United States Patent [19]
Gallatin et al.

[11] Patent Number: 5,837,478
[45] Date of Patent: Nov. 17, 1998

[54] METHOD OF IDENTIFYING MODULATORS OF BINDING BETWEEN AND VCAM-1

[75] Inventors: W. Michael Gallatin, Mercer Island; Monica Van der Vieren, Seattle, both of Wash.

[73] Assignee: ICOS Corporation, Bothell, Wash.

[21] Appl. No.: 943,363

[22] Filed: Oct. 3, 1997

Related U.S. Application Data

[63] Continuation-in-part of Ser. No. 605,672, Feb. 22, 1996, which is a continuation-in-part of Ser. No. 362,652, Dec. 21, 1994, Pat. No. 5,766,850, which is a continuation-in-part of Ser. No. 286,889, Aug. 5, 1994, Pat. No. 5,470,953, which is a continuation-in-part of Ser. No. 173,497, Dec. 23, 1993, Pat. No. 5,437,958.

[51] Int. Cl.$^6$ .......................... G01N 33/53; G01N 33/566
[52] U.S. Cl. ........................... 435/7.24; 435/7.1; 435/7.2; 435/7.21; 435/7.8
[58] Field of Search .............................. 435/7.1, 7.2, 7.24

[56] References Cited

U.S. PATENT DOCUMENTS

| | | |
|---|---|---|
| 4,271,139 | 6/1981 | Hart . |
| 4,568,649 | 2/1986 | Bertoglio-Matte . |
| 5,437,958 | 8/1995 | Gallatin et al. . |
| 5,470,953 | 11/1995 | Gallatin et al. . |
| 5,728,533 | 3/1998 | Gallatin et al. . |

OTHER PUBLICATIONS

Adams, et al., "Experimental graft arteriosclerosis; 1. The Lewis–To–F–344 Allograft Model," *Transplantation*, 53:1115–1119 (1992).
Adams et al., "Experimental graft arteriosclerosis: II. Immunocytochemical analysis of lesion development," *Transplantation*, 56:794–799 (1993).
Anderson, et al., "Exact definition of species–specific and cross–reactive epitopes of the 65–kilodalton protein of mycobacterium leprae using synthetic peptides," *J.Immunol.* 141:607–613 (1988).
Arfors, et al., "A monoclonal antibody to the membrane glycoprotein complex CD18 inhibits polymorphonuclear leukocyte accumulation and plasma leakage in vivo," *Blood* 69:338–340 (1987).
El–Gabalway et al. Arthritis and Rheumatism 39:1913–1921 (1996).
Grayson et al. J. Allergy Clin. Immunol. 101(No.1 Part 2)S51 Abstract 220 (1998).
Van Der Vieren et al.. Immunity 3:683–690 (1995).
Danilenko et al. J. Immunol. 155:35–44 (1995).
Wong et al. Gene 171:291–294 (1996).
Rabb et al. J. Am. Soc. Nephrology 7(9) :1716 (1996) Abstract A2348.
Elangbam et al. Vet. Pathol. 34: 61–73 (1997).
Bernstein et al. Clin. Exp. Immunol. 106: 160–169 (1996).
Arnaout, "Structure and function of the leukocyte adhesion molecules CD11/CD18," *Blood* 75:1037–1050 (1990).
Berman, et al., "Biosynthesis and function of membrane bound and secreted forms of recombinant CD11b/CD18 (Mac–1)," *J. Cell, Biochem* 52:183–195 (1993).
Bochner, et al., "Flow cytometric methods for the analysis of human basophil surface and viability," *J.Immunol.Meth.* 125:265–271 (1989).
Burnett, et al., "The IgA heavy–chain gene family in rabbit: cloning and sequence analysis of 13 Cα genes," *EMBO J.* 8:4041–4047 (1989).
Capecchi, "Altering the genome by homologous recombination," *Science* 244:1288–1292 (1989).
Chang, et al., "A general method for facilitating heterodimeric pairing between two proteins: application to expression of α and β T–cell receptor extracellular segments," *Proc.Natl.Acad.Sci.(USA)*, 91:11408–11412 (1994).
Chisaka, et al., "Developmental defects of the ear, cranial nerves and hindbrain resulting from targeted disruption of the mouse homeobox gene *Hox–1.6*," *Nature* 355:516–520 (1992).
Cobbold, et al., "Non–lineage, LFA–1 family, and leucocyte common antigens: new and previously defined clusters," *Leukocyte Typing III*, McMicael (ed), Oxford Press, p. 788 (1987).
Collins, et al., "The HL–60 promyelocytic leukemia cell line: proliferation, differentiation, and cellular oncogene expression," *Blood*, 70:1233–1244 (1987).
Corbi, et al., "cDNA cloning and complete primary structure of the α subunit of a leukocyte adhesion glycoprotein, p150, 95," *EMBO J.* 6:4023–4028 (1987).
Corbi, et al., "The human leukocyte adhesion glycoprotein Mac–1 (complement receptor type 3, CD116 α subunit," *J.Biol.Chem.* 263:12403–12411 (1988).
Cromartie, et al., "Arthritis in rats after systemic injection of streptococcal cells or cell walls." *J.Exp.Med.* 146:1585–1602 (1977).
Dana, et al., "Deficiency of a surface membrane glycoprotein (Mo1) in man," *J.Clin.Invest.* 73:153–159 (1984).
Danilenko, et al., "Canine leukocyte cell adhesion molecules (LeuCams): characterization of the CD11/CD18 family," *Tissue Antigens* 40:13–21 (1992).
Deng, et al., "Location of crossovers during gene targeting with insertion and replacement vectors," *Mol.Cell.Biol.* 13:2134–2140 (1993).
Diamond, et al., "The I domain is a major recognition site on the leukocyte integrin Mac–1 (CD11b/CD18) for four distinct adhesion ligands," *J.Cell, Biol.* 120:1031–1043 (1993).
Fleming, et al., "Structural Analysis of the CD11b gene and phylogenetic analysis of the α–integrin gene family demonstrate remarkable conservation of genomic organization and suggest early diversification during evolution," *J.Immunol.* 150:480–490 (1993).
Frohman, "Race: Rapid amplification of cDNA ends" in *PCR Protocols: A Guide to Methods and Applications*, Innis, et al. (eds.) Academic press:New York (1990) pp. 28–38.

(List continued on next page.)

*Primary Examiner*—Lila Feisee
*Assistant Examiner*—Phillip Gambel
*Attorney, Agent, or Firm*—Marshall, O'Toole, Gerstein, Murray & Borun

[57] ABSTRACT

Methods to identify modulators of $\alpha_d$ binding to VCAM-1 are disclosed.

4 Claims, 4 Drawing Sheets

OTHER PUBLICATIONS

Greve, et al., "The major human rhinovirus receptor is ICAM–1," *Cell* 56:839 (1989).

Hanenberg, et al., "Macrophage infiltration precedes and is a prerequisite for lymphocytic insulitis in pancreatic islets of prediabetic BB rats," *Diatetologia* 32:126–134 (1989).

Hansel, et al., "Purification of human blood eosinophils by negative selection using immunomagnetic beads," *J.Immunol.Meth.* 122:97–103 (1989).

Hart and Greenwald, "Scintillation proximity assay (SPA)—a new method of immunoassay," *Mol.Immunol.* 12:265–267 (1979).

Hart and Greenwald, "Scintillation proximity assay of antigen–antibody binding kinetics: concise communication," *J.Nuc.Med.* 20:1062–1065 (1979).

Hildreth & Orentas, "Involvement of a leukocyte adhesion receptor (LFA–1) in HIV–induced syncytium formation," *Science* 244:1075–1078 (1989).

Huitinga, et al., "Treatment with anti–CR3 antibodies ED7 and ED8 suppresses experimental allergic encephalomyelitis in Lewis rats," *Eur. J. Immunol* 23:709–715 (1993).

Hynes, et al., Integrins: Versatility, Modulation, and Signaling in Cell Adhesion, *Cell* 69:11–25 (1992).

Ingalls and Golenbock, "CD11c/CD18, A transmembrane signaling receptor for lipopolysaccharide," *J.Exp.Med.,* 181:1473–1479 (1995).

Jutila, et al., "In vivo distribution and characterization of two novel mononuclear phagocyte differentiation antigens in mice," *J.Leukocyte Biol.* 54:30–39 (1993).

Karin and Richards, "Human metallothionein genes—primary structure of the metallothionein–II gene and a related processed protein," *Nature* 299:797–802 (1982).

Kishimoto, et al., "Heterologous mutations of the β subunit common to the LFA–1, Mac–1 and p1150,95 glycoproteins cause leukocyte adhesion deficiency," *Cell* 50:193–202 (1987).

Kishimoto, et al., "Cloning of the β subunit of the leukocyte adhesion proteins: homology to an extracellular matrix receptor defines a novel supergene family," *Cell* 48:681–690 (1987).

Kroncke, et al., "Activated macrophages kill pancreatic syngeneic islet cells via arginine–dependent nitric oxide generation," *BBRC* 175:752–758 (1991).

Landis, et al., "A novel LFA–1 activation epitope maps to the I domain," *J.Cell.Biol.* 120:1519–1527 (1993).

Larson, et al., "Primary sructure of the leukocyte function–associated molecule–1 α subunit; an integrin with an embedded domain defining a protein superfamily," *J.Cell. Biol.* 108:703–712 (1989).

Larson and Springer, "Structure and function of leukocyte integrins," *Immunol.Rev.* 114:181–217 (1990).

Lawrence, et al., "Purification and characterization of human skin mast cells," *J.Immunol.* 139:3062–2069 (1987).

Letvin, et al., "Conservation of myeloid surface antigens on primary granulocyte," *Blood* 61:408–410 (1983).

Luk, et al., "Biotinylated lipopolysaccharide binds to endotoxin receptor in endothelial and moncytic cells," *Alan.Biochem.* 232:217–224 (1995).

MacMicking, et al., "Altered responses to bacterial infection and endotoxic shock in mice lacking inducible nitric oxide synthase," *Cell* 81:641–650 (1995).

McCabe, "Production of single–stranded DNA by asymmetric PCR," in *PCR Protocols; A Guide to Methods and Applicants,* Innis et al. (ed) *Academic Press;* New York (1990) pp. 76–83.

Merrill, et al., "Microglial cell cytotoxicity of oligodendrocytes is mediated through nitric oxide," *Immunol.* 151:2132 (1993).

Metlay, et al., "The distinct leukocyte integrins of mouse spleen dendritic cells as identified with new hamster monoclonal antibodies," *J.Exp.Med.* 141:1753–1771 (1990).

Michishita, et al., "A novel divalent cation–binding site in the A domain of the β2 integrin CR3 (CD11b/CD18) is essential for ligand binding," *Cell* 72:857–867 (1993).

Moore, et al., "Canine leukocyte integrins; characteization of a CD18 homologue," *Tissue Antigens* 36:211–220 (1990).

Mulligan, et al., "Tissue injury caused by deposition of immune complexes is L–arginine dependent," *Proc.Natl.Acad.Sci.(USA)* 88:6338–6342 (1991).

Nourshargh, et al., "Accumulation of [111]In–neutrophils in rabbit skin in allergic and non–allergic inflammatory reactions in vivo," *J.Immunol.* 142;3193–3198 (1989).

Patarroyo, et al., "Leukocyte–cell adhesion: a molecular process fundamental in leukocyte physiology," *Immunol.Rev.* 114:67–108 (1990).

Price, et al., "In vivo inhibition of neutrophil function in the rabbit using monoclonal antibody to CD18," *J.Immunol.* 139:4174–4177 (1987).

Randi and Hogg, "I domain of $β_2$ integrin lymphocyte function–associated antigen–1 contains a binding site for ligand intercellular adhesion molecule–1," *J.Biol.Chem.* 269:12395–12398 (1994).

Rojiani et al., "In vitro interaction of a polypeptide homologous to human Ro/SS–A antigen (calreticulin) with a highly conserved amino acid sequence in the cytoplasmic domain of integrin α subunits," *Biochemistry* 30:9859–9866 (1991).

Rosenfeld, et al., "Fatty streak initiation in Watanabe heritable hyperlipemic and comparably hypercholesterolemic fat–fed rabbits" *Arteriosclerosis* 7:9–23 (1987).

Rosenfeld, et al., "Fatty steak expansion and maturation in Watanabe heritable hyperlipemic and comparably hypercholesterolemic fat–fed rabbits" *Arteriosclerosis* 7:24–34 (1987).

Sadhu, et al., "LFA–1 Binding site in ICAM–3 contains a conserved motif and non–contiguous amino acids" *Cell Adhesion and Communication,* 2:429–440 (1994).

Sambrook, et al., (eds), "Immobilization of Bacteriophage λ Plaques on nitrocellulose filters or nylon membranes" in *Molecular Cloning: a laboratory manual,* Cold Spring Harbor Press:Cold Spring Harbor, NY (1989) p.2.110.

Sanchez–Madrid, et al., "A human leukocyte differentiation antigen family with distinct αa–subunits and a common β–subunit," *J.Exp.Med.* 154:1517 (1981).

Schall, "Biology of the rantes/sis cytokine family" *Cytokine,* 3:165–183 (1991).

Schneiderman, et al., "Expression of 12 rabbit IgA Cα genes as chimeric rabbit–mouse IgA antibodies," *Proc.Natl.Acad. Sci. (USA)* 86:7562–7565 (1989).

Schwab, et al., "Pro–and anti–inflammatory roles of interleukin–1 recurrence of bacterial cell wall–induced arthritis in rats," *Infection and Immunity* 59:4436–4442 (1991).

Searle, et al., "Regulation, linkage, and sequence of mouse metallothionein I and II genes," *Mol.Cell.Biol.* 4:1221–1230 (1984).

Shaw, et al., "Molecular cloning of the human mucosal lymphocyte integrin $\alpha^E$ subunit," *J.Biol.Chem.* 269:6016–6025 (1994).

Smith, et al., "Cooperative interactions of LFA–1 and Mac–1 with intercellular adhesion molecule–1 in facilitating adherence and transendothelial migration of human neutrophils in vitro," *J.Clin.Invest.* 83:2008–2017 (1989).

Springer, "Adhesion molecules of the immune system," *Nature* 346:425–434 (1990).

Tamura, et al., "Epithelial interin$\alpha_6\beta_4$: complete primary structure of $\alpha_6$ and variant forms of $\beta_4$," *J.Cell.Biol.* 111:1593–1604 (1990).

Ueda, et al., "Identification of the complement iC3b binding site in the $\beta2$ integrin CR3 (CD11b/CD18)," *Proc.Natl.Acad.Sci. (USA)* 91:10680–10684 (1994).

Varshney, et al., "Structure, organization, and regulation of human metallothionein $I^F$ gene; differential and cell–type specific expression in response to heavy metals and glucocorticoids," *Mol.Cell.Biol.* 6:26–36 (1986).

Warner, et al., "A rapid Percoll technique for the purification of human basophils," *J.Immunol.Meth.* 106:107–110 (1987).

Wright, "Multiple receptors for endotoxin," *Curr.Opin.Immunol.* 3:83–90 (1991).

Yamada, et al., "Mucosal injury and inflammation in a model of chronic granulomatous colitis in rats," *Gastroenterology* 104:759–771 (1993).

Zhou, et al., "Differential ligand binding specificities of recombinant Cd11b/Cd18 integrin I–domain" *J.Biol. Chem.* 269: 17076–17079 (1994).

Denholm and Wolber, "A simple method for the purification of human peripheral blood monocytes", *Immunol. Meth.* 144:247–251 (1991).

Rabb, et al., "Alterations in Soluble and Leukocyte Surface L–Selectin (CD62L) in Hemodialysis Patients[1.1]", *J.Am.Soc.Nephrol.* 6:1445–1450 (1995).

Rabb, et al., "Cell Adhesion Molecules and the Kidney", *Am.J.Kidnet.Dis.* 23:155–166 (1994).

Ward and Reynolds, "A Heterogeneous Lymhoocytic Leukemia in F344 Rats", *Am.J.Pathol.* 110:1–10 (1982).

Stromberg, "Large Granular Lymphocyte Leukemia in F344 Rats", *Am.J.Pathol.* 119:517–519 (1985).

Reynolds, et al., "Nature Killer Activity in the Rat", *J.Immunol.* 132;534–540 (1984).

```
αD     TF-GT--VLL  LSVLASYHGF  NLDVEEPTIF  QEDAGGFGQS  VVQFGGSRLV   47
CD11B  MA-LR--VLL  LTALTLCHGF  NLDTENAMTF  QENARGFGQS  VVQLQGSRVV   47
CD11C  MTRTRAALLL  FTALATSLGF  NLDTEELTAF  RVDSAGFGDS  VVQYANSWVV   50

αD     VGAPLEVVAA  NQTGRLYDCA  AATGMCQPIP  LHIRPEAVNM  SLGLTLAAST   97
CD11B  VGAPQEIVAA  NRGSLYQCD   YSTGSCEPIR  LQVPVEAVNM  SLGLSLAATT   97
CD11C  VGAPQKIIAA  NQIGGLYQCG  YSTGACEPIG  LQVPPEAVNM  SLGLSLASTT  100

αD     NGSRLLACGP  TLHRVCGENS  YSKGSCLLLG  SR-WEIIQTV  PDATPECPHQ  146
CD11B  SPPQLLACGP  TVHQTCSENT  YVKGLCFLFG  SNLRQQPQKF  PEALRGCPQE  147
CD11C  SPSQLLACGP  TVHHECGRNM  YLTGLCFLLG  PT--QLTQRL  PVSRQECPRQ  148

αD     EMDIVFLIDG  SGSIDQNDFN  QMKGFVQAVM  GQFEGTDTLF  ALMQYSNLLK  196
CD11B  DSDIAFLIDG  SGSIIPHDFR  RMKEFVSTVM  EQLKKSKTLF  SLMQYSEEFR  197
CD11C  EQDIVFLIDG  SGSISSRNFA  TMMNFVRAVI  SQFQRPSTQF  SLMQFSNKFQ  198

αD     IHFTFQFRT   SPSQQSLVDP  IVQLKGLTFT  ATGILTVVTQ  LFHHKNGARK  246
CD11B  IHFTFKEFQN  NPNPRSLVKP  ITQLLGRTHT  ATGIRKVVRE  LFNITNGARK  247
CD11C  THFTFEEFRR  TSNPLSLLAS  VHQLQGFTYT  ATAIQNVVHR  LFHASYGARR  248

αD     SAKKILIVIT  DGQKYKDPLE  YSDVIPQAEK  AGIIRYAIGV  GHAFQGPTAR  296
CD11B  NAFKILVVIT  DGEKFGDPLG  YEDVIPEADR  EGVIRYVIGV  GDAFRSEKSR  297
CD11C  DAIKILIVIT  DGKKEGDSLD  YKDVIPMADA  AGIIRYAIGV  GLAFQNRRNSW 298
```

FIGURE 1A

```
αD    QELNTISSAP PODHVFKVDN FAALGSIQKQ LQEKIYAVEG TQSRASSSFQ    346
CD11b QELNTIASKP PRDHVFQVNN FEALKTIQNQ LREKIFAIEG TQTGSSSSFE    347
CD11c KELNDIASKP SQEHIFKVED FDALKDIQNQ LKEKIFAIEG TETISSSSFE    348

αD    HEMSQEGFST ALTMDGLFLG AVGSFSWSGG AFLYPPNMSP TFINMSQENV    396
CD11b HEMSQEGFSA AITSNGPLLS TVGSYDWAGG VFLYTSKEKS TFINMTRVDS    397
CD11c LEMAQEGFSA VFTPDGPVLG AVGSFTWSGG AFLYPPNMSP TFINMSQENV    398

αD    DMRDSYLGYS TELALWKGVQ NLVLGAPRYQ HTGKAVIFTQ VSRQWRKKAE    446
CD11b DMNDAYLGYA AAIILRNRVQ SLVLGAPRYQ HIGLVAMFRQ NTGMWESNAN    447
CD11c DMRDSYLGYS TELALWKGVQ SLVLGAPRYQ HIGKAVIFIQ VSRQWRMKAE    448

αD    VTGTQIGSYF GASLCSVDVD SDGSTDLILI GAPHYYEQTR GGQVSVCPLP    496
CD11b VKGTQIGAYF GASLCSVDVD SNGSTDLVLI GAPHYYEQTR GGQVSVCPLP    497
CD11c VIGTQIGSYF GASLCSVDVD TDGSTDLVLI GAPHYYEQTR GGQVSVCPLP    498

αD    RGQRVQWQCD AVLRGEQGHP WGRFGAALTV LGDVNEDKLI DVAIGAPGEQ    546
CD11b RGQRARWQCD AVLYGEQGQP WGRFGAALTV LGDVNGDKLT DVAIGAPGEE    547
CD11c RGWRRMW-CD AVLYGEQGHP WGRFGAALTV LGDVNGDKLT DVVIGAPGEE    547

αD    ENRGAVYLFH GASESGISPS HSQRIASSQL SPRLQYFGQA LSGGQDLTQD    596
CD11b DNRGAVYLFH GTSGSGISPS HSQRIAGSKL SPRLQYFGQS LSGGQDLTMD    597
CD11c ENRGAVYLFH GVLGPSISPS HSQRIAGSQL SSRLQYFGQA LSGGQDLTQD    597
```

FIGURE 1B

```
αD    GLMDLAVGAR GQVLLLLRSLP VLKVGVAMRF SPVEVAKAVY RCWEEKPSAL  646
CD11B GLVDLTVGAQ GHVLLLLRSQP VLRVKAIMEF NPREVARNVF ECNDQVVKGK  647
CD11C GLVDLAVGAR GQVLLLLRTRP VLWVGVSMQF IPAEIPRSAF ECREQVVSEQ  647

αD    EAGDATVCLT IQKSSLDQL- -GDIQSSVRF DLALDPGRLT SRAIFNETKN   694
CD11B EAGEVRVCLH VQKSTRDRLR EGQIQSVVTY DLALDSGRPH SRAVFNETKN   697
CD11C TLVQSNICLY IDKRSKNLLG SRDLQSSVTL DLALAPGRLS PRAIFQETKN   697

αD    PTLTTRKTLG LGIHCETLKL LLPDCVEDVV SPIILHLNFS LVREPIPSPQ   744
CD11B STRRQTQVLG LTQTCETLKL QLPNCIEDPV SPIVLRLNFS LVGTPLSAFG   747
CD11C RSLSRVRVLG LKAHCENFNL LLPSCVEDSV IPIILRLNFT LVGKPLLAFR   747

αD    NLRPVLAVGS QDLFTASLPF EKNCGQDGLC EGDLGVTLSF SGLQTLTVGS   794
CD11B NLRPVLAEDA QRLFTALFPF EKNCGNDNIC QDDLSITFSF MSLDCLVVGG   797
CD11C NLRPMLAALA QRYFTASLPF EKNCGADHIC QDNLGISFSF PGLKSLLVGS   797

αD    SLELNVIVTV WNAGEDSYGT VVSLYYPAGL SHRRVSGAQK QPHQSALRLA   844
CD11B PREFNVTVTV RNDGEDSYRT QVTFFFPLDL SYRKVSTLQN QRSQRSWRLA   847
CD11C NLELNAEVMV WNDGEDSYGT TITFSHPAGL SYRYVAEGQK QGQLRSLHLT   847

αD    CETVPTED-- EGLRSSRCSV NHPIFHEGSN GTFIVTFDVS Y---KATLG    888
CD11B CESASSTEVS GALKSTSCSI NHPIFPENSE ---- -VTFNIT FDVDSKASLG 893
CD11C CCSA-PVGSQ GTW-STSCRI NHLIFRGGAQ ---- ----ITFLAT FDVSPKAVGL 891
```

FIGURE 1C

|       |                |                |                |                |                |                |      |
|-------|----------------|----------------|----------------|----------------|----------------|----------------|------|
| αD    | DRMLMRASAS     | SENNKASSSK     | ATFQLELPVK     | YAVYTMISRQ     | EESTKYFNFA     |                | 938  |
| CD11B | NKLLLKANVT     | SENNMPRTNK     | TEFQLELPVK     | YAVYMVVTSH     | GVSTKYLNFT     |                | 943  |
| CD11C | DRLLLIANVS     | SENNIPRTSK     | TIFQLELPVK     | YAVYIVVSSH     | EQFTKYLNFS     |                | 941  |
|       |                |                |                |                |                |                |      |
| αD    | TS-DEKKMKE     | AEHRYRVNNL     | SQRDLAISIN     | FWPVLLNGV      | AVWDVVMEAP     |                | 987  |
| CD11B | AS-ENTS-RV     | MQHQYQVSNL     | GQRSLPISLV     | FLVPVRLNQT     | VIWDRPQVTF     |                | 991  |
| CD11C | ESEEKES-HV     | AMHRYQVNNL     | GQRDLPVSIN     | FWPVELNQE      | AVWMDVEVSH     |                | 990  |
|       |                |                |                |                |                |                |      |
| αD    | SQSLP--CVS     | ERKPPQHSDF     | LTQISRSPML     | DCSIADCLQF     | RCDVPSFSVQ     |                | 1035 |
| CD11B | SENLSSTCHT     | KERLPSHSDF     | LAELRKAPVV     | NCSIAVCQRI     | QCDIPFFGIQ     |                | 1041 |
| CD11C | PQNPSLRCSS     | EKIAPPASDF     | LAHIQKNPVL     | DCSIAGCLRF     | RCDVPSFSVQ     |                | 1040 |
|       |                |                |                |                |                |                |      |
| αD    | EELDFTLKGN     | LSFGWVRETL     | QKKVLVVSVA     | EITFDTSVYS     | QLPGQEAFMR     |                | 1085 |
| CD11B | EEFNATLKGN     | LSFDWYIKTS     | HNHLLIVSTA     | EILFNDSVFT     | LLPGQGAFVR     |                | 1091 |
| CD11C | EELDFTLKGN     | LSFGWVRQIL     | QKKVSVSVA      | EIIFDTSVYS     | QLPGQEAFMR     |                | 1090 |
|       |                |                |                |                |                |                |      |
| αD    | AQMEMVLEED     | EVYNAIPIIM     | GSSVGALLLL     | ALITATLYKL     | GFFKRHYKEM     |                | 1135 |
| CD11B | SQTETKVEPF     | EVPNPLPLIV     | GSSVGGLLLL     | ALITAALYKL     | GFFKRQYKDM     |                | 1141 |
| CD11C | AQTITVLEKY     | KVHNPIPLIV     | GSSIGGLLLL     | ALITAVLYKV     | GFFKRQYKEM     |                | 1140 |
|       |                |                |                |                |                |                |      |
| αD    | LEDKPED---     | -----TATFS     | GDDFSCVAPN     | VPLS           |                |                | 1161 |
| CD11B | M---SEG---     | -----GP--P     | GAE-----PQ     | ----           |                |                | 1153 |
| CD11C | M---EEANGQ     | IAPENGT--Q     | TPS-----PP     | SEK            |                |                | 1163 |

FIGURE 1D

SEQUENCE LISTING ( 1 ) GENERAL INFORMATION:

( i i i ) NUMBER OF SEQUENCES: 114

( 2 ) INFORMATION FOR SEQ ID NO:1:

( i ) SEQUENCE CHARACTERISTICS:
        ( A ) LENGTH: 3726 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..3485

( x i ) SEQUENCE DESCRIPTION: SEQ ID NO:1:

```
TG ACC TTC GGC ACT GTG CTT CTT CTG AGT GTC CTG GCT TCT TAT CAT            47
   Thr Phe Gly Thr Val Leu Leu Leu Ser Val Leu Ala Ser Tyr His
    1               5                  10                  15

GGA TTC AAC CTG GAT GTG GAG GAG CCT ACG ATC TTC CAG GAG GAT GCA           95
Gly Phe Asn Leu Asp Val Glu Glu Pro Thr Ile Phe Gln Glu Asp Ala
                20                  25                  30

GGC GGC TTT GGG CAG AGC GTG GTG CAG TTC GGT GGA TCT CGA CTC GTG          143
Gly Gly Phe Gly Gln Ser Val Val Gln Phe Gly Gly Ser Arg Leu Val
            35                  40                  45

GTG GGA GCA CCC CTG GAG GTG GTG GCG GCC AAC CAG ACG GGA CGG CTG          191
Val Gly Ala Pro Leu Glu Val Val Ala Ala Asn Gln Thr Gly Arg Leu
        50                  55                  60

TAT GAC TGC GCA GCT GCC ACC GGC ATG TGC CAG CCC ATC CCG CTG CAC          239
Tyr Asp Cys Ala Ala Ala Thr Gly Met Cys Gln Pro Ile Pro Leu His
    65                  70                  75

ATC CGC CCT GAG GCC GTG AAC ATG TCC TTG GGC CTG ACC CTG GCA GCC          287
Ile Arg Pro Glu Ala Val Asn Met Ser Leu Gly Leu Thr Leu Ala Ala
80                  85                  90                  95

TCC ACC AAC GGC TCC CGG CTC CTG GCC TGT GGC CCG ACC CTG CAC AGA          335
Ser Thr Asn Gly Ser Arg Leu Leu Ala Cys Gly Pro Thr Leu His Arg
                100                 105                 110

GTC TGT GGG GAG AAC TCA TAC TCA AAG GGT TCC TGC CTC CTG CTG GGC          383
Val Cys Gly Glu Asn Ser Tyr Ser Lys Gly Ser Cys Leu Leu Leu Gly
            115                 120                 125

TCG CGC TGG GAG ATC ATC CAG ACA GTC CCC GAC GCC ACG CCA GAG TGT          431
Ser Arg Trp Glu Ile Ile Gln Thr Val Pro Asp Ala Thr Pro Glu Cys
        130                 135                 140

CCA CAT CAA GAG ATG GAC ATC GTC TTC CTG ATT GAC GGC TCT GGA AGC          479
Pro His Gln Glu Met Asp Ile Val Phe Leu Ile Asp Gly Ser Gly Ser
    145                 150                 155

ATT GAC CAA AAT GAC TTT AAC CAG ATG AAG GGC TTT GTC CAA GCT GTC          527
Ile Asp Gln Asn Asp Phe Asn Gln Met Lys Gly Phe Val Gln Ala Val
160                 165                 170                 175

ATG GGC CAG TTT GAG GGC ACT GAC ACC CTG TTT GCA CTG ATG CAG TAC          575
Met Gly Gln Phe Glu Gly Thr Asp Thr Leu Phe Ala Leu Met Gln Tyr
                180                 185                 190

TCA AAC CTC CTG AAG ATC CAC TTC ACC TTC ACC CAA TTC CGG ACC AGC          623
```

```
                Ser  Asn  Leu  Leu  Lys  Ile  His  Phe  Thr  Phe  Thr  Gln  Phe  Arg  Thr  Ser
                               195                      200                      205

CCG  AGC  CAG  CAG  AGC  CTG  GTG  GAT  CCC  ATC  GTC  CAA  CTG  AAA  GGC  CTG                   671
Pro  Ser  Gln  Gln  Ser  Leu  Val  Asp  Pro  Ile  Val  Gln  Leu  Lys  Gly  Leu
          210                      215                      220

ACG  TTC  ACG  GCC  ACG  GGC  ATC  CTG  ACA  GTG  GTG  ACA  CAG  CTA  TTT  CAT                   719
Thr  Phe  Thr  Ala  Thr  Gly  Ile  Leu  Thr  Val  Val  Thr  Gln  Leu  Phe  His
          225                      230                      235

CAT  AAG  AAT  GGG  GCC  CGA  AAA  AGT  GCC  AAG  AAG  ATC  CTC  ATT  GTC  ATC                   767
His  Lys  Asn  Gly  Ala  Arg  Lys  Ser  Ala  Lys  Lys  Ile  Leu  Ile  Val  Ile
240                      245                      250                      255

ACA  GAT  GGG  CAG  AAG  TAC  AAA  GAC  CCC  CTG  GAA  TAC  AGT  GAT  GTC  ATC                   815
Thr  Asp  Gly  Gln  Lys  Tyr  Lys  Asp  Pro  Leu  Glu  Tyr  Ser  Asp  Val  Ile
                    260                      265                      270

CCC  CAG  GCA  GAG  AAG  GCT  GGC  ATC  ATC  CGC  TAC  GCT  ATC  GGG  GTG  GGA                   863
Pro  Gln  Ala  Glu  Lys  Ala  Gly  Ile  Ile  Arg  Tyr  Ala  Ile  Gly  Val  Gly
               275                      280                      285

CAC  GCT  TTC  CAG  GGA  CCC  ACT  GCC  AGG  CAG  GAG  CTG  AAT  ACC  ATC  AGC                   911
His  Ala  Phe  Gln  Gly  Pro  Thr  Ala  Arg  Gln  Glu  Leu  Asn  Thr  Ile  Ser
          290                      295                      300

TCA  GCG  CCT  CCG  CAG  GAC  CAC  GTG  TTC  AAG  GTG  GAC  AAC  TTT  GCA  GCC                   959
Ser  Ala  Pro  Pro  Gln  Asp  His  Val  Phe  Lys  Val  Asp  Asn  Phe  Ala  Ala
305                      310                      315

CTT  GGC  AGC  ATC  CAG  AAG  CAG  CTG  CAG  GAG  AAG  ATC  TAT  GCA  GTT  GAG                  1007
Leu  Gly  Ser  Ile  Gln  Lys  Gln  Leu  Gln  Glu  Lys  Ile  Tyr  Ala  Val  Glu
320                      325                      330                      335

GGA  ACC  CAG  TCC  AGG  GCA  AGC  AGC  TCC  TTC  CAG  CAC  GAG  ATG  TCC  CAA                  1055
Gly  Thr  Gln  Ser  Arg  Ala  Ser  Ser  Ser  Phe  Gln  His  Glu  Met  Ser  Gln
                    340                      345                      350

GAA  GGC  TTC  AGC  ACA  GCC  CTC  ACA  ATG  GAT  GGC  CTC  TTC  CTG  GGG  GCT                  1103
Glu  Gly  Phe  Ser  Thr  Ala  Leu  Thr  Met  Asp  Gly  Leu  Phe  Leu  Gly  Ala
               355                      360                      365

GTG  GGG  AGC  TTT  AGC  TGG  TCT  GGA  GGT  GCC  TTC  CTG  TAT  CCC  CCA  AAT                  1151
Val  Gly  Ser  Phe  Ser  Trp  Ser  Gly  Gly  Ala  Phe  Leu  Tyr  Pro  Pro  Asn
          370                      375                      380

ATG  AGC  CCC  ACC  TTC  ATC  AAC  ATG  TCT  CAG  GAG  AAT  GTG  GAC  ATG  AGG                  1199
Met  Ser  Pro  Thr  Phe  Ile  Asn  Met  Ser  Gln  Glu  Asn  Val  Asp  Met  Arg
385                      390                      395

GAC  TCT  TAC  CTG  GGT  TAC  TCC  ACC  GAG  CTA  GCC  CTG  TGG  AAG  GGG  GTA                  1247
Asp  Ser  Tyr  Leu  Gly  Tyr  Ser  Thr  Glu  Leu  Ala  Leu  Trp  Lys  Gly  Val
400                      405                      410                      415

CAG  AAC  CTG  GTC  CTG  GGG  GCC  CCC  CGC  TAC  CAG  CAT  ACC  GGG  AAG  GCT                  1295
Gln  Asn  Leu  Val  Leu  Gly  Ala  Pro  Arg  Tyr  Gln  His  Thr  Gly  Lys  Ala
                    420                      425                      430

GTC  ATC  TTC  ACC  CAG  GTG  TCC  AGG  CAA  TGG  AGG  AAG  AAG  GCC  GAA  GTC                  1343
Val  Ile  Phe  Thr  Gln  Val  Ser  Arg  Gln  Trp  Arg  Lys  Lys  Ala  Glu  Val
               435                      440                      445

ACA  GGG  ACG  CAG  ATC  GGC  TCC  TAC  TTC  GGG  GCC  TCC  CTC  TGC  TCC  GTG                  1391
Thr  Gly  Thr  Gln  Ile  Gly  Ser  Tyr  Phe  Gly  Ala  Ser  Leu  Cys  Ser  Val
          450                      455                      460

GAT  GTG  GAC  AGC  GAT  GGC  AGC  ACC  GAC  CTG  ATC  CTC  ATT  GGG  GCC  CCC                  1439
Asp  Val  Asp  Ser  Asp  Gly  Ser  Thr  Asp  Leu  Ile  Leu  Ile  Gly  Ala  Pro
     465                      470                      475

CAT  TAC  TAT  GAG  CAG  ACC  CGA  GGG  GGC  CAG  GTG  TCC  GTG  TGT  CCC  TTG                  1487
His  Tyr  Tyr  Glu  Gln  Thr  Arg  Gly  Gly  Gln  Val  Ser  Val  Cys  Pro  Leu
480                      485                      490                      495

CCT  AGG  GGG  CAG  AGG  GTG  CAG  TGG  CAG  TGT  GAC  GCT  GTT  CTC  CGT  GGT                  1535
Pro  Arg  Gly  Gln  Arg  Val  Gln  Trp  Gln  Cys  Asp  Ala  Val  Leu  Arg  Gly
                    500                      505                      510

GAG  CAG  GGC  CAC  CCC  TGG  GGC  CGC  TTT  GGG  GCA  GCC  CTG  ACA  GTG  TTG                  1583
```

```
Glu Gln Gly His Pro Trp Gly Arg Phe Gly Ala Ala Leu Thr Val Leu
            515             520                 525

GGG GAT GTG AAT GAG GAC AAG CTG ATA GAC GTG GCC ATT GGG GCC CCG    1631
Gly Asp Val Asn Glu Asp Lys Leu Ile Asp Val Ala Ile Gly Ala Pro
        530             535                 540

GGA GAG CAG GAG AAC CGG GGT GCT GTC TAC CTG TTT CAC GGA GCC TCA    1679
Gly Glu Gln Glu Asn Arg Gly Ala Val Tyr Leu Phe His Gly Ala Ser
545                 550                 555

GAA TCC GGC ATC AGC CCC TCC CAC AGC CAG CGG ATT GCC AGC TCC CAG    1727
Glu Ser Gly Ile Ser Pro Ser His Ser Gln Arg Ile Ala Ser Ser Gln
560                 565                 570                 575

CTC TCC CCC AGG CTG CAG TAT TTT GGG CAG GCG CTG AGT GGG GGT CAG    1775
Leu Ser Pro Arg Leu Gln Tyr Phe Gly Gln Ala Leu Ser Gly Gly Gln
                580                 585                 590

GAC CTC ACC CAG GAT GGA CTG ATG GAC CTG GCC GTG GGG GCC CGG GGC    1823
Asp Leu Thr Gln Asp Gly Leu Met Asp Leu Ala Val Gly Ala Arg Gly
            595                 600                 605

CAG GTG CTC CTG CTC AGG AGT CTG CCG GTG CTG AAA GTG GGG GTG GCC    1871
Gln Val Leu Leu Leu Arg Ser Leu Pro Val Leu Lys Val Gly Val Ala
        610                 615                 620

ATG AGA TTC AGC CCT GTG GAG GTG GCC AAG GCT GTG TAC CGG TGC TGG    1919
Met Arg Phe Ser Pro Val Glu Val Ala Lys Ala Val Tyr Arg Cys Trp
625                 630                 635

GAA GAG AAG CCC AGT GCC CTG GAA GCT GGG GAC GCC ACC GTC TGT CTC    1967
Glu Glu Lys Pro Ser Ala Leu Glu Ala Gly Asp Ala Thr Val Cys Leu
640                 645                 650                 655

ACC ATC CAG AAA AGC TCA CTG GAC CAG CTA GGT GAC ATC CAA AGC TCT    2015
Thr Ile Gln Lys Ser Ser Leu Asp Gln Leu Gly Asp Ile Gln Ser Ser
                660                 665                 670

GTC AGG TTT GAT CTG GCA CTG GAC CCA GGT CGT CTG ACT TCT CGT GCC    2063
Val Arg Phe Asp Leu Ala Leu Asp Pro Gly Arg Leu Thr Ser Arg Ala
            675                 680                 685

ATT TTC AAT GAA ACC AAG AAC CCC ACT TTG ACT CGA AGA AAA ACC CTG    2111
Ile Phe Asn Glu Thr Lys Asn Pro Thr Leu Thr Arg Arg Lys Thr Leu
        690                 695                 700

GGA CTG GGG ATT CAC TGT GAA ACC CTG AAG CTG CTT TTG CCA GAT TGT    2159
Gly Leu Gly Ile His Cys Glu Thr Leu Lys Leu Leu Leu Pro Asp Cys
705                 710                 715

GTG GAG GAT GTG GTG AGC CCC ATC ATT CTG CAC CTC AAC TTC TCA CTG    2207
Val Glu Asp Val Val Ser Pro Ile Ile Leu His Leu Asn Phe Ser Leu
720                 725                 730                 735

GTG AGA GAG CCC ATC CCC TCC CCC CAG AAC CTG CGT CCT GTG CTG GCC    2255
Val Arg Glu Pro Ile Pro Ser Pro Gln Asn Leu Arg Pro Val Leu Ala
                740                 745                 750

GTG GGC TCA CAA GAC CTC TTC ACT GCT TCT CTC CCC TTC GAG AAG AAC    2303
Val Gly Ser Gln Asp Leu Phe Thr Ala Ser Leu Pro Phe Glu Lys Asn
            755                 760                 765

TGT GGG CAA GAT GGC CTC TGT GAA GGG GAC CTG GGT GTC ACC CTC AGC    2351
Cys Gly Gln Asp Gly Leu Cys Glu Gly Asp Leu Gly Val Thr Leu Ser
        770                 775                 780

TTC TCA GGC CTG CAG ACC CTG ACC GTG GGG AGC TCC CTG GAG CTC AAC    2399
Phe Ser Gly Leu Gln Thr Leu Thr Val Gly Ser Ser Leu Glu Leu Asn
785                 790                 795

GTG ATT GTG ACT GTG TGG AAC GCA GGT GAG GAT TCC TAC GGA ACC GTG    2447
Val Ile Val Thr Val Trp Asn Ala Gly Glu Asp Ser Tyr Gly Thr Val
800                 805                 810                 815

GTC AGC CTC TAC TAT CCA GCA GGG CTG TCG CAC CGA CGG GTG TCA GGA    2495
Val Ser Leu Tyr Tyr Pro Ala Gly Leu Ser His Arg Arg Val Ser Gly
                820                 825                 830

GCC CAG AAG CAG CCC CAT CAG AGT GCC CTG CGC CTG GCA TGT GAG ACA    2543
```

-continued

| | | | | | | | | | | | | | | | |
|---|---|---|---|---|---|---|---|---|---|---|---|---|---|---|---|
| Ala | Gln | Lys | Gln | Pro | His | Gln | Ser | Ala | Leu | Arg | Leu | Ala | Cys | Glu | Thr |
| | | 835 | | | | | 840 | | | | | 845 | | | |

| GTG | CCC | ACT | GAG | GAT | GAG | GGC | CTA | AGA | AGC | AGC | CGC | TGC | AGT | GTC | AAC | 2591 |
|---|---|---|---|---|---|---|---|---|---|---|---|---|---|---|---|---|
| Val | Pro | Thr | Glu | Asp | Glu | Gly | Leu | Arg | Ser | Ser | Arg | Cys | Ser | Val | Asn | |
| | | 850 | | | | | 855 | | | | | 860 | | | | |

| CAC | CCC | ATC | TTC | CAT | GAG | GGC | TCT | AAC | GGC | ACC | TTC | ATA | GTC | ACA | TTC | 2639 |
|---|---|---|---|---|---|---|---|---|---|---|---|---|---|---|---|---|
| His | Pro | Ile | Phe | His | Glu | Gly | Ser | Asn | Gly | Thr | Phe | Ile | Val | Thr | Phe | |
| | 865 | | | | | 870 | | | | | 875 | | | | | |

| GAT | GTC | TCC | TAC | AAG | GCC | ACC | CTG | GGA | GAC | AGG | ATG | CTT | ATG | AGG | GCC | 2687 |
|---|---|---|---|---|---|---|---|---|---|---|---|---|---|---|---|---|
| Asp | Val | Ser | Tyr | Lys | Ala | Thr | Leu | Gly | Asp | Arg | Met | Leu | Met | Arg | Ala | |
| 880 | | | | | 885 | | | | | 890 | | | | | 895 | |

| AGT | GCA | AGC | AGT | GAG | AAC | AAT | AAG | GCT | TCA | AGC | AGC | AAG | GCC | ACC | TTC | 2735 |
|---|---|---|---|---|---|---|---|---|---|---|---|---|---|---|---|---|
| Ser | Ala | Ser | Ser | Glu | Asn | Asn | Lys | Ala | Ser | Ser | Ser | Lys | Ala | Thr | Phe | |
| | | | | 900 | | | | | 905 | | | | | 910 | | |

| CAG | CTG | GAG | CTC | CCG | GTG | AAG | TAT | GCA | GTC | TAC | ACC | ATG | ATC | AGC | AGG | 2783 |
|---|---|---|---|---|---|---|---|---|---|---|---|---|---|---|---|---|
| Gln | Leu | Glu | Leu | Pro | Val | Lys | Tyr | Ala | Val | Tyr | Thr | Met | Ile | Ser | Arg | |
| | | | 915 | | | | | 920 | | | | | 925 | | | |

| CAG | GAA | GAA | TCC | ACC | AAG | TAC | TTC | AAC | TTT | GCA | ACC | TCC | GAT | GAG | AAG | 2831 |
|---|---|---|---|---|---|---|---|---|---|---|---|---|---|---|---|---|
| Gln | Glu | Glu | Ser | Thr | Lys | Tyr | Phe | Asn | Phe | Ala | Thr | Ser | Asp | Glu | Lys | |
| | | 930 | | | | | 935 | | | | | 940 | | | | |

| AAA | ATG | AAA | GAG | GCT | GAG | CAT | CGA | TAC | CGT | GTG | AAT | AAC | CTC | AGC | CAG | 2879 |
|---|---|---|---|---|---|---|---|---|---|---|---|---|---|---|---|---|
| Lys | Met | Lys | Glu | Ala | Glu | His | Arg | Tyr | Arg | Val | Asn | Asn | Leu | Ser | Gln | |
| | 945 | | | | | 950 | | | | | 955 | | | | | |

| CGA | GAT | CTG | GCC | ATC | AGC | ATT | AAC | TTC | TGG | GTT | CCT | GTC | CTG | CTG | AAC | 2927 |
|---|---|---|---|---|---|---|---|---|---|---|---|---|---|---|---|---|
| Arg | Asp | Leu | Ala | Ile | Ser | Ile | Asn | Phe | Trp | Val | Pro | Val | Leu | Leu | Asn | |
| 960 | | | | | 965 | | | | | 970 | | | | | 975 | |

| GGG | GTG | GCT | GTG | TGG | GAT | GTG | GTC | ATG | GAG | GCC | CCA | TCT | CAG | AGT | CTC | 2975 |
|---|---|---|---|---|---|---|---|---|---|---|---|---|---|---|---|---|
| Gly | Val | Ala | Val | Trp | Asp | Val | Val | Met | Glu | Ala | Pro | Ser | Gln | Ser | Leu | |
| | | | | 980 | | | | | 985 | | | | | 990 | | |

| CCC | TGT | GTT | TCA | GAG | AGA | AAA | CCT | CCC | CAG | CAT | TCT | GAC | TTC | CTG | ACC | 3023 |
|---|---|---|---|---|---|---|---|---|---|---|---|---|---|---|---|---|
| Pro | Cys | Val | Ser | Glu | Arg | Lys | Pro | Pro | Gln | His | Ser | Asp | Phe | Leu | Thr | |
| | | | 995 | | | | | 1000 | | | | | 1005 | | | |

| CAG | ATT | TCA | AGA | AGT | CCC | ATG | CTG | GAC | TGC | TCC | ATT | GCT | GAC | TGC | CTG | 3071 |
|---|---|---|---|---|---|---|---|---|---|---|---|---|---|---|---|---|
| Gln | Ile | Ser | Arg | Ser | Pro | Met | Leu | Asp | Cys | Ser | Ile | Ala | Asp | Cys | Leu | |
| | | | 1010 | | | | | 1015 | | | | | 1020 | | | |

| CAG | TTC | CGC | TGT | GAC | GTC | CCC | TCC | TTC | AGC | GTC | CAG | GAG | GAG | CTG | GAT | 3119 |
|---|---|---|---|---|---|---|---|---|---|---|---|---|---|---|---|---|
| Gln | Phe | Arg | Cys | Asp | Val | Pro | Ser | Phe | Ser | Val | Gln | Glu | Glu | Leu | Asp | |
| | 1025 | | | | | 1030 | | | | | 1035 | | | | | |

| TTC | ACC | CTG | AAG | GGC | AAT | CTC | AGT | TTC | GGC | TGG | GTC | CGC | GAG | ACA | TTG | 3167 |
|---|---|---|---|---|---|---|---|---|---|---|---|---|---|---|---|---|
| Phe | Thr | Leu | Lys | Gly | Asn | Leu | Ser | Phe | Gly | Trp | Val | Arg | Glu | Thr | Leu | |
| 1040 | | | | | 1045 | | | | | 1050 | | | | | 1055 | |

| CAG | AAG | AAG | GTG | TTG | GTC | GTG | AGT | GTG | GCT | GAA | ATT | ACG | TTC | GAC | ACA | 3215 |
|---|---|---|---|---|---|---|---|---|---|---|---|---|---|---|---|---|
| Gln | Lys | Lys | Val | Leu | Val | Val | Ser | Val | Ala | Glu | Ile | Thr | Phe | Asp | Thr | |
| | | | | 1060 | | | | | 1065 | | | | | 1070 | | |

| TCC | GTG | TAC | TCC | CAG | CTT | CCA | GGA | CAG | GAG | GCA | TTT | ATG | AGA | GCT | CAG | 3263 |
|---|---|---|---|---|---|---|---|---|---|---|---|---|---|---|---|---|
| Ser | Val | Tyr | Ser | Gln | Leu | Pro | Gly | Gln | Glu | Ala | Phe | Met | Arg | Ala | Gln | |
| | | | 1075 | | | | | 1080 | | | | | 1085 | | | |

| ATG | GAG | ATG | GTG | CTA | GAA | GAA | GAC | GAG | GTC | TAC | AAT | GCC | ATT | CCC | ATC | 3311 |
|---|---|---|---|---|---|---|---|---|---|---|---|---|---|---|---|---|
| Met | Glu | Met | Val | Leu | Glu | Glu | Asp | Glu | Val | Tyr | Asn | Ala | Ile | Pro | Ile | |
| | | 1090 | | | | | 1095 | | | | | 1100 | | | | |

| ATC | ATG | GGC | AGC | TCT | GTG | GGG | GCT | CTG | CTA | CTG | CTG | GCG | CTC | ATC | ACA | 3359 |
|---|---|---|---|---|---|---|---|---|---|---|---|---|---|---|---|---|
| Ile | Met | Gly | Ser | Ser | Val | Gly | Ala | Leu | Leu | Leu | Leu | Ala | Leu | Ile | Thr | |
| | | 1105 | | | | | 1110 | | | | | 1115 | | | | |

| GCC | ACA | CTG | TAC | AAG | CTT | GGC | TTC | TTC | AAA | CGC | CAC | TAC | AAG | GAA | ATG | 3407 |
|---|---|---|---|---|---|---|---|---|---|---|---|---|---|---|---|---|
| Ala | Thr | Leu | Tyr | Lys | Leu | Gly | Phe | Phe | Lys | Arg | His | Tyr | Lys | Glu | Met | |
| 1120 | | | | | 1125 | | | | | 1130 | | | | | 1135 | |

| CTG | GAG | GAC | AAG | CCT | GAA | GAC | ACT | GCC | ACA | TTC | AGT | GGG | GAC | GAT | TTC | 3455 |
|---|---|---|---|---|---|---|---|---|---|---|---|---|---|---|---|---|
| Leu | Glu | Asp | Lys | Pro | Glu | Asp | Thr | Ala | Thr | Phe | Ser | Gly | Asp | Asp | Phe | |
| | | | 1140 | | | | | 1145 | | | | | 1150 | | | |

| AGC | TGT | GTG | GCC | CCA | AAT | GTG | CCT | TTG | TCC | TAATAATCCA | CTTTCCTGTT | 3505 |
|---|---|---|---|---|---|---|---|---|---|---|---|---|

```
Ser  Cys  Val  Ala  Pro  Asn  Val  Pro  Leu  Ser
               1155                     1160
```

TATCTCTACC ACTGTGGGCT GGACTTGCTT GCAACCATAA ATCAACTTAC ATGGAAACAA    3565

CTTCTGCATA GATCTGCACT GGCCTAAGCA ACCTACCAGG TGCTAAGCAC CTTCTCGGAG    3625

AGATAGAGAT TGTAATGTTT TTACATATCT GTCCATCTTT TTCAGCAATG ACCCACTTTT    3685

TACAGAAGCA GGCATGGTGC CAGCATAAAT TTTCATATGC T                       3726

( 2 ) INFORMATION FOR SEQ ID NO:2:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Thr  Phe  Gly  Thr  Val  Leu  Leu  Leu  Ser  Val  Leu  Ala  Ser  Tyr  His  Gly
1              5                        10                       15

Phe  Asn  Leu  Asp  Val  Glu  Glu  Pro  Thr  Ile  Phe  Gln  Glu  Asp  Ala  Gly
          20                       25                       30

Gly  Phe  Gly  Gln  Ser  Val  Val  Gln  Phe  Gly  Gly  Ser  Arg  Leu  Val  Val
               35                       40                  45

Gly  Ala  Pro  Leu  Glu  Val  Val  Ala  Ala  Asn  Gln  Thr  Gly  Arg  Leu  Tyr
     50                       55                  60

Asp  Cys  Ala  Ala  Ala  Thr  Gly  Met  Cys  Gln  Pro  Ile  Pro  Leu  His  Ile
65                       70                  75                            80

Arg  Pro  Glu  Ala  Val  Asn  Met  Ser  Leu  Gly  Leu  Thr  Leu  Ala  Ala  Ser
                    85                       90                       95

Thr  Asn  Gly  Ser  Arg  Leu  Leu  Ala  Cys  Gly  Pro  Thr  Leu  His  Arg  Val
               100                      105                 110

Cys  Gly  Glu  Asn  Ser  Tyr  Ser  Lys  Gly  Ser  Cys  Leu  Leu  Leu  Gly  Ser
          115                      120                      125

Arg  Trp  Glu  Ile  Ile  Gln  Thr  Val  Pro  Asp  Ala  Thr  Pro  Glu  Cys  Pro
     130                      135                 140

His  Gln  Glu  Met  Asp  Ile  Val  Phe  Leu  Ile  Asp  Gly  Ser  Gly  Ser  Ile
145                      150                 155                           160

Asp  Gln  Asn  Asp  Phe  Asn  Gln  Met  Lys  Gly  Phe  Val  Gln  Ala  Val  Met
               165                      170                      175

Gly  Gln  Phe  Glu  Gly  Thr  Asp  Thr  Leu  Phe  Ala  Leu  Met  Gln  Tyr  Ser
               180                      185                 190

Asn  Leu  Leu  Lys  Ile  His  Phe  Thr  Phe  Thr  Gln  Phe  Arg  Thr  Ser  Pro
          195                      200                 205

Ser  Gln  Gln  Ser  Leu  Val  Asp  Pro  Ile  Val  Gln  Leu  Lys  Gly  Leu  Thr
     210                      215                 220

Phe  Thr  Ala  Thr  Gly  Ile  Leu  Thr  Val  Val  Thr  Gln  Leu  Phe  His  His
225                      230                 235                           240

Lys  Asn  Gly  Ala  Arg  Lys  Ser  Ala  Lys  Lys  Ile  Leu  Ile  Val  Ile  Thr
               245                      250                      255

Asp  Gly  Gln  Lys  Tyr  Lys  Asp  Pro  Leu  Glu  Tyr  Ser  Asp  Val  Ile  Pro
               260                      265                 270

Gln  Ala  Glu  Lys  Ala  Gly  Ile  Ile  Arg  Tyr  Ala  Ile  Gly  Val  Gly  His
     275                      280                 285

Ala  Phe  Gln  Gly  Pro  Thr  Ala  Arg  Gln  Glu  Leu  Asn  Thr  Ile  Ser  Ser
     290                      295                 300
```

```
Ala  Pro  Pro  Gln  Asp  His  Val  Phe  Lys  Val  Asp  Asn  Phe  Ala  Ala  Leu
305                 310                 315                           320

Gly  Ser  Ile  Gln  Lys  Gln  Leu  Gln  Glu  Lys  Ile  Tyr  Ala  Val  Glu  Gly
                    325                 330                           335

Thr  Gln  Ser  Arg  Ala  Ser  Ser  Ser  Gln  His  Glu  Met  Ser  Gln  Glu
               340                 345                      350

Gly  Phe  Ser  Thr  Ala  Leu  Thr  Met  Asp  Gly  Leu  Phe  Leu  Gly  Ala  Val
               355                 360                      365

Gly  Ser  Phe  Ser  Trp  Ser  Gly  Ala  Phe  Leu  Tyr  Pro  Pro  Asn  Met
     370                 375                      380

Ser  Pro  Thr  Phe  Ile  Asn  Met  Ser  Gln  Glu  Asn  Val  Asp  Met  Arg  Asp
385                      390                 395                           400

Ser  Tyr  Leu  Gly  Tyr  Ser  Thr  Glu  Leu  Ala  Leu  Trp  Lys  Gly  Val  Gln
                    405                      410                      415

Asn  Leu  Val  Leu  Gly  Ala  Pro  Arg  Tyr  Gln  His  Thr  Gly  Lys  Ala  Val
               420                 425                           430

Ile  Phe  Thr  Gln  Val  Ser  Arg  Gln  Trp  Arg  Lys  Lys  Ala  Glu  Val  Thr
               435                 440                      445

Gly  Thr  Gln  Ile  Gly  Ser  Tyr  Phe  Gly  Ala  Ser  Leu  Cys  Ser  Val  Asp
     450                      455                      460

Val  Asp  Ser  Asp  Gly  Ser  Thr  Asp  Leu  Ile  Leu  Ile  Gly  Ala  Pro  His
465                      470                 475                           480

Tyr  Tyr  Glu  Gln  Thr  Arg  Gly  Gly  Gln  Val  Ser  Val  Cys  Pro  Leu  Pro
                    485                 490                      495

Arg  Gly  Gln  Arg  Val  Gln  Trp  Gln  Cys  Asp  Ala  Val  Leu  Arg  Gly  Glu
               500                 505                      510

Gln  Gly  His  Pro  Trp  Gly  Arg  Phe  Gly  Ala  Ala  Leu  Thr  Val  Leu  Gly
          515                 520                      525

Asp  Val  Asn  Glu  Asp  Lys  Leu  Ile  Asp  Val  Ala  Ile  Gly  Ala  Pro  Gly
     530                 535                 540

Glu  Gln  Glu  Asn  Arg  Gly  Ala  Val  Tyr  Leu  Phe  His  Gly  Ala  Ser  Glu
545                 550                 555                           560

Ser  Gly  Ile  Ser  Pro  Ser  His  Ser  Gln  Arg  Ile  Ala  Ser  Ser  Gln  Leu
                    565                 570                      575

Ser  Pro  Arg  Leu  Gln  Tyr  Phe  Gly  Gln  Ala  Leu  Ser  Gly  Gly  Gln  Asp
               580                 585                      590

Leu  Thr  Gln  Asp  Gly  Leu  Met  Asp  Leu  Ala  Val  Gly  Ala  Arg  Gly  Gln
          595                 600                      605

Val  Leu  Leu  Leu  Arg  Ser  Leu  Pro  Val  Leu  Lys  Val  Gly  Val  Ala  Met
     610                 615                 620

Arg  Phe  Ser  Pro  Val  Glu  Val  Ala  Lys  Ala  Val  Tyr  Arg  Cys  Trp  Glu
625                 630                 635                           640

Glu  Lys  Pro  Ser  Ala  Leu  Glu  Ala  Gly  Asp  Ala  Thr  Val  Cys  Leu  Thr
               645                 650                      655

Ile  Gln  Lys  Ser  Ser  Leu  Asp  Gln  Leu  Gly  Asp  Ile  Gln  Ser  Ser  Val
               660                 665                      670

Arg  Phe  Asp  Leu  Ala  Leu  Asp  Pro  Gly  Arg  Leu  Thr  Ser  Arg  Ala  Ile
          675                 680                      685

Phe  Asn  Glu  Thr  Lys  Asn  Pro  Thr  Leu  Thr  Arg  Arg  Lys  Thr  Leu  Gly
     690                 695                      700

Leu  Gly  Ile  His  Cys  Glu  Thr  Leu  Lys  Leu  Leu  Leu  Pro  Asp  Cys  Val
705                      710                 715                           720

Glu  Asp  Val  Val  Ser  Pro  Ile  Ile  Leu  His  Leu  Asn  Phe  Ser  Leu  Val
               725                 730                      735
```

-continued

```
Arg  Glu  Pro  Ile  Pro  Ser  Pro  Gln  Asn  Leu  Arg  Pro  Val  Leu  Ala  Val
               740                      745                     750

Gly  Ser  Gln  Asp  Leu  Phe  Thr  Ala  Ser  Leu  Pro  Phe  Glu  Lys  Asn  Cys
          755                      760                     765

Gly  Gln  Asp  Gly  Leu  Cys  Glu  Gly  Asp  Leu  Gly  Val  Thr  Leu  Ser  Phe
          770                 775                     780

Ser  Gly  Leu  Gln  Thr  Leu  Thr  Val  Gly  Ser  Ser  Leu  Glu  Leu  Asn  Val
785                      790                     795                          800

Ile  Val  Thr  Val  Trp  Asn  Ala  Gly  Glu  Asp  Ser  Tyr  Gly  Thr  Val  Val
                    805                      810                     815

Ser  Leu  Tyr  Tyr  Pro  Ala  Gly  Leu  Ser  His  Arg  Arg  Val  Ser  Gly  Ala
                    820                      825                     830

Gln  Lys  Gln  Pro  His  Gln  Ser  Ala  Leu  Arg  Leu  Ala  Cys  Glu  Thr  Val
               835                      840                     845

Pro  Thr  Glu  Asp  Glu  Gly  Leu  Arg  Ser  Ser  Arg  Cys  Ser  Val  Asn  His
     850                      855                     860

Pro  Ile  Phe  His  Glu  Gly  Ser  Asn  Gly  Thr  Phe  Ile  Val  Thr  Phe  Asp
865                      870                      875                          880

Val  Ser  Tyr  Lys  Ala  Thr  Leu  Gly  Asp  Arg  Met  Leu  Met  Arg  Ala  Ser
                    885                      890                     895

Ala  Ser  Ser  Glu  Asn  Asn  Lys  Ala  Ser  Ser  Lys  Ala  Thr  Phe  Gln
               900                      905                     910

Leu  Glu  Leu  Pro  Val  Lys  Tyr  Ala  Val  Tyr  Thr  Met  Ile  Ser  Arg  Gln
               915                      920                     925

Glu  Glu  Ser  Thr  Lys  Tyr  Phe  Asn  Phe  Ala  Thr  Ser  Asp  Glu  Lys  Lys
     930                      935                     940

Met  Lys  Glu  Ala  Glu  His  Arg  Tyr  Arg  Val  Asn  Asn  Leu  Ser  Gln  Arg
945                      950                      955                          960

Asp  Leu  Ala  Ile  Ser  Ile  Asn  Phe  Trp  Val  Pro  Val  Leu  Leu  Asn  Gly
                    965                      970                     975

Val  Ala  Val  Trp  Asp  Val  Val  Met  Glu  Ala  Pro  Ser  Gln  Ser  Leu  Pro
               980                      985                     990

Cys  Val  Ser  Glu  Arg  Lys  Pro  Pro  Gln  His  Ser  Asp  Phe  Leu  Thr  Gln
          995                      1000                    1005

Ile  Ser  Arg  Ser  Pro  Met  Leu  Asp  Cys  Ser  Ile  Ala  Asp  Cys  Leu  Gln
     1010                     1015                    1020

Phe  Arg  Cys  Asp  Val  Pro  Ser  Phe  Ser  Val  Gln  Glu  Glu  Leu  Asp  Phe
1025                     1030                     1035                         1040

Thr  Leu  Lys  Gly  Asn  Leu  Ser  Phe  Gly  Trp  Val  Arg  Glu  Thr  Leu  Gln
               1045                     1050                    1055

Lys  Lys  Val  Leu  Val  Val  Ser  Val  Ala  Glu  Ile  Thr  Phe  Asp  Thr  Ser
               1060                     1065                    1070

Val  Tyr  Ser  Gln  Leu  Pro  Gly  Gln  Glu  Ala  Phe  Met  Arg  Ala  Gln  Met
          1075                     1080                    1085

Glu  Met  Val  Leu  Glu  Glu  Asp  Glu  Val  Tyr  Asn  Ala  Ile  Pro  Ile  Ile
     1090                     1095                    1100

Met  Gly  Ser  Ser  Val  Gly  Ala  Leu  Leu  Leu  Leu  Ala  Leu  Ile  Thr  Ala
1105                     1110                     1115                         1120

Thr  Leu  Tyr  Lys  Leu  Gly  Phe  Phe  Lys  Arg  His  Tyr  Lys  Glu  Met  Leu
                    1125                     1130                    1135

Glu  Asp  Lys  Pro  Glu  Asp  Thr  Ala  Thr  Phe  Ser  Gly  Asp  Asp  Phe  Ser
               1140                     1145                    1150

Cys  Val  Ala  Pro  Asn  Val  Pro  Lys  Ser
```

1155                1160

(2) INFORMATION FOR SEQ ID NO:3:

(i) SEQUENCE CHARACTERISTICS:
        (A) LENGTH: 1153 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met  Ala  Leu  Arg  Val  Leu  Leu  Leu  Thr  Ala  Leu  Thr  Leu  Cys  His  Gly
 1              5                        10                       15

Phe  Asn  Leu  Asp  Thr  Glu  Asn  Ala  Met  Thr  Phe  Gln  Glu  Asn  Ala  Arg
            20                       25                       30

Gly  Phe  Gly  Gln  Ser  Val  Val  Gln  Leu  Gln  Gly  Ser  Arg  Val  Val  Val
        35                       40                       45

Gly  Ala  Pro  Gln  Glu  Ile  Val  Ala  Ala  Asn  Gln  Arg  Gly  Ser  Leu  Tyr
    50                       55                       60

Gln  Cys  Asp  Tyr  Ser  Thr  Gly  Ser  Cys  Glu  Pro  Ile  Arg  Leu  Gln  Val
65                       70                       75                       80

Pro  Val  Glu  Ala  Val  Asn  Met  Ser  Leu  Gly  Leu  Ser  Leu  Ala  Ala  Thr
                    85                       90                       95

Thr  Ser  Pro  Pro  Gln  Leu  Leu  Ala  Cys  Gly  Pro  Thr  Val  His  Gln  Thr
                100                      105                      110

Cys  Ser  Glu  Asn  Thr  Tyr  Val  Lys  Gly  Leu  Cys  Phe  Leu  Phe  Gly  Ser
            115                      120                      125

Asn  Leu  Arg  Gln  Gln  Pro  Gln  Lys  Phe  Pro  Glu  Ala  Leu  Arg  Gly  Cys
        130                      135                      140

Pro  Gln  Glu  Asp  Ser  Asp  Ile  Ala  Phe  Leu  Ile  Asp  Gly  Ser  Gly  Ser
145                      150                      155                      160

Ile  Ile  Pro  His  Asp  Phe  Arg  Arg  Met  Lys  Glu  Phe  Val  Ser  Thr  Val
                    165                      170                      175

Met  Glu  Gln  Leu  Lys  Lys  Ser  Lys  Thr  Leu  Phe  Ser  Leu  Met  Gln  Tyr
                180                      185                      190

Ser  Glu  Glu  Phe  Arg  Ile  His  Phe  Thr  Phe  Lys  Glu  Phe  Gln  Asn  Asn
            195                      200                      205

Pro  Asn  Pro  Arg  Ser  Leu  Val  Lys  Pro  Ile  Thr  Gln  Leu  Leu  Gly  Arg
        210                      215                      220

Thr  His  Thr  Ala  Thr  Gly  Ile  Arg  Lys  Val  Val  Arg  Glu  Leu  Phe  Asn
225                      230                      235                      240

Ile  Thr  Asn  Gly  Ala  Arg  Lys  Asn  Ala  Phe  Lys  Ile  Leu  Val  Val  Ile
                    245                      250                      255

Thr  Asp  Gly  Glu  Lys  Phe  Gly  Asp  Pro  Leu  Gly  Tyr  Glu  Asp  Val  Ile
                260                      265                      270

Pro  Glu  Ala  Asp  Arg  Glu  Gly  Val  Ile  Arg  Tyr  Val  Ile  Gly  Val  Gly
            275                      280                      285

Asp  Ala  Phe  Arg  Ser  Glu  Lys  Ser  Arg  Gln  Glu  Leu  Asn  Thr  Ile  Ala
        290                      295                      300

Ser  Lys  Pro  Pro  Arg  Asp  His  Val  Phe  Gln  Val  Asn  Asn  Phe  Glu  Ala
305                      310                      315                      320

Leu  Lys  Thr  Ile  Gln  Asn  Gln  Leu  Arg  Glu  Lys  Ile  Phe  Ala  Ile  Glu
                    325                      330                      335

Gly  Thr  Gln  Thr  Gly  Ser  Ser  Ser  Phe  Glu  His  Glu  Met  Ser  Gln
                340                      345                      350
```

```
Glu  Gly  Phe  Ser  Ala  Ala  Ile  Thr  Ser  Asn  Gly  Pro  Leu  Leu  Ser  Thr
          355                 360                      365

Val  Gly  Ser  Tyr  Asp  Trp  Ala  Gly  Val  Phe  Leu  Tyr  Thr  Ser  Lys
     370                 375                      380

Glu  Lys  Ser  Thr  Phe  Ile  Asn  Met  Thr  Arg  Val  Asp  Ser  Asp  Met  Asn
385                      390                 395                           400

Asp  Ala  Tyr  Leu  Gly  Tyr  Ala  Ala  Ala  Ile  Ile  Leu  Arg  Asn  Arg  Val
                    405                      410                           415

Gln  Ser  Leu  Val  Leu  Gly  Ala  Pro  Arg  Tyr  Gln  His  Ile  Gly  Leu  Val
                    420                 425                      430

Ala  Met  Phe  Arg  Gln  Asn  Thr  Gly  Met  Trp  Glu  Ser  Asn  Ala  Asn  Val
               435                 440                      445

Lys  Gly  Thr  Gln  Ile  Gly  Ala  Tyr  Phe  Gly  Ala  Ser  Leu  Cys  Ser  Val
     450                      455                 460

Asp  Val  Asp  Ser  Asn  Gly  Ser  Thr  Asp  Leu  Val  Leu  Ile  Gly  Ala  Pro
465                      470                 475                           480

His  Tyr  Tyr  Glu  Gln  Thr  Arg  Gly  Gly  Gln  Val  Ser  Val  Cys  Pro  Leu
                    485                 490                      495

Pro  Arg  Gly  Gln  Arg  Ala  Arg  Trp  Gln  Cys  Asp  Ala  Val  Leu  Tyr  Gly
               500                 505                      510

Glu  Gln  Gly  Gln  Pro  Trp  Gly  Arg  Phe  Gly  Ala  Ala  Leu  Thr  Val  Leu
          515                      520                      525

Gly  Asp  Val  Asn  Gly  Asp  Lys  Leu  Thr  Asp  Val  Ala  Ile  Gly  Ala  Pro
     530                      535                      540

Gly  Glu  Glu  Asp  Asn  Arg  Gly  Ala  Val  Tyr  Leu  Phe  His  Gly  Thr  Ser
545                      550                 555                           560

Gly  Ser  Gly  Ile  Ser  Pro  Ser  His  Ser  Gln  Arg  Ile  Ala  Gly  Ser  Lys
               565                      570                           575

Leu  Ser  Pro  Arg  Leu  Gln  Tyr  Phe  Gly  Gln  Ser  Leu  Ser  Gly  Gly  Gln
               580                 585                      590

Asp  Leu  Thr  Met  Asp  Gly  Leu  Val  Asp  Leu  Thr  Val  Gly  Ala  Gln  Gly
          595                 600                 605

His  Val  Leu  Leu  Leu  Arg  Ser  Gln  Pro  Val  Leu  Arg  Val  Lys  Ala  Ile
610                      615                      620

Met  Glu  Phe  Asn  Pro  Arg  Glu  Val  Ala  Arg  Asn  Val  Phe  Glu  Cys  Asn
625                      630                 635                           640

Asp  Gln  Val  Val  Lys  Gly  Lys  Glu  Ala  Gly  Glu  Val  Arg  Val  Cys  Leu
               645                 650                      655

His  Val  Gln  Lys  Ser  Thr  Arg  Asp  Arg  Leu  Arg  Glu  Gly  Gln  Ile  Gln
               660                 665                      670

Ser  Val  Val  Thr  Tyr  Asp  Leu  Ala  Leu  Asp  Ser  Gly  Arg  Pro  His  Ser
          675                 680                      685

Arg  Ala  Val  Phe  Asn  Glu  Thr  Lys  Asn  Ser  Thr  Arg  Arg  Gln  Thr  Gln
     690                      695                 700

Val  Leu  Gly  Leu  Thr  Gln  Thr  Cys  Glu  Thr  Leu  Lys  Leu  Gln  Leu  Pro
705                      710                 715                           720

Asn  Cys  Ile  Glu  Asp  Pro  Val  Ser  Pro  Ile  Val  Leu  Arg  Leu  Asn  Phe
               725                 730                      735

Ser  Leu  Val  Gly  Thr  Pro  Leu  Ser  Ala  Phe  Gly  Asn  Leu  Arg  Pro  Val
               740                 745                      750

Leu  Ala  Glu  Asp  Ala  Gln  Arg  Leu  Phe  Thr  Ala  Leu  Phe  Pro  Phe  Glu
               755                 760                      765

Lys  Asn  Cys  Gly  Asn  Asp  Asn  Ile  Cys  Gln  Asp  Asp  Leu  Ser  Ile  Thr
```

|       |       |       |       | 770   |       |       |       |       | 775   |       |       |       |       | 780   |       |
|-------|-------|-------|-------|-------|-------|-------|-------|-------|-------|-------|-------|-------|-------|-------|-------|
| Phe   | Ser   | Phe   | Met   | Ser   | Leu   | Asp   | Cys   | Leu   | Val   | Val   | Gly   | Gly   | Pro   | Arg   | Glu   |
| 785   |       |       |       |       | 790   |       |       |       |       | 795   |       |       |       |       | 800   |
| Phe   | Asn   | Val   | Thr   | Val   | Thr   | Val   | Arg   | Asn   | Asp   | Gly   | Glu   | Asp   | Ser   | Tyr   | Arg   |
|       |       |       |       | 805   |       |       |       |       | 810   |       |       |       |       | 815   |       |
| Thr   | Gln   | Val   | Thr   | Phe   | Phe   | Phe   | Pro   | Leu   | Asp   | Leu   | Ser   | Tyr   | Arg   | Lys   | Val   |
|       |       |       | 820   |       |       |       |       | 825   |       |       |       |       | 830   |       |       |
| Ser   | Thr   | Leu   | Gln   | Asn   | Gln   | Arg   | Ser   | Gln   | Arg   | Ser   | Trp   | Arg   | Leu   | Ala   | Cys   |
|       |       |       | 835   |       |       |       |       | 840   |       |       |       |       | 845   |       |       |
| Glu   | Ser   | Ala   | Ser   | Ser   | Thr   | Glu   | Val   | Ser   | Gly   | Ala   | Leu   | Lys   | Ser   | Thr   | Ser   |
|       |       | 850   |       |       |       |       | 855   |       |       |       |       | 860   |       |       |       |
| Cys   | Ser   | Ile   | Asn   | His   | Pro   | Ile   | Phe   | Pro   | Glu   | Asn   | Ser   | Glu   | Val   | Thr   | Phe   |
| 865   |       |       |       |       | 870   |       |       |       |       | 875   |       |       |       |       | 880   |
| Asn   | Ile   | Thr   | Phe   | Asp   | Val   | Asp   | Ser   | Lys   | Ala   | Ser   | Leu   | Gly   | Asn   | Lys   | Leu   |
|       |       |       |       | 885   |       |       |       |       | 890   |       |       |       |       | 895   |       |
| Leu   | Leu   | Lys   | Ala   | Asn   | Val   | Thr   | Ser   | Glu   | Asn   | Asn   | Met   | Pro   | Arg   | Thr   | Asn   |
|       |       |       | 900   |       |       |       |       | 905   |       |       |       |       | 910   |       |       |
| Lys   | Thr   | Glu   | Phe   | Gln   | Leu   | Glu   | Leu   | Pro   | Val   | Lys   | Tyr   | Ala   | Val   | Tyr   | Met   |
|       |       | 915   |       |       |       |       | 920   |       |       |       |       | 925   |       |       |       |
| Val   | Val   | Thr   | Ser   | His   | Gly   | Val   | Ser   | Thr   | Lys   | Tyr   | Leu   | Asn   | Phe   | Thr   | Ala   |
|       |       | 930   |       |       |       |       | 935   |       |       |       |       | 940   |       |       |       |
| Ser   | Glu   | Asn   | Thr   | Ser   | Arg   | Val   | Met   | Gln   | His   | Gln   | Tyr   | Gln   | Val   | Ser   | Asn   |
| 945   |       |       |       |       | 950   |       |       |       |       | 955   |       |       |       |       | 960   |
| Leu   | Gly   | Gln   | Arg   | Ser   | Leu   | Pro   | Ile   | Ser   | Leu   | Val   | Phe   | Leu   | Val   | Pro   | Val   |
|       |       |       |       | 965   |       |       |       |       | 970   |       |       |       |       | 975   |       |
| Arg   | Leu   | Asn   | Gln   | Thr   | Val   | Ile   | Trp   | Asp   | Arg   | Pro   | Gln   | Val   | Thr   | Phe   | Ser   |
|       |       |       | 980   |       |       |       |       | 985   |       |       |       |       | 990   |       |       |
| Glu   | Asn   | Leu   | Ser   | Ser   | Thr   | Cys   | His   | Thr   | Lys   | Glu   | Arg   | Leu   | Pro   | Ser   | His   |
|       |       | 995   |       |       |       |       | 1000  |       |       |       |       | 1005  |       |       |       |
| Ser   | Asp   | Phe   | Leu   | Ala   | Glu   | Leu   | Arg   | Lys   | Ala   | Pro   | Val   | Val   | Asn   | Cys   | Ser   |
|       |       | 1010  |       |       |       |       | 1015  |       |       |       |       | 1020  |       |       |       |
| Ile   | Ala   | Val   | Cys   | Gln   | Arg   | Ile   | Gln   | Cys   | Asp   | Ile   | Pro   | Phe   | Phe   | Gly   | Ile   |
| 1025  |       |       |       |       | 1030  |       |       |       |       | 1035  |       |       |       |       | 1040  |
| Gln   | Glu   | Glu   | Phe   | Asn   | Ala   | Thr   | Leu   | Lys   | Gly   | Asn   | Leu   | Ser   | Phe   | Asp   | Trp   |
|       |       |       |       | 1045  |       |       |       |       | 1050  |       |       |       |       | 1055  |       |
| Tyr   | Ile   | Lys   | Thr   | Ser   | His   | Asn   | His   | Leu   | Leu   | Ile   | Val   | Ser   | Thr   | Ala   | Glu   |
|       |       |       | 1060  |       |       |       |       | 1065  |       |       |       |       | 1070  |       |       |
| Ile   | Leu   | Phe   | Asn   | Asp   | Ser   | Val   | Phe   | Thr   | Leu   | Leu   | Pro   | Gly   | Gln   | Gly   | Ala   |
|       |       |       | 1075  |       |       |       |       | 1080  |       |       |       |       | 1085  |       |       |
| Phe   | Val   | Arg   | Ser   | Gln   | Thr   | Glu   | Thr   | Lys   | Val   | Glu   | Pro   | Phe   | Glu   | Val   | Pro   |
|       |       |       | 1090  |       |       |       |       | 1095  |       |       |       |       | 1100  |       |       |
| Asn   | Pro   | Leu   | Pro   | Leu   | Ile   | Val   | Gly   | Ser   | Ser   | Val   | Gly   | Gly   | Leu   | Leu   | Leu   |
| 1105  |       |       |       |       | 1110  |       |       |       |       | 1115  |       |       |       |       | 1120  |
| Leu   | Ala   | Leu   | Ile   | Thr   | Ala   | Ala   | Leu   | Tyr   | Lys   | Leu   | Gly   | Phe   | Phe   | Lys   | Arg   |
|       |       |       |       | 1125  |       |       |       |       | 1130  |       |       |       |       | 1135  |       |
| Gln   | Tyr   | Lys   | Asp   | Met   | Met   | Ser   | Glu   | Gly   | Gly   | Pro   | Pro   | Gly   | Ala   | Glu   | Pro   |
|       |       |       | 1140  |       |       |       |       | 1145  |       |       |       |       | 1150  |       |       |
| Gln   |       |       |       |       |       |       |       |       |       |       |       |       |       |       |       |

( 2 ) INFORMATION FOR SEQ ID NO:4:

( i ) SEQUENCE CHARACTERISTICS:
        ( A ) LENGTH: 1163 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO:4:

| Met | Thr | Arg | Thr | Arg | Ala | Ala | Leu | Leu | Leu | Phe | Thr | Ala | Leu | Ala | Thr |
|---|---|---|---|---|---|---|---|---|---|---|---|---|---|---|---|
| 1 | | | | 5 | | | | | 10 | | | | | 15 | |

| Ser | Leu | Gly | Phe | Asn | Leu | Asp | Thr | Glu | Glu | Leu | Thr | Ala | Phe | Arg | Val |
|---|---|---|---|---|---|---|---|---|---|---|---|---|---|---|---|
| | | | 20 | | | | 25 | | | | | 30 | | | |

| Asp | Ser | Ala | Gly | Phe | Gly | Asp | Ser | Val | Val | Gln | Tyr | Ala | Asn | Ser | Trp |
|---|---|---|---|---|---|---|---|---|---|---|---|---|---|---|---|
| | | 35 | | | | 40 | | | | | 45 | | | | |

| Val | Val | Val | Gly | Ala | Pro | Gln | Lys | Ile | Ile | Ala | Ala | Asn | Gln | Ile | Gly |
|---|---|---|---|---|---|---|---|---|---|---|---|---|---|---|---|
| | 50 | | | | 55 | | | | | 60 | | | | | |

| Gly | Leu | Tyr | Gln | Cys | Gly | Tyr | Ser | Thr | Gly | Ala | Cys | Glu | Pro | Ile | Gly |
|---|---|---|---|---|---|---|---|---|---|---|---|---|---|---|---|
| 65 | | | | 70 | | | | | 75 | | | | | 80 | |

| Leu | Gln | Val | Pro | Pro | Glu | Ala | Val | Asn | Met | Ser | Leu | Gly | Leu | Ser | Leu |
|---|---|---|---|---|---|---|---|---|---|---|---|---|---|---|---|
| | | | | 85 | | | | | 90 | | | | | 95 | |

| Ala | Ser | Thr | Thr | Ser | Pro | Ser | Gln | Leu | Leu | Ala | Cys | Gly | Pro | Thr | Val |
|---|---|---|---|---|---|---|---|---|---|---|---|---|---|---|---|
| | | | 100 | | | | 105 | | | | | 110 | | | |

| His | His | Glu | Cys | Gly | Arg | Asn | Met | Tyr | Leu | Thr | Gly | Leu | Cys | Phe | Leu |
|---|---|---|---|---|---|---|---|---|---|---|---|---|---|---|---|
| | | 115 | | | | 120 | | | | | 125 | | | | |

| Leu | Gly | Pro | Thr | Gln | Leu | Thr | Gln | Arg | Leu | Pro | Val | Ser | Arg | Gln | Glu |
|---|---|---|---|---|---|---|---|---|---|---|---|---|---|---|---|
| | 130 | | | | 135 | | | | | 140 | | | | | |

| Cys | Pro | Arg | Gln | Glu | Gln | Asp | Ile | Val | Phe | Leu | Ile | Asp | Gly | Ser | Gly |
|---|---|---|---|---|---|---|---|---|---|---|---|---|---|---|---|
| 145 | | | | | 150 | | | | | 155 | | | | | 160 |

| Ser | Ile | Ser | Ser | Arg | Asn | Phe | Ala | Thr | Met | Met | Asn | Phe | Val | Arg | Ala |
|---|---|---|---|---|---|---|---|---|---|---|---|---|---|---|---|
| | | | | 165 | | | | | 170 | | | | | 175 | |

| Val | Ile | Ser | Gln | Phe | Gln | Arg | Pro | Ser | Thr | Gln | Phe | Ser | Leu | Met | Gln |
|---|---|---|---|---|---|---|---|---|---|---|---|---|---|---|---|
| | | | 180 | | | | | 185 | | | | | 190 | | |

| Phe | Ser | Asn | Lys | Phe | Gln | Thr | His | Phe | Thr | Phe | Glu | Glu | Phe | Arg | Arg |
|---|---|---|---|---|---|---|---|---|---|---|---|---|---|---|---|
| | | 195 | | | | | 200 | | | | | 205 | | | |

| Thr | Ser | Asn | Pro | Leu | Ser | Leu | Leu | Ala | Ser | Val | His | Gln | Leu | Gln | Gly |
|---|---|---|---|---|---|---|---|---|---|---|---|---|---|---|---|
| | 210 | | | | | 215 | | | | | 220 | | | | |

| Phe | Thr | Tyr | Thr | Ala | Thr | Ala | Ile | Gln | Asn | Val | Val | His | Arg | Leu | Phe |
|---|---|---|---|---|---|---|---|---|---|---|---|---|---|---|---|
| 225 | | | | | 230 | | | | | 235 | | | | | 240 |

| His | Ala | Ser | Tyr | Gly | Ala | Arg | Arg | Asp | Ala | Ile | Lys | Ile | Leu | Ile | Val |
|---|---|---|---|---|---|---|---|---|---|---|---|---|---|---|---|
| | | | | 245 | | | | | 250 | | | | | 255 | |

| Ile | Thr | Asp | Gly | Lys | Lys | Glu | Gly | Asp | Ser | Leu | Asp | Tyr | Lys | Asp | Val |
|---|---|---|---|---|---|---|---|---|---|---|---|---|---|---|---|
| | | | 260 | | | | | 265 | | | | | 270 | | |

| Ile | Pro | Met | Ala | Asp | Ala | Ala | Gly | Ile | Ile | Arg | Tyr | Ala | Ile | Gly | Val |
|---|---|---|---|---|---|---|---|---|---|---|---|---|---|---|---|
| | | 275 | | | | | 280 | | | | | 285 | | | |

| Gly | Leu | Ala | Phe | Gln | Asn | Arg | Asn | Ser | Trp | Lys | Glu | Leu | Asn | Asp | Ile |
|---|---|---|---|---|---|---|---|---|---|---|---|---|---|---|---|
| | 290 | | | | | 295 | | | | | 300 | | | | |

| Ala | Ser | Lys | Pro | Ser | Gln | Glu | His | Ile | Phe | Lys | Val | Glu | Asp | Phe | Asp |
|---|---|---|---|---|---|---|---|---|---|---|---|---|---|---|---|
| 305 | | | | | 310 | | | | | 315 | | | | | 320 |

| Ala | Leu | Lys | Asp | Ile | Gln | Asn | Gln | Leu | Lys | Glu | Lys | Ile | Phe | Ala | Ile |
|---|---|---|---|---|---|---|---|---|---|---|---|---|---|---|---|
| | | | | 325 | | | | | 330 | | | | | 335 | |

| Glu | Gly | Thr | Glu | Thr | Ile | Ser | Ser | Ser | Ser | Phe | Glu | Leu | Glu | Met | Ala |
|---|---|---|---|---|---|---|---|---|---|---|---|---|---|---|---|
| | | | 340 | | | | | 345 | | | | | 350 | | |

| Gln | Glu | Gly | Phe | Ser | Ala | Val | Phe | Thr | Pro | Asp | Gly | Pro | Val | Leu | Gly |
|---|---|---|---|---|---|---|---|---|---|---|---|---|---|---|---|
| | | 355 | | | | | 360 | | | | | 365 | | | |

| Ala | Val | Gly | Ser | Phe | Thr | Trp | Ser | Gly | Gly | Ala | Phe | Leu | Tyr | Pro | Pro |
|---|---|---|---|---|---|---|---|---|---|---|---|---|---|---|---|
| | 370 | | | | | 375 | | | | | 380 | | | | |

| Asn | Met | Ser | Pro | Thr | Phe | Ile | Asn | Met | Ser | Gln | Glu | Asn | Val | Asp | Met |
|---|---|---|---|---|---|---|---|---|---|---|---|---|---|---|---|
| 385 | | | | | 390 | | | | | 395 | | | | | 400 |

-continued

| | | | | | | | | | | | | | | | |
|---|---|---|---|---|---|---|---|---|---|---|---|---|---|---|---|
|Arg|Asp|Ser|Tyr|Leu 405|Gly|Tyr|Ser|Thr|Glu 410|Leu|Ala|Leu|Trp|Lys 415|Gly|
|Val|Gln|Ser|Leu 420|Val|Leu|Gly|Ala|Pro 425|Arg|Tyr|Gln|His|Ile 430|Gly|Lys|
|Ala|Val|Ile 435|Phe|Ile|Gln|Val|Ser 440|Arg|Gln|Trp|Arg|Met 445|Lys|Ala|Glu|
|Val|Ile|Gly 450|Thr|Gln|Ile|Gly|Ser 455|Tyr|Phe|Gly|Ala 460|Ser|Leu|Cys|Ser|
|Val 465|Asp|Val|Asp|Thr|Asp 470|Gly|Ser|Thr|Asp 475|Leu|Val|Leu|Ile|Gly|Ala 480|
|Pro|His|Tyr|Tyr|Glu 485|Gln|Thr|Arg|Gly|Gly 490|Gln|Val|Ser|Val|Cys 495|Pro|
|Leu|Pro|Arg|Gly 500|Trp|Arg|Arg|Trp|Trp 505|Cys|Asp|Ala|Val|Leu 510|Tyr|Gly|
|Glu|Gln|Gly|His 515|Pro|Trp|Gly|Arg 520|Phe|Gly|Ala|Ala|Leu 525|Thr|Val|Leu|
|Gly|Asp|Val|Asn 530|Gly|Asp|Lys 535|Leu|Thr|Asp|Val|Val 540|Ile|Gly|Ala|Pro|
|Gly 545|Glu|Glu|Glu|Asn|Arg 550|Gly|Ala|Val|Tyr|Leu 555|Phe|His|Gly|Val|Leu 560|
|Gly|Pro|Ser|Ile|Ser 565|Pro|Ser|His|Ser|Gln 570|Arg|Ile|Ala|Gly|Ser 575|Gln|
|Leu|Ser|Ser|Arg 580|Leu|Gln|Tyr|Phe|Gly 585|Gln|Ala|Leu|Ser|Gly 590|Gly|Gln|
|Asp|Leu|Thr 595|Gln|Asp|Gly|Leu|Val 600|Asp|Leu|Ala|Val|Gly 605|Ala|Arg|Gly|
|Gln|Val 610|Leu|Leu|Leu|Arg|Thr 615|Arg|Pro|Val|Leu|Trp 620|Val|Gly|Val|Ser|
|Met 625|Gln|Phe|Ile|Pro|Ala 630|Glu|Ile|Pro|Arg|Ser 635|Ala|Phe|Glu|Cys|Arg 640|
|Glu|Gln|Val|Val|Ser 645|Glu|Gln|Thr|Leu|Val 650|Gln|Ser|Asn|Ile|Cys 655|Leu|
|Tyr|Ile|Asp|Lys 660|Arg|Ser|Lys|Asn|Leu 665|Leu|Gly|Ser|Arg|Asp 670|Leu|Gln|
|Ser|Ser|Val|Thr 675|Leu|Asp|Leu|Ala 680|Leu|Ala|Pro|Gly|Arg 685|Leu|Ser|Pro|
|Arg|Ala|Ile|Phe 690|Gln|Glu|Thr|Lys 695|Asn|Arg|Ser|Leu|Ser 700|Arg|Val|Arg|
|Val 705|Leu|Gly|Leu|Lys|Ala 710|His|Cys|Glu|Asn|Phe 715|Asn|Leu|Leu|Leu|Pro 720|
|Ser|Cys|Val|Glu|Asp 725|Ser|Val|Ile|Pro|Ile 730|Ile|Leu|Arg|Leu|Asn 735|Phe|
|Thr|Leu|Val|Gly 740|Lys|Pro|Leu|Leu|Ala 745|Phe|Arg|Asn|Leu|Arg 750|Pro|Met|
|Leu|Ala|Ala 755|Leu|Ala|Gln|Arg|Tyr 760|Phe|Thr|Ala|Ser|Leu 765|Pro|Phe|Glu|
|Lys|Asn|Cys 770|Gly|Ala|Asp|His|Ile 775|Cys|Gln|Asp|Asn|Leu 780|Gly|Ile|Ser|
|Phe 785|Ser|Phe|Pro|Gly|Leu 790|Lys|Ser|Leu|Leu|Val 795|Gly|Ser|Asn|Leu|Glu 800|
|Leu|Asn|Ala|Glu|Val 805|Met|Val|Trp|Asn|Asp 810|Gly|Glu|Asp|Ser|Tyr 815|Gly|
|Thr|Thr|Ile|Thr|Phe|Ser|His|Pro|Ala|Gly|Leu|Ser|Tyr|Arg|Tyr|Val|

```
                                820                           825                           830
        Ala  Glu  Gly  Gln  Lys  Gln  Gly  Gln  Leu  Arg  Ser  Leu  His  Leu  Thr  Cys
                      835                           840                           845
        Cys  Ser  Ala  Pro  Val  Gly  Ser  Gln  Gly  Thr  Trp  Ser  Thr  Ser  Cys  Arg
                      850                           855                           860
        Ile  Asn  His  Leu  Ile  Phe  Arg  Gly  Gly  Ala  Gln  Ile  Thr  Phe  Leu  Ala
        865                      870                           875                      880
        Thr  Phe  Asp  Val  Ser  Pro  Lys  Ala  Val  Gly  Leu  Asp  Arg  Leu  Leu  Leu
                                885                           890                           895
        Ile  Ala  Asn  Val  Ser  Ser  Glu  Asn  Asn  Ile  Pro  Arg  Thr  Ser  Lys  Thr
                      900                           905                           910
        Ile  Phe  Gln  Leu  Glu  Leu  Pro  Val  Lys  Tyr  Ala  Val  Tyr  Ile  Val  Val
                      915                           920                           925
        Ser  Ser  His  Glu  Gln  Phe  Thr  Lys  Tyr  Leu  Asn  Phe  Ser  Glu  Ser  Glu
                      930                           935                           940
        Glu  Lys  Glu  Ser  His  Val  Ala  Met  His  Arg  Tyr  Gln  Val  Asn  Asn  Leu
        945                      950                           955                      960
        Gly  Gln  Arg  Asp  Leu  Pro  Val  Ser  Ile  Asn  Phe  Trp  Val  Pro  Val  Glu
                                965                           970                           975
        Leu  Asn  Gln  Glu  Ala  Val  Trp  Met  Asp  Val  Glu  Val  Ser  His  Pro  Gln
                      980                           985                           990
        Asn  Pro  Ser  Leu  Arg  Cys  Ser  Ser  Glu  Lys  Ile  Ala  Pro  Pro  Ala  Ser
                      995                           1000                          1005
        Asp  Phe  Leu  Ala  His  Ile  Gln  Lys  Asn  Pro  Val  Leu  Asp  Cys  Ser  Ile
                      1010                          1015                          1020
        Ala  Gly  Cys  Leu  Arg  Phe  Arg  Cys  Asp  Val  Pro  Ser  Phe  Ser  Val  Gln
        1025                     1030                          1035                     1040
        Glu  Glu  Leu  Asp  Phe  Thr  Leu  Lys  Gly  Asn  Leu  Ser  Phe  Gly  Trp  Val
                                1045                          1050                          1055
        Arg  Gln  Ile  Leu  Gln  Lys  Lys  Val  Ser  Val  Val  Ser  Val  Ala  Glu  Ile
                      1060                          1065                          1070
        Ile  Phe  Asp  Thr  Ser  Val  Tyr  Ser  Gln  Leu  Pro  Gly  Gln  Glu  Ala  Phe
                      1075                          1080                          1085
        Met  Arg  Ala  Gln  Thr  Ile  Thr  Val  Leu  Glu  Lys  Tyr  Lys  Val  His  Asn
                      1090                          1095                          1100
        Pro  Ile  Pro  Leu  Ile  Val  Gly  Ser  Ser  Ile  Gly  Gly  Leu  Leu  Leu  Leu
        1105                     1110                          1115                     1120
        Ala  Leu  Ile  Thr  Ala  Val  Leu  Tyr  Lys  Val  Gly  Phe  Phe  Lys  Arg  Gln
                                1125                          1130                          1135
        Tyr  Lys  Glu  Met  Met  Glu  Glu  Ala  Asn  Gly  Gln  Ile  Ala  Pro  Glu  Asn
                      1140                          1145                          1150
        Gly  Thr  Gln  Thr  Pro  Ser  Pro  Pro  Ser  Glu  Lys
                      1155                          1160
```

( 2 ) INFORMATION FOR SEQ ID NO:5:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

```
        Phe  Asn  Leu  Asp  Val  Glu  Glu  Pro  Met  Val  Phe  Gln
        1                      5                           10
```

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TTYAAYYTGG AYGTNGARGA RCCNATGGTN TTYCA     35

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

TTCAACCTGG ACGTGGAGGA GCCCATGGTG TTCCAA     36

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

TTCAACCTGG ACGTNGAASA NCCCATGGTC TTCCAA     36

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

TTYAAYYTNG AYGTNGARGA RCC     23

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TTYAAYYTGG ACGTNGAAGA     20

( 2 ) INFORMATION FOR SEQ ID NO:11:

( i ) SEQUENCE CHARACTERISTICS:
        ( A ) LENGTH: 17 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

TGRAANACCA TNGGYTC 17

(2) INFORMATION FOR SEQ ID NO:12:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

TTGGAAGACC ATNGGYTC 18

(2) INFORMATION FOR SEQ ID NO:13:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

ATTAACCCTC ACTAAAG 17

(2) INFORMATION FOR SEQ ID NO:14:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

AATACGACTC ACTATAG 17

(2) INFORMATION FOR SEQ ID NO:15:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:15:

Val Phe Gln Glu Xaa Gly Ala Gly Phe Gly Gln
1               5                   10

(2) INFORMATION FOR SEQ ID NO:16:

(i) SEQUENCE CHARACTERISTICS:
(A) LENGTH: 14 amino acids
(B) TYPE: amino acid
(D) TOPOLOGY: linear (ii) MOLECULE TYPE: peptide (  x  i  ) SEQUENCE DESCRIPTION: SEQ ID NO:16:

Leu Tyr Asp Xaa Val Ala Ala Thr Gly Leu Xaa Gln Pro Ile
1               5                   10

( 2 ) INFORMATION FOR SEQ ID NO:17:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:17:

Pro Leu Glu Tyr Xaa Asp Val Ile Pro Gln Ala Glu
1               5                   10

( 2 ) INFORMATION FOR SEQ ID NO:18:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:18:

Phe Gln Glu Gly Phe Ser Xaa Val Leu Xaa
1               5                   10

( 2 ) INFORMATION FOR SEQ ID NO:19:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:19:

Thr Ser Pro Thr Phe Ile Xaa Met Ser Gln Glu Asn Val Asp
1               5                   10

( 2 ) INFORMATION FOR SEQ ID NO:20:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:20:

Leu Val Val Gly Ala Pro Leu Glu Val Val Ala Val Xaa Gln Thr Gly
1               5                   10                  15
Arg ( 2 ) INFORMATION FOR SEQ ID NO:21:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:21:

Leu Asp Xaa Lys Pro Xaa Asp Thr Ala (2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Phe  Gly  Glu  Gln  Phe  Ser  Glu
 1                 5
```

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

```
RAANCCYTCY TGRAAACTYT C                                    21
```

(2) INFORMATION FOR SEQ ID NO:24:

(i) SEQUENCE CHARACTERISTICS:
        (A) LENGTH: 1006 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

```
TTCAACCTGG ACGTGGAGGA GCCCATGGTG TTCAAGAGGA TGGAGCTGGC TTTGGACAGA      60
GCGTGGCCCA GCTTGGCGGA TCTAGACTCG TGGTGGGAGC CCCCTGGAG GTGGTGGCGG      120
TCAACCAAAC AGGAAGGTTG TATGACTGTG TGGCTGCCAC TGGCCTTGTC AACCCATACC     180
CCTGCACACA CCCCCAGATG CTGTGAACAT GTCCCTGGGT CTGTCCCTGT CAGCCGCCGC     240
CAGTCGCCCC TGGCTGCTGG CCTGTGGCCC AACCATGCAC AGAGCCTGTG GGAGAATAT     300
GTATGCAGAA GGCTTTTGCC TCCTGTTGGA CTCCCATCTG CAGACCATTT GGACAGTACC     360
TGCTGCCCTA CCAGAGTGTC CAAGTCAAGA GATGGACATT GTCTTCCTGA TTGATGGTTC     420
TGGCAGTATG AGCAAAGTGA CTTTAAACAA ATGAAGGATT TGTGAGAGCT GTGATGGGAC     480
AGTTTGAGGG CACCCAAACC CTGTTCTCAC TGATACAGTA TCCCACCTCC CTGAAGATCC     540
ACTTCACCTT CACGCAATTC CAGAGCAGCT GGAACCCTCT GAGCCTGGTG GATCCCATTG     600
TCCAACTGGA CGGCCTGACA TATACAGCCA CGGGCATCCG GAAAGTGGTG GAGGAACTGT     660
TTCATAGTAA GAATGGGGCC CGTAAAAGTG CCAAGAAGAT CCTCATTGTC ATCACAGATG     720
GCAAAAATAC AAAGACCCCC TGGAGTACGA GGACGTATCC CCAGGCAGAG AGAGCGGATC     780
ATCCGCTATG CCATTGGGGT GGGAGATGCT TTCTGGAAAC CCAGTGCCAA GCAGGAGCTG     840
GACAACATTG GCTCAGAGCC GGCTCAGGAC CATGTGTTCA GGGTGGACAA CTTTGCAGCA     900
CTCAGCAGCA TCCAGGAGCA GCTGCAGGAG AAGATCTTTG CACTCGAAGG AACCCAGTCG     960
ACGACAAGTA GCTCTTTCCA ACATGAGATG TTCCAAGAAG GGTTCA                   1006
```

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

GTNTTYCARG ARGAYGG                                        17

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

CCACTGTCAG GATGCCCGTG                                    20

( 2 ) INFORMATION FOR SEQ ID NO:27:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

AGTTACGAAT TCGCCACCAT GGCTCTACGG GTGCTTCTTC TG          42

( 2 ) INFORMATION FOR SEQ ID NO:28:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

AGTTACGAAT TCGCCACCAT GACTCGGACT GTGCTTCTTC TG          42

( 2 ) INFORMATION FOR SEQ ID NO:29:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

AGTTACGAAT TCGCCACCAT GACCTTCGGC ACTGTG                36

( 2 ) INFORMATION FOR SEQ ID NO:30:

( i ) SEQUENCE CHARACTERISTICS:
        ( A ) LENGTH: 20 base pairs (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:30:

TTGCTGACTG CCTGCAGTTC                                                                              20

(2) INFORMATION FOR SEQ ID NO:31:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:31:

GTTCTGACGC GTAATGGCAT TGTAGACCTC GTCTTC                                                            36

(2) INFORMATION FOR SEQ ID NO:32:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:32:

ACGTATGCAG GATCCCATCA AGAGATGGAC ATCGCT                                                            36

(2) INFORMATION FOR SEQ ID NO:33:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:33:

ACTGCATGTC TCGAGGCTGA AGCCTTCTTG GGACATC                                                           37

(2) INFORMATION FOR SEQ ID NO:34:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:34:

TATAGACTGC TGGGTAGTCC CCAC                                                                         24

(2) INFORMATION FOR SEQ ID NO:35:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (i i) MOLECULE TYPE: DNA ( x i ) SEQUENCE DESCRIPTION: SEQ ID NO:35:

TGAAGATTGG GGGTAAATAA CAGA 24

( 2 ) INFORMATION FOR SEQ ID NO:36:

( i ) SEQUENCE CHARACTERISTICS:
        ( A ) LENGTH: 3528 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..3456

( x i ) SEQUENCE DESCRIPTION: SEQ ID NO:36:

```
GGC TGG GCC CTG GCT TCC TGT CAT GGG TCT AAC CTG GAT GTG GAG GAA      48
Gly Trp Ala Leu Ala Ser Cys His Gly Ser Asn Leu Asp Val Glu Glu
 1               5                  10                  15

CCC ATC GTG TTC AGA GAG GAT GCA GCC AGC TTT GGA CAG ACT GTG GTG      96
Pro Ile Val Phe Arg Glu Asp Ala Ala Ser Phe Gly Gln Thr Val Val
             20                  25                  30

CAG TTT GGT GGA TCT CGA CTC GTG GTG GGA GCC CCT CTG GAG GCG GTG     144
Gln Phe Gly Gly Ser Arg Leu Val Val Gly Ala Pro Leu Glu Ala Val
         35                  40                  45

GCA GTC AAC CAA ACA GGA CGG TTG TAT GAC TGT GCA CCT GCC ACT GGC     192
Ala Val Asn Gln Thr Gly Arg Leu Tyr Asp Cys Ala Pro Ala Thr Gly
     50                  55                  60

ATG TGC CAG CCC ATC GTA CTG CGC AGT CCC CTA GAG GCA GTG AAC ATG     240
Met Cys Gln Pro Ile Val Leu Arg Ser Pro Leu Glu Ala Val Asn Met
 65                  70                  75                  80

TCC CTG GGC CTG TCT CTG GTG ACT GCC ACC AAT AAC GCC CAG TTG CTG     288
Ser Leu Gly Leu Ser Leu Val Thr Ala Thr Asn Asn Ala Gln Leu Leu
                 85                  90                  95

GCT TGT GGT CCA ACT GCA CAG AGA GCT TGT GTG AAG AAC ATG TAT GCG     336
Ala Cys Gly Pro Thr Ala Gln Arg Ala Cys Val Lys Asn Met Tyr Ala
            100                 105                 110

AAA GGT TCC TGC CTC CTT CTC GGC TCC AGC TTG CAG TTC ATC CAG GCA     384
Lys Gly Ser Cys Leu Leu Leu Gly Ser Ser Leu Gln Phe Ile Gln Ala
        115                 120                 125

GTC CCT GCC TCC ATG CCA GAG TGT CCA AGA CAA GAG ATG GAC ATT GCT     432
Val Pro Ala Ser Met Pro Glu Cys Pro Arg Gln Glu Met Asp Ile Ala
    130                 135                 140

TTC CTG ATT GAT GGT TCT GGC AGC ATT AAC CAA AGG GAC TTT GCC CAG     480
Phe Leu Ile Asp Gly Ser Gly Ser Ile Asn Gln Arg Asp Phe Ala Gln
145                 150                 155                 160

ATG AAG GAC TTT GTC AAA GCT TTG ATG GGA GAG TTT GCG AGC ACC AGC     528
Met Lys Asp Phe Val Lys Ala Leu Met Gly Glu Phe Ala Ser Thr Ser
                165                 170                 175

ACC TTG TTC TCC CTG ATG CAA TAC TCG AAC ATC CTG AAG ACC CAT TTT     576
Thr Leu Phe Ser Leu Met Gln Tyr Ser Asn Ile Leu Lys Thr His Phe
            180                 185                 190

ACC TTC ACT GAA TTC AAG AAC ATC CTG GAC CCT CAG AGC CTG GTG GAT     624
Thr Phe Thr Glu Phe Lys Asn Ile Leu Asp Pro Gln Ser Leu Val Asp
        195                 200                 205

CCC ATT GTC CAG CTG CAA GGC CTG ACC TAC ACA GCC ACA GGC ATC CGG     672
Pro Ile Val Gln Leu Gln Gly Leu Thr Tyr Thr Ala Thr Gly Ile Arg
    210                 215                 220

ACA GTG ATG GAA GAG CTA TTT CAT AGC AAG AAT GGG TCC CGT AAA AGT     720
Thr Val Met Glu Glu Leu Phe His Ser Lys Asn Gly Ser Arg Lys Ser
```

-continued

```
            225                         230                         235                         240
GCC   AAG   AAG   ATC   CTC   CTT   GTC   ATC   ACA   GAT   GGG   CAG   AAA   TAC   AGA   GAC         768
Ala   Lys   Lys   Ile   Leu   Leu   Val   Ile   Thr   Asp   Gly   Gln   Lys   Tyr   Arg   Asp
                        245                         250                         255

CCC   CTG   GAG   TAT   AGT   GAT   GTC   ATT   CCC   GCC   GCA   GAC   AAA   GCT   GGC   ATC         816
Pro   Leu   Glu   Tyr   Ser   Asp   Val   Ile   Pro   Ala   Ala   Asp   Lys   Ala   Gly   Ile
                        260                         265                         270

ATT   CGT   TAT   GCT   ATT   GGG   GTG   GGA   GAT   GCC   TTC   CAG   GAG   CCC   ACT   GCC         864
Ile   Arg   Tyr   Ala   Ile   Gly   Val   Gly   Asp   Ala   Phe   Gln   Glu   Pro   Thr   Ala
                        275                         280                         285

CTG   AAG   GAG   CTG   AAC   ACC   ATT   GGC   TCA   GCT   CCC   CCA   CAG   GAC   CAC   GTG         912
Leu   Lys   Glu   Leu   Asn   Thr   Ile   Gly   Ser   Ala   Pro   Pro   Gln   Asp   His   Val
      290                         295                         300

TTC   AAG   GTA   GGC   AAC   TTT   GCA   GCA   CTT   CGC   AGC   ATC   CAG   AGG   CAA   CTT         960
Phe   Lys   Val   Gly   Asn   Phe   Ala   Ala   Leu   Arg   Ser   Ile   Gln   Arg   Gln   Leu
305                         310                         315                         320

CAG   GAG   AAA   ATC   TTC   GCC   ATT   GAG   GGA   ACT   CAA   TCA   AGG   TCA   AGT   AGT        1008
Gln   Glu   Lys   Ile   Phe   Ala   Ile   Glu   Gly   Thr   Gln   Ser   Arg   Ser   Ser   Ser
                        325                         330                         335

TCC   TTT   CAG   CAC   GAG   ATG   TCA   CAA   GAA   GGT   TTC   AGT   TCA   GCT   CTC   ACA        1056
Ser   Phe   Gln   His   Glu   Met   Ser   Gln   Glu   Gly   Phe   Ser   Ser   Ala   Leu   Thr
                  340                         345                         350

TCG   GAT   GGA   CCC   GTT   CTG   GGG   GCC   GYG   GGA   AGC   TTC   AGC   TGG   TCC   GGA        1104
Ser   Asp   Gly   Pro   Val   Leu   Gly   Ala   Xaa   Gly   Ser   Phe   Ser   Trp   Ser   Gly
            355                         360                         365

GGT   GCC   TTC   TTA   TAT   CCC   CCA   AAT   ACG   AGA   CCC   ACC   TTT   ATC   AAC   ATG        1152
Gly   Ala   Phe   Leu   Tyr   Pro   Pro   Asn   Thr   Arg   Pro   Thr   Phe   Ile   Asn   Met
      370                         375                         380

TCT   CAG   GAG   AAT   GTG   GAC   ATG   AGA   GAC   TCC   TAC   CTG   GGT   TAC   TCC   ACC        1200
Ser   Gln   Glu   Asn   Val   Asp   Met   Arg   Asp   Ser   Tyr   Leu   Gly   Tyr   Ser   Thr
385                         390                         395                         400

GCA   GTG   GCC   TTT   TGG   AAG   GGG   GTT   CAC   AGC   CTG   ATC   CTG   GGG   GCC   CCG        1248
Ala   Val   Ala   Phe   Trp   Lys   Gly   Val   His   Ser   Leu   Ile   Leu   Gly   Ala   Pro
                        405                         410                         415

CGT   CAC   CAG   CAC   ACG   GGG   AAG   GTT   GTC   ATC   TTT   ACC   CAG   GAA   GCC   AGG        1296
Arg   His   Gln   His   Thr   Gly   Lys   Val   Val   Ile   Phe   Thr   Gln   Glu   Ala   Arg
                  420                         425                         430

CAT   TGG   AGG   CCC   AAG   TCT   GAA   GTC   AGA   GGG   ACA   CAG   ATC   GGC   TCC   TAC        1344
His   Trp   Arg   Pro   Lys   Ser   Glu   Val   Arg   Gly   Thr   Gln   Ile   Gly   Ser   Tyr
            435                         440                         445

TTC   GGG   GCC   TCT   CTC   TGT   TCT   GTG   GAC   GTG   GAT   AGA   GAT   GGC   AGC   ACY        1392
Phe   Gly   Ala   Ser   Leu   Cys   Ser   Val   Asp   Val   Asp   Arg   Asp   Gly   Ser   Xaa
      450                         455                         460

GAC   CTG   GTC   CTG   ATC   GGA   GCC   CCC   CAT   TAC   TAT   GAG   CAG   ACC   CGA   GGG        1440
Asp   Leu   Val   Leu   Ile   Gly   Ala   Pro   His   Tyr   Tyr   Glu   Gln   Thr   Arg   Gly
465                         470                         475                         480

GGG   CAG   GTC   TCA   GTG   TKC   CCC   GTG   CCC   GGT   GTG   AGG   GGC   AGG   TGG   CAG        1488
Gly   Gln   Val   Ser   Val   Xaa   Pro   Val   Pro   Gly   Val   Arg   Gly   Arg   Trp   Gln
                        485                         490                         495

TGT   GAG   GCC   ACC   CTC   CAC   GGG   GAG   CAG   GRC   CAT   CCT   TGG   GGC   CGC   TTT        1536
Cys   Glu   Ala   Thr   Leu   His   Gly   Glu   Gln   Xaa   His   Pro   Trp   Gly   Arg   Phe
                  500                         505                         510

GGG   GTG   GCT   CTG   ACA   GTG   CTG   GGG   GAC   GTA   AAC   GGG   GAC   AAT   CTG   GCA        1584
Gly   Val   Ala   Leu   Thr   Val   Leu   Gly   Asp   Val   Asn   Gly   Asp   Asn   Leu   Ala
            515                         520                         525

GAC   GTG   GCT   ATT   GGT   GCC   CCT   GGA   GAG   GAG   GAG   AGC   AGA   GGT   GCT   GTC        1632
Asp   Val   Ala   Ile   Gly   Ala   Pro   Gly   Glu   Glu   Glu   Ser   Arg   Gly   Ala   Val
530                         535                         540

TAC   ATA   TTT   CAT   GGA   GCC   TCG   AGA   CTG   GAG   ATC   ATG   CCC   TCA   CCC   AGC        1680
Tyr   Ile   Phe   His   Gly   Ala   Ser   Arg   Leu   Glu   Ile   Met   Pro   Ser   Pro   Ser
```

```
545                         550                         555                         560
CAG CGG GTC ACT GGC TCC CAG CTC TCC CTG AGA CTG CAG TAT TTT GGG    1728
Gln Arg Val Thr Gly Ser Gln Leu Ser Leu Arg Leu Gln Tyr Phe Gly
            565                         570                         575

CAG TCA TTG AGT GGG GGT CAG GAC CTT ACA CAG GAT GGC CTG GTG GAC    1776
Gln Ser Leu Ser Gly Gly Gln Asp Leu Thr Gln Asp Gly Leu Val Asp
            580                         585                         590

CTG GCC GTG GGA GCC CAG GGG CAC GTA CTG CTC CTC AGG AGT CTG CCT    1824
Leu Ala Val Gly Ala Gln Gly His Val Leu Leu Leu Arg Ser Leu Pro
            595                         600                         605

CTG CTG AAA GTG GAG CTC TCC ATA AGA TTC GCC CCC ATG GAG GTG GCA    1872
Leu Leu Lys Val Glu Leu Ser Ile Arg Phe Ala Pro Met Glu Val Ala
    610                         615                         620

AAG GCT GTG TAC CAG TGC TGG GAA AGG ACT CCC ACT GTC CTC GAA GCT    1920
Lys Ala Val Tyr Gln Cys Trp Glu Arg Thr Pro Thr Val Leu Glu Ala
625                         630                         635                         640

GGA GAG GCC ACT GTC TGT CTC ACT GTC CAC AAA GGC TCA CCT GAC CTG    1968
Gly Glu Ala Thr Val Cys Leu Thr Val His Lys Gly Ser Pro Asp Leu
            645                         650                         655

TTA GGT AAT GTC CAA GGC TCT GTC AGG TAT GAT CTG GCG TTA GAT CCG    2016
Leu Gly Asn Val Gln Gly Ser Val Arg Tyr Asp Leu Ala Leu Asp Pro
            660                         665                         670

GGC CGC CTG ATT TCT CGT GCC ATT TTT GAT GAG ACT AAG AAC TGC ACT    2064
Gly Arg Leu Ile Ser Arg Ala Ile Phe Asp Glu Thr Lys Asn Cys Thr
            675                         680                         685

TTG ACG GGA AGG AAG ACT CTG GGG CTT GGT GAT CAC TGC GAA ACA GTG    2112
Leu Thr Gly Arg Lys Thr Leu Gly Leu Gly Asp His Cys Glu Thr Val
            690                         695                         700

AAG CTG CTT TTG CCG GAC TGT GTG GAA GAT GCA GTG AGC CCT ATC ATC    2160
Lys Leu Leu Leu Pro Asp Cys Val Glu Asp Ala Val Ser Pro Ile Ile
705                         710                         715                         720

CTG CGC CTC AAC TTT TCC CTG GTG AGA GAC TCT GCT TCA CCC AGG AAC    2208
Leu Arg Leu Asn Phe Ser Leu Val Arg Asp Ser Ala Ser Pro Arg Asn
            725                         730                         735

CTG CAT CCT GTG CTG GCT GTG GGC TCA CAA GAC CAC ATA ACT GCT TCT    2256
Leu His Pro Val Leu Ala Val Gly Ser Gln Asp His Ile Thr Ala Ser
            740                         745                         750

CTG CCG TTT GAG AAG AAC TGT AAG CAA GAA CTC CTG TGT GAG GGG GAC    2304
Leu Pro Phe Glu Lys Asn Cys Lys Gln Glu Leu Leu Cys Glu Gly Asp
            755                         760                         765

CTG GGC ATC AGC TTT AAC TTC TCA GGC CTG CAG GTC TTG GTG GTG GGA    2352
Leu Gly Ile Ser Phe Asn Phe Ser Gly Leu Gln Val Leu Val Val Gly
            770                         775                         780

GGC TCC CCA GAG CTC ACT GTG ACA GTC ACT GTG TGG AAT GAG GGT GAG    2400
Gly Ser Pro Glu Leu Thr Val Thr Val Thr Val Trp Asn Glu Gly Glu
785                         790                         795                         800

GAC AGC TAT GGA ACT TTA GTC AAG TTC TAC TAC CCA GCA GGG CTA TCT    2448
Asp Ser Tyr Gly Thr Leu Val Lys Phe Tyr Tyr Pro Ala Gly Leu Ser
            805                         810                         815

TAC CGA CGG GTA ACA GGG ACT CAG CAA CCT CAT CAG TAC CCA CTA CGC    2496
Tyr Arg Arg Val Thr Gly Thr Gln Gln Pro His Gln Tyr Pro Leu Arg
            820                         825                         830

TTG GCC TGT GAG GCT GAG CCC GCT GCC CAG GAG GAC CTG AGG AGC AGC    2544
Leu Ala Cys Glu Ala Glu Pro Ala Ala Gln Glu Asp Leu Arg Ser Ser
            835                         840                         845

AGC TGT AGC ATT AAT CAC CCC ATC TTC CGA GAA GGT GCA AAG ACC ACC    2592
Ser Cys Ser Ile Asn His Pro Ile Phe Arg Glu Gly Ala Lys Thr Thr
    850                         855                         860

TTC ATG ATC ACA TTC GAT GTC TCC TAC AAG GCC TTC CTA GGA GAC AGG    2640
Phe Met Ile Thr Phe Asp Val Ser Tyr Lys Ala Phe Leu Gly Asp Arg
```

-continued

| | | | | | | | | | | | | | | | | |
|---|---|---|---|---|---|---|---|---|---|---|---|---|---|---|---|---|
| 865 | | | | | | 870 | | | | | 875 | | | | 880 | |
| TTG | CTT | CTG | AGG | GCC | AAA | GCC | AGC | AGT | GAG | AAT | AAT | AAG | CCT | GAT | ACC | 2688 |
| Leu | Leu | Leu | Arg | Ala | Lys | Ala | Ser | Ser | Glu | Asn | Asn | Lys | Pro | Asp | Thr | |
| | | | 885 | | | | | 890 | | | | | | 895 | | |
| AAC | AAG | ACT | GCC | TTC | CAG | CTG | GAG | CTC | CCA | GTG | AAG | TAC | ACC | GTC | TAT | 2736 |
| Asn | Lys | Thr | Ala | Phe | Gln | Leu | Glu | Leu | Pro | Val | Lys | Tyr | Thr | Val | Tyr | |
| | | | 900 | | | | | 905 | | | | | 910 | | | |
| ACC | CTG | ATC | AGT | AGG | CAA | GAA | GAT | TCC | ACC | AAC | CAT | GTC | AAC | TTT | TCA | 2784 |
| Thr | Leu | Ile | Ser | Arg | Gln | Glu | Asp | Ser | Thr | Asn | His | Val | Asn | Phe | Ser | |
| | | 915 | | | | | 920 | | | | 925 | | | | | |
| TCT | TCC | CAC | GGG | GGG | AGA | AGG | CAA | GAA | GCC | GCA | CAT | CGC | TAT | CGT | GTG | 2832 |
| Ser | Ser | His | Gly | Gly | Arg | Arg | Gln | Glu | Ala | Ala | His | Arg | Tyr | Arg | Val | |
| | 930 | | | | | 935 | | | | | 940 | | | | | |
| AAT | AAC | CTG | AGT | CCA | CTG | AAG | CTG | GCC | GTC | AGA | GTT | AAC | TTC | TGG | GTC | 2880 |
| Asn | Asn | Leu | Ser | Pro | Leu | Lys | Leu | Ala | Val | Arg | Val | Asn | Phe | Trp | Val | |
| 945 | | | | | 950 | | | | | 955 | | | | | 960 | |
| CCT | GTC | CTT | CTG | AAC | GGT | GTG | GCT | GTG | TGG | GAC | GTG | ACT | CTG | AGC | AGC | 2928 |
| Pro | Val | Leu | Leu | Asn | Gly | Val | Ala | Val | Trp | Asp | Val | Thr | Leu | Ser | Ser | |
| | | | | 965 | | | | | 970 | | | | | 975 | | |
| CCA | GCA | CAG | GGT | GTC | TCC | TGC | GTG | TCC | CAG | ATG | AAA | CCT | CCT | CAG | AAT | 2976 |
| Pro | Ala | Gln | Gly | Val | Ser | Cys | Val | Ser | Gln | Met | Lys | Pro | Pro | Gln | Asn | |
| | | | 980 | | | | | 985 | | | | | 990 | | | |
| CCC | GAC | TTT | CTG | ACC | CAG | ATT | CAG | AGA | CGT | TCT | GTG | CTG | GAC | TGC | TCC | 3024 |
| Pro | Asp | Phe | Leu | Thr | Gln | Ile | Gln | Arg | Arg | Ser | Val | Leu | Asp | Cys | Ser | |
| | | 995 | | | | | 1000 | | | | | 1005 | | | | |
| ATT | GCT | GAC | TGC | CTG | CAC | TCC | CGC | TGT | GAC | ATC | CCC | TCC | TTG | GAC | ATC | 3072 |
| Ile | Ala | Asp | Cys | Leu | His | Ser | Arg | Cys | Asp | Ile | Pro | Ser | Leu | Asp | Ile | |
| | | 1010 | | | | 1015 | | | | | 1020 | | | | | |
| CAG | GAT | GAA | CTT | GAC | TTC | ATT | CTG | AGG | GGC | AAC | CTC | AGC | TTC | GGC | TGG | 3120 |
| Gln | Asp | Glu | Leu | Asp | Phe | Ile | Leu | Arg | Gly | Asn | Leu | Ser | Phe | Gly | Trp | |
| 1025 | | | | | 1030 | | | | | | 1035 | | | | 1040 | |
| GTC | AGT | CAG | ACA | TTG | CAG | GAA | AAG | GTG | TTG | CTT | GTG | AGT | GAG | GCT | GAA | 3168 |
| Val | Ser | Gln | Thr | Leu | Gln | Glu | Lys | Val | Leu | Leu | Val | Ser | Glu | Ala | Glu | |
| | | | | 1045 | | | | | 1050 | | | | | 1055 | | |
| ATC | ACT | TTC | GAC | ACA | TCT | GTG | TAC | TCC | CAG | CTG | CCA | GGA | CAG | GAG | GCA | 3216 |
| Ile | Thr | Phe | Asp | Thr | Ser | Val | Tyr | Ser | Gln | Leu | Pro | Gly | Gln | Glu | Ala | |
| | | | 1060 | | | | | 1065 | | | | | 1070 | | | |
| TTT | CTG | AGA | GCC | CAG | GTG | GAG | ACA | ACG | TTA | GAA | GAA | TAC | GTG | GTC | TAT | 3264 |
| Phe | Leu | Arg | Ala | Gln | Val | Glu | Thr | Thr | Leu | Glu | Glu | Tyr | Val | Val | Tyr | |
| | | 1075 | | | | | 1080 | | | | | 1085 | | | | |
| GAG | CCC | ATC | TTC | CTC | GTG | GCG | GGC | AGC | TCG | GTG | GGA | GGT | CTG | CTG | TTA | 3312 |
| Glu | Pro | Ile | Phe | Leu | Val | Ala | Gly | Ser | Ser | Val | Gly | Gly | Leu | Leu | Leu | |
| | | 1090 | | | | 1095 | | | | | 1100 | | | | | |
| CTG | GCT | CTC | ATC | ACA | GTG | GTA | CTG | TAC | AAG | CTT | GGC | TYC | TYC | AAA | CGT | 3360 |
| Leu | Ala | Leu | Ile | Thr | Val | Val | Leu | Tyr | Lys | Leu | Gly | Xaa | Xaa | Lys | Arg | |
| 1105 | | | | | 1110 | | | | | 1115 | | | | | 1120 | |
| CAG | TAC | AAA | GAA | ATG | CTG | GAC | GGC | AAG | GCT | GCA | GAT | CCT | GTC | ACA | GCC | 3408 |
| Gln | Tyr | Lys | Glu | Met | Leu | Asp | Gly | Lys | Ala | Ala | Asp | Pro | Val | Thr | Ala | |
| | | | | 1125 | | | | | 1130 | | | | | 1135 | | |
| GGC | CAG | GCA | GAT | TTC | GGC | TGT | GAG | ACT | CCT | CCA | TAT | CTC | | | | |
| Gly | Gln | Ala | Asp | Phe | Gly | Cys | Glu | Thr | Pro | Pro | Tyr | Leu | | | | |
| | | | 1140 | | | | | 1145 | | | | | | | | |
| | | | | | | | | | | | GTG | AGC | TAGGAATCCA | | | 3463 |
| | | | | | | | | | | | Val | Ser | | | | |
| | | | | | | | | | | | 1150 | | | | | |

CTCTCCTGCC TATCTCTGNA ATGAAGATTG GTCCTGCCTA TGAGTCTACT GGCATGGGAA   3523

CGAGT   3528

( 2 ) INFORMATION FOR SEQ ID NO:37:

( i ) SEQUENCE CHARACTERISTICS:
  ( A ) LENGTH: 1151 amino acids
  ( B ) TYPE: amino acid
  ( D ) TOPOLOGY: linear ( i i ) MOLECULE TYPE: protein ( x i ) SEQUENCE DESCRIPTION: SEQ ID NO:37:

```
Gly Trp Ala Leu Ala Ser Cys His Gly Ser Asn Leu Asp Val Glu Glu
 1               5                  10                  15

Pro Ile Val Phe Arg Glu Asp Ala Ala Ser Phe Gly Gln Thr Val Val
                20                  25                  30

Gln Phe Gly Gly Ser Arg Leu Val Val Gly Ala Pro Leu Glu Ala Val
                35                  40                  45

Ala Val Asn Gln Thr Gly Arg Leu Tyr Asp Cys Ala Pro Ala Thr Gly
                50                  55                  60

Met Cys Gln Pro Ile Val Leu Arg Ser Pro Leu Glu Ala Val Asn Met
 65                  70                  75                  80

Ser Leu Gly Leu Ser Leu Val Thr Thr Asn Asn Ala Gln Leu Leu
                    85                  90                  95

Ala Cys Gly Pro Thr Ala Gln Arg Ala Cys Val Lys Asn Met Tyr Ala
                100                 105                 110

Lys Gly Ser Cys Leu Leu Leu Gly Ser Ser Leu Gln Phe Ile Gln Ala
                115                 120                 125

Val Pro Ala Ser Met Pro Glu Cys Pro Arg Gln Glu Met Asp Ile Ala
130                 135                 140

Phe Leu Ile Asp Gly Ser Gly Ser Ile Asn Gln Arg Asp Phe Ala Gln
145                 150                 155                 160

Met Lys Asp Phe Val Lys Ala Leu Met Gly Glu Phe Ala Ser Thr Ser
                    165                 170                 175

Thr Leu Phe Ser Leu Met Gln Tyr Ser Asn Ile Leu Lys Thr His Phe
                    180                 185                 190

Thr Phe Thr Glu Phe Lys Asn Ile Leu Asp Pro Gln Ser Leu Val Asp
                195                 200                 205

Pro Ile Val Gln Leu Gln Gly Leu Thr Tyr Thr Ala Thr Gly Ile Arg
    210                 215                 220

Thr Val Met Glu Glu Leu Phe His Ser Lys Asn Gly Ser Arg Lys Ser
225                 230                 235                 240

Ala Lys Lys Ile Leu Leu Val Ile Thr Asp Gly Gln Lys Tyr Arg Asp
                    245                 250                 255

Pro Leu Glu Tyr Ser Asp Val Ile Pro Ala Ala Asp Lys Ala Gly Ile
                    260                 265                 270

Ile Arg Tyr Ala Ile Gly Val Gly Asp Ala Phe Gln Glu Pro Thr Ala
                275                 280                 285

Leu Lys Glu Leu Asn Thr Ile Gly Ser Ala Pro Pro Gln Asp His Val
    290                 295                 300

Phe Lys Val Gly Asn Phe Ala Ala Leu Arg Ser Ile Gln Arg Gln Leu
305                 310                 315                 320

Gln Glu Lys Ile Phe Ala Ile Glu Gly Thr Gln Ser Arg Ser Ser Ser
                325                 330                 335

Ser Phe Gln His Glu Met Ser Gln Glu Gly Phe Ser Ser Ala Leu Thr
                340                 345                 350

Ser Asp Gly Pro Val Leu Gly Ala Xaa Gly Ser Phe Ser Trp Ser Gly
                355                 360                 365

Gly Ala Phe Leu Tyr Pro Pro Asn Thr Arg Pro Thr Phe Ile Asn Met
```

```
       370                    375                        380
Ser  Gln  Glu  Asn  Val  Asp  Met  Arg  Asp  Ser  Tyr  Leu  Gly  Tyr  Ser  Thr
385                      390                      395                      400

Ala  Val  Ala  Phe  Trp  Lys  Gly  Val  His  Ser  Leu  Ile  Leu  Gly  Ala  Pro
               405                      410                      415

Arg  His  Gln  His  Thr  Gly  Lys  Val  Val  Ile  Phe  Thr  Gln  Glu  Ala  Arg
                    420                      425                      430

His  Trp  Arg  Pro  Lys  Ser  Glu  Val  Arg  Gly  Thr  Gln  Ile  Gly  Ser  Tyr
               435                      440                      445

Phe  Gly  Ala  Ser  Leu  Cys  Ser  Val  Asp  Val  Asp  Arg  Asp  Gly  Ser  Xaa
          450                      455                      460

Asp  Leu  Val  Leu  Ile  Gly  Ala  Pro  His  Tyr  Tyr  Glu  Gln  Thr  Arg  Gly
465                           470                      475                      480

Gly  Gln  Val  Ser  Val  Xaa  Pro  Val  Pro  Gly  Val  Arg  Gly  Arg  Trp  Gln
                    485                      490                      495

Cys  Glu  Ala  Thr  Leu  His  Gly  Glu  Gln  Xaa  His  Pro  Trp  Gly  Arg  Phe
               500                      505                      510

Gly  Val  Ala  Leu  Thr  Val  Leu  Gly  Asp  Val  Asn  Gly  Asp  Asn  Leu  Ala
          515                      520                      525

Asp  Val  Ala  Ile  Gly  Ala  Pro  Gly  Glu  Glu  Ser  Arg  Gly  Ala  Val
     530                      535                      540

Tyr  Ile  Phe  His  Gly  Ala  Ser  Arg  Leu  Glu  Ile  Met  Pro  Ser  Pro  Ser
545                           550                      555                      560

Gln  Arg  Val  Thr  Gly  Ser  Gln  Leu  Ser  Leu  Arg  Leu  Gln  Tyr  Phe  Gly
                    565                      570                      575

Gln  Ser  Leu  Ser  Gly  Gly  Gln  Asp  Leu  Thr  Gln  Asp  Gly  Leu  Val  Asp
               580                      585                      590

Leu  Ala  Val  Gly  Ala  Gln  Gly  His  Val  Leu  Leu  Leu  Arg  Ser  Leu  Pro
          595                      600                      605

Leu  Leu  Lys  Val  Glu  Leu  Ser  Ile  Arg  Phe  Ala  Pro  Met  Glu  Val  Ala
610                      615                      620

Lys  Ala  Val  Tyr  Gln  Cys  Trp  Glu  Arg  Thr  Pro  Thr  Val  Leu  Glu  Ala
625                      630                      635                      640

Gly  Glu  Ala  Thr  Val  Cys  Leu  Thr  Val  His  Lys  Gly  Ser  Pro  Asp  Leu
               645                      650                      655

Leu  Gly  Asn  Val  Gln  Gly  Ser  Val  Arg  Tyr  Asp  Leu  Ala  Leu  Asp  Pro
               660                      665                      670

Gly  Arg  Leu  Ile  Ser  Arg  Ala  Ile  Phe  Asp  Glu  Thr  Lys  Asn  Cys  Thr
          675                      680                      685

Leu  Thr  Gly  Arg  Lys  Thr  Leu  Gly  Leu  Gly  Asp  His  Cys  Glu  Thr  Val
     690                      695                      700

Lys  Leu  Leu  Leu  Pro  Asp  Cys  Val  Glu  Asp  Ala  Val  Ser  Pro  Ile  Ile
705                      710                      715                      720

Leu  Arg  Leu  Asn  Phe  Ser  Leu  Val  Arg  Asp  Ser  Ala  Ser  Pro  Arg  Asn
                    725                      730                      735

Leu  His  Pro  Val  Leu  Ala  Val  Gly  Ser  Gln  Asp  His  Ile  Thr  Ala  Ser
               740                      745                      750

Leu  Pro  Phe  Glu  Lys  Asn  Cys  Lys  Gln  Glu  Leu  Leu  Cys  Glu  Gly  Asp
          755                      760                      765

Leu  Gly  Ile  Ser  Phe  Asn  Phe  Ser  Gly  Leu  Gln  Val  Leu  Val  Val  Gly
     770                      775                      780

Gly  Ser  Pro  Glu  Leu  Thr  Val  Thr  Val  Thr  Val  Trp  Asn  Glu  Gly  Glu
785                      790                      795                      800
```

-continued

```
Asp  Ser  Tyr  Gly  Thr  Leu  Val  Lys  Phe  Tyr  Tyr  Pro  Ala  Gly  Leu  Ser
               805                      810                      815

Tyr  Arg  Arg  Val  Thr  Gly  Thr  Gln  Gln  Pro  His  Gln  Tyr  Pro  Leu  Arg
               820                      825                      830

Leu  Ala  Cys  Glu  Ala  Glu  Pro  Ala  Ala  Gln  Glu  Asp  Leu  Arg  Ser  Ser
               835                      840                      845

Ser  Cys  Ser  Ile  Asn  His  Pro  Ile  Phe  Arg  Glu  Gly  Ala  Lys  Thr  Thr
     850                      855                      860

Phe  Met  Ile  Thr  Phe  Asp  Val  Ser  Tyr  Lys  Ala  Phe  Leu  Gly  Asp  Arg
865                      870                      875                      880

Leu  Leu  Leu  Arg  Ala  Lys  Ala  Ser  Ser  Glu  Asn  Asn  Lys  Pro  Asp  Thr
                    885                      890                      895

Asn  Lys  Thr  Ala  Phe  Gln  Leu  Glu  Leu  Pro  Val  Lys  Tyr  Thr  Val  Tyr
                900                      905                      910

Thr  Leu  Ile  Ser  Arg  Gln  Glu  Asp  Ser  Thr  Asn  His  Val  Asn  Phe  Ser
               915                      920                      925

Ser  Ser  His  Gly  Gly  Arg  Arg  Gln  Glu  Ala  Ala  His  Arg  Tyr  Arg  Val
     930                      935                      940

Asn  Asn  Leu  Ser  Pro  Leu  Lys  Leu  Ala  Val  Arg  Val  Asn  Phe  Trp  Val
945                      950                      955                           960

Pro  Val  Leu  Leu  Asn  Gly  Val  Ala  Val  Trp  Asp  Val  Thr  Leu  Ser  Ser
               965                      970                      975

Pro  Ala  Gln  Gly  Val  Ser  Cys  Val  Ser  Gln  Met  Lys  Pro  Pro  Gln  Asn
               980                      985                      990

Pro  Asp  Phe  Leu  Thr  Gln  Ile  Gln  Arg  Arg  Ser  Val  Leu  Asp  Cys  Ser
               995                      1000                     1005

Ile  Ala  Asp  Cys  Leu  His  Ser  Arg  Cys  Asp  Ile  Pro  Ser  Leu  Asp  Ile
     1010                     1015                     1020

Gln  Asp  Glu  Leu  Asp  Phe  Ile  Leu  Arg  Gly  Asn  Leu  Ser  Phe  Gly  Trp
1025                     1030                     1035                     1040

Val  Ser  Gln  Thr  Leu  Gln  Glu  Lys  Val  Leu  Leu  Val  Ser  Glu  Ala  Glu
                    1045                     1050                     1055

Ile  Thr  Phe  Asp  Thr  Ser  Val  Tyr  Ser  Gln  Leu  Pro  Gly  Gln  Glu  Ala
               1060                     1065                     1070

Phe  Leu  Arg  Ala  Gln  Val  Glu  Thr  Thr  Leu  Glu  Glu  Tyr  Val  Val  Tyr
          1075                     1080                     1085

Glu  Pro  Ile  Phe  Leu  Val  Ala  Gly  Ser  Ser  Val  Gly  Gly  Leu  Leu  Leu
     1090                     1095                     1100

Leu  Ala  Leu  Ile  Thr  Val  Val  Leu  Tyr  Lys  Leu  Gly  Xaa  Xaa  Lys  Arg
1105                     1110                     1115                     1120

Gln  Tyr  Lys  Glu  Met  Leu  Asp  Gly  Lys  Ala  Ala  Asp  Pro  Val  Thr  Ala
               1125                     1130                     1135

Gly  Gln  Ala  Asp  Phe  Gly  Cys  Glu  Thr  Pro  Pro  Tyr  Leu  Val  Ser
               1140                     1145                     1150
```

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

GTCCAAGCTG TCATGGGCCA G                           21

( 2 ) INFORMATION FOR SEQ ID NO:39:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

GTCCAGCAGA CTGAAGAGCA CGG        23

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

TGTAAAACGA CGGCCAGT        18

( 2 ) INFORMATION FOR SEQ ID NO:41:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

GGAAACAGCT ATGACCATG        19

( 2 ) INFORMATION FOR SEQ ID NO:42:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

GGACATGTTC ACTGCCTCTA GG        22

( 2 ) INFORMATION FOR SEQ ID NO:43:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GGCGGACAGT CAGACGACTG TCCTG        25

( 2 ) INFORMATION FOR SEQ ID NO:44:

( i ) SEQUENCE CHARACTERISTICS:

(A) LENGTH: 38 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:44:

CTGGTTCGGC CCACCTCTGA AGGTTCCAGA ATCGATAG                                    38

(2) INFORMATION FOR SEQ ID NO:45:

(i) SEQUENCE CHARACTERISTICS:
(A) LENGTH: 3519 base pairs
(B) TYPE: nucleic acid
(C) STRANDEDNESS: single
(D) TOPOLOGY: linear (i i) MOLECULE TYPE: cDNA (i x) FEATURE:
(A) NAME/KEY: CDS
(B) LOCATION: 52..3519

(x i) SEQUENCE DESCRIPTION: SEQ ID NO:45:

| | | | | | | | | | | | | | | | | | |
|---|---|---|---|---|---|---|---|---|---|---|---|---|---|---|---|---|---|
| GCTTTCTGAA | GGTTCCAGAA | TCGATAGTGA | ATTCGTGGGC | ACTGCTCAGA | T | ATG | GTC | | | | | | | | | | 57 |
| | | | | | | Met | Val | | | | | | | | | | |
| | | | | | | | 1 | | | | | | | | | | |

| CGT | GGA | GTT | GTG | ATC | CTC | CTG | TGT | GGC | TGG | GCC | CTG | GCT | TCC | TGT | CAT | 105 |
|---|---|---|---|---|---|---|---|---|---|---|---|---|---|---|---|---|
| Arg | Gly | Val | Val | Ile | Leu | Leu | Cys | Gly | Trp | Ala | Leu | Ala | Ser | Cys | His | |
| | 5 | | | | | 10 | | | | | | 15 | | | | |

| GGG | TCT | AAC | CTG | GAT | GTG | GAG | AAG | CCC | GTC | GTG | TTC | AAA | GAG | GAT | GCA | 153 |
|---|---|---|---|---|---|---|---|---|---|---|---|---|---|---|---|---|
| Gly | Ser | Asn | Leu | Asp | Val | Glu | Lys | Pro | Val | Val | Phe | Lys | Glu | Asp | Ala | |
| | 20 | | | | 25 | | | | | 30 | | | | | | |

| GCC | AGC | TTC | GGA | CAG | ACT | GTG | GTG | CAG | TTT | GGT | GGA | TCT | CGA | CTC | GTG | 201 |
|---|---|---|---|---|---|---|---|---|---|---|---|---|---|---|---|---|
| Ala | Ser | Phe | Gly | Gln | Thr | Val | Val | Gln | Phe | Gly | Gly | Ser | Arg | Leu | Val | |
| 35 | | | | 40 | | | | 45 | | | | | | 50 | | |

| GTG | GGA | GCC | CCT | CTG | GAG | GCG | GTG | GCA | GTC | AAC | CAA | ACA | GGA | CAG | TCG | 249 |
|---|---|---|---|---|---|---|---|---|---|---|---|---|---|---|---|---|
| Val | Gly | Ala | Pro | Leu | Glu | Ala | Val | Ala | Val | Asn | Gln | Thr | Gly | Gln | Ser | |
| | | | | 55 | | | | 60 | | | | | | 65 | | |

| TCT | GAC | TGT | CCG | CCT | GCC | ACT | GGC | GTG | TGC | CAG | CCC | ATC | TTA | CTG | CAC | 297 |
|---|---|---|---|---|---|---|---|---|---|---|---|---|---|---|---|---|
| Ser | Asp | Cys | Pro | Pro | Ala | Thr | Gly | Val | Cys | Gln | Pro | Ile | Leu | Leu | His | |
| | | 70 | | | | | 75 | | | | | 80 | | | | |

| ATT | CCC | CTA | GAG | GCA | GTG | AAC | ATG | TCC | CTG | GGC | CTG | TCT | CTG | GTG | GCT | 345 |
|---|---|---|---|---|---|---|---|---|---|---|---|---|---|---|---|---|
| Ile | Pro | Leu | Glu | Ala | Val | Asn | Met | Ser | Leu | Gly | Leu | Ser | Leu | Val | Ala | |
| | | 85 | | | | | 90 | | | | 95 | | | | | |

| GAC | ACC | AAT | AAC | TCC | CAG | TTG | CTG | GCT | TGT | GGT | CCA | ACT | GCA | CAG | AGA | 393 |
|---|---|---|---|---|---|---|---|---|---|---|---|---|---|---|---|---|
| Asp | Thr | Asn | Asn | Ser | Gln | Leu | Leu | Ala | Cys | Gly | Pro | Thr | Ala | Gln | Arg | |
| | 100 | | | | | 105 | | | | 110 | | | | | | |

| GCT | TGT | GCA | AAG | AAC | ATG | TAT | GCA | AAA | GGT | TCC | TGC | CTC | CTT | CTG | GGC | 441 |
|---|---|---|---|---|---|---|---|---|---|---|---|---|---|---|---|---|
| Ala | Cys | Ala | Lys | Asn | Met | Tyr | Ala | Lys | Gly | Ser | Cys | Leu | Leu | Leu | Gly | |
| 115 | | | | | 120 | | | | 125 | | | | | | 130 | |

| TCC | AGC | TTG | CAG | TTC | ATC | CAG | GCA | ATC | CCT | GCT | ACC | ATG | CCA | GAG | TGT | 489 |
|---|---|---|---|---|---|---|---|---|---|---|---|---|---|---|---|---|
| Ser | Ser | Leu | Gln | Phe | Ile | Gln | Ala | Ile | Pro | Ala | Thr | Met | Pro | Glu | Cys | |
| | | | | 135 | | | | 140 | | | | | 145 | | | |

| CCA | GGA | CAA | GAG | ATG | GAC | ATT | GCT | TTC | CTG | ATT | GAT | GGC | TCC | GGC | AGC | 537 |
|---|---|---|---|---|---|---|---|---|---|---|---|---|---|---|---|---|
| Pro | Gly | Gln | Glu | Met | Asp | Ile | Ala | Phe | Leu | Ile | Asp | Gly | Ser | Gly | Ser | |
| | | | 150 | | | | | 155 | | | | | 160 | | | |

| ATT | GAT | CAA | AGT | GAC | TTT | ACC | CAG | ATG | AAG | GAC | TTC | GTC | AAA | GCT | TTG | 585 |
|---|---|---|---|---|---|---|---|---|---|---|---|---|---|---|---|---|
| Ile | Asp | Gln | Ser | Asp | Phe | Thr | Gln | Met | Lys | Asp | Phe | Val | Lys | Ala | Leu | |
| | | 165 | | | | | 170 | | | | 175 | | | | | |

| ATG | GGC | CAG | TTG | GCG | AGC | ACC | AGC | ACC | TCG | TTC | TCC | CTG | ATG | CAA | TAC | 633 |
|---|---|---|---|---|---|---|---|---|---|---|---|---|---|---|---|---|
| Met | Gly | Gln | Leu | Ala | Ser | Thr | Ser | Thr | Ser | Phe | Ser | Leu | Met | Gln | Tyr | |
| | 180 | | | | 185 | | | | | 190 | | | | | | |

| | | | | | | | | | | | | | | | | |
|---|---|---|---|---|---|---|---|---|---|---|---|---|---|---|---|---|
| TCA | AAC | ATC | CTG | AAG | ACT | CAT | TTT | ACC | TTC | ACG | GAA | TTC | AAG | AGC | AGC | 681 |
| Ser | Asn | Ile | Leu | Lys | Thr | His | Phe | Thr | Phe | Thr | Glu | Phe | Lys | Ser | Ser | |
| 195 | | | | | 200 | | | | 205 | | | | | | 210 | |
| CTG | AGC | CCT | CAG | AGC | CTG | GTG | GAT | GCC | ATC | GTC | CAG | CTC | CAA | GGC | CTG | 729 |
| Leu | Ser | Pro | Gln | Ser | Leu | Val | Asp | Ala | Ile | Val | Gln | Leu | Gln | Gly | Leu | |
| | | | 215 | | | | 220 | | | | | | 225 | | | |
| ACG | TAC | ACA | GCC | TCG | GGC | ATC | CAG | AAA | GTG | GTG | AAA | GAG | CTA | TTT | CAT | 777 |
| Thr | Tyr | Thr | Ala | Ser | Gly | Ile | Gln | Lys | Val | Val | Lys | Glu | Leu | Phe | His | |
| | | | 230 | | | | | 235 | | | | | 240 | | | |
| AGC | AAG | AAT | GGG | GCC | CGA | AAA | AGT | GCC | AAG | AAG | ATA | CTA | ATT | GTC | ATC | 825 |
| Ser | Lys | Asn | Gly | Ala | Arg | Lys | Ser | Ala | Lys | Lys | Ile | Leu | Ile | Val | Ile | |
| | | 245 | | | | | 250 | | | | | 255 | | | | |
| ACA | GAT | GGG | CAG | AAA | TTC | AGA | GAC | CCC | CTG | GAG | TAT | AGA | CAT | GTC | ATC | 873 |
| Thr | Asp | Gly | Gln | Lys | Phe | Arg | Asp | Pro | Leu | Glu | Tyr | Arg | His | Val | Ile | |
| | 260 | | | | | 265 | | | | | 270 | | | | | |
| CCT | GAA | GCA | GAG | AAA | GCT | GGG | ATC | ATT | CGC | TAT | GCT | ATA | GGG | GTG | GGA | 921 |
| Pro | Glu | Ala | Glu | Lys | Ala | Gly | Ile | Ile | Arg | Tyr | Ala | Ile | Gly | Val | Gly | |
| 275 | | | | | 280 | | | | 285 | | | | | | 290 | |
| GAT | GCC | TTC | CGG | GAA | CCC | ACT | GCC | CTA | CAG | GAG | CTG | AAC | ACC | ATT | GGC | 969 |
| Asp | Ala | Phe | Arg | Glu | Pro | Thr | Ala | Leu | Gln | Glu | Leu | Asn | Thr | Ile | Gly | |
| | | | | 295 | | | | 300 | | | | | 305 | | | |
| TCA | GCT | CCC | TCG | CAG | GAC | CAC | GTG | TTC | AAG | GTG | GGC | AAT | TTT | GTA | GCA | 1017 |
| Ser | Ala | Pro | Ser | Gln | Asp | His | Val | Phe | Lys | Val | Gly | Asn | Phe | Val | Ala | |
| | | | 310 | | | | | 315 | | | | | 320 | | | |
| CTT | CGC | AGC | ATC | CAG | CGG | CAA | ATT | CAG | GAG | AAA | ATC | TTT | GCC | ATT | GAA | 1065 |
| Leu | Arg | Ser | Ile | Gln | Arg | Gln | Ile | Gln | Glu | Lys | Ile | Phe | Ala | Ile | Glu | |
| | | 325 | | | | | 330 | | | | | 335 | | | | |
| GGA | ACC | GAA | TCA | AGG | TCA | AGT | AGT | TCC | TTT | CAG | CAC | GAG | ATG | TCA | CAA | 1113 |
| Gly | Thr | Glu | Ser | Arg | Ser | Ser | Ser | Ser | Phe | Gln | His | Glu | Met | Ser | Gln | |
| | 340 | | | | | 345 | | | | | 350 | | | | | |
| GAA | GGT | TTC | AGC | TCA | GCT | CTC | TCA | ATG | GAT | GGA | CCA | GTT | CTG | GGG | GCT | 1161 |
| Glu | Gly | Phe | Ser | Ser | Ala | Leu | Ser | Met | Asp | Gly | Pro | Val | Leu | Gly | Ala | |
| 355 | | | | | 360 | | | | 365 | | | | | | 370 | |
| GTG | GGA | GGC | TTC | AGC | TGG | TCT | GGA | GGT | GCC | TTC | TTG | TAC | CCC | TCA | AAT | 1209 |
| Val | Gly | Gly | Phe | Ser | Trp | Ser | Gly | Gly | Ala | Phe | Leu | Tyr | Pro | Ser | Asn | |
| | | | | 375 | | | | 380 | | | | | | 385 | | |
| ATG | AGA | TCC | ACC | TTC | ATC | AAC | ATG | TCT | CAG | GAG | AAC | GAG | GAT | ATG | AGG | 1257 |
| Met | Arg | Ser | Thr | Phe | Ile | Asn | Met | Ser | Gln | Glu | Asn | Glu | Asp | Met | Arg | |
| | | | 390 | | | | | 395 | | | | | 400 | | | |
| GAC | GCT | TAC | CTG | GGT | TAC | TCC | ACC | GCA | CTG | GCC | TTT | TGG | AAG | GGG | GTC | 1305 |
| Asp | Ala | Tyr | Leu | Gly | Tyr | Ser | Thr | Ala | Leu | Ala | Phe | Trp | Lys | Gly | Val | |
| | | 405 | | | | | 410 | | | | | 415 | | | | |
| CAC | AGC | CTG | ATC | CTG | GGG | GCC | CCT | CGC | CAC | CAG | CAC | ACG | GGG | AAG | GTT | 1353 |
| His | Ser | Leu | Ile | Leu | Gly | Ala | Pro | Arg | His | Gln | His | Thr | Gly | Lys | Val | |
| | 420 | | | | | 425 | | | | | 430 | | | | | |
| GTC | ATC | TTT | ACC | CAG | GAA | TCC | AGG | CAC | TGG | AGG | CCC | AAG | TCT | GAA | GTC | 1401 |
| Val | Ile | Phe | Thr | Gln | Glu | Ser | Arg | His | Trp | Arg | Pro | Lys | Ser | Glu | Val | |
| 435 | | | | | 440 | | | | 445 | | | | | | 450 | |
| AGA | GGG | ACA | CAG | ATC | GGC | TCC | TAC | TTT | GGG | GCA | TCT | CTC | TGT | TCT | GTG | 1449 |
| Arg | Gly | Thr | Gln | Ile | Gly | Ser | Tyr | Phe | Gly | Ala | Ser | Leu | Cys | Ser | Val | |
| | | | | 455 | | | | 460 | | | | | | 465 | | |
| GAC | ATG | GAT | AGA | GAT | GGC | AGC | ACT | GAC | CTG | GTC | CTG | ATT | GGA | GTC | CCC | 1497 |
| Asp | Met | Asp | Arg | Asp | Gly | Ser | Thr | Asp | Leu | Val | Leu | Ile | Gly | Val | Pro | |
| | | | 470 | | | | | 475 | | | | | 480 | | | |
| CAT | TAC | TAT | GAG | CAC | ACC | CGA | GGG | GGG | CAG | GTG | TCG | GTG | TGC | CCC | ATG | 1545 |
| His | Tyr | Tyr | Glu | His | Thr | Arg | Gly | Gly | Gln | Val | Ser | Val | Cys | Pro | Met | |
| | | 485 | | | | | 490 | | | | | 495 | | | | |
| CCT | GGT | GTG | AGG | AGC | AGG | TGG | CAT | TGT | GGG | ACC | ACC | CTC | CAT | GGG | GAG | 1593 |
| Pro | Gly | Val | Arg | Ser | Arg | Trp | His | Cys | Gly | Thr | Thr | Leu | His | Gly | Glu | |
| | 500 | | | | | 505 | | | | | 510 | | | | | |

-continued

| | | | | | | | | | | | | | | | | |
|---|---|---|---|---|---|---|---|---|---|---|---|---|---|---|---|---|
| CAG | GGC | CAT | CCT | TGG | GGC | CGC | TTT | GGG | GCG | GCT | CTG | ACA | GTG | CTA | GGG | 1641 |
| Gln | Gly | His | Pro | Trp | Gly | Arg | Phe | Gly | Ala | Ala | Leu | Thr | Val | Leu | Gly | |
| 515 | | | | 520 | | | | | 525 | | | | | | 530 | |
| GAC | GTG | AAT | GGG | GAC | AGT | CTG | GCG | GAT | GTG | GCT | ATT | GGT | GCA | CCC | GGA | 1689 |
| Asp | Val | Asn | Gly | Asp | Ser | Leu | Ala | Asp | Val | Ala | Ile | Gly | Ala | Pro | Gly | |
| | | | | 535 | | | | 540 | | | | | | 545 | | |
| GAG | GAG | GAG | AAC | AGA | GGT | GCT | GTC | TAC | ATA | TTT | CAT | GGA | GCC | TCG | AGA | 1737 |
| Glu | Glu | Glu | Asn | Arg | Gly | Ala | Val | Tyr | Ile | Phe | His | Gly | Ala | Ser | Arg | |
| | | | 550 | | | | | 555 | | | | | 560 | | | |
| CAG | GAC | ATC | GCT | CCC | TCG | CCT | AGC | CAG | CGG | GTC | ACT | GGC | TCC | CAG | CTC | 1785 |
| Gln | Asp | Ile | Ala | Pro | Ser | Pro | Ser | Gln | Arg | Val | Thr | Gly | Ser | Gln | Leu | |
| | | 565 | | | | | 570 | | | | | 575 | | | | |
| TTC | CTG | AGG | CTC | CAA | TAT | TTT | GGG | CAG | TCA | TTA | AGT | GGG | GGT | CAG | GAC | 1833 |
| Phe | Leu | Arg | Leu | Gln | Tyr | Phe | Gly | Gln | Ser | Leu | Ser | Gly | Gly | Gln | Asp | |
| | 580 | | | | | 585 | | | | | 590 | | | | | |
| CTT | ACA | CAG | GAT | GGC | CTG | GTG | GAC | CTG | GCC | GTG | GGA | GCC | CAG | GGG | CAC | 1881 |
| Leu | Thr | Gln | Asp | Gly | Leu | Val | Asp | Leu | Ala | Val | Gly | Ala | Gln | Gly | His | |
| 595 | | | | | 600 | | | | | 605 | | | | | 610 | |
| GTG | CTG | CTG | CTT | AGG | AGT | CTG | CCT | TTG | CTG | AAA | GTG | GGG | ATC | TCC | ATT | 1929 |
| Val | Leu | Leu | Leu | Arg | Ser | Leu | Pro | Leu | Leu | Lys | Val | Gly | Ile | Ser | Ile | |
| | | | | 615 | | | | | 620 | | | | | 625 | | |
| AGA | TTT | GCC | CCC | TCA | GAG | GTG | GCA | AAG | ACT | GTG | TAC | CAG | TGC | TGG | GGA | 1977 |
| Arg | Phe | Ala | Pro | Ser | Glu | Val | Ala | Lys | Thr | Val | Tyr | Gln | Cys | Trp | Gly | |
| | | | 630 | | | | | 635 | | | | | 640 | | | |
| AGG | ACT | CCC | ACT | GTC | CTC | GAA | GCT | GGA | GAG | GCC | ACC | GTC | TGT | CTC | ACT | 2025 |
| Arg | Thr | Pro | Thr | Val | Leu | Glu | Ala | Gly | Glu | Ala | Thr | Val | Cys | Leu | Thr | |
| | | 645 | | | | | 650 | | | | | 655 | | | | |
| GTC | CGC | AAA | GGT | TCA | CCT | GAC | CTG | TTA | GGT | GAT | GTC | CAA | AGC | TCT | GTC | 2073 |
| Val | Arg | Lys | Gly | Ser | Pro | Asp | Leu | Leu | Gly | Asp | Val | Gln | Ser | Ser | Val | |
| | 660 | | | | | 665 | | | | | 670 | | | | | |
| AGG | TAT | GAT | CTG | GCG | TTG | GAT | CCG | GGC | CGT | CTG | ATT | TCT | CGT | GCC | ATT | 2121 |
| Arg | Tyr | Asp | Leu | Ala | Leu | Asp | Pro | Gly | Arg | Leu | Ile | Ser | Arg | Ala | Ile | |
| 675 | | | | | 680 | | | | | 685 | | | | | 690 | |
| TTT | GAT | GAG | ACG | AAG | AAC | TGC | ACT | TTG | ACC | CGA | AGG | AAG | ACT | CTG | GGG | 2169 |
| Phe | Asp | Glu | Thr | Lys | Asn | Cys | Thr | Leu | Thr | Arg | Arg | Lys | Thr | Leu | Gly | |
| | | | | 695 | | | | 700 | | | | | 705 | | | |
| CTT | GGT | GAT | CAC | TGC | GAA | ACA | ATG | AAG | CTG | CTT | TTG | CCA | GAC | TGT | GTG | 2217 |
| Leu | Gly | Asp | His | Cys | Glu | Thr | Met | Lys | Leu | Leu | Leu | Pro | Asp | Cys | Val | |
| | | | 710 | | | | | 715 | | | | | 720 | | | |
| GAG | GAT | GCA | GTG | ACC | CCT | ATC | ATC | CTG | CGC | CTT | AAC | TTA | TCC | CTG | GCA | 2265 |
| Glu | Asp | Ala | Val | Thr | Pro | Ile | Ile | Leu | Arg | Leu | Asn | Leu | Ser | Leu | Ala | |
| | | 725 | | | | | 730 | | | | | 735 | | | | |
| GGG | GAC | TCT | GCT | CCA | TCC | AGG | AAC | CTT | CGT | CCT | GTG | CTG | GCT | GTG | GGC | 2313 |
| Gly | Asp | Ser | Ala | Pro | Ser | Arg | Asn | Leu | Arg | Pro | Val | Leu | Ala | Val | Gly | |
| | 740 | | | | | 745 | | | | | 750 | | | | | |
| TCA | CAA | GAC | CAT | GTA | ACA | GCT | TCT | TTC | CCG | TTT | GAG | AAG | AAC | TGT | GAG | 2361 |
| Ser | Gln | Asp | His | Val | Thr | Ala | Ser | Phe | Pro | Phe | Glu | Lys | Asn | Cys | Glu | |
| 755 | | | | | 760 | | | | | 765 | | | | | 770 | |
| GGG | AAC | CTG | GGC | GTC | AGC | TTC | AAC | TTC | TCA | GGC | CTG | CAG | GTC | TTG | GAG | 2409 |
| Gly | Asn | Leu | Gly | Val | Ser | Phe | Asn | Phe | Ser | Gly | Leu | Gln | Val | Leu | Glu | |
| | | | | 775 | | | | | 780 | | | | | 785 | | |
| GTA | GGA | AGC | TCC | CCA | GAG | CTC | ACT | GTG | ACA | GTA | ACA | GTT | TGG | AAT | GAG | 2457 |
| Val | Gly | Ser | Ser | Pro | Glu | Leu | Thr | Val | Thr | Val | Thr | Val | Trp | Asn | Glu | |
| | | | 790 | | | | | 795 | | | | | 800 | | | |
| GGT | GAG | GAC | AGC | TAT | GGA | ACC | TTA | ATC | AAG | TTC | TAC | TAC | CCA | GCA | GAG | 2505 |
| Gly | Glu | Asp | Ser | Tyr | Gly | Thr | Leu | Ile | Lys | Phe | Tyr | Tyr | Pro | Ala | Glu | |
| | | 805 | | | | | 810 | | | | | 815 | | | | |
| CTA | TCT | TAC | CGA | CGG | GTG | ACA | AGA | GCC | CAG | CAA | CCT | CAT | CCG | TAC | CCA | 2553 |
| Leu | Ser | Tyr | Arg | Arg | Val | Thr | Arg | Ala | Gln | Gln | Pro | His | Pro | Tyr | Pro | |
| | 820 | | | | | 825 | | | | | 830 | | | | | |

```
CTA  CGC  CTG  GCA  TGT  GAG  GCT  GAG  CCC  ACG  GGC  CAG  GAG  AGC  CTG  AGG       2601
Leu  Arg  Leu  Ala  Cys  Glu  Ala  Glu  Pro  Thr  Gly  Gln  Glu  Ser  Leu  Arg
835            840                      845                      850

AGC  AGC  AGC  TGT  AGC  ATC  AAT  CAC  CCC  ATC  TTC  CGA  GAA  GGT  GCC  AAG       2649
Ser  Ser  Ser  Cys  Ser  Ile  Asn  His  Pro  Ile  Phe  Arg  Glu  Gly  Ala  Lys
               855                      860                      865

GCC  ACC  TTC  ATG  ATC  ACA  TTT  GAT  GTC  TCC  TAC  AAG  GCC  TTC  CTG  GGA       2697
Ala  Thr  Phe  Met  Ile  Thr  Phe  Asp  Val  Ser  Tyr  Lys  Ala  Phe  Leu  Gly
               870                      875                      880

GAC  AGG  TTG  CTT  CTG  AGG  GCC  AGC  GCA  AGC  AGT  GAG  AAT  AAT  AAG  CCT       2745
Asp  Arg  Leu  Leu  Leu  Arg  Ala  Ser  Ala  Ser  Ser  Glu  Asn  Asn  Lys  Pro
          885                      890                      895

GAA  ACC  AGC  AAG  ACT  GCC  TTC  CAG  CTG  GAG  CTT  CCG  GTG  AAG  TAC  ACG       2793
Glu  Thr  Ser  Lys  Thr  Ala  Phe  Gln  Leu  Glu  Leu  Pro  Val  Lys  Tyr  Thr
900                      905                      910

GTC  TAT  ACC  GTG  ATC  AGT  AGG  CAG  GAA  GAT  TCT  ACC  AAG  CAT  TTC  AAC       2841
Val  Tyr  Thr  Val  Ile  Ser  Arg  Gln  Glu  Asp  Ser  Thr  Lys  His  Phe  Asn
915                      920                      925                      930

TTC  TCA  TCT  TCC  CAC  GGG  GAG  AGA  CAG  AAA  GAG  GCC  GAA  CAT  CGA  TAT       2889
Phe  Ser  Ser  Ser  His  Gly  Glu  Arg  Gln  Lys  Glu  Ala  Glu  His  Arg  Tyr
                    935                      940                      945

CGT  GTG  AAT  AAC  CTG  AGT  CCA  TTG  ACG  CTG  GCC  ATC  AGC  GTT  AAC  TTC       2937
Arg  Val  Asn  Asn  Leu  Ser  Pro  Leu  Thr  Leu  Ala  Ile  Ser  Val  Asn  Phe
          950                      955                      960

TGG  GTC  CCC  ATC  CTT  CTG  AAT  GGT  GTG  GCC  GTG  TGG  GAT  GTG  ACT  CTG       2985
Trp  Val  Pro  Ile  Leu  Leu  Asn  Gly  Val  Ala  Val  Trp  Asp  Val  Thr  Leu
          965                      970                      975

AGG  AGC  CCA  GCA  CAG  GGT  GTC  TCC  TGT  GTG  TCA  CAG  AGG  GAA  CCT  CCT       3033
Arg  Ser  Pro  Ala  Gln  Gly  Val  Ser  Cys  Val  Ser  Gln  Arg  Glu  Pro  Pro
     980                      985                      990

CAA  CAT  TCC  GAC  CTT  CTG  ACC  CAG  ATC  CAA  GGA  CGC  TCT  GTG  CTG  GAC       3081
Gln  His  Ser  Asp  Leu  Leu  Thr  Gln  Ile  Gln  Gly  Arg  Ser  Val  Leu  Asp
995                      1000                     1005                     1010

TGC  GCC  ATC  GCC  GAC  TGC  CTG  CAC  CTC  CGC  TGT  GAC  ATC  CCC  TCC  TTG       3129
Cys  Ala  Ile  Ala  Asp  Cys  Leu  His  Leu  Arg  Cys  Asp  Ile  Pro  Ser  Leu
               1015                     1020                     1025

GGC  ACC  CTG  GAT  GAG  CTT  GAC  TTC  ATT  CTG  AAG  GGC  AAC  CTC  AGC  TTC       3177
Gly  Thr  Leu  Asp  Glu  Leu  Asp  Phe  Ile  Leu  Lys  Gly  Asn  Leu  Ser  Phe
               1030                     1035                     1040

GGC  TGG  ATC  AGT  CAG  ACA  TTG  CAG  AAA  AAG  GTG  TTG  CTC  CTG  AGT  GAG       3225
Gly  Trp  Ile  Ser  Gln  Thr  Leu  Gln  Lys  Lys  Val  Leu  Leu  Leu  Ser  Glu
               1045                     1050                     1055

GCT  GAA  ATC  ACA  TTC  AAC  ACA  TCT  GTG  TAT  TCC  CAG  CTG  CCG  GGA  CAG       3273
Ala  Glu  Ile  Thr  Phe  Asn  Thr  Ser  Val  Tyr  Ser  Gln  Leu  Pro  Gly  Gln
     1060                     1065                     1070

GAG  GCA  TTT  CTG  AGA  GCC  CAG  GTG  TCA  ACG  ATG  CTA  GAA  GAA  TAC  GTG       3321
Glu  Ala  Phe  Leu  Arg  Ala  Gln  Val  Ser  Thr  Met  Leu  Glu  Glu  Tyr  Val
1075                     1080                     1085                     1090

GTC  TAT  GAG  CCC  GTC  TTC  CTC  ATG  GTG  TTC  AGC  TCA  GTG  GGA  GGT  CTG       3369
Val  Tyr  Glu  Pro  Val  Phe  Leu  Met  Val  Phe  Ser  Ser  Val  Gly  Gly  Leu
               1095                     1100                     1105

CTG  TTA  CTG  GCT  CTC  ATC  ACT  GTG  GCG  CTG  TAC  AAG  CTT  GGC  TTC  TTC       3417
Leu  Leu  Leu  Ala  Leu  Ile  Thr  Val  Ala  Leu  Tyr  Lys  Leu  Gly  Phe  Phe
               1110                     1115                     1120

AAA  CGT  CAG  TAT  AAA  GAG  ATG  CTG  GAT  CTA  CCA  TCT  GCA  GAT  CCT  GAC       3465
Lys  Arg  Gln  Tyr  Lys  Glu  Met  Leu  Asp  Leu  Pro  Ser  Ala  Asp  Pro  Asp
          1125                     1130                     1135

CCA  GCC  GGC  CAG  GCA  GAT  TCC  AAC  CAT  GAG  ACT  CCT  CCA  CAT  CTC  ACG       3513
Pro  Ala  Gly  Gln  Ala  Asp  Ser  Asn  His  Glu  Thr  Pro  Pro  His  Leu  Thr
1140                     1145                     1150
```

| TCC TAG | | 3519 |
|---|---|---|
| Ser |||
| 1155 |||

(2) INFORMATION FOR SEQ ID NO:46:

(i) SEQUENCE CHARACTERISTICS:
        (A) LENGTH: 1155 amino acids
        (B) TYPE: amino acid
        (D) TOPOLOGY: linear (ii) MOLECULE TYPE: protein (xi) SEQUENCE DESCRIPTION: SEQ ID NO:46:

```
Met Val Arg Gly Val Val Ile Leu Leu Cys Gly Trp Ala Leu Ala Ser
 1               5                  10                  15
Cys His Gly Ser Asn Leu Asp Val Glu Lys Pro Val Val Phe Lys Glu
                20                  25                  30
Asp Ala Ala Ser Phe Gly Gln Thr Val Val Gln Phe Gly Gly Ser Arg
            35                  40                  45
Leu Val Val Gly Ala Pro Leu Glu Ala Val Ala Val Asn Gln Thr Gly
        50                  55                  60
Gln Ser Ser Asp Cys Pro Pro Ala Thr Gly Val Cys Gln Pro Ile Leu
65                  70                  75                  80
Leu His Ile Pro Leu Glu Ala Val Asn Met Ser Leu Gly Leu Ser Leu
                85                  90                  95
Val Ala Asp Thr Asn Asn Ser Gln Leu Leu Ala Cys Gly Pro Thr Ala
            100                 105                 110
Gln Arg Ala Cys Ala Lys Asn Met Tyr Ala Lys Gly Ser Cys Leu Leu
        115                 120                 125
Leu Gly Ser Ser Leu Gln Phe Ile Gln Ala Ile Pro Ala Thr Met Pro
    130                 135                 140
Glu Cys Pro Gly Gln Glu Met Asp Ile Ala Phe Leu Ile Asp Gly Ser
145                 150                 155                 160
Gly Ser Ile Asp Gln Ser Asp Phe Thr Gln Met Lys Asp Phe Val Lys
                165                 170                 175
Ala Leu Met Gly Gln Leu Ala Ser Thr Ser Thr Ser Phe Ser Leu Met
            180                 185                 190
Gln Tyr Ser Asn Ile Leu Lys Thr His Phe Thr Phe Thr Glu Phe Lys
        195                 200                 205
Ser Ser Leu Ser Pro Gln Ser Leu Val Asp Ala Ile Val Gln Leu Gln
    210                 215                 220
Gly Leu Thr Tyr Thr Ala Ser Gly Ile Gln Lys Val Val Lys Glu Leu
225                 230                 235                 240
Phe His Ser Lys Asn Gly Ala Arg Lys Ser Ala Lys Lys Ile Leu Ile
                245                 250                 255
Val Ile Thr Asp Gly Gln Lys Phe Arg Asp Pro Leu Glu Tyr Arg His
            260                 265                 270
Val Ile Pro Glu Ala Glu Lys Ala Gly Ile Ile Arg Tyr Ala Ile Gly
        275                 280                 285
Val Gly Asp Ala Phe Arg Glu Pro Thr Ala Leu Gln Glu Leu Asn Thr
    290                 295                 300
Ile Gly Ser Ala Pro Ser Gln Asp His Val Phe Lys Val Gly Asn Phe
305                 310                 315                 320
Val Ala Leu Arg Ser Ile Gln Arg Gln Ile Gln Glu Lys Ile Phe Ala
                325                 330                 335
Ile Glu Gly Thr Glu Ser Arg Ser Ser Ser Ser Phe Gln His Glu Met
```

-continued

```
                        340                          345                          350
Ser   Gln   Glu   Gly   Phe   Ser   Ser   Ala   Leu   Ser   Met   Asp   Gly   Pro   Val   Leu
            355                           360                           365
Gly   Ala   Val   Gly   Gly   Phe   Ser   Trp   Ser   Gly   Gly   Ala   Phe   Leu   Tyr   Pro
      370                           375                           380
Ser   Asn   Met   Arg   Ser   Thr   Phe   Ile   Asn   Met   Ser   Gln   Glu   Asn   Glu   Asp
385                           390                           395                           400
Met   Arg   Asp   Ala   Tyr   Leu   Gly   Tyr   Ser   Thr   Ala   Leu   Ala   Phe   Trp   Lys
                  405                           410                           415
Gly   Val   His   Ser   Leu   Ile   Leu   Gly   Ala   Pro   Arg   His   Gln   His   Thr   Gly
                  420                           425                           430
Lys   Val   Val   Ile   Phe   Thr   Gln   Glu   Ser   Arg   His   Trp   Arg   Pro   Lys   Ser
            435                           440                           445
Glu   Val   Arg   Gly   Thr   Gln   Ile   Gly   Ser   Tyr   Phe   Gly   Ala   Ser   Leu   Cys
      450                           455                           460
Ser   Val   Asp   Met   Asp   Arg   Asp   Gly   Ser   Thr   Asp   Leu   Val   Leu   Ile   Gly
465                           470                           475                           480
Val   Pro   His   Tyr   Tyr   Glu   His   Thr   Arg   Gly   Gly   Gln   Val   Ser   Val   Cys
                        485                           490                           495
Pro   Met   Pro   Gly   Val   Arg   Ser   Arg   Trp   His   Cys   Gly   Thr   Thr   Leu   His
                  500                           505                           510
Gly   Glu   Gln   Gly   His   Pro   Trp   Gly   Arg   Phe   Gly   Ala   Ala   Leu   Thr   Val
            515                           520                           525
Leu   Gly   Asp   Val   Asn   Gly   Asp   Ser   Leu   Ala   Asp   Val   Ala   Ile   Gly   Ala
      530                           535                           540
Pro   Gly   Glu   Glu   Glu   Asn   Arg   Gly   Ala   Val   Tyr   Ile   Phe   His   Gly   Ala
545                           550                           555                           560
Ser   Arg   Gln   Asp   Ile   Ala   Pro   Ser   Pro   Ser   Gln   Arg   Val   Thr   Gly   Ser
                        565                           570                           575
Gln   Leu   Phe   Leu   Arg   Leu   Gln   Tyr   Phe   Gly   Gln   Ser   Leu   Ser   Gly   Gly
                  580                           585                           590
Gln   Asp   Leu   Thr   Gln   Asp   Gly   Leu   Val   Asp   Leu   Ala   Val   Gly   Ala   Gln
            595                           600                           605
Gly   His   Val   Leu   Leu   Leu   Arg   Ser   Leu   Pro   Leu   Leu   Lys   Val   Gly   Ile
      610                           615                           620
Ser   Ile   Arg   Phe   Ala   Pro   Ser   Glu   Val   Ala   Lys   Thr   Val   Tyr   Gln   Cys
625                           630                           635                           640
Trp   Gly   Arg   Thr   Pro   Thr   Val   Leu   Glu   Ala   Gly   Glu   Ala   Thr   Val   Cys
                        645                           650                           655
Leu   Thr   Val   Arg   Lys   Gly   Ser   Pro   Asp   Leu   Leu   Gly   Asp   Val   Gln   Ser
                  660                           665                           670
Ser   Val   Arg   Tyr   Asp   Leu   Ala   Leu   Asp   Pro   Gly   Arg   Leu   Ile   Ser   Arg
            675                           680                           685
Ala   Ile   Phe   Asp   Glu   Thr   Lys   Asn   Cys   Thr   Leu   Thr   Arg   Arg   Lys   Thr
      690                           695                           700
Leu   Gly   Leu   Gly   Asp   His   Cys   Glu   Thr   Met   Lys   Leu   Leu   Leu   Pro   Asp
705                           710                           715                           720
Cys   Val   Glu   Asp   Ala   Val   Thr   Pro   Ile   Ile   Leu   Arg   Leu   Asn   Leu   Ser
                        725                           730                           735
Leu   Ala   Gly   Asp   Ser   Ala   Pro   Ser   Arg   Asn   Leu   Arg   Pro   Val   Leu   Ala
                  740                           745                           750
Val   Gly   Ser   Gln   Asp   His   Val   Thr   Ala   Ser   Phe   Pro   Phe   Glu   Lys   Asn
            755                           760                           765
```

|     |     |     |     |     |     |     |     |     |     |     |     |     |     |
| --- | --- | --- | --- | --- | --- | --- | --- | --- | --- | --- | --- | --- | --- |
| Cys | Glu | Gly | Asn | Leu | Gly | Val | Ser | Phe | Asn | Phe | Ser | Gly | Leu | Gln | Val |
|     | 770 |     |     |     | 775 |     |     |     | 780 |     |     |     |     |
| Leu | Glu | Val | Gly | Ser | Ser | Pro | Glu | Leu | Thr | Val | Thr | Val | Thr | Val | Trp |
| 785 |     |     |     |     | 790 |     |     |     | 795 |     |     |     |     | 800 |
| Asn | Glu | Gly | Glu | Asp | Ser | Tyr | Gly | Thr | Leu | Ile | Lys | Phe | Tyr | Tyr | Pro |
|     |     |     |     | 805 |     |     |     |     | 810 |     |     |     |     | 815 |
| Ala | Glu | Leu | Ser | Tyr | Arg | Arg | Val | Thr | Arg | Ala | Gln | Gln | Pro | His | Pro |
|     |     |     | 820 |     |     |     |     | 825 |     |     |     |     | 830 |
| Tyr | Pro | Leu | Arg | Leu | Ala | Cys | Glu | Ala | Glu | Pro | Thr | Gly | Gln | Glu | Ser |
|     |     | 835 |     |     |     |     | 840 |     |     |     |     | 845 |     |
| Leu | Arg | Ser | Ser | Ser | Cys | Ser | Ile | Asn | His | Pro | Ile | Phe | Arg | Glu | Gly |
|     | 850 |     |     |     |     | 855 |     |     |     |     | 860 |     |     |     |
| Ala | Lys | Ala | Thr | Phe | Met | Ile | Thr | Phe | Asp | Val | Ser | Tyr | Lys | Ala | Phe |
| 865 |     |     |     |     | 870 |     |     |     |     | 875 |     |     |     |     | 880 |
| Leu | Gly | Asp | Arg | Leu | Leu | Leu | Arg | Ala | Ser | Ala | Ser | Ser | Glu | Asn | Asn |
|     |     |     |     | 885 |     |     |     |     | 890 |     |     |     |     | 895 |
| Lys | Pro | Glu | Thr | Ser | Lys | Thr | Ala | Phe | Gln | Leu | Glu | Leu | Pro | Val | Lys |
|     |     |     | 900 |     |     |     |     | 905 |     |     |     |     | 910 |     |
| Tyr | Thr | Val | Tyr | Thr | Val | Ile | Ser | Arg | Gln | Glu | Asp | Ser | Thr | Lys | His |
|     |     | 915 |     |     |     |     | 920 |     |     |     |     | 925 |     |     |
| Phe | Asn | Phe | Ser | Ser | Ser | His | Gly | Glu | Arg | Gln | Lys | Glu | Ala | Glu | His |
|     | 930 |     |     |     |     | 935 |     |     |     |     | 940 |     |     |     |
| Arg | Tyr | Arg | Val | Asn | Asn | Leu | Ser | Pro | Leu | Thr | Leu | Ala | Ile | Ser | Val |
| 945 |     |     |     |     | 950 |     |     |     |     | 955 |     |     |     |     | 960 |
| Asn | Phe | Trp | Val | Pro | Ile | Leu | Leu | Asn | Gly | Val | Ala | Val | Trp | Asp | Val |
|     |     |     |     | 965 |     |     |     |     | 970 |     |     |     |     | 975 |     |
| Thr | Leu | Arg | Ser | Pro | Ala | Gln | Gly | Val | Ser | Cys | Val | Ser | Gln | Arg | Glu |
|     |     |     | 980 |     |     |     |     | 985 |     |     |     |     | 990 |     |
| Pro | Pro | Gln | His | Ser | Asp | Leu | Leu | Thr | Gln | Ile | Gln | Gly | Arg | Ser | Val |
|     |     | 995 |     |     |     |     | 1000 |     |     |     |     | 1005 |     |     |
| Leu | Asp | Cys | Ala | Ile | Ala | Asp | Cys | Leu | His | Leu | Arg | Cys | Asp | Ile | Pro |
|     |     | 1010 |     |     |     |     | 1015 |     |     |     |     | 1020 |     |     |
| Ser | Leu | Gly | Thr | Leu | Asp | Glu | Leu | Asp | Phe | Ile | Leu | Lys | Gly | Asn | Leu |
| 1025 |     |     |     |     | 1030 |     |     |     |     | 1035 |     |     |     |     | 1040 |
| Ser | Phe | Gly | Trp | Ile | Ser | Gln | Thr | Leu | Gln | Lys | Lys | Val | Leu | Leu | Leu |
|     |     |     |     | 1045 |     |     |     |     | 1050 |     |     |     |     | 1055 |
| Ser | Glu | Ala | Glu | Ile | Thr | Phe | Asn | Thr | Ser | Val | Tyr | Ser | Gln | Leu | Pro |
|     |     |     |     | 1060 |     |     |     |     | 1065 |     |     |     |     | 1070 |
| Gly | Gln | Glu | Ala | Phe | Leu | Arg | Ala | Gln | Val | Ser | Thr | Met | Leu | Glu | Glu |
|     |     |     | 1075 |     |     |     |     | 1080 |     |     |     |     | 1085 |     |
| Tyr | Val | Val | Tyr | Glu | Pro | Val | Phe | Leu | Met | Val | Phe | Ser | Ser | Val | Gly |
|     |     | 1090 |     |     |     |     | 1095 |     |     |     |     | 1100 |     |     |
| Gly | Leu | Leu | Leu | Leu | Ala | Leu | Ile | Thr | Val | Ala | Leu | Tyr | Lys | Leu | Gly |
| 1105 |     |     |     |     | 1110 |     |     |     |     | 1115 |     |     |     |     | 1120 |
| Phe | Phe | Lys | Arg | Gln | Tyr | Lys | Glu | Met | Leu | Asp | Leu | Pro | Ser | Ala | Asp |
|     |     |     |     | 1125 |     |     |     |     | 1130 |     |     |     |     | 1135 |
| Pro | Asp | Pro | Ala | Gly | Gln | Ala | Asp | Ser | Asn | His | Glu | Thr | Pro | Pro | His |
|     |     |     | 1140 |     |     |     |     | 1145 |     |     |     |     | 1150 |
| Leu | Thr | Ser |
|     |     | 1155 |

( 2 ) INFORMATION FOR SEQ ID NO:47:

( i ) SEQUENCE CHARACTERISTICS:
        ( A ) LENGTH: 49 base pairs (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:47:

AGTTACGGAT CCGGCACCAT GACCTTCGGC ACTGTGATCC TCCTGTGTG 49

(2) INFORMATION FOR SEQ ID NO:48:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:48:

GCTGGACGAT GGCATCCAC 19

(2) INFORMATION FOR SEQ ID NO:49:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:49:

GTAGAGTTAC GGATCCGGCA CCAT 24

(2) INFORMATION FOR SEQ ID NO:50:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:50:

GCAGCCAGCT TCGGACAGAC 20

(2) INFORMATION FOR SEQ ID NO:51:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:51:

CCATGTCCAC AGAACAGAGA G 21

(2) INFORMATION FOR SEQ ID NO:52:

(i) SEQUENCE CHARACTERISTICS:
            (A) LENGTH: 3803 base pairs
            (B) TYPE: nucleic acid
            (C) STRANDEDNESS: single
            (D) TOPOLOGY: linear (i i) MOLECULE TYPE: cDNA ( i x ) FEATURE:
    ( A ) NAME/KEY: CDS
    ( B ) LOCATION: 1..3486

( x i ) SEQUENCE DESCRIPTION: SEQ ID NO:52:

```
ATG GTC CGT GGA GTT GTG ATC CTC CTG TGT GGC TGG GCC CTG GCT TCC    48
Met Val Arg Gly Val Val Ile Leu Leu Cys Gly Trp Ala Leu Ala Ser
 1           5                   10                  15

TGT CAT GGG TCT AAC CTG GAT GTG GAG AAG CCC GTC GTG TTC AAA GAG    96
Cys His Gly Ser Asn Leu Asp Val Glu Lys Pro Val Val Phe Lys Glu
             20                  25                  30

GAT GCA GCC AGC TTC GGA CAG ACT GTG GTG CAG TTT GGT GGA TCT CGA   144
Asp Ala Ala Ser Phe Gly Gln Thr Val Val Gln Phe Gly Gly Ser Arg
         35                  40                  45

CTC GTG GTG GGA GCC CCT CTG GAG GCG GTG GCA GTC AAC CAA ACA GGA   192
Leu Val Val Gly Ala Pro Leu Glu Ala Val Ala Val Asn Gln Thr Gly
     50                  55                  60

CAG TCG TCT GAC TGT CCG CCT GCC ACT GGC GTG TGC CAG CCC ATC TTA   240
Gln Ser Ser Asp Cys Pro Pro Ala Thr Gly Val Cys Gln Pro Ile Leu
 65                  70                  75                  80

CTG CAC ATT CCC CTA GAG GCA GTG AAC ATG TCC CTG GGC CTG TCT CTG   288
Leu His Ile Pro Leu Glu Ala Val Asn Met Ser Leu Gly Leu Ser Leu
             85                  90                  95

GTG GCT GAC ACC AAT AAC TCC CAG TTG CTG GCT TGT GGT CCA ACT GCA   336
Val Ala Asp Thr Asn Asn Ser Gln Leu Leu Ala Cys Gly Pro Thr Ala
            100                 105                 110

CAG AGA GCT TGT GCA AAG AAC ATG TAT GCA AAA GGT TCC TGC CTC CTT   384
Gln Arg Ala Cys Ala Lys Asn Met Tyr Ala Lys Gly Ser Cys Leu Leu
        115                 120                 125

CTG GGC TCC AGC TTG CAG TTC ATC CAG GCA ATC CCT GCT ACC ATG CCA   432
Leu Gly Ser Ser Leu Gln Phe Ile Gln Ala Ile Pro Ala Thr Met Pro
    130                 135                 140

GAG TGT CCA GGA CAA GAG ATG GAC ATT GCT TTC CTG ATT GAT GGC TCC   480
Glu Cys Pro Gly Gln Glu Met Asp Ile Ala Phe Leu Ile Asp Gly Ser
145                 150                 155                 160

GGC AGC ATT GAT CAA AGT GAC TTT ACC CAG ATG AAG GAC TTC GTC AAA   528
Gly Ser Ile Asp Gln Ser Asp Phe Thr Gln Met Lys Asp Phe Val Lys
                165                 170                 175

GCT TTG ATG GGC CAG TTG GCG AGC ACC AGC ACC TCG TTC TCC CTG ATG   576
Ala Leu Met Gly Gln Leu Ala Ser Thr Ser Thr Ser Phe Ser Leu Met
            180                 185                 190

CAA TAC TCA AAC ATC CTG AAG ACT CAT TTT ACC TTC ACG GAA TTC AAG   624
Gln Tyr Ser Asn Ile Leu Lys Thr His Phe Thr Phe Thr Glu Phe Lys
        195                 200                 205

AGC AGC CTG AGC CCT CAG AGC CTG GTG GAT GCC ATC GTC CAG CTC CAA   672
Ser Ser Leu Ser Pro Gln Ser Leu Val Asp Ala Ile Val Gln Leu Gln
    210                 215                 220

GGC CTG ACG TAC ACA GCC TCG GGC ATC CAG AAA GTG GTG AAA GAG CTA   720
Gly Leu Thr Tyr Thr Ala Ser Gly Ile Gln Lys Val Val Lys Glu Leu
225                 230                 235                 240

TTT CAT AGC AAG AAT GGG GCC CGA AAA AGT GCC AAG AAG ATA CTA ATT   768
Phe His Ser Lys Asn Gly Ala Arg Lys Ser Ala Lys Lys Ile Leu Ile
                245                 250                 255

GTC ATC ACA GAT GGG CAG AAA TTC AGA GAC CCC TTG GAG TAT AGA CAT   816
Val Ile Thr Asp Gly Gln Lys Phe Arg Asp Pro Leu Glu Tyr Arg His
            260                 265                 270

GTC ATC CCT GAA GCA GAG AAA GCT GGG ATC ATT CGC TAT GCT ATA GGG   864
Val Ile Pro Glu Ala Glu Lys Ala Gly Ile Ile Arg Tyr Ala Ile Gly
        275                 280                 285

GTG GGA GAT GCC TTC CGG GAA CCC ACT GCC CTA CAG GAG CTG AAC ACC   912
```

-continued

| | | | | | | | | | | | | | | | |
|---|---|---|---|---|---|---|---|---|---|---|---|---|---|---|---|
| Val | Gly | Asp | Ala | Phe | Arg | Glu | Pro | Thr | Ala | Leu | Gln | Glu | Leu | Asn | Thr |
| 290 | | | | 295 | | | | | 300 | | | | | | |

| ATT | GGC | TCA | GCT | CCC | TCG | CAG | GAC | CAC | GTG | TTC | AAG | GTG | GGC | AAT | TTT | 960 |
|---|---|---|---|---|---|---|---|---|---|---|---|---|---|---|---|---|
| Ile | Gly | Ser | Ala | Pro | Ser | Gln | Asp | His | Val | Phe | Lys | Val | Gly | Asn | Phe | |
| 305 | | | | 310 | | | | | 315 | | | | | 320 | | |

| GTA | GCA | CTT | CGC | AGC | ATC | CAG | CGG | CAA | ATT | CAG | GAG | AAA | ATC | TTT | GCC | 1008 |
|---|---|---|---|---|---|---|---|---|---|---|---|---|---|---|---|---|
| Val | Ala | Leu | Arg | Ser | Ile | Gln | Arg | Gln | Ile | Gln | Glu | Lys | Ile | Phe | Ala | |
| | | | | 325 | | | | | 330 | | | | | 335 | | |

| ATT | GAA | GGA | ACC | GAA | TCA | AGG | TCA | AGT | AGT | TCC | TTT | CAG | CAC | GAG | ATG | 1056 |
|---|---|---|---|---|---|---|---|---|---|---|---|---|---|---|---|---|
| Ile | Glu | Gly | Thr | Glu | Ser | Arg | Ser | Ser | Ser | Ser | Phe | Gln | His | Glu | Met | |
| | | | 340 | | | | | 345 | | | | | 350 | | | |

| TCA | CAA | GAA | GGT | TTC | AGC | TCA | GCT | CTC | TCA | ATG | GAT | GGA | CCA | GTT | CTG | 1104 |
|---|---|---|---|---|---|---|---|---|---|---|---|---|---|---|---|---|
| Ser | Gln | Glu | Gly | Phe | Ser | Ser | Ala | Leu | Ser | Met | Asp | Gly | Pro | Val | Leu | |
| | | | 355 | | | | | 360 | | | | | 365 | | | |

| GGG | GCT | GTG | GGA | GGC | TTC | AGC | TGG | TCT | GGA | GGT | GCC | TTC | TTG | TAC | CCC | 1152 |
|---|---|---|---|---|---|---|---|---|---|---|---|---|---|---|---|---|
| Gly | Ala | Val | Gly | Gly | Phe | Ser | Trp | Ser | Gly | Gly | Ala | Phe | Leu | Tyr | Pro | |
| 370 | | | | | 375 | | | | | 380 | | | | | | |

| TCA | AAT | ATG | AGA | TCC | ACC | TTC | ATC | AAC | ATG | TCT | CAG | GAG | AAC | GAG | GAT | 1200 |
|---|---|---|---|---|---|---|---|---|---|---|---|---|---|---|---|---|
| Ser | Asn | Met | Arg | Ser | Thr | Phe | Ile | Asn | Met | Ser | Gln | Glu | Asn | Glu | Asp | |
| 385 | | | | | 390 | | | | | 395 | | | | | 400 | |

| ATG | AGG | GAC | GCT | TAC | CTG | GGT | TAC | TCC | ACC | GCA | CTG | GCC | TTT | TGG | AAG | 1248 |
|---|---|---|---|---|---|---|---|---|---|---|---|---|---|---|---|---|
| Met | Arg | Asp | Ala | Tyr | Leu | Gly | Tyr | Ser | Thr | Ala | Leu | Ala | Phe | Trp | Lys | |
| | | | | 405 | | | | | 410 | | | | | 415 | | |

| GGG | GTC | CAC | AGC | CTG | ATC | CTG | GGG | GCC | CCT | CGC | CAC | CAG | CAC | ACG | GGG | 1296 |
|---|---|---|---|---|---|---|---|---|---|---|---|---|---|---|---|---|
| Gly | Val | His | Ser | Leu | Ile | Leu | Gly | Ala | Pro | Arg | His | Gln | His | Thr | Gly | |
| | | | 420 | | | | | 425 | | | | | 430 | | | |

| AAG | GTT | GTC | ATC | TTT | ACC | CAG | GAA | TCC | AGG | CAC | TGG | AGG | CCC | AAG | TCT | 1344 |
|---|---|---|---|---|---|---|---|---|---|---|---|---|---|---|---|---|
| Lys | Val | Val | Ile | Phe | Thr | Gln | Glu | Ser | Arg | His | Trp | Arg | Pro | Lys | Ser | |
| | | 435 | | | | | 440 | | | | | 445 | | | | |

| GAA | GTC | AGA | GGG | ACA | CAG | ATC | GGC | TCC | TAC | TTT | GGG | GCA | TCT | CTC | TGT | 1392 |
|---|---|---|---|---|---|---|---|---|---|---|---|---|---|---|---|---|
| Glu | Val | Arg | Gly | Thr | Gln | Ile | Gly | Ser | Tyr | Phe | Gly | Ala | Ser | Leu | Cys | |
| | 450 | | | | | 455 | | | | | 460 | | | | | |

| TCT | GTG | GAC | ATG | GAT | AGA | GAT | GGC | AGC | ACT | GAC | CTG | GTC | CTG | ATT | GGA | 1440 |
|---|---|---|---|---|---|---|---|---|---|---|---|---|---|---|---|---|
| Ser | Val | Asp | Met | Asp | Arg | Asp | Gly | Ser | Thr | Asp | Leu | Val | Leu | Ile | Gly | |
| 465 | | | | | 470 | | | | | 475 | | | | | 480 | |

| GTC | CCC | CAT | TAC | TAT | GAG | CAC | ACC | CGA | GGG | GGG | CAG | GTG | TCG | GTG | TGC | 1488 |
|---|---|---|---|---|---|---|---|---|---|---|---|---|---|---|---|---|
| Val | Pro | His | Tyr | Tyr | Glu | His | Thr | Arg | Gly | Gly | Gln | Val | Ser | Val | Cys | |
| | | | | 485 | | | | | 490 | | | | | 495 | | |

| CCC | ATG | CCT | GGT | GTG | AGG | AGC | AGG | TGG | CAT | TGT | GGG | ACC | ACC | CTC | CAT | 1536 |
|---|---|---|---|---|---|---|---|---|---|---|---|---|---|---|---|---|
| Pro | Met | Pro | Gly | Val | Arg | Ser | Arg | Trp | His | Cys | Gly | Thr | Thr | Leu | His | |
| | | | 500 | | | | | 505 | | | | | 510 | | | |

| GGG | GAG | CAG | GGC | CAT | CCT | TGG | GGC | CGC | TTT | GGG | GCG | GCT | CTG | ACA | GTG | 1584 |
|---|---|---|---|---|---|---|---|---|---|---|---|---|---|---|---|---|
| Gly | Glu | Gln | Gly | His | Pro | Trp | Gly | Arg | Phe | Gly | Ala | Ala | Leu | Thr | Val | |
| | | | 515 | | | | | 520 | | | | | 525 | | | |

| CTA | GGG | GAC | GTG | AAT | GGG | GAC | AGT | CTG | GCG | GAT | GTG | GCT | ATT | GGT | GCA | 1632 |
|---|---|---|---|---|---|---|---|---|---|---|---|---|---|---|---|---|
| Leu | Gly | Asp | Val | Asn | Gly | Asp | Ser | Leu | Ala | Asp | Val | Ala | Ile | Gly | Ala | |
| | 530 | | | | | 535 | | | | | 540 | | | | | |

| CCC | GGA | GAG | GAG | GAG | AAC | AGA | GGT | GCT | GTC | TAC | ATA | TTT | CAT | GGA | GCC | 1680 |
|---|---|---|---|---|---|---|---|---|---|---|---|---|---|---|---|---|
| Pro | Gly | Glu | Glu | Glu | Asn | Arg | Gly | Ala | Val | Tyr | Ile | Phe | His | Gly | Ala | |
| 545 | | | | | 550 | | | | | 555 | | | | | 560 | |

| TCG | AGA | CAG | GAC | ATC | GCT | CCC | TCG | CCT | AGC | CAG | CGG | GTC | ACT | GGC | TCC | 1728 |
|---|---|---|---|---|---|---|---|---|---|---|---|---|---|---|---|---|
| Ser | Arg | Gln | Asp | Ile | Ala | Pro | Ser | Pro | Ser | Gln | Arg | Val | Thr | Gly | Ser | |
| | | | | 565 | | | | | 570 | | | | | 575 | | |

| CAG | CTC | TTC | CTG | AGG | CTC | CAA | TAT | TTT | GGG | CAG | TCA | TTA | AGT | GGG | GGT | 1776 |
|---|---|---|---|---|---|---|---|---|---|---|---|---|---|---|---|---|
| Gln | Leu | Phe | Leu | Arg | Leu | Gln | Tyr | Phe | Gly | Gln | Ser | Leu | Ser | Gly | Gly | |
| | | | 580 | | | | | 585 | | | | | 590 | | | |

| CAG | GAC | CTT | ACA | CAG | GAT | GGC | CTG | GTG | GAC | CTG | GCC | GTG | GGA | GCC | CAG | 1824 |
|---|---|---|---|---|---|---|---|---|---|---|---|---|---|---|---|---|
| Gln | Asp | Leu | Thr | Gln | Asp | Gly | Leu | Val | Asp | Leu | Ala | Val | Gly | Ala | Gln | |
| | | 595 | | | | | 600 | | | | | 605 | | | | |

| GGG | CAC | GTG | CTG | CTG | CTT | AGG | AGT | CTG | CCT | TTG | CTG | AAA | GTG | GGG | ATC | 1872 |

| | | | | | | | | | | | | | | | | |
|---|---|---|---|---|---|---|---|---|---|---|---|---|---|---|---|---|
| Gly | His | Val | Leu | Leu | Leu | Arg | Ser | Leu | Pro | Leu | Leu | Lys | Val | Gly | Ile | |
| | 610 | | | | | 615 | | | | 620 | | | | | | |
| TCC | ATT | AGA | TTT | GCC | CCC | TCA | GAG | GTG | GCA | AAG | ACT | GTG | TAC | CAG | TGC | 1920 |
| Ser | Ile | Arg | Phe | Ala | Pro | Ser | Glu | Val | Ala | Lys | Thr | Val | Tyr | Gln | Cys | |
| 625 | | | | | 630 | | | | 635 | | | | | 640 | | |
| TGG | GGA | AGG | ACT | CCC | ACT | GTC | CTC | GAA | GCT | GGA | GAG | GCC | ACC | GTC | TGT | 1968 |
| Trp | Gly | Arg | Thr | Pro | Thr | Val | Leu | Glu | Ala | Gly | Glu | Ala | Thr | Val | Cys | |
| | | | | 645 | | | | 650 | | | | | 655 | | | |
| CTC | ACT | GTC | CGC | AAA | GGT | TCA | CCT | GAC | CTG | TTA | GGT | GAT | GTC | CAA | AGC | 2016 |
| Leu | Thr | Val | Arg | Lys | Gly | Ser | Pro | Asp | Leu | Leu | Gly | Asp | Val | Gln | Ser | |
| | | | 660 | | | | 665 | | | | | 670 | | | | |
| TCT | GTC | AGG | TAT | GAT | CTG | GCG | TTG | GAT | CCG | GGC | CGT | CTG | ATT | TCT | CGT | 2064 |
| Ser | Val | Arg | Tyr | Asp | Leu | Ala | Leu | Asp | Pro | Gly | Arg | Leu | Ile | Ser | Arg | |
| | | 675 | | | | 680 | | | | | 685 | | | | | |
| GCC | ATT | TTT | GAT | GAG | ACG | AAG | AAC | TGC | ACT | TTG | ACC | CGA | AGG | AAG | ACT | 2112 |
| Ala | Ile | Phe | Asp | Glu | Thr | Lys | Asn | Cys | Thr | Leu | Thr | Arg | Arg | Lys | Thr | |
| | 690 | | | | | 695 | | | | | 700 | | | | | |
| CTG | GGG | CTT | GGT | GAT | CAC | TGC | GAA | ACA | ATG | AAG | CTG | CTT | TTG | CCA | GAC | 2160 |
| Leu | Gly | Leu | Gly | Asp | His | Cys | Glu | Thr | Met | Lys | Leu | Leu | Leu | Pro | Asp | |
| 705 | | | | | 710 | | | | 715 | | | | | 720 | | |
| TGT | GTG | GAG | GAT | GCA | GTG | ACC | CCT | ATC | ATC | CTG | CGC | CTT | AAC | TTA | TCC | 2208 |
| Cys | Val | Glu | Asp | Ala | Val | Thr | Pro | Ile | Ile | Leu | Arg | Leu | Asn | Leu | Ser | |
| | | | | 725 | | | | 730 | | | | | 735 | | | |
| CTG | GCA | GGG | GAC | TCT | GCT | CCA | TCC | AGG | AAC | CTT | CGT | CCT | GTG | CTG | GCT | 2256 |
| Leu | Ala | Gly | Asp | Ser | Ala | Pro | Ser | Arg | Asn | Leu | Arg | Pro | Val | Leu | Ala | |
| | | | 740 | | | | 745 | | | | | 750 | | | | |
| GTG | GGC | TCA | CAA | GAC | CAT | GTA | ACA | GCT | TCT | TTC | CCG | TTT | GAG | AAG | AAC | 2304 |
| Val | Gly | Ser | Gln | Asp | His | Val | Thr | Ala | Ser | Phe | Pro | Phe | Glu | Lys | Asn | |
| | | 755 | | | | 760 | | | | | 765 | | | | | |
| TGT | AAG | CAG | GAG | CTC | CTG | TGT | GAG | GGG | AAC | CTG | GGC | GTC | AGC | TTC | AAC | 2352 |
| Cys | Lys | Gln | Glu | Leu | Leu | Cys | Glu | Gly | Asn | Leu | Gly | Val | Ser | Phe | Asn | |
| | 770 | | | | | 775 | | | | | 780 | | | | | |
| TTC | TCA | GGC | CTG | CAG | GTC | TTG | GAG | GTA | GGA | AGC | TCC | CCA | GAG | CTC | ACT | 2400 |
| Phe | Ser | Gly | Leu | Gln | Val | Leu | Glu | Val | Gly | Ser | Ser | Pro | Glu | Leu | Thr | |
| 785 | | | | | 790 | | | | 795 | | | | | 800 | | |
| GTG | ACA | GTA | ACA | GTT | TGG | AAT | GAG | GGT | GAG | GAC | AGC | TAT | GGA | ACC | TTA | 2448 |
| Val | Thr | Val | Thr | Val | Trp | Asn | Glu | Gly | Glu | Asp | Ser | Tyr | Gly | Thr | Leu | |
| | | | | 805 | | | | 810 | | | | | 815 | | | |
| ATC | AAG | TTC | TAC | TAC | CCA | GCA | GAG | CTA | TCT | TAC | CGA | CGG | GTG | ACA | AGA | 2496 |
| Ile | Lys | Phe | Tyr | Tyr | Pro | Ala | Glu | Leu | Ser | Tyr | Arg | Arg | Val | Thr | Arg | |
| | | | 820 | | | | 825 | | | | | 830 | | | | |
| GCC | CAG | CAA | CCT | CAT | CCG | TAC | CCA | CTA | CGC | CTG | GCA | TGT | GAG | GCT | GAG | 2544 |
| Ala | Gln | Gln | Pro | His | Pro | Tyr | Pro | Leu | Arg | Leu | Ala | Cys | Glu | Ala | Glu | |
| | | 835 | | | | 840 | | | | | 845 | | | | | |
| CCC | ACG | GGC | CAG | GAG | AGC | CTG | AGG | AGC | AGC | TGT | AGC | ATC | AAT | CAC | | 2592 |
| Pro | Thr | Gly | Gln | Glu | Ser | Leu | Arg | Ser | Ser | Cys | Ser | Ile | Asn | His | | |
| | 850 | | | | | 855 | | | | | 860 | | | | | |
| CCC | ATC | TTC | CGA | GAA | GGT | GCC | AAG | GCC | ACC | TTC | ATG | ATC | ACA | TTT | GAT | 2640 |
| Pro | Ile | Phe | Arg | Glu | Gly | Ala | Lys | Ala | Thr | Phe | Met | Ile | Thr | Phe | Asp | |
| 865 | | | | | 870 | | | | 875 | | | | | 880 | | |
| GTC | TCC | TAC | AAG | GCC | TTC | CTG | GGA | GAC | AGG | TTG | CTT | CTG | AGG | GCC | AGC | 2688 |
| Val | Ser | Tyr | Lys | Ala | Phe | Leu | Gly | Asp | Arg | Leu | Leu | Leu | Arg | Ala | Ser | |
| | | | | 885 | | | | 890 | | | | | 895 | | | |
| GCA | AGC | AGT | GAG | AAT | AAT | AAG | CCT | GAA | ACC | AGC | AAG | ACT | GCC | TTC | CAG | 2736 |
| Ala | Ser | Ser | Glu | Asn | Asn | Lys | Pro | Glu | Thr | Ser | Lys | Thr | Ala | Phe | Gln | |
| | | | 900 | | | | 905 | | | | | 910 | | | | |
| CTG | GAG | CTT | CCG | GTG | AAG | TAC | ACG | GTC | TAT | ACC | GTG | ATC | AGT | AGG | CAG | 2784 |
| Leu | Glu | Leu | Pro | Val | Lys | Tyr | Thr | Val | Tyr | Thr | Val | Ile | Ser | Arg | Gln | |
| | | 915 | | | | 920 | | | | | 925 | | | | | |
| GAA | GAT | TCT | ACC | AAG | CAT | TTC | AAC | TTC | TCA | TCT | TCC | CAC | GGG | GAG | AGA | 2832 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Glu | Asp | Ser | Thr | Lys | His | Phe | Asn | Phe | Ser | Ser | Ser | His | Gly | Glu | Arg |      |
|     | 930 |     |     |     | 935 |     |     |     |     | 940 |     |     |     |     |     |      |
| CAG | AAA | GAG | GCC | GAA | CAT | CGA | TAT | CGT | GTG | AAT | AAC | CTG | AGT | CCA | TTG | 2880 |
| Gln | Lys | Glu | Ala | Glu | His | Arg | Tyr | Arg | Val | Asn | Asn | Leu | Ser | Pro | Leu |      |
| 945 |     |     |     |     | 950 |     |     |     |     | 955 |     |     |     |     | 960 |      |
| ACG | CTG | GCC | ATC | AGC | GTT | AAC | TTC | TGG | GTC | CCC | ATC | CTT | CTG | AAT | GGT | 2928 |
| Thr | Leu | Ala | Ile | Ser | Val | Asn | Phe | Trp | Val | Pro | Ile | Leu | Leu | Asn | Gly |      |
|     |     |     |     | 965 |     |     |     |     | 970 |     |     |     |     |     | 975 |      |
| GTG | GCC | GTG | TGG | GAT | GTG | ACT | CTG | AGG | AGC | CCA | GCA | CAG | GGT | GTC | TCC | 2976 |
| Val | Ala | Val | Trp | Asp | Val | Thr | Leu | Arg | Ser | Pro | Ala | Gln | Gly | Val | Ser |      |
|     |     |     |     | 980 |     |     |     |     | 985 |     |     |     |     | 990 |     |      |
| TGT | GTG | TCA | CAG | AGG | GAA | CCT | CCT | CAA | CAT | TCC | GAC | CTT | CTG | ACC | CAG | 3024 |
| Cys | Val | Ser | Gln | Arg | Glu | Pro | Pro | Gln | His | Ser | Asp | Leu | Leu | Thr | Gln |      |
|     |     | 995 |     |     |     |     | 1000 |     |     |     |     | 1005 |     |     |     |      |
| ATC | CAA | GGA | CGC | TCT | GTG | CTG | GAC | TGC | GCC | ATC | GCC | GAC | TGC | CTG | CAC | 3072 |
| Ile | Gln | Gly | Arg | Ser | Val | Leu | Asp | Cys | Ala | Ile | Ala | Asp | Cys | Leu | His |      |
|     | 1010 |     |     |     |     | 1015 |     |     |     |     | 1020 |     |     |     |     |      |
| CTC | CGC | TGT | GAC | ATC | CCC | TCC | TTG | GGC | ACC | CTG | GAT | GAG | CTT | GAC | TTC | 3120 |
| Leu | Arg | Cys | Asp | Ile | Pro | Ser | Leu | Gly | Thr | Leu | Asp | Glu | Leu | Asp | Phe |      |
| 1025 |     |     |     |     | 1030 |     |     |     |     | 1035 |     |     |     |     | 1040 |      |
| ATT | CTG | AAG | GGC | AAC | CTC | AGC | TTC | GGC | TGG | ATC | AGT | CAG | ACA | TTG | CAG | 3168 |
| Ile | Leu | Lys | Gly | Asn | Leu | Ser | Phe | Gly | Trp | Ile | Ser | Gln | Thr | Leu | Gln |      |
|     |     |     |     | 1045 |     |     |     |     | 1050 |     |     |     |     | 1055 |     |      |
| AAA | AAG | GTG | TTG | CTC | CTG | AGT | GAG | GCT | GAA | ATC | ACA | TTC | AAC | ACA | TCT | 3216 |
| Lys | Lys | Val | Leu | Leu | Leu | Ser | Glu | Ala | Glu | Ile | Thr | Phe | Asn | Thr | Ser |      |
|     |     |     | 1060 |     |     |     |     | 1065 |     |     |     |     | 1070 |     |     |      |
| GTG | TAT | TCC | CAG | CTG | CCG | GGA | CAG | GAG | GCA | TTT | CTG | AGA | GCC | CAG | GTG | 3264 |
| Val | Tyr | Ser | Gln | Leu | Pro | Gly | Gln | Glu | Ala | Phe | Leu | Arg | Ala | Gln | Val |      |
|     |     | 1075 |     |     |     |     | 1080 |     |     |     |     | 1085 |     |     |     |      |
| TCA | ACG | ATG | CTA | GAA | GAA | TAC | GTG | GTC | TAT | GAG | CCC | GTC | TTC | CTC | ATG | 3312 |
| Ser | Thr | Met | Leu | Glu | Glu | Tyr | Val | Val | Tyr | Glu | Pro | Val | Phe | Leu | Met |      |
| 1090 |     |     |     |     | 1095 |     |     |     |     | 1100 |     |     |     |     |     |      |
| GTG | TTC | AGC | TCA | GTG | GGA | GGT | CTG | CTG | TTA | CTG | GCT | CTC | ATC | ACT | GTG | 3360 |
| Val | Phe | Ser | Ser | Val | Gly | Gly | Leu | Leu | Leu | Leu | Ala | Leu | Ile | Thr | Val |      |
| 1105 |     |     |     |     | 1110 |     |     |     |     | 1115 |     |     |     |     | 1120 |      |
| GCG | CTG | TAC | AAG | CTT | GGC | TTC | TTC | AAA | CGT | CAG | TAT | AAA | GAG | ATG | CTG | 3408 |
| Ala | Leu | Tyr | Lys | Leu | Gly | Phe | Phe | Lys | Arg | Gln | Tyr | Lys | Glu | Met | Leu |      |
|     |     |     |     | 1125 |     |     |     |     | 1130 |     |     |     |     | 1135 |     |      |
| GAT | CTA | CCA | TCT | GCA | GAT | CCT | GAC | CCA | GCC | GGC | CAG | GCA | GAT | TCC | AAC | 3456 |
| Asp | Leu | Pro | Ser | Ala | Asp | Pro | Asp | Pro | Ala | Gly | Gln | Ala | Asp | Ser | Asn |      |
|     |     |     |     | 1140 |     |     |     |     | 1145 |     |     |     |     | 1150 |     |      |
| CAT | GAG | ACT | CCT | CCA | CAT | CTC | ACG | TCC | TAGGAATCTA | CTTTCCTGTA |     |     |     |     |     | 3503 |
| His | Glu | Thr | Pro | Pro | His | Leu | Thr | Ser |     |     |     |     |     |     |     |      |
|     |     |     |     | 1155 |     |     |     | 1160 |     |     |     |     |     |     |     |      |
| TATCTCCACA | ATTACGAGAT | TGGTTTTGCT | TTTGCCTATG | AATCTACTGG | CATGGGAACA |     |     |     |     |     |     |     |     |     |     | 3563 |
| AGTTCTCTTC | AGCTCTGGGC | TAGCCTGGGA | AACTTCCCAG | AAATGATGCC | CTACCTCCTG |     |     |     |     |     |     |     |     |     |     | 3623 |
| AGCTGGAGA  | TTTTTATGGT | TTGCCCATGT | GTCAGATTTC | AGTGCTGATC | CACTTTTTTT |     |     |     |     |     |     |     |     |     |     | 3683 |
| GCAAGAGCAG | GAATGGGGTC | AGCATAAATT | TACATATGGA | TAAGAACTAA | CACAAGACTG |     |     |     |     |     |     |     |     |     |     | 3743 |
| AGTAATATGC | TCAATATTCA | ATGTATTGCT | TGTATAAATT | TTTAAAAAAT | AAAATGAAAN |     |     |     |     |     |     |     |     |     |     | 3803 |

( 2 ) INFORMATION FOR SEQ ID NO:53:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

```
Met Val Arg Gly Val Val Ile Leu Leu Cys Gly Trp Ala Leu Ala Ser
 1               5                    10                  15
Cys His Gly Ser Asn Leu Asp Val Glu Lys Pro Val Val Phe Lys Glu
                 20                  25                  30
Asp Ala Ala Ser Phe Gly Gln Thr Val Val Gln Phe Gly Ser Arg
             35              40                  45
Leu Val Val Gly Ala Pro Leu Glu Ala Val Ala Val Asn Gln Thr Gly
         50              55                  60
Gln Ser Ser Asp Cys Pro Pro Ala Thr Gly Val Cys Gln Pro Ile Leu
 65              70                  75                      80
Leu His Ile Pro Leu Glu Ala Val Asn Met Ser Leu Gly Leu Ser Leu
                 85                  90                  95
Val Ala Asp Thr Asn Asn Ser Gln Leu Leu Ala Cys Gly Pro Thr Ala
            100             105                 110
Gln Arg Ala Cys Ala Lys Asn Met Tyr Ala Lys Gly Ser Cys Leu Leu
        115              120                 125
Leu Gly Ser Ser Leu Gln Phe Ile Gln Ala Ile Pro Ala Thr Met Pro
    130             135                 140
Glu Cys Pro Gly Gln Glu Met Asp Ile Ala Phe Leu Ile Asp Gly Ser
145             150                 155                     160
Gly Ser Ile Asp Gln Ser Asp Phe Thr Gln Met Lys Asp Phe Val Lys
            165                 170                 175
Ala Leu Met Gly Gln Leu Ala Ser Thr Ser Thr Ser Phe Ser Leu Met
            180                 185                 190
Gln Tyr Ser Asn Ile Leu Lys Thr His Phe Thr Phe Thr Glu Phe Lys
        195                 200                 205
Ser Ser Leu Ser Pro Gln Ser Leu Val Asp Ala Ile Val Gln Leu Gln
    210                 215                 220
Gly Leu Thr Tyr Thr Ala Ser Gly Ile Gln Lys Val Val Lys Glu Leu
225                 230                 235                 240
Phe His Ser Lys Asn Gly Ala Arg Lys Ser Ala Lys Lys Ile Leu Ile
                245                 250                 255
Val Ile Thr Asp Gly Gln Lys Phe Arg Asp Pro Leu Glu Tyr Arg His
            260                 265                 270
Val Ile Pro Glu Ala Glu Lys Ala Gly Ile Ile Arg Tyr Ala Ile Gly
        275                 280                 285
Val Gly Asp Ala Phe Arg Glu Pro Thr Ala Leu Gln Glu Leu Asn Thr
    290                 295                 300
Ile Gly Ser Ala Pro Ser Gln Asp His Val Phe Lys Val Gly Asn Phe
305                 310                 315                 320
Val Ala Leu Arg Ser Ile Gln Arg Gln Ile Gln Glu Lys Ile Phe Ala
                325                 330                 335
Ile Glu Gly Thr Glu Ser Arg Ser Ser Ser Phe Gln His Glu Met
            340                 345                 350
Ser Gln Glu Gly Phe Ser Ser Ala Leu Ser Met Asp Gly Pro Val Leu
        355                 360                 365
Gly Ala Val Gly Gly Phe Ser Trp Ser Gly Gly Ala Phe Leu Tyr Pro
    370                 375                 380
Ser Asn Met Arg Ser Thr Phe Ile Asn Met Ser Gln Glu Asn Glu Asp
385                 390                 395                 400
Met Arg Asp Ala Tyr Leu Gly Tyr Ser Thr Ala Leu Ala Phe Trp Lys
                405                 410                 415
Gly Val His Ser Leu Ile Leu Gly Ala Pro Arg His Gln His Thr Gly
```

-continued

|     |     |     | 420 |     |     |     | 425 |     |     |     | 430 |     |     |     |
|-----|-----|-----|-----|-----|-----|-----|-----|-----|-----|-----|-----|-----|-----|-----|
| Lys | Val | Val | Ile | Phe | Thr | Gln | Glu | Ser | Arg | His | Trp | Arg | Pro | Lys | Ser |
|     |     | 435 |     |     |     |     | 440 |     |     |     |     | 445 |     |     |
| Glu | Val | Arg | Gly | Thr | Gln | Ile | Gly | Ser | Tyr | Phe | Gly | Ala | Ser | Leu | Cys |
|     | 450 |     |     |     |     | 455 |     |     |     |     | 460 |     |     |     |
| Ser | Val | Asp | Met | Asp | Arg | Asp | Gly | Ser | Thr | Asp | Leu | Val | Leu | Ile | Gly |
| 465 |     |     |     |     | 470 |     |     |     |     | 475 |     |     |     |     | 480 |
| Val | Pro | His | Tyr | Tyr | Glu | His | Thr | Arg | Gly | Gly | Gln | Val | Ser | Val | Cys |
|     |     |     |     | 485 |     |     |     |     | 490 |     |     |     |     | 495 |     |
| Pro | Met | Pro | Gly | Val | Arg | Ser | Arg | Trp | His | Cys | Gly | Thr | Thr | Leu | His |
|     |     |     | 500 |     |     |     |     |     | 505 |     |     |     |     | 510 |     |
| Gly | Glu | Gln | Gly | His | Pro | Trp | Gly | Arg | Phe | Gly | Ala | Ala | Leu | Thr | Val |
|     |     | 515 |     |     |     |     | 520 |     |     |     |     |     | 525 |     |     |
| Leu | Gly | Asp | Val | Asn | Gly | Asp | Ser | Leu | Ala | Asp | Val | Ala | Ile | Gly | Ala |
|     | 530 |     |     |     |     | 535 |     |     |     |     | 540 |     |     |     |     |
| Pro | Gly | Glu | Glu | Glu | Asn | Arg | Gly | Ala | Val | Tyr | Ile | Phe | His | Gly | Ala |
| 545 |     |     |     |     | 550 |     |     |     |     | 555 |     |     |     |     | 560 |
| Ser | Arg | Gln | Asp | Ile | Ala | Pro | Ser | Pro | Ser | Gln | Arg | Val | Thr | Gly | Ser |
|     |     |     |     | 565 |     |     |     |     | 570 |     |     |     |     | 575 |     |
| Gln | Leu | Phe | Leu | Arg | Leu | Gln | Tyr | Phe | Gly | Gln | Ser | Leu | Ser | Gly | Gly |
|     |     |     | 580 |     |     |     |     | 585 |     |     |     |     | 590 |     |     |
| Gln | Asp | Leu | Thr | Gln | Asp | Gly | Leu | Val | Asp | Leu | Ala | Val | Gly | Ala | Gln |
|     |     | 595 |     |     |     |     | 600 |     |     |     |     | 605 |     |     |     |
| Gly | His | Val | Leu | Leu | Leu | Arg | Ser | Leu | Pro | Leu | Leu | Lys | Val | Gly | Ile |
|     | 610 |     |     |     |     | 615 |     |     |     |     | 620 |     |     |     |     |
| Ser | Ile | Arg | Phe | Ala | Pro | Ser | Glu | Val | Ala | Lys | Thr | Val | Tyr | Gln | Cys |
| 625 |     |     |     |     | 630 |     |     |     |     | 635 |     |     |     |     | 640 |
| Trp | Gly | Arg | Thr | Pro | Thr | Val | Leu | Glu | Ala | Gly | Glu | Ala | Thr | Val | Cys |
|     |     |     |     | 645 |     |     |     |     | 650 |     |     |     |     | 655 |     |
| Leu | Thr | Val | Arg | Lys | Gly | Ser | Pro | Asp | Leu | Leu | Gly | Asp | Val | Gln | Ser |
|     |     |     | 660 |     |     |     |     | 665 |     |     |     |     | 670 |     |     |
| Ser | Val | Arg | Tyr | Asp | Leu | Ala | Leu | Asp | Pro | Gly | Arg | Leu | Ile | Ser | Arg |
|     |     | 675 |     |     |     |     | 680 |     |     |     |     | 685 |     |     |     |
| Ala | Ile | Phe | Asp | Glu | Thr | Lys | Asn | Cys | Thr | Leu | Thr | Arg | Arg | Lys | Thr |
|     | 690 |     |     |     |     | 695 |     |     |     |     | 700 |     |     |     |     |
| Leu | Gly | Leu | Gly | Asp | His | Cys | Glu | Thr | Met | Lys | Leu | Leu | Leu | Pro | Asp |
| 705 |     |     |     |     | 710 |     |     |     |     | 715 |     |     |     |     | 720 |
| Cys | Val | Glu | Asp | Ala | Val | Thr | Pro | Ile | Ile | Leu | Arg | Leu | Asn | Leu | Ser |
|     |     |     |     | 725 |     |     |     |     | 730 |     |     |     |     | 735 |     |
| Leu | Ala | Gly | Asp | Ser | Ala | Pro | Ser | Arg | Asn | Leu | Arg | Pro | Val | Leu | Ala |
|     |     |     | 740 |     |     |     |     | 745 |     |     |     |     | 750 |     |     |
| Val | Gly | Ser | Gln | Asp | His | Val | Thr | Ala | Ser | Phe | Pro | Phe | Glu | Lys | Asn |
|     |     | 755 |     |     |     |     | 760 |     |     |     |     | 765 |     |     |     |
| Cys | Lys | Gln | Glu | Leu | Leu | Cys | Glu | Gly | Asn | Leu | Gly | Val | Ser | Phe | Asn |
|     | 770 |     |     |     |     | 775 |     |     |     |     | 780 |     |     |     |     |
| Phe | Ser | Gly | Leu | Gln | Val | Leu | Glu | Val | Gly | Ser | Ser | Pro | Glu | Leu | Thr |
| 785 |     |     |     |     | 790 |     |     |     |     | 795 |     |     |     |     | 800 |
| Val | Thr | Val | Thr | Val | Trp | Asn | Glu | Gly | Glu | Asp | Ser | Tyr | Gly | Thr | Leu |
|     |     |     |     | 805 |     |     |     |     | 810 |     |     |     |     | 815 |     |
| Ile | Lys | Phe | Tyr | Tyr | Pro | Ala | Glu | Leu | Ser | Tyr | Arg | Arg | Val | Thr | Arg |
|     |     |     |     | 820 |     |     |     |     | 825 |     |     |     |     | 830 |     |
| Ala | Gln | Gln | Pro | His | Pro | Tyr | Pro | Leu | Arg | Leu | Ala | Cys | Glu | Ala | Glu |
|     |     | 835 |     |     |     |     | 840 |     |     |     |     | 845 |     |     |     |

| Pro | Thr | Gly | Gln | Glu | Ser | Leu | Arg | Ser | Ser | Ser | Cys | Ser | Ile | Asn | His |
|     | 850 |     |     |     | 855 |     |     |     |     | 860 |     |     |     |     |     |

| Pro | Ile | Phe | Arg | Glu | Gly | Ala | Lys | Ala | Thr | Phe | Met | Ile | Thr | Phe | Asp |
| 865 |     |     |     |     | 870 |     |     |     | 875 |     |     |     |     |     | 880 |

| Val | Ser | Tyr | Lys | Ala | Phe | Leu | Gly | Asp | Arg | Leu | Leu | Leu | Arg | Ala | Ser |
|     |     |     |     | 885 |     |     |     |     | 890 |     |     |     |     | 895 |     |

| Ala | Ser | Ser | Glu | Asn | Asn | Lys | Pro | Glu | Thr | Ser | Lys | Thr | Ala | Phe | Gln |
|     |     |     | 900 |     |     |     |     | 905 |     |     |     |     | 910 |     |     |

| Leu | Glu | Leu | Pro | Val | Lys | Tyr | Thr | Val | Tyr | Thr | Val | Ile | Ser | Arg | Gln |
|     |     | 915 |     |     |     |     | 920 |     |     |     |     | 925 |     |     |     |

| Glu | Asp | Ser | Thr | Lys | His | Phe | Asn | Phe | Ser | Ser | Ser | His | Gly | Glu | Arg |
|     | 930 |     |     |     |     | 935 |     |     |     |     | 940 |     |     |     |     |

| Gln | Lys | Glu | Ala | Glu | His | Arg | Tyr | Arg | Val | Asn | Asn | Leu | Ser | Pro | Leu |
| 945 |     |     |     |     | 950 |     |     |     |     | 955 |     |     |     |     | 960 |

| Thr | Leu | Ala | Ile | Ser | Val | Asn | Phe | Trp | Val | Pro | Ile | Leu | Leu | Asn | Gly |
|     |     |     |     | 965 |     |     |     |     | 970 |     |     |     |     | 975 |     |

| Val | Ala | Val | Trp | Asp | Val | Thr | Leu | Arg | Ser | Pro | Ala | Gln | Gly | Val | Ser |
| 980 |     |     |     |     |     |     |     | 985 |     |     |     |     | 990 |     |     |

| Cys | Val | Ser | Gln | Arg | Glu | Pro | Pro | Gln | His | Ser | Asp | Leu | Leu | Thr | Gln |
|     |     | 995 |     |     |     |     | 1000|     |     |     |     |     | 1005|     |     |

| Ile | Gln | Gly | Arg | Ser | Val | Leu | Asp | Cys | Ala | Ile | Ala | Asp | Cys | Leu | His |
|     |     | 1010|     |     |     |     | 1015|     |     |     |     | 1020|     |     |     |

| Leu | Arg | Cys | Asp | Ile | Pro | Ser | Leu | Gly | Thr | Leu | Asp | Glu | Leu | Asp | Phe |
| 1025|     |     |     |     | 1030|     |     |     |     | 1035|     |     |     |     | 1040|

| Ile | Leu | Lys | Gly | Asn | Leu | Ser | Phe | Gly | Trp | Ile | Ser | Gln | Thr | Leu | Gln |
|     |     |     |     | 1045|     |     |     |     | 1050|     |     |     |     | 1055|     |

| Lys | Lys | Val | Leu | Leu | Leu | Ser | Glu | Ala | Glu | Ile | Thr | Phe | Asn | Thr | Ser |
|     |     |     |     | 1060|     |     |     |     | 1065|     |     |     |     | 1070|     |

| Val | Tyr | Ser | Gln | Leu | Pro | Gly | Gln | Glu | Ala | Phe | Leu | Arg | Ala | Gln | Val |
|     |     |     | 1075|     |     |     |     | 1080|     |     |     |     | 1085|     |     |

| Ser | Thr | Met | Leu | Glu | Glu | Tyr | Val | Val | Tyr | Glu | Pro | Val | Phe | Leu | Met |
|     |     |     | 1090|     |     |     |     | 1095|     |     |     |     | 1100|     |     |

| Val | Phe | Ser | Ser | Val | Gly | Gly | Leu | Leu | Leu | Leu | Ala | Leu | Ile | Thr | Val |
| 1105|     |     |     |     | 1110|     |     |     |     | 1115|     |     |     |     | 1120|

| Ala | Leu | Tyr | Lys | Leu | Gly | Phe | Phe | Lys | Arg | Gln | Tyr | Lys | Glu | Met | Leu |
|     |     |     |     | 1125|     |     |     |     | 1130|     |     |     |     | 1135|     |

| Asp | Leu | Pro | Ser | Ala | Asp | Pro | Asp | Pro | Ala | Gly | Gln | Ala | Asp | Ser | Asn |
|     |     |     |     | 1140|     |     |     |     | 1145|     |     |     |     | 1150|     |

| His | Glu | Thr | Pro | Pro | His | Leu | Thr | Ser |
|     |     |     | 1155|     |     |     |     | 1160|

( 2 ) INFORMATION FOR SEQ ID NO:54:

( i ) SEQUENCE CHARACTERISTICS:
        ( A ) LENGTH: 3597 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 40..3525

( x i ) SEQUENCE DESCRIPTION: SEQ ID NO:54:

```
AGCTTTACAG CTCTCTACTT CTCAGTGCAC TGCTCAGTG ATG GCC GGT GGA GTT      54
                                            Met Ala Gly Gly Val
                                             1               5
```

```
GTG ATC CTC CTG TGT GGC TGG GTC CTG GCT TCC TGT CAT GGG TCT AAC      102
Val Ile Leu Leu Cys Gly Trp Val Leu Ala Ser Cys His Gly Ser Asn
            10                      15                      20

CTG GAT GTG GAG GAA CCC ATC GTG TTC AGA GAG GAT GCA GCC AGC TTT      150
Leu Asp Val Glu Glu Pro Ile Val Phe Arg Glu Asp Ala Ala Ser Phe
                25                      30                      35

GGA CAG ACT GTG GTG CAG TTT GGT GGA TCT CGA CTC GTG GTG GGA GCC      198
Gly Gln Thr Val Val Gln Phe Gly Gly Ser Arg Leu Val Val Gly Ala
            40                      45                      50

CCT CTG GAG GCG GTG GCA GTC AAC CAA ACA GGA CGG TTG TAT GAC TGT      246
Pro Leu Glu Ala Val Ala Val Asn Gln Thr Gly Arg Leu Tyr Asp Cys
        55                      60                      65

GCA CCT GCC ACT GGC ATG TGC AGC CCC ATC GTA CTG CGC AGT CCC CTA      294
Ala Pro Ala Thr Gly Met Cys Gln Pro Ile Val Leu Arg Ser Pro Leu
    70                      75                      80                      85

GAG GCA GTG AAC ATG TCC CTG GGC CTG TCT CTG GTG ACT GCC ACC AAT      342
Glu Ala Val Asn Met Ser Leu Gly Leu Ser Leu Val Thr Ala Thr Asn
                    90                      95                      100

AAC GCC CAG TTG CTG GCT TGT GGT CCA ACT GCA CAG AGA GCT TGT GTG      390
Asn Ala Gln Leu Leu Ala Cys Gly Pro Thr Ala Gln Arg Ala Cys Val
                105                     110                     115

AAG AAC ATG TAT GCG AAA GGT TCC TGC CTC CTT CTC GGC TCC AGC TTG      438
Lys Asn Met Tyr Ala Lys Gly Ser Cys Leu Leu Leu Gly Ser Ser Leu
        120                     125                     130

CAG TTC ATC CAG GCA GTC CCT GCC TCC ATG CCA GAG TGT CCA AGA CAA      486
Gln Phe Ile Gln Ala Val Pro Ala Ser Met Pro Glu Cys Pro Arg Gln
    135                     140                     145

GAG ATG GAC ATT GCT TTC CTG ATT GAT GGT TCT GGC AGC ATT AAC CAA      534
Glu Met Asp Ile Ala Phe Leu Ile Asp Gly Ser Gly Ser Ile Asn Gln
150                     155                     160                     165

AGG GAC TTT GCC CAG ATG AAG GAC TTT GTC AAA GCT TTG ATG GGA GAG      582
Arg Asp Phe Ala Gln Met Lys Asp Phe Val Lys Ala Leu Met Gly Glu
                170                     175                     180

TTT GCG AGC ACC AGC ACC TTG TTC TCC CTG ATG CAA TAC TCG AAC ATC      630
Phe Ala Ser Thr Ser Thr Leu Phe Ser Leu Met Gln Tyr Ser Asn Ile
            185                     190                     195

CTG AAG ACC CAT TTT ACC TTC ACT GAA TTC AAG AAC ATC CTG GAC CCT      678
Leu Lys Thr His Phe Thr Phe Thr Glu Phe Lys Asn Ile Leu Asp Pro
        200                     205                     210

CAG AGC CTG GTG GAT CCC ATT GTC CAG CTG CAA GGC CTG ACC TAC ACA      726
Gln Ser Leu Val Asp Pro Ile Val Gln Leu Gln Gly Leu Thr Tyr Thr
    215                     220                     225

GCC ACA GGC ATC CGG ACA GTG ATG GAA GAG CTA TTT CAT AGC AAG AAT      774
Ala Thr Gly Ile Arg Thr Val Met Glu Glu Leu Phe His Ser Lys Asn
230                     235                     240                     245

GGG TCC CGT AAA AGT GCC AAG AAG ATC CTC CTT GTC ATC ACA GAT GGG      822
Gly Ser Arg Lys Ser Ala Lys Lys Ile Leu Leu Val Ile Thr Asp Gly
                250                     255                     260

CAG AAA TAC AGA GAC CCC CTG GAG TAT AGT GAT GTC ATT CCC GCC GCA      870
Gln Lys Tyr Arg Asp Pro Leu Glu Tyr Ser Asp Val Ile Pro Ala Ala
            265                     270                     275

GAC AAA GCT GGC ATC ATT CGT TAT GCT ATT GGG GTG GGA GAT GCC TTC      918
Asp Lys Ala Gly Ile Ile Arg Tyr Ala Ile Gly Val Gly Asp Ala Phe
        280                     285                     290

CAG GAG CCC ACT GCC CTG AAG GAG CTG AAC ACC ATT GGC TCA GCT CCC      966
Gln Glu Pro Thr Ala Leu Lys Glu Leu Asn Thr Ile Gly Ser Ala Pro
    295                     300                     305

CCA CAG GAC CAC GTG TTC AAG GTA GGC AAC TTT GCA GCA CTT CGC AGC      1014
Pro Gln Asp His Val Phe Lys Val Gly Asn Phe Ala Ala Leu Arg Ser
310                     315                     320                     325
```

| | | | | | | | | | | | | | | | |
|---|---|---|---|---|---|---|---|---|---|---|---|---|---|---|---|
| ATC | CAG | AGG | CAA | CTT | CAG | GAG | AAA | ATC | TTC | GCC | ATT | GAG | GGA | ACT | CAA | 1062
| Ile | Gln | Arg | Gln | Leu | Gln | Glu | Lys | Ile | Phe | Ala | Ile | Glu | Gly | Thr | Gln |
| | | | | 330 | | | | 335 | | | | 340 | | | |
| TCA | AGG | TCA | AGT | AGT | TCC | TTT | CAG | CAC | GAG | ATG | TCA | CAA | GAA | GGT | TTC | 1110
| Ser | Arg | Ser | Ser | Ser | Ser | Phe | Gln | His | Glu | Met | Ser | Gln | Glu | Gly | Phe |
| | | | 345 | | | | | 350 | | | | | 355 | | |
| AGT | TCA | GCT | CTC | ACA | TCG | GAT | GGA | CCC | GTT | CTG | GGG | GCC | GTG | GGA | AGC | 1158
| Ser | Ser | Ala | Leu | Thr | Ser | Asp | Gly | Pro | Val | Leu | Gly | Ala | Val | Gly | Ser |
| | | 360 | | | | | 365 | | | | | 370 | | | |
| TTC | AGC | TGG | TCC | GGA | GGT | GCC | TTC | TTA | TAT | CCC | CCA | AAT | ACG | AGA | CCC | 1206
| Phe | Ser | Trp | Ser | Gly | Gly | Ala | Phe | Leu | Tyr | Pro | Pro | Asn | Thr | Arg | Pro |
| | 375 | | | | | 380 | | | | | 385 | | | | |
| ACC | TTT | ATC | AAC | ATG | TCT | CAG | GAG | AAT | GTG | GAC | ATG | AGA | GAC | TCC | TAC | 1254
| Thr | Phe | Ile | Asn | Met | Ser | Gln | Glu | Asn | Val | Asp | Met | Arg | Asp | Ser | Tyr |
| 390 | | | | | 395 | | | | | 400 | | | | | 405 |
| CTG | GGT | TAC | TCC | ACC | GCA | GTG | GCC | TTT | TGG | AAG | GGG | GTT | CAC | AGC | CTG | 1302
| Leu | Gly | Tyr | Ser | Thr | Ala | Val | Ala | Phe | Trp | Lys | Gly | Val | His | Ser | Leu |
| | | | | 410 | | | | 415 | | | | 420 | | | |
| ATC | CTG | GGG | GCC | CCG | CGT | CAC | CAG | CAC | ACG | GGG | AAG | GTT | GTC | ATC | TTT | 1350
| Ile | Leu | Gly | Ala | Pro | Arg | His | Gln | His | Thr | Gly | Lys | Val | Val | Ile | Phe |
| | | | 425 | | | | | 430 | | | | | 435 | | |
| ACC | CAG | GAA | GCC | AGG | CAT | TGG | AGG | CCC | AAG | TCT | GAA | GTC | AGA | GGG | ACA | 1398
| Thr | Gln | Glu | Ala | Arg | His | Trp | Arg | Pro | Lys | Ser | Glu | Val | Arg | Gly | Thr |
| | | 440 | | | | | 445 | | | | | 450 | | | |
| CAG | ATC | GGC | TCC | TAC | TTC | GGG | GCC | TCT | CTC | TGT | TCT | GTG | GAC | GTG | GAT | 1446
| Gln | Ile | Gly | Ser | Tyr | Phe | Gly | Ala | Ser | Leu | Cys | Ser | Val | Asp | Val | Asp |
| | 455 | | | | | 460 | | | | | 465 | | | | |
| AGA | GAT | GGC | AGC | ACY | GAC | CTG | GTC | CTG | ATC | GGA | GCC | CCC | CAT | TAC | TAT | 1494
| Arg | Asp | Gly | Ser | Xaa | Asp | Leu | Val | Leu | Ile | Gly | Ala | Pro | His | Tyr | Tyr |
| 470 | | | | | 475 | | | | | 480 | | | | | 485 |
| GAG | CAG | ACC | CGA | GGG | GGG | CAG | GTC | TCA | GTG | TTC | CCC | GTG | CCC | GGT | GTG | 1542
| Glu | Gln | Thr | Arg | Gly | Gly | Gln | Val | Ser | Val | Phe | Pro | Val | Pro | Gly | Val |
| | | | | 490 | | | | 495 | | | | 500 | | | |
| AGG | GGC | AGG | TGG | CAG | TGT | GAG | GCC | ACC | CTC | CAC | GGG | GAG | CAG | GGC | CAT | 1590
| Arg | Gly | Arg | Trp | Gln | Cys | Glu | Ala | Thr | Leu | His | Gly | Glu | Gln | Gly | His |
| | | | 505 | | | | | 510 | | | | | 515 | | |
| CCT | TGG | GGC | CGC | TTT | GGG | GTG | GCT | CTG | ACA | GTG | CTG | GGG | GAC | GTA | AAC | 1638
| Pro | Trp | Gly | Arg | Phe | Gly | Val | Ala | Leu | Thr | Val | Leu | Gly | Asp | Val | Asn |
| | | 520 | | | | | 525 | | | | | 530 | | | |
| GGG | GAC | AAT | CTG | GCA | GAC | GTG | GCT | ATT | GGT | GCC | CCT | GGA | GAG | GAG | GAG | 1686
| Gly | Asp | Asn | Leu | Ala | Asp | Val | Ala | Ile | Gly | Ala | Pro | Gly | Glu | Glu | Glu |
| | 535 | | | | | 540 | | | | | 545 | | | | |
| AGC | AGA | GGT | GCT | GTC | TAC | ATA | TTT | CAT | GGA | GCC | TCG | AGA | CTG | GAG | ATC | 1734
| Ser | Arg | Gly | Ala | Val | Tyr | Ile | Phe | His | Gly | Ala | Ser | Arg | Leu | Glu | Ile |
| 550 | | | | | 555 | | | | | 560 | | | | | 565 |
| ATG | CCC | TCA | CCC | AGC | CAG | CGG | GTC | ACT | GGC | TCC | CAG | CTC | TCC | CTG | AGA | 1782
| Met | Pro | Ser | Pro | Ser | Gln | Arg | Val | Thr | Gly | Ser | Gln | Leu | Ser | Leu | Arg |
| | | | | 570 | | | | 575 | | | | 580 | | | |
| CTG | CAG | TAT | TTT | GGG | CAG | TCA | TTG | AGT | GGG | GGT | CAG | GAC | CTT | ACA | CAG | 1830
| Leu | Gln | Tyr | Phe | Gly | Gln | Ser | Leu | Ser | Gly | Gly | Gln | Asp | Leu | Thr | Gln |
| | | | 585 | | | | | 590 | | | | | 595 | | |
| GAT | GGC | CTG | GTG | GAC | CTG | GCC | GTG | GGA | GCC | CAG | GGG | CAC | GTA | CTG | CTG | 1878
| Asp | Gly | Leu | Val | Asp | Leu | Ala | Val | Gly | Ala | Gln | Gly | His | Val | Leu | Leu |
| | | 600 | | | | | 605 | | | | | 610 | | | |
| CTC | AGG | AGT | CTG | CCT | CTG | CTG | AAA | GTG | GAG | CTC | TCC | ATA | AGA | TTC | GCC | 1926
| Leu | Arg | Ser | Leu | Pro | Leu | Leu | Lys | Val | Glu | Leu | Ser | Ile | Arg | Phe | Ala |
| | 615 | | | | | 620 | | | | | 625 | | | | |
| CCC | ATG | GAG | GTG | GCA | AAG | GCT | GTG | TAC | CAG | TGC | TGG | GAA | AGG | ACT | CCC | 1974
| Pro | Met | Glu | Val | Ala | Lys | Ala | Val | Tyr | Gln | Cys | Trp | Glu | Arg | Thr | Pro |
| 630 | | | | | 635 | | | | | 640 | | | | | 645 |

| | | | | | | | | | | | | | | | | |
|---|---|---|---|---|---|---|---|---|---|---|---|---|---|---|---|---|
| ACT | GTC | CTC | GAA | GCT | GGA | GAG | GCC | ACT | GTC | TGT | CTC | ACT | GTC | CAC | AAA | 2022 |
| Thr | Val | Leu | Glu | Ala | Gly | Glu | Ala | Thr | Val | Cys | Leu | Thr | Val | His | Lys | |
| | | | | 650 | | | | 655 | | | | | | 660 | | |
| GGC | TCA | CCT | GAC | CTG | TTA | GGT | AAT | GTC | CAA | GGC | TCT | GTC | AGG | TAT | GAT | 2070 |
| Gly | Ser | Pro | Asp | Leu | Leu | Gly | Asn | Val | Gln | Gly | Ser | Val | Arg | Tyr | Asp | |
| | | | 665 | | | | | 670 | | | | | 675 | | | |
| CTG | GCG | TTA | GAT | CCG | GGC | CGC | CTG | ATT | TCT | CGT | GCC | ATT | TTT | GAT | GAG | 2118 |
| Leu | Ala | Leu | Asp | Pro | Gly | Arg | Leu | Ile | Ser | Arg | Ala | Ile | Phe | Asp | Glu | |
| | | | 680 | | | | | 685 | | | | | 690 | | | |
| ACT | AAG | AAC | TGC | ACT | TTG | ACG | GGA | AGG | AAG | ACT | CTG | GGG | CTT | GGT | GAT | 2166 |
| Thr | Lys | Asn | Cys | Thr | Leu | Thr | Gly | Arg | Lys | Thr | Leu | Gly | Leu | Gly | Asp | |
| | | 695 | | | | | 700 | | | | | 705 | | | | |
| CAC | TGC | GAA | ACA | GTG | AAG | CTG | CTT | TTG | CCG | GAC | TGT | GTG | GAA | GAT | GCA | 2214 |
| His | Cys | Glu | Thr | Val | Lys | Leu | Leu | Leu | Pro | Asp | Cys | Val | Glu | Asp | Ala | |
| 710 | | | | | 715 | | | | | 720 | | | | | 725 | |
| GTG | AGC | CCT | ATC | ATC | CTG | CGC | CTC | AAC | TTT | TCC | CTG | GTG | AGA | GAC | TCT | 2262 |
| Val | Ser | Pro | Ile | Ile | Leu | Arg | Leu | Asn | Phe | Ser | Leu | Val | Arg | Asp | Ser | |
| | | | | 730 | | | | | 735 | | | | | 740 | | |
| GCT | TCA | CCC | AGG | AAC | CTG | CAT | CCT | GTG | CTG | GCT | GTG | GGC | TCA | CAA | GAC | 2310 |
| Ala | Ser | Pro | Arg | Asn | Leu | His | Pro | Val | Leu | Ala | Val | Gly | Ser | Gln | Asp | |
| | | | 745 | | | | | 750 | | | | | 755 | | | |
| CAC | ATA | ACT | GCT | TCT | CTG | CCG | TTT | GAG | AAG | AAC | TGT | AAG | CAA | GAA | CTC | 2358 |
| His | Ile | Thr | Ala | Ser | Leu | Pro | Phe | Glu | Lys | Asn | Cys | Lys | Gln | Glu | Leu | |
| | | 760 | | | | | 765 | | | | | 770 | | | | |
| CTG | TGT | GAG | GGG | GAC | CTG | GGC | ATC | AGC | TTT | AAC | TTC | TCA | GGC | CTG | CAG | 2406 |
| Leu | Cys | Glu | Gly | Asp | Leu | Gly | Ile | Ser | Phe | Asn | Phe | Ser | Gly | Leu | Gln | |
| | 775 | | | | | 780 | | | | | 785 | | | | | |
| GTC | TTG | GTG | GTG | GGA | GGC | TCC | CCA | GAG | CTC | ACT | GTG | ACA | GTC | ACT | GTG | 2454 |
| Val | Leu | Val | Val | Gly | Gly | Ser | Pro | Glu | Leu | Thr | Val | Thr | Val | Thr | Val | |
| 790 | | | | | 795 | | | | | 800 | | | | | 805 | |
| TGG | AAT | GAG | GGT | GAG | GAC | AGC | TAT | GGA | ACT | TTA | GTC | AAG | TTC | TAC | TAC | 2502 |
| Trp | Asn | Glu | Gly | Glu | Asp | Ser | Tyr | Gly | Thr | Leu | Val | Lys | Phe | Tyr | Tyr | |
| | | | | 810 | | | | | 815 | | | | | 820 | | |
| CCA | GCA | GGG | CTA | TCT | TAC | CGA | CGG | GTA | ACA | GGG | ACT | CAG | CAA | CCT | CAT | 2550 |
| Pro | Ala | Gly | Leu | Ser | Tyr | Arg | Arg | Val | Thr | Gly | Thr | Gln | Gln | Pro | His | |
| | | | 825 | | | | | 830 | | | | | 835 | | | |
| CAG | TAC | CCA | CTA | CGC | TTG | GCC | TGT | GAG | GCT | GAG | CCC | GCT | GCC | CAG | GAG | 2598 |
| Gln | Tyr | Pro | Leu | Arg | Leu | Ala | Cys | Glu | Ala | Glu | Pro | Ala | Ala | Gln | Glu | |
| | | 840 | | | | | 845 | | | | | 850 | | | | |
| GAC | CTG | AGG | AGC | AGC | AGC | TGT | AGC | ATT | AAT | CAC | CCC | ATC | TTC | CGA | GAA | 2646 |
| Asp | Leu | Arg | Ser | Ser | Ser | Cys | Ser | Ile | Asn | His | Pro | Ile | Phe | Arg | Glu | |
| | 855 | | | | | 860 | | | | | 865 | | | | | |
| GGT | GCA | AAG | ACC | ACC | TTC | ATG | ATC | ACA | TTC | GAT | GTC | TCC | TAC | AAG | GCC | 2694 |
| Gly | Ala | Lys | Thr | Thr | Phe | Met | Ile | Thr | Phe | Asp | Val | Ser | Tyr | Lys | Ala | |
| 870 | | | | | 875 | | | | | 880 | | | | | 885 | |
| TTC | CTA | GGA | GAC | AGG | TTG | CTT | CTG | AGG | GCC | AAA | GCC | AGC | AGT | GAG | AAT | 2742 |
| Phe | Leu | Gly | Asp | Arg | Leu | Leu | Leu | Arg | Ala | Lys | Ala | Ser | Ser | Glu | Asn | |
| | | | | 890 | | | | | 895 | | | | | 900 | | |
| AAT | AAG | CCT | GAT | ACC | AAC | AAG | ACT | GCC | TTC | CAG | CTG | GAG | CTC | CCA | GTG | 2790 |
| Asn | Lys | Pro | Asp | Thr | Asn | Lys | Thr | Ala | Phe | Gln | Leu | Glu | Leu | Pro | Val | |
| | | | 905 | | | | | 910 | | | | | 915 | | | |
| AAG | TAC | ACC | GTC | TAT | ACC | CTG | ATC | AGT | AGG | CAA | GAA | GAT | TCC | ACC | AAC | 2838 |
| Lys | Tyr | Thr | Val | Tyr | Thr | Leu | Ile | Ser | Arg | Gln | Glu | Asp | Ser | Thr | Asn | |
| | | 920 | | | | | 925 | | | | | 930 | | | | |
| CAT | GTC | AAC | TTT | TCA | TCT | TCC | CAC | GGG | GGG | AGA | AGG | CAA | GAA | GCC | GCA | 2886 |
| His | Val | Asn | Phe | Ser | Ser | Ser | His | Gly | Gly | Arg | Arg | Gln | Glu | Ala | Ala | |
| | 935 | | | | | 940 | | | | | 945 | | | | | |
| CAT | CGC | TAT | CGT | GTG | AAT | AAC | CTG | AGT | CCA | CTG | AAG | CTG | GCC | GTC | AGA | 2934 |
| His | Arg | Tyr | Arg | Val | Asn | Asn | Leu | Ser | Pro | Leu | Lys | Leu | Ala | Val | Arg | |
| 950 | | | | | 955 | | | | | 960 | | | | | 965 | |

| | | | | | | | | | | | | | | | | |
|---|---|---|---|---|---|---|---|---|---|---|---|---|---|---|---|---|
| GTT | AAC | TTC | TGG | GTC | CCT | GTC | CTT | CTG | AAC | GGT | GTG | GCT | GTG | TGG | GAC | 2982 |
| Val | Asn | Phe | Trp | Val | Pro | Val | Leu | Leu | Asn | Gly | Val | Ala | Val | Trp | Asp | |
| | | | 970 | | | | | 975 | | | | | | 980 | | |
| GTG | ACT | CTG | AGC | AGC | CCA | GCA | CAG | GGT | GTC | TCC | TGC | GTG | TCC | CAG | ATG | 3030 |
| Val | Thr | Leu | Ser | Ser | Pro | Ala | Gln | Gly | Val | Ser | Cys | Val | Ser | Gln | Met | |
| | | | 985 | | | | | 990 | | | | | 995 | | | |
| AAA | CCT | CCT | CAG | AAT | CCC | GAC | TTT | CTG | ACC | CAG | ATT | CAG | AGA | CGT | TCT | 3078 |
| Lys | Pro | Pro | Gln | Asn | Pro | Asp | Phe | Leu | Thr | Gln | Ile | Gln | Arg | Arg | Ser | |
| | | | 1000 | | | | | 1005 | | | | | 1010 | | | |
| GTG | CTG | GAC | TGC | TCC | ATT | GCT | GAC | TGC | CTG | CAC | TTC | CGC | TGT | GAC | ATC | 3126 |
| Val | Leu | Asp | Cys | Ser | Ile | Ala | Asp | Cys | Leu | His | Phe | Arg | Cys | Asp | Ile | |
| | | | 1015 | | | | | 1020 | | | | | 1025 | | | |
| CCC | TCC | TTG | GAC | ATC | CAG | GAT | GAA | CTT | GAC | TTC | ATT | CTG | AGG | GGC | AAC | 3174 |
| Pro | Ser | Leu | Asp | Ile | Gln | Asp | Glu | Leu | Asp | Phe | Ile | Leu | Arg | Gly | Asn | |
| 1030 | | | | | 1035 | | | | | 1040 | | | | | 1045 | |
| CTC | AGC | TTC | GGC | TGG | GTC | AGT | CAG | ACA | TTG | CAG | GAA | AAG | GTG | TTG | CTT | 3222 |
| Leu | Ser | Phe | Gly | Trp | Val | Ser | Gln | Thr | Leu | Gln | Glu | Lys | Val | Leu | Leu | |
| | | | | 1050 | | | | | 1055 | | | | | 1060 | | |
| GTG | AGT | GAG | GCT | GAA | ATC | ACT | TTC | GAC | ACA | TCT | GTG | TAC | TCC | CAG | CTG | 3270 |
| Val | Ser | Glu | Ala | Glu | Ile | Thr | Phe | Asp | Thr | Ser | Val | Tyr | Ser | Gln | Leu | |
| | | | 1065 | | | | | 1070 | | | | | 1075 | | | |
| CCA | GGA | CAG | GAG | GCA | TTT | CTG | AGA | GCC | CAG | GTG | GAG | ACA | ACG | TTA | GAA | 3318 |
| Pro | Gly | Gln | Glu | Ala | Phe | Leu | Arg | Ala | Gln | Val | Glu | Thr | Thr | Leu | Glu | |
| | | | 1080 | | | | | 1085 | | | | | 1090 | | | |
| GAA | TAC | GTG | GTC | TAT | GAG | CCC | ATC | TTC | CTC | GTG | GCG | GGC | AGC | TCG | GTG | 3366 |
| Glu | Tyr | Val | Val | Tyr | Glu | Pro | Ile | Phe | Leu | Val | Ala | Gly | Ser | Ser | Val | |
| | | | 1095 | | | | | 1100 | | | | | 1105 | | | |
| GGA | GGT | CTG | CTG | TTA | CTG | GCT | CTC | ATC | ACA | GTG | GTA | CTG | TAC | AAG | CTT | 3414 |
| Gly | Gly | Leu | Leu | Leu | Leu | Ala | Leu | Ile | Thr | Val | Val | Leu | Tyr | Lys | Leu | |
| 1110 | | | | | 1115 | | | | | 1120 | | | | | 1125 | |
| GGC | TTC | TYC | AAA | CGT | CAG | TAC | AAA | GAA | ATG | CTG | GAC | GGC | AAG | GCT | GCA | 3462 |
| Gly | Phe | Xaa | Lys | Arg | Gln | Tyr | Lys | Glu | Met | Leu | Asp | Gly | Lys | Ala | Ala | |
| | | | | 1130 | | | | | 1135 | | | | | 1140 | | |
| GAT | CCT | GTC | ACA | GCC | GGC | CAG | GCA | GAT | TTC | GGC | TGT | GAG | ACT | CCT | CCA | 3510 |
| Asp | Pro | Val | Thr | Ala | Gly | Gln | Ala | Asp | Phe | Gly | Cys | Glu | Thr | Pro | Pro | |
| | | | 1145 | | | | | 1150 | | | | | 1155 | | | |
| TAT | CTC | GTG | AGC | TAGGAATCCA | | CTCTCCTGCC | | TATCTCTGCA | | ATGAAGATTG | | | | | | 3562 |
| Tyr | Leu | Val | Ser | | | | | | | | | | | | | |
| | | | 1160 | | | | | | | | | | | | | |
| GTCCTGCCTA | | TGAGTCTACT | | GGCATGGGAA | | CGAGT | | | | | | | | | | 3597 |

( 2 ) INFORMATION FOR SEQ ID NO:55:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:55:

| | | | | | | | | | | | | | | |
|---|---|---|---|---|---|---|---|---|---|---|---|---|---|---|
| Met | Ala | Gly | Gly | Val | Val | Ile | Leu | Leu | Cys | Gly | Trp | Val | Leu | Ala | Ser |
| 1 | | | | 5 | | | | | 10 | | | | | 15 | |
| Cys | His | Gly | Ser | Asn | Leu | Asp | Val | Glu | Glu | Pro | Ile | Val | Phe | Arg | Glu |
| | | | 20 | | | | | 25 | | | | | 30 | | |
| Asp | Ala | Ala | Ser | Phe | Gly | Gln | Thr | Val | Val | Gln | Phe | Gly | Gly | Ser | Arg |
| | | 35 | | | | | 40 | | | | | 45 | | | |
| Leu | Val | Val | Gly | Ala | Pro | Leu | Glu | Ala | Val | Ala | Val | Asn | Gln | Thr | Gly |
| | 50 | | | | | 55 | | | | | 60 | | | | |
| Arg | Leu | Tyr | Asp | Cys | Ala | Pro | Ala | Thr | Gly | Met | Cys | Gln | Pro | Ile | Val |

```
       65                    70                    75                    80
Leu  Arg  Ser  Pro  Leu  Glu  Ala  Val  Asn  Met  Ser  Leu  Gly  Leu  Ser  Leu
                    85                    90                              95
Val  Thr  Ala  Thr  Asn  Asn  Ala  Gln  Leu  Leu  Ala  Cys  Gly  Pro  Thr  Ala
               100                    105                   110
Gln  Arg  Ala  Cys  Val  Lys  Asn  Met  Tyr  Ala  Lys  Gly  Ser  Cys  Leu  Leu
          115                    120                    125
Leu  Gly  Ser  Ser  Leu  Gln  Phe  Ile  Gln  Ala  Val  Pro  Ala  Ser  Met  Pro
     130                    135                    140
Glu  Cys  Pro  Arg  Gln  Glu  Met  Asp  Ile  Ala  Phe  Leu  Ile  Asp  Gly  Ser
145                    150                    155                         160
Gly  Ser  Ile  Asn  Gln  Arg  Asp  Phe  Ala  Gln  Met  Lys  Asp  Phe  Val  Lys
                    165                    170                    175
Ala  Leu  Met  Gly  Glu  Phe  Ala  Ser  Thr  Ser  Thr  Leu  Phe  Ser  Leu  Met
               180                    185                    190
Gln  Tyr  Ser  Asn  Ile  Leu  Lys  Thr  His  Phe  Thr  Phe  Thr  Glu  Phe  Lys
          195                    200                    205
Asn  Ile  Leu  Asp  Pro  Gln  Ser  Leu  Val  Asp  Pro  Ile  Val  Gln  Leu  Gln
     210                    215                    220
Gly  Leu  Thr  Tyr  Thr  Ala  Thr  Gly  Ile  Arg  Thr  Val  Met  Glu  Glu  Leu
225                    230                    235                         240
Phe  His  Ser  Lys  Asn  Gly  Ser  Arg  Lys  Ser  Ala  Lys  Lys  Ile  Leu  Leu
                    245                    250                         255
Val  Ile  Thr  Asp  Gly  Gln  Lys  Tyr  Arg  Asp  Pro  Leu  Glu  Tyr  Ser  Asp
               260                    265                    270
Val  Ile  Pro  Ala  Ala  Asp  Lys  Ala  Gly  Ile  Ile  Arg  Tyr  Ala  Ile  Gly
          275                    280                    285
Val  Gly  Asp  Ala  Phe  Gln  Glu  Pro  Thr  Ala  Leu  Lys  Glu  Leu  Asn  Thr
     290                    295                    300
Ile  Gly  Ser  Ala  Pro  Pro  Gln  Asp  His  Val  Phe  Lys  Val  Gly  Asn  Phe
305                    310                    315                         320
Ala  Ala  Leu  Arg  Ser  Ile  Gln  Arg  Gln  Leu  Gln  Glu  Lys  Ile  Phe  Ala
                    325                    330                         335
Ile  Glu  Gly  Thr  Gln  Ser  Arg  Ser  Ser  Ser  Phe  Gln  His  Glu  Met
               340                    345                    350
Ser  Gln  Glu  Gly  Phe  Ser  Ser  Ala  Leu  Thr  Ser  Asp  Gly  Pro  Val  Leu
          355                    360                    365
Gly  Ala  Val  Gly  Ser  Phe  Ser  Trp  Ser  Gly  Gly  Ala  Phe  Leu  Tyr  Pro
     370                    375                    380
Pro  Asn  Thr  Arg  Pro  Thr  Phe  Ile  Asn  Met  Ser  Gln  Glu  Asn  Val  Asp
385                    390                    395                         400
Met  Arg  Asp  Ser  Tyr  Leu  Gly  Tyr  Ser  Thr  Ala  Val  Ala  Phe  Trp  Lys
                    405                    410                         415
Gly  Val  His  Ser  Leu  Ile  Leu  Gly  Ala  Pro  Arg  His  Gln  His  Thr  Gly
               420                    425                    430
Lys  Val  Val  Ile  Phe  Thr  Gln  Glu  Ala  Arg  His  Trp  Arg  Pro  Lys  Ser
          435                    440                    445
Glu  Val  Arg  Gly  Thr  Gln  Ile  Gly  Ser  Tyr  Phe  Gly  Ala  Ser  Leu  Cys
     450                    455                    460
Ser  Val  Asp  Val  Asp  Arg  Asp  Gly  Ser  Xaa  Asp  Leu  Val  Leu  Ile  Gly
465                    470                    475                         480
Ala  Pro  His  Tyr  Tyr  Glu  Gln  Thr  Arg  Gly  Gly  Gln  Val  Ser  Val  Phe
                    485                    490                         495
```

| Pro | Val | Pro | Gly | Val | Arg | Gly | Arg | Trp | Gln | Cys | Glu | Ala | Thr | Leu | His |
|---|---|---|---|---|---|---|---|---|---|---|---|---|---|---|---|
| | | | 500 | | | | 505 | | | | | | 510 | | |
| Gly | Glu | Gln | Gly | His | Pro | Trp | Gly | Arg | Phe | Gly | Val | Ala | Leu | Thr | Val |
| | | | 515 | | | | 520 | | | | | 525 | | | |
| Leu | Gly | Asp | Val | Asn | Gly | Asp | Asn | Leu | Ala | Asp | Val | Ala | Ile | Gly | Ala |
| | 530 | | | | | 535 | | | | | 540 | | | | |
| Pro | Gly | Glu | Glu | Glu | Ser | Arg | Gly | Ala | Val | Tyr | Ile | Phe | His | Gly | Ala |
| 545 | | | | | 550 | | | | | 555 | | | | | 560 |
| Ser | Arg | Leu | Glu | Ile | Met | Pro | Ser | Pro | Ser | Gln | Arg | Val | Thr | Gly | Ser |
| | | | | 565 | | | | 570 | | | | | 575 | | |
| Gln | Leu | Ser | Leu | Arg | Leu | Gln | Tyr | Phe | Gly | Gln | Ser | Leu | Ser | Gly | Gly |
| | | | 580 | | | | 585 | | | | | 590 | | | |
| Gln | Asp | Leu | Thr | Gln | Asp | Gly | Leu | Val | Asp | Leu | Ala | Val | Gly | Ala | Gln |
| | | 595 | | | | 600 | | | | | 605 | | | | |
| Gly | His | Val | Leu | Leu | Leu | Arg | Ser | Leu | Pro | Leu | Leu | Lys | Val | Glu | Leu |
| | 610 | | | | 615 | | | | | 620 | | | | | |
| Ser | Ile | Arg | Phe | Ala | Pro | Met | Glu | Val | Ala | Lys | Ala | Val | Tyr | Gln | Cys |
| 625 | | | | | 630 | | | | 635 | | | | | | 640 |
| Trp | Glu | Arg | Thr | Pro | Thr | Val | Leu | Glu | Ala | Gly | Glu | Ala | Thr | Val | Cys |
| | | | | 645 | | | | | 650 | | | | | 655 | |
| Leu | Thr | Val | His | Lys | Gly | Ser | Pro | Asp | Leu | Leu | Gly | Asn | Val | Gln | Gly |
| | | | 660 | | | | 665 | | | | | 670 | | | |
| Ser | Val | Arg | Tyr | Asp | Leu | Ala | Leu | Asp | Pro | Gly | Arg | Leu | Ile | Ser | Arg |
| | | 675 | | | | 680 | | | | | 685 | | | | |
| Ala | Ile | Phe | Asp | Glu | Thr | Lys | Asn | Cys | Thr | Leu | Thr | Gly | Arg | Lys | Thr |
| | 690 | | | | 695 | | | | | 700 | | | | | |
| Leu | Gly | Leu | Gly | Asp | His | Cys | Glu | Thr | Val | Lys | Leu | Leu | Leu | Pro | Asp |
| 705 | | | | | 710 | | | | 715 | | | | | | 720 |
| Cys | Val | Glu | Asp | Ala | Val | Ser | Pro | Ile | Ile | Leu | Arg | Leu | Asn | Phe | Ser |
| | | | | 725 | | | | 730 | | | | | 735 | | |
| Leu | Val | Arg | Asp | Ser | Ala | Ser | Pro | Arg | Asn | Leu | His | Pro | Val | Leu | Ala |
| | | | 740 | | | | 745 | | | | | 750 | | | |
| Val | Gly | Ser | Gln | Asp | His | Ile | Thr | Ala | Ser | Leu | Pro | Phe | Glu | Lys | Asn |
| | | 755 | | | | 760 | | | | | 765 | | | | |
| Cys | Lys | Gln | Glu | Leu | Leu | Cys | Glu | Gly | Asp | Leu | Gly | Ile | Ser | Phe | Asn |
| | 770 | | | | | 775 | | | | | 780 | | | | |
| Phe | Ser | Gly | Leu | Gln | Val | Leu | Val | Val | Gly | Gly | Ser | Pro | Glu | Leu | Thr |
| 785 | | | | | 790 | | | | | 795 | | | | | 800 |
| Val | Thr | Val | Thr | Val | Trp | Asn | Glu | Gly | Glu | Asp | Ser | Tyr | Gly | Thr | Leu |
| | | | | 805 | | | | 810 | | | | | 815 | | |
| Val | Lys | Phe | Tyr | Tyr | Pro | Ala | Gly | Leu | Ser | Tyr | Arg | Arg | Val | Thr | Gly |
| | | | 820 | | | | 825 | | | | | 830 | | | |
| Thr | Gln | Gln | Pro | His | Gln | Tyr | Pro | Leu | Arg | Leu | Ala | Cys | Glu | Ala | Glu |
| | | | 835 | | | | 840 | | | | | 845 | | | |
| Pro | Ala | Ala | Gln | Glu | Asp | Leu | Arg | Ser | Ser | Ser | Cys | Ser | Ile | Asn | His |
| | 850 | | | | | 855 | | | | | 860 | | | | |
| Pro | Ile | Phe | Arg | Glu | Gly | Ala | Lys | Thr | Thr | Phe | Met | Ile | Thr | Phe | Asp |
| 865 | | | | | 870 | | | | | 875 | | | | | 880 |
| Val | Ser | Tyr | Lys | Ala | Phe | Leu | Gly | Asp | Arg | Leu | Leu | Leu | Arg | Ala | Lys |
| | | | | 885 | | | | | 890 | | | | | 895 | |
| Ala | Ser | Ser | Glu | Asn | Asn | Lys | Pro | Asp | Thr | Asn | Lys | Thr | Ala | Phe | Gln |
| | | | | 900 | | | | 905 | | | | | 910 | | |
| Leu | Glu | Leu | Pro | Val | Lys | Tyr | Thr | Val | Tyr | Thr | Leu | Ile | Ser | Arg | Gln |
| | | | 915 | | | | 920 | | | | | 925 | | | |

```
Glu  Asp  Ser  Thr  Asn  His  Val  Asn  Phe  Ser  Ser  Ser  His  Gly  Gly  Arg
     930                 935                 940

Arg  Gln  Glu  Ala  Ala  His  Arg  Tyr  Arg  Val  Asn  Asn  Leu  Ser  Pro  Leu
945                      950                 955                           960

Lys  Leu  Ala  Val  Arg  Val  Asn  Phe  Trp  Val  Pro  Val  Leu  Leu  Asn  Gly
                    965                 970                      975

Val  Ala  Val  Trp  Asp  Val  Thr  Leu  Ser  Ser  Pro  Ala  Gln  Gly  Val  Ser
               980                      985                      990

Cys  Val  Ser  Gln  Met  Lys  Pro  Pro  Gln  Asn  Pro  Asp  Phe  Leu  Thr  Gln
          995                      1000                1005

Ile  Gln  Arg  Arg  Ser  Val  Leu  Asp  Cys  Ser  Ile  Ala  Asp  Cys  Leu  His
          1010                1015                1020

Phe  Arg  Cys  Asp  Ile  Pro  Ser  Leu  Asp  Ile  Gln  Asp  Glu  Leu  Asp  Phe
1025                1030                     1035                          1040

Ile  Leu  Arg  Gly  Asn  Leu  Ser  Phe  Gly  Trp  Val  Ser  Gln  Thr  Leu  Gln
                    1045                     1050                1055

Glu  Lys  Val  Leu  Leu  Val  Ser  Glu  Ala  Glu  Ile  Thr  Phe  Asp  Thr  Ser
               1060                1065                     1070

Val  Tyr  Ser  Gln  Leu  Pro  Gly  Gln  Glu  Ala  Phe  Leu  Arg  Ala  Gln  Val
          1075                1080                     1085

Glu  Thr  Thr  Leu  Glu  Glu  Tyr  Val  Val  Tyr  Glu  Pro  Ile  Phe  Leu  Val
     1090                1095                1100

Ala  Gly  Ser  Ser  Val  Gly  Gly  Leu  Leu  Leu  Leu  Ala  Leu  Ile  Thr  Val
1105                1110                     1115                          1120

Val  Leu  Tyr  Lys  Leu  Gly  Xaa  Xaa  Lys  Arg  Gln  Tyr  Lys  Glu  Met  Leu
                    1125                1130                     1135

Asp  Gly  Lys  Ala  Ala  Asp  Pro  Val  Thr  Xaa  Gly  Gln  Ala  Asp  Phe  Gly
               1140                     1145                1150

Cys  Glu  Thr  Pro  Pro  Tyr  Leu  Val  Ser
          1155                1160
```

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

CCTGTCATGG GTCTAACCTG          20

( 2 ) INFORMATION FOR SEQ ID NO:57:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

AGGTTAGACC CATGACAGG          19

( 2 ) INFORMATION FOR SEQ ID NO:58:

( i ) SEQUENCE CHARACTERISTICS:

( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:58:

GGCCTTGCAG CTGGACAATG 20

( 2 ) INFORMATION FOR SEQ ID NO:59:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:59:

CCAAAGCTGG CTGCATCCTC TC 22

( 2 ) INFORMATION FOR SEQ ID NO:60:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:60:

CCGCCTGCCA CTGGCGTGTG C 21

( 2 ) INFORMATION FOR SEQ ID NO:61:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:61:

CCCAGATGAA GGACTTCGTC AA 22

( 2 ) INFORMATION FOR SEQ ID NO:62:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:62:

GCTGGGATCA TTCGCTATGC 20

( 2 ) INFORMATION FOR SEQ ID NO:63:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear (ii) MOLECULE TYPE: DNA (xi) SEQUENCE DESCRIPTION: SEQ ID NO:63:

CAATGGATGG ACCAGTTCTG G   21

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:64:

CAGATCGGCT CCTACTTTGG   20

(2) INFORMATION FOR SEQ ID NO:65:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

CATGGAGCCT CGAGACAGG   19

(2) INFORMATION FOR SEQ ID NO:66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:66:

CCACTGTCCT CGAAGCTGGA G   21

(2) INFORMATION FOR SEQ ID NO:67:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:67:

CTTCGTCCTG TGCTGGCTGT GGGCTC   26

(2) INFORMATION FOR SEQ ID NO:68:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:68:

CGCCTGGCAT GTGAGGCTGA G   21

( 2 ) INFORMATION FOR SEQ ID NO:69:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:69:

CCGTGATCAG TAGGCAGGAA G                          21

( 2 ) INFORMATION FOR SEQ ID NO:70:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:70:

GTCACAGAGG GAACCTCC                            18

( 2 ) INFORMATION FOR SEQ ID NO:71:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:71:

GCTCCTGAGT GAGGCTGAAA TCA                      23

( 2 ) INFORMATION FOR SEQ ID NO:72:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:72:

GAGATGCTGG ATCTACCATC TGC                      23

( 2 ) INFORMATION FOR SEQ ID NO:73:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:73:

CTGAGCTGGG AGATTTTTAT GG                       22

( 2 ) INFORMATION FOR SEQ ID NO:74:

( i ) SEQUENCE CHARACTERISTICS:

( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:74:

GTGGATCAGC ACTGAAATCT G 21

( 2 ) INFORMATION FOR SEQ ID NO:75:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:75:

CGTTTGAAGA AGCCAAGCTT G 21

( 2 ) INFORMATION FOR SEQ ID NO:76:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:76:

CACAGCGGAG GTGCAGGCAG 20

( 2 ) INFORMATION FOR SEQ ID NO:77:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:77:

CTCACTGCTT GCGCTGGC 18

( 2 ) INFORMATION FOR SEQ ID NO:78:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:78:

CGGTAAGATA GCTCTGCTGG 20

( 2 ) INFORMATION FOR SEQ ID NO:79:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:79:

GAGCCCACAG CCAGCACAGG 20

( 2 ) INFORMATION FOR SEQ ID NO:80:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:80:

GATCCAACGC CAGATCATAC C 21

( 2 ) INFORMATION FOR SEQ ID NO:81:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:81:

CACGGCCAGG TCCACCAGGC 20

( 2 ) INFORMATION FOR SEQ ID NO:82:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:82:

CACGTCCCCT AGCACTGTCA G 21

( 2 ) INFORMATION FOR SEQ ID NO:83:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:83:

TTGACGAAGT CCTTCATCTG GG 22

( 2 ) INFORMATION FOR SEQ ID NO:84:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:84:

GAACTGCAAG CTGGAGCCCA G 21

( 2 ) INFORMATION FOR SEQ ID NO:85:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:85:

CTGGATGCTG CGAAGTGCTA C          21

( 2 ) INFORMATION FOR SEQ ID NO:86:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: cDNA ( x i ) SEQUENCE DESCRIPTION: SEQ ID NO:86:

GCCTTGGAGC TGGACGATGG C          21

( 2 ) INFORMATION FOR SEQ ID NO:87:

( i ) SEQUENCE CHARACTERISTICS:
           ( A ) LENGTH: 33 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:87:

GTAAGATCTC CAGAGTGTCC AAGACAAGAG ATG          33

( 2 ) INFORMATION FOR SEQ ID NO:88:

( i ) SEQUENCE CHARACTERISTICS:
           ( A ) LENGTH: 33 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:88:

CTTCTCGAGT GTGAGAGCTG AACTGAAACC TTC          33

( 2 ) INFORMATION FOR SEQ ID NO:89:

( i ) SEQUENCE CHARACTERISTICS:
           ( A ) LENGTH: 32 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:89:

CGCTGTGACG TCAGAGTTGA GTCCAAATAT GG          32

( 2 ) INFORMATION FOR SEQ ID NO:90:

( i ) SEQUENCE CHARACTERISTICS:

(A) LENGTH: 21 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:90:

GGTGACACTA TAGAATAGGG C                                                            21

(2) INFORMATION FOR SEQ ID NO:91:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:91:

AAGCAGGAGCTCCTGTGT                                                                 18

(2) INFORMATION FOR SEQ ID NO:92:

(i) SEQUENCE CHARACTERISTICS:
(A) LENGTH: 852 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 61..852

(xi) SEQUENCE DESCRIPTION: SEQ ID NO:92:

```
TGATCTCCCT CCAGGCCACT GTTCCCTCTC CACTTCCCCT CACCGCTGCA CTGCTCAGAG                  60

ATG GCC CTT GGG GCT GTG GTC CTC CTT GGG GTC CTG GCT TCT TAC CAC                  108
Met Ala Leu Gly Ala Val Val Leu Leu Gly Val Leu Ala Ser Tyr His
 1               5                  10                  15

GGA TTC AAC TTG GAC GTG ATG AGC GGT GAT CTT CCA GGA AGA CGC AGC                  156
Gly Phe Asn Leu Asp Val Met Ser Gly Asp Leu Pro Gly Arg Arg Ser
                20                  25                  30

GGG CTT CGG GCA GAG CGT GAT GCA GTT TGG GGA TCT CGA CTC GTG GTG                  204
Gly Leu Arg Ala Glu Arg Asp Ala Val Trp Gly Ser Arg Leu Val Val
            35                  40                  45

GGA GCC CCC CTG GCG GTG GTG TCG GCC AAC CAC ACA GGA CGG CTG TAC                  252
Gly Ala Pro Leu Ala Val Val Ser Ala Asn His Thr Gly Arg Leu Tyr
    50                  55                  60

GAG TGT GCG CCT GCC TCC GGC ACC TGC ACG CCC ATT TTC CCA TTC ATG                  300
Glu Cys Ala Pro Ala Ser Gly Thr Cys Thr Pro Ile Phe Pro Phe Met
 65                 70                  75                  80

CCC CCC GAA GCC GTG AAC ATG TCC CTG GGC CTG TCC CTG GCA GCC TCC                  348
Pro Pro Glu Ala Val Asn Met Ser Leu Gly Leu Ser Leu Ala Ala Ser
                85                  90                  95

CCC AAC CAT TCC CAG CTG CTG GCT TGT GGC CCG ACC GTG CAT AGA GCC                  396
Pro Asn His Ser Gln Leu Leu Ala Cys Gly Pro Thr Val His Arg Ala
                100                 105                 110

TGC GGG GAG GAC GTG TAC GCC CAG GGT TTC TGT GTG CTG CTG GAT GCC                  444
Cys Gly Glu Asp Val Tyr Ala Gln Gly Phe Cys Val Leu Leu Asp Ala
            115                 120                 125

CAC GCA CAG CCC ATC GGG ACT GTG CCA GCT GCC CTG CCC GAG TGC CCA                  492
His Ala Gln Pro Ile Gly Thr Val Pro Ala Ala Leu Pro Glu Cys Pro
    130                 135                 140
```

```
GAT  CAA  GAG  ATG  GAC  ATT  GTC  TTC  CTG  ATT  GAC  GGC  TCT  GGC  AGC  ATT     540
Asp  Gln  Glu  Met  Asp  Ile  Val  Phe  Leu  Ile  Asp  Gly  Ser  Gly  Ser  Ile
145                      150                      155                      160

AGC  TCA  AAT  GAC  TTC  CGC  AAG  ATG  AAG  GAC  TTT  GTC  AGA  GCT  GTG  ATG     588
Ser  Ser  Asn  Asp  Phe  Arg  Lys  Met  Lys  Asp  Phe  Val  Arg  Ala  Val  Met
                    165                      170                      175

GAC  CAG  TTC  AAG  GAC  ACC  AAC  ACC  CAG  TTC  TCG  CTG  ATG  CAG  TAC  TCC     636
Asp  Gln  Phe  Lys  Asp  Thr  Asn  Thr  Gln  Phe  Ser  Leu  Met  Gln  Tyr  Ser
               180                      185                      190

AAT  GTG  CTG  GTG  ACA  CAT  TTC  ACC  TTC  AGC  AGC  TTC  CGG  AAC  AGC  TCC     684
Asn  Val  Leu  Val  Thr  His  Phe  Thr  Phe  Ser  Ser  Phe  Arg  Asn  Ser  Ser
          195                      200                      205

AAT  CCT  CAG  GGC  CTA  GTG  GAG  CCC  ATT  GTG  CAG  CTG  ACA  GGC  CTC  ACG     732
Asn  Pro  Gln  Gly  Leu  Val  Glu  Pro  Ile  Val  Gln  Leu  Thr  Gly  Leu  Thr
210                      215                      220

TTC  ACG  GCC  ACA  GGG  ATC  CTG  AAA  GTG  GTG  ACA  GAG  CTG  TTT  CAA  ACC     780
Phe  Thr  Ala  Thr  Gly  Ile  Leu  Lys  Val  Val  Thr  Glu  Leu  Phe  Gln  Thr
225                      230                      235                      240

AAG  AAC  GGG  GCC  CGC  GAA  AGT  GCC  AAG  AAG  ATC  CTC  ATC  GTC  ATC  ACA     828
Lys  Asn  Gly  Ala  Arg  Glu  Ser  Ala  Lys  Lys  Ile  Leu  Ile  Val  Ile  Thr
                    245                      250                      255

GAT  GGG  CAG  AAG  TAC  AAA  GCG  GCA                                            852
Asp  Gly  Gln  Lys  Tyr  Lys  Ala  Ala
               260
```

( 2 ) INFORMATION FOR SEQ ID NO:93:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:93:

```
Met  Ala  Leu  Gly  Ala  Val  Val  Leu  Leu  Gly  Val  Leu  Ala  Ser  Tyr  His
 1                  5                      10                      15

Gly  Phe  Asn  Leu  Asp  Val  Met  Ser  Gly  Asp  Leu  Pro  Gly  Arg  Arg  Ser
                20                      25                      30

Gly  Leu  Arg  Ala  Glu  Arg  Asp  Ala  Val  Trp  Gly  Ser  Arg  Leu  Val  Val
          35                      40                      45

Gly  Ala  Pro  Leu  Ala  Val  Val  Ser  Ala  Asn  His  Thr  Gly  Arg  Leu  Tyr
     50                      55                      60

Glu  Cys  Ala  Pro  Ala  Ser  Gly  Thr  Cys  Thr  Pro  Ile  Phe  Pro  Phe  Met
65                      70                      75                      80

Pro  Pro  Glu  Ala  Val  Asn  Met  Ser  Leu  Gly  Leu  Ser  Leu  Ala  Ala  Ser
               85                       90                       95

Pro  Asn  His  Ser  Gln  Leu  Leu  Ala  Cys  Gly  Pro  Thr  Val  His  Arg  Ala
                    100                      105                      110

Cys  Gly  Glu  Asp  Val  Tyr  Ala  Gln  Gly  Phe  Cys  Val  Leu  Leu  Asp  Ala
               115                      120                      125

His  Ala  Gln  Pro  Ile  Gly  Thr  Val  Pro  Ala  Ala  Leu  Pro  Glu  Cys  Pro
          130                      135                      140

Asp  Gln  Glu  Met  Asp  Ile  Val  Phe  Leu  Ile  Asp  Gly  Ser  Gly  Ser  Ile
145                      150                      155                      160

Ser  Ser  Asn  Asp  Phe  Arg  Lys  Met  Lys  Asp  Phe  Val  Arg  Ala  Val  Met
                    165                      170                      175

Asp  Gln  Phe  Lys  Asp  Thr  Asn  Thr  Gln  Phe  Ser  Leu  Met  Gln  Tyr  Ser
               180                      185                      190
```

```
Asn  Val  Leu  Val  Thr  His  Phe  Thr  Phe  Ser  Ser  Phe  Arg  Asn  Ser  Ser
          195                      200                      205
Asn  Pro  Gln  Gly  Leu  Val  Glu  Pro  Ile  Val  Gln  Leu  Thr  Gly  Leu  Thr
     210                      215                      220
Phe  Thr  Ala  Thr  Gly  Ile  Leu  Lys  Val  Val  Thr  Glu  Leu  Phe  Gln  Thr
225                      230                      235                      240
Lys  Asn  Gly  Ala  Arg  Glu  Ser  Ala  Lys  Lys  Ile  Leu  Ile  Val  Ile  Thr
                    245                      250                      255
Asp  Gly  Gln  Lys  Tyr  Lys  Ala  Ala
                    260
```

( 2 ) INFORMATION FOR SEQ ID NO:94:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:94:

```
CTGGTCTGGA  GGTGCCTTCC  TG                                                    22
```

( 2 ) INFORMATION FOR SEQ ID NO:95:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:95:

```
CCTGAGCAGG  AGCACCTGGC  C                                                     21
```

( 2 ) INFORMATION FOR SEQ ID NO:96:

( i ) SEQUENCE CHARACTERISTICS:
        ( A ) LENGTH: 2499 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:96:

```
ATGACCTTCG  GCACTGTGCT  TCTTCTGAGT  GTCCTGGCTT  CTTATCATGG  ATTCAACCTG       60
GATGTGGAGG  AGCCTACGAT  CTTCCAGGAG  GATGCAGGCG  GCTTTGGGCA  GAGCGTGGTG      120
CAGTTCGGTG  GATCTCGACT  CGTGGTGGGA  GCACCCCTGG  AGGTGGTGGC  GGCCAACCAG      180
ACGGGACGGC  TGTATGACTG  CGCAGCTGCC  ACCGGCATGT  GCCAGCCCAT  CCCGCTGCAC      240
ATCCGCCCTG  AGGCCGTGAA  CATGTCCTTG  GGCCTGACCC  TGGCAGCCTC  CACCAACGGC      300
TCCCGGCTCC  TGGCCTGTGG  CCCGACCCTG  CACAGAGTCT  GTGGGGAGAA  CTCATACTCA      360
AAGGGTTCCT  GCCTCCTGCT  GGGCTCGCGC  TGGGAGATCA  TCCAGACAGT  CCCCGACGCC      420
ACGCCAGAGT  GTCCACATCA  AGAGATGGAC  ATCGTCTTCC  TGATTGACGG  CTCTGGAAGC      480
ATTGACCAAA  ATGACTTTAA  CCAGATGAAG  GGCTTTGTCC  AAGCTGTCAT  GGGCCAGTTT      540
GAGGGCACTG  ACACCCTGTT  TGCACTGATG  CAGTACTCAA  ACCTCCTGAA  GATCCACTTC      600
ACCTTCACCC  AATTCCGGAC  CAGCCCGAGC  CAGCAGAGCC  TGGTGGATCC  CATCGTCCAA      660
```

| | | | | | | |
|---|---|---|---|---|---|---|
| CTGAAAGGCC | TGACGTTCAC | GGCCACGGGC | ATCCTGACAG | TGGTGACACA | GCTATTTCAT | 720 |
| CATAAGAATG | GGGCCCGAAA | AAGTGCCAAG | AAGATCCTCA | TTGTCATCAC | AGATGGGCAG | 780 |
| AAGTACAAAG | ACCCCCTGGA | ATACAGTGAT | GTCATCCCCC | AGGCAGAGAA | GGCTGGCATC | 840 |
| ATCCGCTACG | CTATCGGGGT | GGGACACGCT | TTCCAGGGAC | CCACTGCCAG | GCAGGAGCTG | 900 |
| AATACCATCA | GCTCAGCGCC | TCCGCAGGAC | CACGTGTTCA | AGGTGGACAA | CTTTGCAGCC | 960 |
| CTTGGCAGCA | TCCAGAAGCA | GCTGCAGGAG | AAGATCTATG | CAGTTGAGGG | AACCCAGTCC | 1020 |
| AGGGCAAGCA | GCTCCTTCCA | GCACGAGATG | TCCCAAGAAG | GCTTCAGCAC | AGCCCTCACA | 1080 |
| ATGGATGGCC | TCTTCCTGGG | GGCTGTGGGG | AGCTTTAGCT | GGTCTGGAGG | TGCCTTCCTG | 1140 |
| TATCCCCCAA | ATATGAGCCC | CACCTTCATC | AACATGTCTC | AGGAGAATGT | GGACATGAGG | 1200 |
| GACTCTTACC | TGGGTTACTC | CACCGAGCTA | GCCCTGTGGA | AGGGGTACA | GAACCTGGTC | 1260 |
| CTGGGGGCCC | CCCGCTACCA | GCATACCGGG | AAGGCTGTCA | TCTTCACCCA | GGTGTCCAGG | 1320 |
| CAATGGAGGA | AGAAGGCCGA | AGTCACAGGG | ACGCAGATCG | GCTCCTACTT | CGGGGCCTCC | 1380 |
| CTCTGCTCCG | TGGATGTGGA | CAGCGATGGC | AGCACCGACC | TGATCCTCAT | TGGGGCCCCC | 1440 |
| CATTACTATG | AGCAGACCCG | AGGGGGCCAG | GTGTCCGTGT | GTCCCTTGCC | TAGGGGGAGG | 1500 |
| GTGCAGTGGC | AGTGTGACGC | TGTTCTCCGT | GGTGAGCAGG | GCCACCCCTG | GGGCCGCTTT | 1560 |
| GGGGCAGCCC | TGACAGTGTT | GGGGGATGTG | AATGAGGACA | AGCTGATAGA | CGTGGCCATT | 1620 |
| GGGGCCCCGG | GAGAGCAGGA | GAACCGGGGT | GCTGTCTACC | TGTTTCACGG | AGCCTCAGAA | 1680 |
| TCCGGCATCA | GCCCCTCCCA | CAGCCAGCGG | ATTGCCAGCT | CCCAGCTCTC | CCCCAGGCTG | 1740 |
| CAGTATTTTG | GGCAGGCGCT | GAGTGGGGGT | CAGGACCTCA | CCCAGGATGG | ACTGATGGAC | 1800 |
| CTGGCCGTGG | GGGCCCGGGG | CCAGGTGCTC | CTGCTCAGGA | GTCTGCCGGT | GCTGAAAGTG | 1860 |
| GGGGTGGCCA | TGAGATTCAG | CCCTGTGGAG | GTGGCCAAGG | CTGTGTACCG | GTGCTGGGAA | 1920 |
| GAGAAGCCCA | GTGCCCTGGA | AGCTGGGGAC | GCCACCGTCT | GTCTCACCAT | CCAGAAAAGC | 1980 |
| TCACTGGACC | AGCTAGGTGA | CATCCAAAGC | TCTGTCAGGT | TTGATCTGGC | ACTGGACCCA | 2040 |
| GGTCGTCTGA | CTTCTCGTGC | CATTTTCAAT | GAAACCAAGA | ACCCCACTTT | GACTCGAAGA | 2100 |
| AAAACCCTGG | GACTGGGGAT | TCACTGTGAA | ACCCTGAAGC | TGCTTTTGCC | AGTGAGGACT | 2160 |
| TTGGGTTCTG | GGAAGGGGGA | GAGAGGAGGA | GCCCAAGGCT | GGCCTGGAGC | ACCCCGTTC | 2220 |
| TCTGCTGAGC | GAGGTGGGAA | GGGTTAGGAT | GTTGGGGCTG | GAGAGAGGGA | CATTAGGGCA | 2280 |
| GGAGAACCTG | GCTCCACGGC | TTGGAGGGAG | CACTGTCAGG | GCAGTGGGGA | GTGGATGCAG | 2340 |
| TGGAGGAGGA | CTTGTGGTGG | AGCGTAGAGA | GGACAGCAGG | TTCTTGAAAG | CCTGTTCTCT | 2400 |
| CTCAGGATTG | TGTGGAGGAT | GTGGTGAGCC | CCATCATTCT | GCACCTCAAC | TTCTCACTGG | 2460 |
| TGAGAGAGCC | CATCCCCTCC | CCCCAGAACC | TGCGTCCTG | | | 2499 |

(2) INFORMATION FOR SEQ ID NO:97:

(i) SEQUENCE CHARACTERISTICS:
        (A) LENGTH: 3956 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:97:

| | | | | | | |
|---|---|---|---|---|---|---|
| TTTAACTGCA | CCAACTTTAA | AATACGCTAT | TGGAGCTGGA | ATTACCGCGG | CTGCTGGCAC | 60 |
| CAGACTTGCC | CTCCAATGGA | TCCTCGTTAA | AGGATTTAAA | GTGGACTCAT | TCCAATTACA | 120 |

-continued

| | | | | | | |
|---|---|---|---|---|---|---|
| GGGCCTCGAA | AGAGTCCTGT | ATTGTTATTT | TTCGTCACTA | CCTCCCCGGG | TCGGGAGTGG | 180 |
| GTAATTTGCG | CGCCTGCTGC | CTTCCTTGGA | TGTGGTAGCC | GTTTCTCAGG | CTCCCTCTCC | 240 |
| GGAATCGAAC | CCTGATTCCC | CGTCACCCGT | GGTCACCATG | GTAGGCACGT | GCAGTTCGGT | 300 |
| GGATCTCGAC | TCGTGGTGGG | AGCACCCCTG | GAGGTGGTGG | CGGCCAACCA | GACGGGACGG | 360 |
| CTGTATGACT | GCGCAGCTGC | CACCGGCATG | TGCCAGCCCA | TCCCGCTGCA | CATCCGCCCT | 420 |
| GAGGCCGTGA | ACATGTCCTT | GGGCCTGACC | CTGGCAGCCT | CCACCAACGG | CTCCCGGCTC | 480 |
| CTGGCCTGTG | GCCCGACCCT | GCACAGAGTC | TGTGGGGAGA | ACTCATACTC | AAAGGGTTCC | 540 |
| TGCCTCCTGC | TGGGCTCGCG | CTGGGAGATC | ATCCAGACAG | TCCCCGACGC | CACGCCAGAG | 600 |
| TGTCCACATC | AAGAGATGGA | CATCGTCTTC | CTGATTGACG | GCTCTGGAAG | CATTGACCAA | 660 |
| AATGACTTTA | ACCAGATGAA | GGGCTTTGTC | CAAGCTGTCA | TGGGCCAGTT | TGAGGGCACT | 720 |
| GACACCCTGT | TTGCACTGAT | GCAGTACTCA | AACCTCCTGA | AGATCCACTT | CACCTTCACC | 780 |
| CAATTCCGGA | CCAGCCCGAG | CCAGCAGAGC | CTGGTGGATC | CCATCGTCCA | ACTGAAAGGC | 840 |
| CTGACGTTCA | CGGCCACGGG | CATCCTGACA | GTGGTGACAC | AGCTATTTCA | TCATAAGAAT | 900 |
| GGGGCCCGAA | AAAGTGCCAA | GAAGATCCTC | ATTGTCATCA | CAGATGGGCA | GAAGTACAAA | 960 |
| GACCCCCTGG | AATACAGTGA | TGTCATCCCC | CAGGCAGAGA | AGGCTGGCAT | CATCCGCTAC | 1020 |
| GCTATCGGGG | TGGACACGC | TTTCCAGGGA | CCCACTGCCA | GGCAGGAGCT | GAATACCATC | 1080 |
| AGCTCAGCGC | CTCCGCAGGA | CCACGTGTTC | AAGGTGGACA | ACTTTGCAGC | CCTTGGCAGC | 1140 |
| ATCCAGAAGC | AGCTGCAGGA | GAAGATCTAT | GCAGTTGAGG | GAACCCAGTC | CAGGGCAAGC | 1200 |
| AGCTCCTTCC | AGCACGAGAT | GTCCCAAGAA | GGCTTCAGCA | CAGCCCTCAC | AATGGATGGC | 1260 |
| CTCTTCCTGG | GGGCTGTGGG | GAGCTTTAGC | TGGTCTGGAG | GTGCCTTCCT | GTATCCCCCA | 1320 |
| AATATGAGCC | CCACCTTCAT | CAACATGTCT | CAGGAGAATG | TGGACATGAG | GGACTCTTAC | 1380 |
| CTGGGTTACT | CCACCGAGCT | AGCCCTGTGG | AAGGGGTAC | AGAACCTGGT | CCTGGGGGCC | 1440 |
| CCCCGCTACC | AGCATACCGG | GAAGGCTGTC | ATCTTCACCC | AGGTGTCCAG | GCAATGGAGG | 1500 |
| AAGAAGGCCG | AAGTCACAGG | GACGCAGATC | GGCTCCTACT | TCGGGGCCTC | CCTCTGCTCC | 1560 |
| GTGGATGTGG | ACAGCGATGG | CAGCACCGAC | CTGATCCTCA | TTGGGGCCCC | CCATTACTAT | 1620 |
| GAGCAGACCC | GAGGGGGCCA | GGTGTCCGTG | TGTCCCTTGC | CTAGGGGGAG | GGTGCAGTGG | 1680 |
| CAGTGTGACG | CTGTTCTCCG | TGGTGAGCAG | GGCCACCCCT | GGGGCCGCTT | TGGGGCAGCC | 1740 |
| CTGACAGTGT | TGGGGGATGT | GAATGAGGAC | AAGCTGATAG | ACGTGGCCAT | TGGGGCCCCG | 1800 |
| GGAGAGCAGG | AGAACCGGGG | TGCTGTCTAC | CTGTTTCACG | GAGCCTCAGA | ATCCGGCATC | 1860 |
| AGCCCCTCCC | ACAGCCAGCG | GATTGCCAGC | TCCAGCTCT | CCCCCAGGCT | GCAGTATTTT | 1920 |
| GGGCAGGCGC | TGAGTGGGGG | TCAGGACCTC | ACCCAGGATG | GACTGATGGA | CCTGGCCGTG | 1980 |
| GGGGCCCGGG | GCCAGGTGCT | CCTGCTCAGG | AGTCTGCCGG | TGCTGAAAGT | GGGGGTGGCC | 2040 |
| ATGAGATTCA | GCCCTGTGGA | GGTGGCCAAG | GCTGTGTACC | GGTGCTGGGA | AGAGAAGCCC | 2100 |
| AGTGCCCTGG | AAGCTGGGGA | CGCCACCGTC | TGTCTCACCA | TCCAGAAAAG | CTCACTGGAC | 2160 |
| CAGCTAGGTG | ACATCCAAAG | CTCTGTCAGG | TTTGATCTGG | CACTGGACCC | AGGTCGTCTG | 2220 |
| ACTTCTCGTG | CCATTTTCAA | TGAAACCAAG | AACCCCACTT | TGACTCGAAG | AAAAACCCTG | 2280 |
| GGACTGGGGA | TTCACTGTGA | AACCCTGAAG | CTGCTTTTGC | AGATTGTGT | GGAGGATGTG | 2340 |
| GTGAGCCCCA | TCATTCTGCA | CCTCAACTTC | TCACTGGTGA | GAGAGCCCAT | CCCCTCCCCC | 2400 |
| CAGAACCTGC | GTCCTGTGCT | GGCCGTGGGC | TCACAAGACC | TCTTCACTGC | TTCTCTCCCC | 2460 |
| TTCGAGAAGA | ACTGTGGGCA | AGATGGCCTC | TGTGAAGGGG | ACCTGGGTGT | CACCCTCAGC | 2520 |

```
TTCTCAGGCC  TGCAGACCCT  GACCGTGGGG  AGCTCCCTGG  AGCTCAACGT  GATTGTGACT       2580

GTGTGGAACG  CAGGTGAGGA  TTCCTACGGA  ACCGTGGTCA  GCCTCTACTA  TCCAGCAGGG       2640

CTGTCGCACC  GACGGGTGTC  AGGAGCCCAG  AAGCAGCCCC  ATCAGAGTGC  CCTGCGCCTG       2700

GCATGTGAGA  CAGTGCCCAC  TGAGGATGAG  GGCCTAAGAA  GCAGCCGCTG  CAGTGTCAAC       2760

CACCCCATCT  TCCATGAGGG  CTCTAACGGC  ACCTTCATAG  TCACATTCGA  TGTCTCCTAC       2820

AAGGCCACCC  TGGGAGACAG  GATGCTTATG  AGGGCCAGTG  CAAGCAGTGA  GAACAATAAG       2880

GCTTCAAGCA  GCAAGGCCAC  CTTCCAGCTG  GAGCTCCCGG  TGAAGTATGC  AGTCTACACC       2940

ATGATCAGCA  GGCAGGAAGA  ATCCACCAAG  TACTTCAACT  TTGCAACCTC  CGATGAGAAG       3000

AAAATGAAAG  AGGCTGAGCA  TCGATACCGT  GTGAATAACC  TCAGCCAGCG  AGATCTGGCC       3060

ATCAGCATTA  ACTTCTGGGT  TCCTGTCCTG  CTGAACGGGG  TGGCTGTGTG  GGATGTGGTC       3120

ATGGAGGCCC  CATCTCAGAG  TCTCCCCTGT  GTTTCAGAGA  GAAAACCTCC  CCAGCATTCT       3180

GACTTCCTGA  CCCAGATTTC  AAGAAGTCCC  ATGCTGGACT  GCTCCATTGC  TGACTGCCTG       3240

CAGTTCCGCT  GTGACGTCCC  CTCCTTCAGC  GTCCAGGAGG  AGCTGGATTT  CACCCTGAAG       3300

GGCAATCTCA  GTTTCGGCTG  GGTCCGCGAG  ACATTGCAGA  AGAAGGTGTT  GGTCGTGAGT       3360

GTGGCTGAAA  TTACGTTCGA  CACATCCGTG  TACTCCCAGC  TTCCAGGACA  GGAGGCATTT       3420

ATGAGAGCTC  AGATGGAGAT  GGTGCTAGAA  GAAGACGAGG  TCTACAATGC  CATTCCCATC       3480

ATCATGGGCA  GCTCTGTGGG  GGCTCTGCTA  CTGCTGGCGC  TCATCACAGC  CACACTGTAC       3540

AAGCTTGGCT  TCTTCAAACG  CCACTACAAG  GAAATGCTGG  AGGACAAGCC  TGAAGACACT       3600

GCCACATTCA  GTGGGGACGA  TTTCAGCTGT  GTGGCCCCAA  ATGTGCCTTT  GTCCTAATAA       3660

TCCACTTTCC  TGTTTATCTC  TACCACTGTG  GGCTGGACTT  GCTTGCAACC  ATAAATCAAC       3720

TTACATGGAA  ACAACTTCTG  CATAGATCTG  CACTGGCCTA  AGCAACCTAC  CAGGTGCTAA       3780

GCACCTTCTC  GGAGAGATAG  AGATTGTCAA  TGTTTTTACA  TATCTGTCCA  TCTTTTTCAG       3840

CAATGACCCA  CTTTTTACAG  AAGCAGGCAT  GGTGCCAGCA  TAAATTTTCA  TATGCTTAAG       3900

AATTGTCACA  TGAAAAAAAA  AAAAAAAAAA  AAAAAAAAAA  AAAAAAAAAA  CTTTAG          3956
```

( 2 ) INFORMATION FOR SEQ ID NO:98:

( i ) SEQUENCE CHARACTERISTICS:
        ( A ) LENGTH: 3785 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..3486

( x i ) SEQUENCE DESCRIPTION: SEQ ID NO:98:

```
ATG  ACC  TTC  GGC  ACT  GTG  CTT  CTT  CTG  AGT  GTC  CTG  GCT  TCT  TAT  CAT       48
Met  Thr  Phe  Gly  Thr  Val  Leu  Leu  Leu  Ser  Val  Leu  Ala  Ser  Tyr  His
 1             5                  10                 15

GGA  TTC  AAC  CTG  GAT  GTG  GAG  GAG  CCT  ACG  ATC  TTC  CAG  GAG  GAT  GCA       96
Gly  Phe  Asn  Leu  Asp  Val  Glu  Glu  Pro  Thr  Ile  Phe  Gln  Glu  Asp  Ala
              20                 25                 30

GGC  GGC  TTT  GGG  CAG  AGC  GTG  GTG  CAG  TTC  GGT  GGA  TCT  CGA  CTC  GTG      144
Gly  Gly  Phe  Gly  Gln  Ser  Val  Val  Gln  Phe  Gly  Gly  Ser  Arg  Leu  Val
         35                  40                 45

GTG  GGA  GCA  CCC  CTG  GAG  GTG  GTG  GCG  GCC  AAC  CAG  ACG  GGA  CGG  CTG      192
Val  Gly  Ala  Pro  Leu  Glu  Val  Val  Ala  Ala  Asn  Gln  Thr  Gly  Arg  Leu
     50                  55                 60
```

```
TAT  GAC  TGC  GCA  GCT  GCC  ACC  GGC  ATG  TGC  CAG  CCC  ATC  CCG  CTG  CAC      240
Tyr  Asp  Cys  Ala  Ala  Ala  Thr  Gly  Met  Cys  Gln  Pro  Ile  Pro  Leu  His
65             70                       75                       80

ATC  CGC  CCT  GAG  GCC  GTG  AAC  ATG  TCC  TTG  GGC  CTG  ACC  CTG  GCA  GCC      288
Ile  Arg  Pro  Glu  Ala  Val  Asn  Met  Ser  Leu  Gly  Leu  Thr  Leu  Ala  Ala
                    85                       90                       95

TCC  ACC  AAC  GGC  TCC  CGG  CTC  CTG  GCC  TGT  GGC  CCG  ACC  CTG  CAC  AGA      336
Ser  Thr  Asn  Gly  Ser  Arg  Leu  Leu  Ala  Cys  Gly  Pro  Thr  Leu  His  Arg
               100                      105                      110

GTC  TGT  GGG  GAG  AAC  TCA  TAC  TCA  AAG  GGT  TCC  TGC  CTC  CTG  CTG  GGC      384
Val  Cys  Gly  Glu  Asn  Ser  Tyr  Ser  Lys  Gly  Ser  Cys  Leu  Leu  Leu  Gly
          115                      120                      125

TCG  CGC  TGG  GAG  ATC  ATC  CAG  ACA  GTC  CCC  GAC  GCC  ACG  CCA  GAG  TGT      432
Ser  Arg  Trp  Glu  Ile  Ile  Gln  Thr  Val  Pro  Asp  Ala  Thr  Pro  Glu  Cys
     130                      135                      140

CCA  CAT  CAA  GAG  ATG  GAC  ATC  GTC  TTC  CTG  ATT  GAC  GGC  TCT  GGA  AGC      480
Pro  His  Gln  Glu  Met  Asp  Ile  Val  Phe  Leu  Ile  Asp  Gly  Ser  Gly  Ser
145                      150                      155                      160

ATT  GAC  CAA  AAT  GAC  TTT  AAC  CAG  ATG  AAG  GGC  TTT  GTC  CAA  GCT  GTC      528
Ile  Asp  Gln  Asn  Asp  Phe  Asn  Gln  Met  Lys  Gly  Phe  Val  Gln  Ala  Val
                    165                      170                      175

ATG  GGC  CAG  TTT  GAG  GGC  ACT  GAC  ACC  CTG  TTT  GCA  CTG  ATG  CAG  TAC      576
Met  Gly  Gln  Phe  Glu  Gly  Thr  Asp  Thr  Leu  Phe  Ala  Leu  Met  Gln  Tyr
               180                      185                      190

TCA  AAC  CTC  CTG  AAG  ATC  CAC  TTC  ACC  TTC  ACC  CAA  TTC  CGG  ACC  AGC      624
Ser  Asn  Leu  Leu  Lys  Ile  His  Phe  Thr  Phe  Thr  Gln  Phe  Arg  Thr  Ser
          195                      200                      205

CCG  AGC  CAG  CAG  AGC  CTG  GTG  GAT  CCC  ATC  GTC  CAA  CTG  AAA  GGC  CTG      672
Pro  Ser  Gln  Gln  Ser  Leu  Val  Asp  Pro  Ile  Val  Gln  Leu  Lys  Gly  Leu
     210                      215                      220

ACG  TTC  ACG  GCC  ACG  GGC  ATC  CTG  ACA  GTG  GTG  ACA  CAG  CTA  TTT  CAT      720
Thr  Phe  Thr  Ala  Thr  Gly  Ile  Leu  Thr  Val  Val  Thr  Gln  Leu  Phe  His
225                      230                      235                      240

CAT  AAG  AAT  GGG  GCC  CGA  AAA  AGT  GCC  AAG  AAG  ATC  CTC  ATT  GTC  ATC      768
His  Lys  Asn  Gly  Ala  Arg  Lys  Ser  Ala  Lys  Lys  Ile  Leu  Ile  Val  Ile
                    245                      250                      255

ACA  GAT  GGG  CAG  AAG  TAC  AAA  GAC  CCC  CTG  GAA  TAC  AGT  GAT  GTC  ATC      816
Thr  Asp  Gly  Gln  Lys  Tyr  Lys  Asp  Pro  Leu  Glu  Tyr  Ser  Asp  Val  Ile
               260                      265                      270

CCC  CAG  GCA  GAG  AAG  GCT  GGC  ATC  ATC  CGC  TAC  GCT  ATC  GGG  GTG  GGA      864
Pro  Gln  Ala  Glu  Lys  Ala  Gly  Ile  Ile  Arg  Tyr  Ala  Ile  Gly  Val  Gly
          275                      280                      285

CAC  GCT  TTC  CAG  GGA  CCC  ACT  GCC  AGG  CAG  GAG  CTG  AAT  ACC  ATC  AGC      912
His  Ala  Phe  Gln  Gly  Pro  Thr  Ala  Arg  Gln  Glu  Leu  Asn  Thr  Ile  Ser
     290                      295                      300

TCA  GCG  CCT  CCG  CAG  GAC  CAC  GTG  TTC  AAG  GTG  GAC  AAC  TTT  GCA  GCC      960
Ser  Ala  Pro  Pro  Gln  Asp  His  Val  Phe  Lys  Val  Asp  Asn  Phe  Ala  Ala
305                      310                      315                      320

CTT  GGC  AGC  ATC  CAG  AAG  CAG  CTG  CAG  GAG  AAG  ATC  TAT  GCA  GTT  GAG     1008
Leu  Gly  Ser  Ile  Gln  Lys  Gln  Leu  Gln  Glu  Lys  Ile  Tyr  Ala  Val  Glu
                    325                      330                      335

GGA  ACC  CAG  TCC  AGG  GCA  AGC  AGC  TCC  TTC  CAG  CAC  GAG  ATG  TCC  CAA     1056
Gly  Thr  Gln  Ser  Arg  Ala  Ser  Ser  Ser  Phe  Gln  His  Glu  Met  Ser  Gln
               340                      345                      350

GAA  GGC  TTC  AGC  ACA  GCC  CTC  ACA  ATG  GAT  GGC  CTC  TTC  CTG  GGG  GCT     1104
Glu  Gly  Phe  Ser  Thr  Ala  Leu  Thr  Met  Asp  Gly  Leu  Phe  Leu  Gly  Ala
     355                      360                      365

GTG  GGG  AGC  TTT  AGC  TGG  TCT  GGA  GGT  GCC  TTC  CTG  TAT  CCC  CCA  AAT     1152
Val  Gly  Ser  Phe  Ser  Trp  Ser  Gly  Gly  Ala  Phe  Leu  Tyr  Pro  Pro  Asn
370                      375                      380
```

| | | | | | | | | | | | | | | | | |
|---|---|---|---|---|---|---|---|---|---|---|---|---|---|---|---|---|
| ATG | AGC | CCC | ACC | TTC | ATC | AAC | ATG | TCT | CAG | GAG | AAT | GTG | GAC | ATG | AGG | 1200 |
| Met | Ser | Pro | Thr | Phe | Ile | Asn | Met | Ser | Gln | Glu | Asn | Val | Asp | Met | Arg | |
| 385 | | | | | 390 | | | | | 395 | | | | | 400 | |
| GAC | TCT | TAC | CTG | GGT | TAC | TCC | ACC | GAG | CTA | GCC | CTG | TGG | AAG | GGG | GTA | 1248 |
| Asp | Ser | Tyr | Leu | Gly | Tyr | Ser | Thr | Glu | Leu | Ala | Leu | Trp | Lys | Gly | Val | |
| | | | | 405 | | | | | 410 | | | | | 415 | | |
| CAG | AAC | CTG | GTC | CTG | GGG | GCC | CCC | CGC | TAC | CAG | CAT | ACC | GGG | AAG | GCT | 1296 |
| Gln | Asn | Leu | Val | Leu | Gly | Ala | Pro | Arg | Tyr | Gln | His | Thr | Gly | Lys | Ala | |
| | | | 420 | | | | | 425 | | | | | 430 | | | |
| GTC | ATC | TTC | ACC | CAG | GTG | TCC | AGG | CAA | TGG | AGG | AAG | AAG | GCC | GAA | GTC | 1344 |
| Val | Ile | Phe | Thr | Gln | Val | Ser | Arg | Gln | Trp | Arg | Lys | Lys | Ala | Glu | Val | |
| | | 435 | | | | | 440 | | | | | 445 | | | | |
| ACA | GGG | ACG | CAG | ATC | GGC | TCC | TAC | TTC | GGG | GCC | TCC | CTC | TGC | TCC | GTG | 1392 |
| Thr | Gly | Thr | Gln | Ile | Gly | Ser | Tyr | Phe | Gly | Ala | Ser | Leu | Cys | Ser | Val | |
| | 450 | | | | | 455 | | | | | 460 | | | | | |
| GAT | GTG | GAC | AGC | GAT | GGC | AGC | ACC | GAC | CTG | ATC | CTC | ATT | GGG | GCC | CCC | 1440 |
| Asp | Val | Asp | Ser | Asp | Gly | Ser | Thr | Asp | Leu | Ile | Leu | Ile | Gly | Ala | Pro | |
| 465 | | | | | 470 | | | | | 475 | | | | | 480 | |
| CAT | TAC | TAT | GAG | CAG | ACC | CGA | GGG | GGC | CAG | GTG | TCC | GTG | TGT | CCC | TTG | 1488 |
| His | Tyr | Tyr | Glu | Gln | Thr | Arg | Gly | Gly | Gln | Val | Ser | Val | Cys | Pro | Leu | |
| | | | | 485 | | | | | 490 | | | | | 495 | | |
| CCT | AGG | GGG | AGG | GTG | CAG | TGG | CAG | TGT | GAC | GCT | GTT | CTC | CGT | GGT | GAG | 1536 |
| Pro | Arg | Gly | Arg | Val | Gln | Trp | Gln | Cys | Asp | Ala | Val | Leu | Arg | Gly | Glu | |
| | | | 500 | | | | | 505 | | | | | 510 | | | |
| CAG | GGC | CAC | CCC | TGG | GGC | CGC | TTT | GGG | GCA | GCC | CTG | ACA | GTG | TTG | GGG | 1584 |
| Gln | Gly | His | Pro | Trp | Gly | Arg | Phe | Gly | Ala | Ala | Leu | Thr | Val | Leu | Gly | |
| | | 515 | | | | | 520 | | | | | 525 | | | | |
| GAT | GTG | AAT | GAG | GAC | AAG | CTG | ATA | GAC | GTG | GCC | ATT | GGG | GCC | CCG | GGA | 1632 |
| Asp | Val | Asn | Glu | Asp | Lys | Leu | Ile | Asp | Val | Ala | Ile | Gly | Ala | Pro | Gly | |
| | 530 | | | | | 535 | | | | | 540 | | | | | |
| GAG | CAG | GAG | AAC | CGG | GGT | GCT | GTC | TAC | CTG | TTT | CAC | GGA | GCC | TCA | GAA | 1680 |
| Glu | Gln | Glu | Asn | Arg | Gly | Ala | Val | Tyr | Leu | Phe | His | Gly | Ala | Ser | Glu | |
| 545 | | | | | 550 | | | | | 555 | | | | | 560 | |
| TCC | GGC | ATC | AGC | CCC | TCC | CAC | AGC | CAG | CGG | ATT | GCC | AGC | TCC | CAG | CTC | 1728 |
| Ser | Gly | Ile | Ser | Pro | Ser | His | Ser | Gln | Arg | Ile | Ala | Ser | Ser | Gln | Leu | |
| | | | | 565 | | | | | 570 | | | | | 575 | | |
| TCC | CCC | AGG | CTG | CAG | TAT | TTT | GGG | CAG | GCG | CTG | AGT | GGG | GGT | CAG | GAC | 1776 |
| Ser | Pro | Arg | Leu | Gln | Tyr | Phe | Gly | Gln | Ala | Leu | Ser | Gly | Gly | Gln | Asp | |
| | | | 580 | | | | | 585 | | | | | 590 | | | |
| CTC | ACC | CAG | GAT | GGA | CTG | ATG | GAC | CTG | GCC | GTG | GGG | GCC | CGG | GGC | CAG | 1824 |
| Leu | Thr | Gln | Asp | Gly | Leu | Met | Asp | Leu | Ala | Val | Gly | Ala | Arg | Gly | Gln | |
| | | 595 | | | | | 600 | | | | | 605 | | | | |
| GTG | CTC | CTG | CTC | AGG | AGT | CTG | CCG | GTG | CTG | AAA | GTG | GGG | GTG | GCC | ATG | 1872 |
| Val | Leu | Leu | Leu | Arg | Ser | Leu | Pro | Val | Leu | Lys | Val | Gly | Val | Ala | Met | |
| | 610 | | | | | 615 | | | | | 620 | | | | | |
| AGA | TTC | AGC | CCT | GTG | GAG | GTG | GCC | AAG | GCT | GTG | TAC | CGG | TGC | TGG | GAA | 1920 |
| Arg | Phe | Ser | Pro | Val | Glu | Val | Ala | Lys | Ala | Val | Tyr | Arg | Cys | Trp | Glu | |
| 625 | | | | | 630 | | | | | 635 | | | | | 640 | |
| GAG | AAG | CCC | AGT | GCC | CTG | GAA | GCT | GGG | GAC | GCC | ACC | GTC | TGT | CTC | ACC | 1968 |
| Glu | Lys | Pro | Ser | Ala | Leu | Glu | Ala | Gly | Asp | Ala | Thr | Val | Cys | Leu | Thr | |
| | | | | 645 | | | | | 650 | | | | | 655 | | |
| ATC | CAG | AAA | AGC | TCA | CTG | GAC | CAG | CTA | GGT | GAC | ATC | CAA | AGC | TCT | GTC | 2016 |
| Ile | Gln | Lys | Ser | Ser | Leu | Asp | Gln | Leu | Gly | Asp | Ile | Gln | Ser | Ser | Val | |
| | | | | 660 | | | | | 665 | | | | | 670 | | |
| AGG | TTT | GAT | CTG | GCA | CTG | GAC | CCA | GGT | CGT | CTG | ACT | TCT | CGT | GCC | ATT | 2064 |
| Arg | Phe | Asp | Leu | Ala | Leu | Asp | Pro | Gly | Arg | Leu | Thr | Ser | Arg | Ala | Ile | |
| | | 675 | | | | | 680 | | | | | 685 | | | | |
| TTC | AAT | GAA | ACC | AAG | AAC | CCC | ACT | TTG | ACT | CGA | AGA | AAA | ACC | CTG | GGA | 2112 |
| Phe | Asn | Glu | Thr | Lys | Asn | Pro | Thr | Leu | Thr | Arg | Arg | Lys | Thr | Leu | Gly | |
| | | | | 690 | | | | | 695 | | | | | 700 | | |

| | | | | | | | | | | | | | | | | |
|---|---|---|---|---|---|---|---|---|---|---|---|---|---|---|---|---|
| CTG | GGG | ATT | CAC | TGT | GAA | ACC | CTG | AAG | CTG | CTT | TTG | CCA | GAT | TGT | GTG | 2160 |
| Leu | Gly | Ile | His | Cys | Glu | Thr | Leu | Lys | Leu | Leu | Leu | Pro | Asp | Cys | Val | |
| 705 | | | | 710 | | | | | 715 | | | | | | 720 | |
| GAG | GAT | GTG | GTG | AGC | CCC | ATC | ATT | CTG | CAC | CTC | AAC | TTC | TCA | CTG | GTG | 2208 |
| Glu | Asp | Val | Val | Ser | Pro | Ile | Ile | Leu | His | Leu | Asn | Phe | Ser | Leu | Val | |
| | | | | 725 | | | | | 730 | | | | | 735 | | |
| AGA | GAG | CCC | ATC | CCC | TCC | CCC | CAG | AAC | CTG | CGT | CCT | GTG | CTG | GCC | GTG | 2256 |
| Arg | Glu | Pro | Ile | Pro | Ser | Pro | Gln | Asn | Leu | Arg | Pro | Val | Leu | Ala | Val | |
| | | | 740 | | | | | 745 | | | | | 750 | | | |
| GGC | TCA | CAA | GAC | CTC | TTC | ACT | GCT | TCT | CTC | CCC | TTC | GAG | AAG | AAC | TGT | 2304 |
| Gly | Ser | Gln | Asp | Leu | Phe | Thr | Ala | Ser | Leu | Pro | Phe | Glu | Lys | Asn | Cys | |
| | | 755 | | | | 760 | | | | | 765 | | | | | |
| GGG | CAA | GAT | GGC | CTC | TGT | GAA | GGG | GAC | CTG | GGT | GTC | ACC | CTC | AGC | TTC | 2352 |
| Gly | Gln | Asp | Gly | Leu | Cys | Glu | Gly | Asp | Leu | Gly | Val | Thr | Leu | Ser | Phe | |
| 770 | | | | | 775 | | | | | 780 | | | | | | |
| TCA | GGC | CTG | CAG | ACC | CTG | ACC | GTG | GGG | AGC | TCC | CTG | GAG | CTC | AAC | GTG | 2400 |
| Ser | Gly | Leu | Gln | Thr | Leu | Thr | Val | Gly | Ser | Ser | Leu | Glu | Leu | Asn | Val | |
| 785 | | | | | 790 | | | | | 795 | | | | | 800 | |
| ATT | GTG | ACT | GTG | TGG | AAC | GCA | GGT | GAG | GAT | TCC | TAC | GGA | ACC | GTG | GTC | 2448 |
| Ile | Val | Thr | Val | Trp | Asn | Ala | Gly | Glu | Asp | Ser | Tyr | Gly | Thr | Val | Val | |
| | | | | 805 | | | | | 810 | | | | | 815 | | |
| AGC | CTC | TAC | TAT | CCA | GCA | GGG | CTG | TCG | CAC | CGA | CGG | GTG | TCA | GGA | GCC | 2496 |
| Ser | Leu | Tyr | Tyr | Pro | Ala | Gly | Leu | Ser | His | Arg | Arg | Val | Ser | Gly | Ala | |
| | | | 820 | | | | | 825 | | | | | 830 | | | |
| CAG | AAG | CAG | CCC | CAT | CAG | AGT | GCC | CTG | CGC | CTG | GCA | TGT | GAG | ACA | GTG | 2544 |
| Gln | Lys | Gln | Pro | His | Gln | Ser | Ala | Leu | Arg | Leu | Ala | Cys | Glu | Thr | Val | |
| | | 835 | | | | 840 | | | | | 845 | | | | | |
| CCC | ACT | GAG | GAT | GAG | GGC | CTA | AGA | AGC | AGC | CGC | TGC | AGT | GTC | AAC | CAC | 2592 |
| Pro | Thr | Glu | Asp | Glu | Gly | Leu | Arg | Ser | Ser | Arg | Cys | Ser | Val | Asn | His | |
| | 850 | | | | | 855 | | | | | 860 | | | | | |
| CCC | ATC | TTC | CAT | GAG | GGC | TCT | AAC | GGC | ACC | TTC | ATA | GTC | ACA | TTC | GAT | 2640 |
| Pro | Ile | Phe | His | Glu | Gly | Ser | Asn | Gly | Thr | Phe | Ile | Val | Thr | Phe | Asp | |
| 865 | | | | | 870 | | | | | 875 | | | | | 880 | |
| GTC | TCC | TAC | AAG | GCC | ACC | CTG | GGA | GAC | AGG | ATG | CTT | ATG | AGG | GCC | AGT | 2688 |
| Val | Ser | Tyr | Lys | Ala | Thr | Leu | Gly | Asp | Arg | Met | Leu | Met | Arg | Ala | Ser | |
| | | | | 885 | | | | | 890 | | | | | 895 | | |
| GCA | AGC | AGT | GAG | AAC | AAT | AAG | GCT | TCA | AGC | AGC | AAG | GCC | ACC | TTC | CAG | 2736 |
| Ala | Ser | Ser | Glu | Asn | Asn | Lys | Ala | Ser | Ser | Ser | Lys | Ala | Thr | Phe | Gln | |
| | | | 900 | | | | | 905 | | | | | 910 | | | |
| CTG | GAG | CTC | CCG | GTG | AAG | TAT | GCA | GTC | TAC | ACC | ATG | ATC | AGC | AGG | CAG | 2784 |
| Leu | Glu | Leu | Pro | Val | Lys | Tyr | Ala | Val | Tyr | Thr | Met | Ile | Ser | Arg | Gln | |
| | | 915 | | | | 920 | | | | | 925 | | | | | |
| GAA | GAA | TCC | ACC | AAG | TAC | TTC | AAC | TTT | GCA | ACC | TCC | GAT | GAG | AAG | AAA | 2832 |
| Glu | Glu | Ser | Thr | Lys | Tyr | Phe | Asn | Phe | Ala | Thr | Ser | Asp | Glu | Lys | Lys | |
| | 930 | | | | | 935 | | | | | 940 | | | | | |
| ATG | AAA | GAG | GCT | GAG | CAT | CGA | TAC | CGT | GTG | AAT | AAC | CTC | AGC | CAG | CGA | 2880 |
| Met | Lys | Glu | Ala | Glu | His | Arg | Tyr | Arg | Val | Asn | Asn | Leu | Ser | Gln | Arg | |
| 945 | | | | | 950 | | | | | 955 | | | | | 960 | |
| GAT | CTG | GCC | ATC | AGC | ATT | AAC | TTC | TGG | GTT | CCT | GTC | CTG | CTG | AAC | GGG | 2928 |
| Asp | Leu | Ala | Ile | Ser | Ile | Asn | Phe | Trp | Val | Pro | Val | Leu | Leu | Asn | Gly | |
| | | | | 965 | | | | | 970 | | | | | 975 | | |
| GTG | GCT | GTG | TGG | GAT | GTG | GTC | ATG | GAG | GCC | CCA | TCT | CAG | AGT | CTC | CCC | 2976 |
| Val | Ala | Val | Trp | Asp | Val | Val | Met | Glu | Ala | Pro | Ser | Gln | Ser | Leu | Pro | |
| | | | | 980 | | | | | 985 | | | | | 990 | | |
| TGT | GTT | TCA | GAG | AGA | AAA | CCT | CCC | CAG | CAT | TCT | GAC | TTC | CTG | ACC | CAG | 3024 |
| Cys | Val | Ser | Glu | Arg | Lys | Pro | Pro | Gln | His | Ser | Asp | Phe | Leu | Thr | Gln | |
| | | 995 | | | | 1000 | | | | | 1005 | | | | | |
| ATT | TCA | AGA | AGT | CCC | ATG | CTG | GAC | TGC | TCC | ATT | GCT | GAC | TGC | CTG | CAG | 3072 |
| Ile | Ser | Arg | Ser | Pro | Met | Leu | Asp | Cys | Ser | Ile | Ala | Asp | Cys | Leu | Gln | |
| | | 1010 | | | | 1015 | | | | | 1020 | | | | | |

```
TTC  CGC  TGT  GAC  GTC  CCC  TCC  TTC  AGC  GTC  CAG  GAG  GAG  CTG  GAT  TTC     3120
Phe  Arg  Cys  Asp  Val  Pro  Ser  Phe  Ser  Val  Gln  Glu  Glu  Leu  Asp  Phe
1025                1030                1035                          1040

ACC  CTG  AAG  GGC  AAT  CTC  AGT  TTC  GGC  TGG  GTC  CGC  GAG  ACA  TTG  CAG     3168
Thr  Leu  Lys  Gly  Asn  Leu  Ser  Phe  Gly  Trp  Val  Arg  Glu  Thr  Leu  Gln
                    1045                1050                          1055

AAG  AAG  GTG  TTG  GTC  GTG  AGT  GTG  GCT  GAA  ATT  ACG  TTC  GAC  ACA  TCC     3216
Lys  Lys  Val  Leu  Val  Val  Ser  Val  Ala  Glu  Ile  Thr  Phe  Asp  Thr  Ser
               1060                1065                     1070

GTG  TAC  TCC  CAG  CTT  CCA  GGA  CAG  GAG  GCA  TTT  ATG  AGA  GCT  CAG  ATG     3264
Val  Tyr  Ser  Gln  Leu  Pro  Gly  Gln  Glu  Ala  Phe  Met  Arg  Ala  Gln  Met
               1075                1080                     1085

GAG  ATG  GTG  CTA  GAA  GAA  GAC  GAG  GTC  TAC  AAT  GCC  ATT  CCC  ATC  ATC     3312
Glu  Met  Val  Leu  Glu  Glu  Asp  Glu  Val  Tyr  Asn  Ala  Ile  Pro  Ile  Ile
1090                     1095                     1100

ATG  GGC  AGC  TCT  GTG  GGG  GCT  CTG  CTA  CTG  CTG  GCG  CTC  ATC  ACA  GCC     3360
Met  Gly  Ser  Ser  Val  Gly  Ala  Leu  Leu  Leu  Leu  Ala  Leu  Ile  Thr  Ala
1105                     1110                1115                          1120

ACA  CTG  TAC  AAG  CTT  GGC  TTC  TTC  AAA  CGC  CAC  TAC  AAG  GAA  ATG  CTG     3408
Thr  Leu  Tyr  Lys  Leu  Gly  Phe  Phe  Lys  Arg  His  Tyr  Lys  Glu  Met  Leu
                    1125                1130                          1135

GAG  GAC  AAG  CCT  GAA  GAC  ACT  GCC  ACA  TTC  AGT  GGG  GAC  GAT  TTC  AGC     3456
Glu  Asp  Lys  Pro  Glu  Asp  Thr  Ala  Thr  Phe  Ser  Gly  Asp  Asp  Phe  Ser
               1140                1145                     1150

TGT  GTG  GCC  CCA  AAT  GTG  CCT  TTG  TCC  TAATAATCCA  CTTTCCTGTT                3503
Cys  Val  Ala  Pro  Asn  Val  Pro  Leu  Ser
               1155                1160

TATCTCTACC  ACTGTGGGCT  GGACTTGCTT  GCAACCATAA  ATCAACTTAC  ATGGAAACAA             3563

CTTCTGCATA  GATCTGCACT  GGCCTAAGCA  ACCTACCAGG  TGCTAAGCAC  CTTCTCGGAG             3623

AGATAGAGAT  TGTCAATGTT  TTTACATATC  TGTCCATCTT  TTTCAGCAAT  GACCCACTTT             3683

TTACAGAAGC  AGGCATGGTG  CCAGCATAAA  TTTTCATATG  CTTAAGAATT  GTCACATGAA             3743

AAAAAAAAAA  AAAAAAAAAA  AAAAAAAAAA  AAAAAACTTT  AG                                 3785
```

( 2 ) INFORMATION FOR SEQ ID NO:99:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:99:

```
Met  Thr  Phe  Gly  Thr  Val  Leu  Leu  Leu  Ser  Val  Leu  Ala  Ser  Tyr  His
1                   5                   10                      15

Gly  Phe  Asn  Leu  Asp  Val  Glu  Glu  Pro  Thr  Ile  Phe  Gln  Glu  Asp  Ala
               20                  25                          30

Gly  Gly  Phe  Gly  Gln  Ser  Val  Val  Gln  Phe  Gly  Gly  Ser  Arg  Leu  Val
          35                   40                       45

Val  Gly  Ala  Pro  Leu  Glu  Val  Val  Ala  Ala  Asn  Gln  Thr  Gly  Arg  Leu
     50                       55                  60

Tyr  Asp  Cys  Ala  Ala  Ala  Thr  Gly  Met  Cys  Gln  Pro  Ile  Pro  Leu  His
65                       70                   75                           80

Ile  Arg  Pro  Glu  Ala  Val  Asn  Met  Ser  Leu  Gly  Leu  Thr  Leu  Ala  Ala
                    85                   90                       95

Ser  Thr  Asn  Gly  Ser  Arg  Leu  Leu  Ala  Cys  Gly  Pro  Thr  Leu  His  Arg
               100                  105                     110
```

-continued

| | | | | | | | | | | | | | | |
|---|---|---|---|---|---|---|---|---|---|---|---|---|---|---|
|Val|Cys|Gly|Glu|Asn|Ser|Tyr|Ser|Lys|Gly|Ser|Cys|Leu|Leu|Gly|
| | |115| | | |120| | | |125| | | | |
|Ser|Arg|Trp|Glu|Ile|Ile|Gln|Thr|Val|Pro|Asp|Ala|Thr|Pro|Glu|Cys|
| |130| | | |135| | | |140| | | | | |
|Pro|His|Gln|Glu|Met|Asp|Ile|Val|Phe|Leu|Ile|Asp|Gly|Ser|Gly|Ser|
|145| | | |150| | | |155| | | | | |160|
|Ile|Asp|Gln|Asn|Asp|Phe|Asn|Gln|Met|Lys|Gly|Phe|Val|Gln|Ala|Val|
| | | |165| | | |170| | | |175| | | |
|Met|Gly|Gln|Phe|Glu|Gly|Thr|Asp|Thr|Leu|Phe|Ala|Leu|Met|Gln|Tyr|
| | |180| | | |185| | | |190| | | | |
|Ser|Asn|Leu|Leu|Lys|Ile|His|Phe|Thr|Phe|Thr|Gln|Phe|Arg|Thr|Ser|
| |195| | | |200| | | |205| | | | | |
|Pro|Ser|Gln|Gln|Ser|Leu|Val|Asp|Pro|Ile|Val|Gln|Leu|Lys|Gly|Leu|
|210| | | |215| | | |220| | | | | | |
|Thr|Phe|Thr|Ala|Thr|Gly|Ile|Leu|Thr|Val|Val|Thr|Gln|Leu|Phe|His|
|225| | | |230| | | |235| | | |240| | |
|His|Lys|Asn|Gly|Ala|Arg|Lys|Ser|Ala|Lys|Lys|Ile|Leu|Ile|Val|Ile|
| | | |245| | | |250| | | |255| | | |
|Thr|Asp|Gly|Gln|Lys|Tyr|Lys|Asp|Pro|Leu|Glu|Tyr|Ser|Asp|Val|Ile|
| | |260| | | |265| | | |270| | | | |
|Pro|Gln|Ala|Glu|Lys|Ala|Gly|Ile|Ile|Arg|Tyr|Ala|Ile|Gly|Val|Gly|
| |275| | | |280| | | |285| | | | | |
|His|Ala|Phe|Gln|Gly|Pro|Thr|Ala|Arg|Gln|Glu|Leu|Asn|Thr|Ile|Ser|
|290| | | |295| | | |300| | | | | | |
|Ser|Ala|Pro|Pro|Gln|Asp|His|Val|Phe|Lys|Val|Asp|Asn|Phe|Ala|Ala|
|305| | | |310| | | |315| | | |320| | |
|Leu|Gly|Ser|Ile|Gln|Lys|Gln|Leu|Gln|Glu|Lys|Ile|Tyr|Ala|Val|Glu|
| | | |325| | | |330| | | |335| | | |
|Gly|Thr|Gln|Ser|Arg|Ala|Ser|Ser|Phe|Gln|His|Glu|Met|Ser|Gln|
| | | |340| | | |345| | | |350| | | |
|Glu|Gly|Phe|Ser|Thr|Ala|Leu|Thr|Met|Asp|Gly|Leu|Phe|Leu|Gly|Ala|
| | |355| | | |360| | | |365| | | | |
|Val|Gly|Ser|Phe|Ser|Trp|Ser|Gly|Gly|Ala|Phe|Leu|Tyr|Pro|Pro|Asn|
| |370| | | |375| | | |380| | | | | |
|Met|Ser|Pro|Thr|Phe|Ile|Asn|Met|Ser|Gln|Glu|Asn|Val|Asp|Met|Arg|
|385| | | |390| | | |395| | | |400| | |
|Asp|Ser|Tyr|Leu|Gly|Tyr|Ser|Thr|Glu|Leu|Ala|Leu|Trp|Lys|Gly|Val|
| | | |405| | | |410| | | |415| | | |
|Gln|Asn|Leu|Val|Leu|Gly|Ala|Pro|Arg|Tyr|Gln|His|Thr|Gly|Lys|Ala|
| | | |420| | | |425| | | |430| | | |
|Val|Ile|Phe|Thr|Gln|Val|Ser|Arg|Gln|Trp|Arg|Lys|Lys|Ala|Glu|Val|
| | |435| | | |440| | | |445| | | | |
|Thr|Gly|Thr|Gln|Ile|Gly|Ser|Tyr|Phe|Gly|Ala|Ser|Leu|Cys|Ser|Val|
| |450| | | |455| | | |460| | | | | |
|Asp|Val|Asp|Ser|Asp|Gly|Ser|Thr|Asp|Leu|Ile|Leu|Ile|Gly|Ala|Pro|
|465| | | |470| | | |475| | | |480| | |
|His|Tyr|Tyr|Glu|Gln|Thr|Arg|Gly|Gly|Gln|Val|Ser|Val|Cys|Pro|Leu|
| | | |485| | | |490| | | |495| | | |
|Pro|Arg|Gly|Arg|Val|Gln|Trp|Gln|Cys|Asp|Ala|Val|Leu|Arg|Gly|Glu|
| | |500| | | |505| | | |510| | | | |
|Gln|Gly|His|Pro|Trp|Gly|Arg|Phe|Gly|Ala|Ala|Leu|Thr|Val|Leu|Gly|
| | |515| | | |520| | | |525| | | | |
|Asp|Val|Asn|Glu|Asp|Lys|Leu|Ile|Asp|Val|Ala|Ile|Gly|Ala|Pro|Gly|
| |530| | | |535| | | |540| | | | | |

| | | | | | | | | | | | | | | | |
|---|---|---|---|---|---|---|---|---|---|---|---|---|---|---|---|
|Glu|Gln|Glu|Asn|Arg|Gly|Ala|Val|Tyr|Leu|Phe|His|Gly|Ala|Ser|Glu|
|545| | | | |550| | | |555| | | | | |560|
|Ser|Gly|Ile|Ser|Pro|Ser|His|Ser|Gln|Arg|Ile|Ala|Ser|Ser|Gln|Leu|
| | | | |565| | | |570| | | | |575| | |
|Ser|Pro|Arg|Leu|Gln|Tyr|Phe|Gly|Gln|Ala|Leu|Ser|Gly|Gly|Gln|Asp|
| | | |580| | | | |585| | | | |590| | |
|Leu|Thr|Gln|Asp|Gly|Leu|Met|Asp|Leu|Ala|Val|Gly|Ala|Arg|Gly|Gln|
| | |595| | | |600| | | | | |605| | | |
|Val|Leu|Leu|Leu|Arg|Ser|Leu|Pro|Val|Leu|Lys|Val|Gly|Val|Ala|Met|
| |610| | | |615| | | | |620| | | | | |
|Arg|Phe|Ser|Pro|Val|Glu|Val|Ala|Lys|Ala|Val|Tyr|Arg|Cys|Trp|Glu|
|625| | | |630| | | |635| | | | | | |640|
|Glu|Lys|Pro|Ser|Ala|Leu|Glu|Ala|Gly|Asp|Ala|Thr|Val|Cys|Leu|Thr|
| | | |645| | | |650| | | | | | |655| |
|Ile|Gln|Lys|Ser|Ser|Leu|Asp|Gln|Leu|Gly|Asp|Ile|Gln|Ser|Ser|Val|
| | | |660| | | |665| | | | |670| | | |
|Arg|Phe|Asp|Leu|Ala|Leu|Asp|Pro|Gly|Arg|Leu|Thr|Ser|Arg|Ala|Ile|
| | |675| | | |680| | | | |685| | | | |
|Phe|Asn|Glu|Thr|Lys|Asn|Pro|Thr|Leu|Thr|Arg|Arg|Lys|Thr|Leu|Gly|
| |690| | | |695| | | | |700| | | | | |
|Leu|Gly|Ile|His|Cys|Glu|Thr|Leu|Lys|Leu|Leu|Leu|Pro|Asp|Cys|Val|
|705| | | |710| | | | |715| | | | | |720|
|Glu|Asp|Val|Val|Ser|Pro|Ile|Ile|Leu|His|Leu|Asn|Phe|Ser|Leu|Val|
| | | |725| | | | |730| | | | |735| | |
|Arg|Glu|Pro|Ile|Pro|Ser|Pro|Gln|Asn|Leu|Arg|Pro|Val|Leu|Ala|Val|
| | | |740| | | |745| | | | |750| | | |
|Gly|Ser|Gln|Asp|Leu|Phe|Thr|Ala|Ser|Leu|Pro|Phe|Glu|Lys|Asn|Cys|
| |755| | | |760| | | | |765| | | | | |
|Gly|Gln|Asp|Gly|Leu|Cys|Glu|Gly|Asp|Leu|Gly|Val|Thr|Leu|Ser|Phe|
|770| | | | |775| | | | |780| | | | | |
|Ser|Gly|Leu|Gln|Thr|Leu|Thr|Val|Gly|Ser|Ser|Leu|Glu|Leu|Asn|Val|
|785| | | |790| | | |795| | | | | | |800|
|Ile|Val|Thr|Val|Trp|Asn|Ala|Gly|Glu|Asp|Ser|Tyr|Gly|Thr|Val|Val|
| | | |805| | | |810| | | | |815| | | |
|Ser|Leu|Tyr|Tyr|Pro|Ala|Gly|Leu|Ser|His|Arg|Arg|Val|Ser|Gly|Ala|
| | |820| | | |825| | | | |830| | | | |
|Gln|Lys|Gln|Pro|His|Gln|Ser|Ala|Leu|Arg|Leu|Ala|Cys|Glu|Thr|Val|
| |835| | | |840| | | | |845| | | | | |
|Pro|Thr|Glu|Asp|Glu|Gly|Leu|Arg|Ser|Ser|Arg|Cys|Ser|Val|Asn|His|
|850| | | | |855| | | | |860| | | | | |
|Pro|Ile|Phe|His|Glu|Gly|Ser|Asn|Gly|Thr|Phe|Ile|Val|Thr|Phe|Asp|
|865| | | | |870| | | | |875| | | | |880|
|Val|Ser|Tyr|Lys|Ala|Thr|Leu|Gly|Asp|Arg|Met|Leu|Met|Arg|Ala|Ser|
| | | |885| | | |890| | | | |895| | | |
|Ala|Ser|Ser|Glu|Asn|Asn|Lys|Ala|Ser|Ser|Lys|Ala|Thr|Phe|Gln|
| | | |900| | | |905| | | |910| | | | |
|Leu|Glu|Leu|Pro|Val|Lys|Tyr|Ala|Val|Tyr|Thr|Met|Ile|Ser|Arg|Gln|
| | |915| | | |920| | | | |925| | | | |
|Glu|Glu|Ser|Thr|Lys|Tyr|Phe|Asn|Phe|Ala|Thr|Ser|Asp|Glu|Lys|Lys|
| |930| | | |935| | | | |940| | | | | |
|Met|Lys|Glu|Ala|Glu|His|Arg|Tyr|Arg|Val|Asn|Asn|Leu|Ser|Gln|Arg|
|945| | | |950| | | | |955| | | | | |960|
|Asp|Leu|Ala|Ile|Ser|Ile|Asn|Phe|Trp|Val|Pro|Val|Leu|Leu|Asn|Gly|

|  |  |  |  |  |  |  |  |  |  |  |  |  |  |  |
|---|---|---|---|---|---|---|---|---|---|---|---|---|---|---|
|  |  |  |  |  | 965 |  |  |  | 970 |  |  |  | 975 |  |
| Val | Ala | Val | Trp | Asp | Val | Val | Met | Glu | Ala | Pro | Ser | Gln | Ser | Leu | Pro |
|  |  |  | 980 |  |  |  |  | 985 |  |  |  | 990 |  |  |
| Cys | Val | Ser | Glu | Arg | Lys | Pro | Pro | Gln | His | Ser | Asp | Phe | Leu | Thr | Gln |
|  |  | 995 |  |  |  |  | 1000 |  |  |  |  | 1005 |  |  |
| Ile | Ser | Arg | Ser | Pro | Met | Leu | Asp | Cys | Ser | Ile | Ala | Asp | Cys | Leu | Gln |
|  |  | 1010 |  |  |  |  | 1015 |  |  |  |  | 1020 |  |  |
| Phe | Arg | Cys | Asp | Val | Pro | Ser | Phe | Ser | Val | Gln | Glu | Leu | Asp | Phe |
| 1025 |  |  |  |  | 1030 |  |  |  |  | 1035 |  |  |  | 1040 |
| Thr | Leu | Lys | Gly | Asn | Leu | Ser | Phe | Gly | Trp | Val | Arg | Glu | Thr | Leu | Gln |
|  |  |  |  | 1045 |  |  |  |  | 1050 |  |  |  |  | 1055 |
| Lys | Lys | Val | Leu | Val | Ser | Val | Ala | Glu | Ile | Thr | Phe | Asp | Thr | Ser |
|  |  |  | 1060 |  |  |  |  | 1065 |  |  |  |  | 1070 |  |
| Val | Tyr | Ser | Gln | Leu | Pro | Gly | Gln | Glu | Ala | Phe | Met | Arg | Ala | Gln | Met |
|  |  |  | 1075 |  |  |  |  | 1080 |  |  |  |  | 1085 |  |
| Glu | Met | Val | Leu | Glu | Glu | Asp | Glu | Val | Tyr | Asn | Ala | Ile | Pro | Ile | Ile |
|  |  |  | 1090 |  |  |  |  | 1095 |  |  |  | 1100 |  |  |
| Met | Gly | Ser | Ser | Val | Gly | Ala | Leu | Leu | Leu | Leu | Ala | Leu | Ile | Thr | Ala |
| 1105 |  |  |  |  | 1110 |  |  |  |  | 1115 |  |  |  |  | 1120 |
| Thr | Leu | Tyr | Lys | Leu | Gly | Phe | Phe | Lys | Arg | His | Tyr | Lys | Glu | Met | Leu |
|  |  |  |  | 1125 |  |  |  |  | 1130 |  |  |  |  | 1135 |
| Glu | Asp | Lys | Pro | Glu | Asp | Thr | Ala | Thr | Phe | Ser | Gly | Asp | Asp | Phe | Ser |
|  |  |  | 1140 |  |  |  |  | 1145 |  |  |  |  | 1150 |  |
| Cys | Val | Ala | Pro | Asn | Val | Pro | Leu | Ser |  |  |  |  |  |  |
|  |  | 1155 |  |  |  |  | 1160 |  |  |  |  |  |  |  |

( 2 ) INFORMATION FOR SEQ ID NO:100:

( i ) SEQUENCE CHARACTERISTICS:
        ( A ) LENGTH: 1318 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 17..1255

( x i ) SEQUENCE DESCRIPTION: SEQ ID NO:100:

| AATTCGGCAC | GAGCTT |  | GGG | GCT | GTG | GTC | CTC | CTT | GGG | GTC | CTG | GCT | TCT | 49 |
|---|---|---|---|---|---|---|---|---|---|---|---|---|---|---|
|  |  |  | Gly | Ala | Val | Val | Leu | Leu | Gly | Val | Leu | Ala | Ser |  |
|  |  |  | 1 |  |  |  | 5 |  |  |  |  | 10 |  |  |
| TAC | CAC | GGA | TTC | AAC | TTG | GAC | GTG | GAT | GAG | CCG | GTG | ATC | TTC | CAG | GAA | 97 |
| Tyr | His | Gly | Phe | Asn | Leu | Asp | Val | Asp | Glu | Pro | Val | Ile | Phe | Gln | Glu |  |
|  |  | 15 |  |  |  |  | 20 |  |  |  |  | 25 |  |  |  |
| GAC | GCA | GCG | GGC | TTC | GGG | CAG | AGC | GTG | ATG | CAG | TTT | GGA | GGA | TCT | CGA | 145 |
| Asp | Ala | Ala | Gly | Phe | Gly | Gln | Ser | Val | Met | Gln | Phe | Gly | Gly | Ser | Arg |  |
|  |  | 30 |  |  |  |  | 35 |  |  |  |  | 40 |  |  |  |
| CTC | GTG | GTG | GGA | GCC | CCC | CTG | GCG | GTG | GTG | TCG | GCC | AAC | CAC | ACA | GGA | 193 |
| Leu | Val | Val | Gly | Ala | Pro | Leu | Ala | Val | Val | Ser | Ala | Asn | His | Thr | Gly |  |
|  |  | 45 |  |  |  |  | 50 |  |  |  |  | 55 |  |  |  |
| CGG | CTG | TAC | GAG | TGT | GCG | CCT | GCC | TCC | GGC | ACC | TGC | ACG | CCC | ATT | TTC | 241 |
| Arg | Leu | Tyr | Glu | Cys | Ala | Pro | Ala | Ser | Gly | Thr | Cys | Thr | Pro | Ile | Phe |  |
| 60 |  |  |  |  | 65 |  |  |  |  | 70 |  |  |  |  | 75 |
| CCA | TTC | ATG | CCC | CCC | GAA | GCC | GTG | AAC | ATG | TCC | CTG | GGC | CTG | TCC | CTG | 289 |
| Pro | Phe | Met | Pro | Pro | Glu | Ala | Val | Asn | Met | Ser | Leu | Gly | Leu | Ser | Leu |  |
|  |  |  |  | 80 |  |  |  |  | 85 |  |  |  |  | 90 |  |
| GCA | GCC | TCC | CCC | AAC | CAT | TCC | CAG | CTG | CTG | GCT | TGT | GGC | CCG | ACC | GTG | 337 |

|     |     |     |     |     |     |     |     |     |     |     |     |     |     |     |     |
|---|---|---|---|---|---|---|---|---|---|---|---|---|---|---|---|
| Ala | Ala | Ser | Pro<br>95 | Asn | His | Ser | Gln | Leu<br>100 | Leu | Ala | Cys | Gly | Pro<br>105 | Thr | Val |

| CAT | AGA | GCC | TGC | GGG | GAG | GAC | GTG | TAC | GCC | CAG | GGT | TTC | TGT | GTG | CTG | 385 |
|---|---|---|---|---|---|---|---|---|---|---|---|---|---|---|---|---|
| His | Arg | Ala<br>110 | Cys | Gly | Glu | Asp | Val<br>115 | Tyr | Ala | Gln | Gly<br>120 | Phe | Cys | Val | Leu | |

| CTG | GAT | GCC | CAC | GCA | CAG | CCC | ATC | GGG | ACT | GTG | CCA | GCT | GCC | CTG | CCC | 433 |
|---|---|---|---|---|---|---|---|---|---|---|---|---|---|---|---|---|
| Leu | Asp<br>125 | Ala | His | Ala | Gln<br>130 | Pro | Ile | Gly | Thr | Val<br>135 | Pro | Ala | Ala | Leu | Pro | |

| GAG | TGC | CCA | GAT | CAA | GAG | ATG | GAC | ATT | GTC | TTC | CTG | ATT | GAC | GGC | TCT | 481 |
|---|---|---|---|---|---|---|---|---|---|---|---|---|---|---|---|---|
| Glu<br>140 | Cys | Pro | Asp | Gln | Glu<br>145 | Met | Asp | Ile | Val | Phe<br>150 | Leu | Ile | Asp | Gly | Ser<br>155 | |

| GGC | AGC | ATT | AGC | TCA | AAT | GAC | TTC | CGC | AAG | ATG | AAG | GAC | TTT | GTC | AGA | 529 |
|---|---|---|---|---|---|---|---|---|---|---|---|---|---|---|---|---|
| Gly | Ser | Ile | Ser | Ser<br>160 | Asn | Asp | Phe | Arg | Lys<br>165 | Met | Lys | Asp | Phe | Val<br>170 | Arg | |

| GCT | GTG | ATG | GAC | CAG | TTC | AAG | GAC | ACC | AAC | ACC | CAG | TTC | TCG | CTG | ATG | 577 |
|---|---|---|---|---|---|---|---|---|---|---|---|---|---|---|---|---|
| Ala | Val | Met | Asp<br>175 | Gln | Phe | Lys | Asp | Thr<br>180 | Asn | Thr | Gln | Phe | Ser<br>185 | Leu | Met | |

| CAG | TAC | TCC | AAT | GTG | CTG | GTG | ACA | CAT | TTC | ACC | TTC | AGC | AGC | TTC | CGG | 625 |
|---|---|---|---|---|---|---|---|---|---|---|---|---|---|---|---|---|
| Gln | Tyr | Ser | Asn<br>190 | Val | Leu | Val | Thr | His<br>195 | Phe | Thr | Phe | Ser | Ser<br>200 | Phe | Arg | |

| AAC | AGC | TCC | AAT | CCT | CAG | GGC | CTA | GTG | GAG | CCC | ATT | GTG | CAG | CTG | ACA | 673 |
|---|---|---|---|---|---|---|---|---|---|---|---|---|---|---|---|---|
| Asn | Ser<br>205 | Ser | Asn | Pro | Gln | Gly<br>210 | Leu | Val | Glu | Pro | Ile<br>215 | Val | Gln | Leu | Thr | |

| GGC | CTC | ACG | TTC | ACG | GCC | ACA | GGG | ATC | CTG | AAA | GTG | GTG | ACA | GAG | CTG | 721 |
|---|---|---|---|---|---|---|---|---|---|---|---|---|---|---|---|---|
| Gly<br>220 | Leu | Thr | Phe | Thr | Ala<br>225 | Thr | Gly | Ile | Leu | Lys<br>230 | Val | Val | Thr | Glu | Leu<br>235 | |

| TTT | CAA | ACC | AAG | AAC | GGG | GCC | CGC | GAA | AGT | GCC | AAG | AAG | ATC | CTC | ATC | 769 |
|---|---|---|---|---|---|---|---|---|---|---|---|---|---|---|---|---|
| Phe | Gln | Thr | Lys | Asn<br>240 | Gly | Ala | Arg | Glu | Ser<br>245 | Ala | Lys | Lys | Ile | Leu<br>250 | Ile | |

| GTC | ATC | ACA | GAT | GGG | CAG | AAG | TAC | AAA | GAC | CCC | CTG | CAC | TAC | AGT | GCT | 817 |
|---|---|---|---|---|---|---|---|---|---|---|---|---|---|---|---|---|
| Val | Ile | Thr | Asp<br>255 | Gly | Gln | Lys | Tyr | Lys<br>260 | Asp | Pro | Leu | His | Tyr<br>265 | Ser | Ala | |

| GTC | ATC | CCA | CAG | GCA | GAG | CAG | GCG | GGC | ATC | ATC | CGC | TAC | GCC | ATC | GGG | 865 |
|---|---|---|---|---|---|---|---|---|---|---|---|---|---|---|---|---|
| Val | Ile | Pro | Gln<br>270 | Ala | Glu | Gln | Ala | Gly<br>275 | Ile | Ile | Arg | Tyr | Ala<br>280 | Ile | Gly | |

| GTG | GGG | GAC | GCG | TTC | CAG | AAA | CCC | ACA | GCC | AGG | CAG | GAG | CTG | GAC | ACC | 913 |
|---|---|---|---|---|---|---|---|---|---|---|---|---|---|---|---|---|
| Val | Gly<br>285 | Asp | Ala | Phe | Gln | Lys<br>290 | Pro | Thr | Ala | Arg | Gln<br>295 | Glu | Leu | Asp | Thr | |

| ATC | GCC | TCC | GAG | CCG | CCC | GAC | GCC | CAC | GTG | TTC | CAG | GTG | GAC | AAT | TTC | 961 |
|---|---|---|---|---|---|---|---|---|---|---|---|---|---|---|---|---|
| Ile | Ala | Ser | Glu<br>300 | Pro | Pro | Asp | Ala | His<br>305 | Val | Phe | Gln | Val | Asp<br>310 | Asn | Phe<br>315 | |

| TCA | GCA | CTC | AGC | AGC | ATC | CAA | AAG | CAG | CTG | TAT | GAC | AGG | ATC | TTT | GCC | 1009 |
|---|---|---|---|---|---|---|---|---|---|---|---|---|---|---|---|---|
| Ser | Ala | Leu | Ser | Ser<br>320 | Ile | Gln | Lys | Gln | Leu<br>325 | Tyr | Asp | Arg | Ile | Phe<br>330 | Ala | |

| GTC | GAG | GGA | ACC | CTG | TCA | TCG | GCA | AGC | ACC | TCC | TTC | CAG | CAT | GAG | ATG | 1057 |
|---|---|---|---|---|---|---|---|---|---|---|---|---|---|---|---|---|
| Val | Glu | Gly | Thr<br>335 | Leu | Ser | Ser | Ala | Ser<br>340 | Thr | Ser | Phe | Gln | His<br>345 | Glu | Met | |

| TCC | CAA | GAG | GGC | TTC | AGC | TCA | CTT | CTC | ACC | ACG | GAA | GGA | CCG | GTG | CTG | 1105 |
|---|---|---|---|---|---|---|---|---|---|---|---|---|---|---|---|---|
| Ser | Gln | Glu<br>350 | Gly | Phe | Ser | Ser | Leu<br>355 | Leu | Thr | Thr | Glu | Gly<br>360 | Pro | Val | Leu | |

| GGG | GCT | GTG | GGC | AGC | TTC | GAT | TGG | TCC | GGG | GGT | GCT | TTC | CTG | TAC | CCC | 1153 |
|---|---|---|---|---|---|---|---|---|---|---|---|---|---|---|---|---|
| Gly | Ala | Val | Gly<br>365 | Ser | Phe | Asp | Trp | Ser<br>370 | Gly | Gly | Ala | Phe | Leu<br>375 | Tyr | Pro | |

| CCC | GGC | GGG | AGC | CCC | ACC | TTC | ATC | AAC | ATG | TCT | CAG | CAG | AAC | GTG | GAC | 1201 |
|---|---|---|---|---|---|---|---|---|---|---|---|---|---|---|---|---|
| Pro<br>380 | Gly | Gly | Ser | Pro | Thr<br>385 | Phe | Ile | Asn | Met | Ser<br>390 | Gln | Gln | Asn | Val | Asp<br>395 | |

| ATG | AGG | GAC | TCC | TAC | CTG | GGT | GAG | GAA | GGG | GTG | GGG | GTG | GGG | ACA | GGT | 1249 |
|---|---|---|---|---|---|---|---|---|---|---|---|---|---|---|---|---|
| Met | Arg | Asp | Ser | Tyr<br>400 | Leu | Gly | Glu | Glu | Gly<br>405 | Val | Gly | Val | Gly<br>410 | Thr | Gly | |

| GGG | AGC | TGAGGCTTGG | GGTGGGGTGG | GGCTGGGCTG | GGAGGGGAGG | GAAGAGGAGG | 1305 |
|---|---|---|---|---|---|---|---|

Gly Ser

GGAGAGGCAA AGA 1318

(2) INFORMATION FOR SEQ ID NO:101:

(i) SEQUENCE CHARACTERISTICS:
        (A) LENGTH: 413 amino acids
        (B) TYPE: amino acid
        (D) TOPOLOGY: linear (ii) MOLECULE TYPE: protein (xi) SEQUENCE DESCRIPTION: SEQ ID NO:101:

```
Gly  Ala  Val  Val  Leu  Leu  Gly  Val  Leu  Ala  Ser  Tyr  His  Gly  Phe  Asn
 1              5                        10                       15
Leu  Asp  Val  Asp  Glu  Pro  Val  Ile  Phe  Gln  Glu  Asp  Ala  Ala  Gly  Phe
               20                        25                      30
Gly  Gln  Ser  Val  Met  Gln  Phe  Gly  Gly  Ser  Arg  Leu  Val  Val  Gly  Ala
              35                        40                      45
Pro  Leu  Ala  Val  Val  Ser  Ala  Asn  His  Thr  Gly  Arg  Leu  Tyr  Glu  Cys
     50                        55                       60
Ala  Pro  Ala  Ser  Gly  Thr  Cys  Thr  Pro  Ile  Phe  Pro  Phe  Met  Pro  Pro
 65                      70                       75                       80
Glu  Ala  Val  Asn  Met  Ser  Leu  Gly  Leu  Ser  Leu  Ala  Ala  Ser  Pro  Asn
                    85                       90                           95
His  Ser  Gln  Leu  Leu  Ala  Cys  Gly  Pro  Thr  Val  His  Arg  Ala  Cys  Gly
                    100                      105                     110
Glu  Asp  Val  Tyr  Ala  Gln  Gly  Phe  Cys  Val  Leu  Leu  Asp  Ala  His  Ala
               115                       120                    125
Gln  Pro  Ile  Gly  Thr  Val  Pro  Ala  Ala  Leu  Pro  Glu  Cys  Pro  Asp  Gln
     130                       135                      140
Glu  Met  Asp  Ile  Val  Phe  Leu  Ile  Asp  Gly  Ser  Gly  Ser  Ile  Ser  Ser
145                       150                      155                      160
Asn  Asp  Phe  Arg  Lys  Met  Lys  Asp  Phe  Val  Arg  Ala  Val  Met  Asp  Gln
                    165                      170                     175
Phe  Lys  Asp  Thr  Asn  Thr  Gln  Phe  Ser  Leu  Met  Gln  Tyr  Ser  Asn  Val
               180                       185                     190
Leu  Val  Thr  His  Phe  Thr  Phe  Ser  Ser  Phe  Arg  Asn  Ser  Asn  Pro
               195                       200                     205
Gln  Gly  Leu  Val  Glu  Pro  Ile  Val  Gln  Leu  Thr  Gly  Leu  Thr  Phe  Thr
     210                       215                      220
Ala  Thr  Gly  Ile  Leu  Lys  Val  Val  Thr  Glu  Leu  Phe  Gln  Thr  Lys  Asn
225                      230                       235                     240
Gly  Ala  Arg  Glu  Ser  Ala  Lys  Lys  Ile  Leu  Ile  Val  Ile  Thr  Asp  Gly
                    245                      250                     255
Gln  Lys  Tyr  Lys  Asp  Pro  Leu  His  Tyr  Ser  Ala  Val  Ile  Pro  Gln  Ala
               260                       265                     270
Glu  Gln  Ala  Gly  Ile  Ile  Arg  Tyr  Ala  Ile  Gly  Val  Gly  Asp  Ala  Phe
          275                       280                      285
Gln  Lys  Pro  Thr  Ala  Arg  Gln  Glu  Leu  Asp  Thr  Ile  Ala  Ser  Glu  Pro
     290                       295                      300
Pro  Asp  Ala  His  Val  Phe  Gln  Val  Asp  Asn  Phe  Ser  Ala  Leu  Ser  Ser
305                      310                       315                     320
Ile  Gln  Lys  Gln  Leu  Tyr  Asp  Arg  Ile  Phe  Ala  Val  Glu  Gly  Thr  Leu
                    325                      330                     335
Ser  Ser  Ala  Ser  Thr  Ser  Phe  Gln  His  Glu  Met  Ser  Gln  Glu  Gly  Phe
```

```
                          340                          345                          350

Ser   Ser   Leu   Leu   Thr   Thr   Glu   Gly   Pro   Val   Leu   Gly   Ala   Val   Gly   Ser
            355                           360                           365

Phe   Asp   Trp   Ser   Gly   Gly   Ala   Phe   Leu   Tyr   Pro   Pro   Gly   Gly   Ser   Pro
      370                           375                           380

Thr   Phe   Ile   Asn   Met   Ser   Gln   Gln   Asn   Val   Asp   Met   Arg   Asp   Ser   Tyr
385                           390                           395                           400

Leu   Gly   Glu   Glu   Gly   Val   Gly   Val   Gly   Thr   Gly   Gly   Ser
                        405                           410
```

( 2 ) INFORMATION FOR SEQ ID NO:102:

( i ) SEQUENCE CHARACTERISTICS:
        ( A ) LENGTH: 1484 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1482

( x i ) SEQUENCE DESCRIPTION: SEQ ID NO:102:

```
GAT   GTC   CAG   AGC   TCC   ATC   AGC   TAT   GAT   CTG   GCA   CTG   GAC   CCA   GGC   CGC      48
Asp   Val   Gln   Ser   Ser   Ile   Ser   Tyr   Asp   Leu   Ala   Leu   Asp   Pro   Gly   Arg
1                       5                           10                          15

CTG   GTC   TCT   CGG   GCC   ATT   TTT   CAA   GAG   ACC   CAG   AAC   CAG   ACT   TTA   ACT      96
Leu   Val   Ser   Arg   Ala   Ile   Phe   Gln   Glu   Thr   Gln   Asn   Gln   Thr   Leu   Thr
                  20                          25                          30

CGA   AGG   AAG   ACC   CTG   GGG   CTG   GGG   CGT   CAC   TGT   GAA   ACC   ATG   AGG   CTA     144
Arg   Arg   Lys   Thr   Leu   Gly   Leu   Gly   Arg   His   Cys   Glu   Thr   Met   Arg   Leu
            35                          40                          45

CTT   TTG   CCA   GAC   TGC   GTA   GAG   GAC   GTG   GTG   AAC   CCC   ATC   GTC   CTG   CAC     192
Leu   Leu   Pro   Asp   Cys   Val   Glu   Asp   Val   Val   Asn   Pro   Ile   Val   Leu   His
      50                          55                          60

CTC   AAC   TTC   TCC   CTG   GAG   GGA   CAG   CCA   ATC   CTC   TCA   TCC   CAG   AAT   CTG     240
Leu   Asn   Phe   Ser   Leu   Glu   Gly   Gln   Pro   Ile   Leu   Ser   Ser   Gln   Asn   Leu
65                          70                          75                          80

CGC   CCT   GTG   CTG   GCC   ACG   GGC   TCG   CAG   GAC   CAC   TTC   ATT   GCC   TCC   CTC     288
Arg   Pro   Val   Leu   Ala   Thr   Gly   Ser   Gln   Asp   His   Phe   Ile   Ala   Ser   Leu
                        85                          90                          95

CCC   TTT   GAG   AAG   AAC   TGC   GGA   CAA   GAT   CGC   CTG   TGT   GAG   GGG   GAC   CTG     336
Pro   Phe   Glu   Lys   Asn   Cys   Gly   Gln   Asp   Arg   Leu   Cys   Glu   Gly   Asp   Leu
                  100                         105                         110

AGC   ATC   AGC   TTC   AAC   TTC   TCG   GGC   TTG   AAT   ACC   CTG   CTG   GTG   GGG   CTC     384
Ser   Ile   Ser   Phe   Asn   Phe   Ser   Gly   Leu   Asn   Thr   Leu   Leu   Val   Gly   Leu
            115                         120                         125

TCC   CTG   GAG   CTC   ACA   GTG   ACA   GTG   ACC   GTG   CGG   AAT   GAG   GGC   GAG   GAC     432
Ser   Leu   Glu   Leu   Thr   Val   Thr   Val   Thr   Val   Arg   Asn   Glu   Gly   Glu   Asp
      130                         135                         140

TCC   TAT   GGG   ACC   GCC   ATC   ACC   CTC   TAC   TAC   CCA   GCA   GGG   CTA   TCC   TAC     480
Ser   Tyr   Gly   Thr   Ala   Ile   Thr   Leu   Tyr   Tyr   Pro   Ala   Gly   Leu   Ser   Tyr
145                         150                         155                         160

AGG   CGG   GTG   TCG   GGC   CAG   ACA   CAA   CCC   TGG   CAG   CGC   CCC   CTG   CAC   CTC     528
Arg   Arg   Val   Ser   Gly   Gln   Thr   Gln   Pro   Trp   Gln   Arg   Pro   Leu   His   Leu
                        165                         170                         175

GCA   TGT   GAG   GCT   GTA   CCT   ACC   GAG   AGC   GAG   GGC   TTG   AGG   AGT   ACC   AGC     576
Ala   Cys   Glu   Ala   Val   Pro   Thr   Glu   Ser   Glu   Gly   Leu   Arg   Ser   Thr   Ser
                  180                         185                         190

TGC   AGC   GTC   AAC   CAC   CCC   ATC   TTC   CAA   GGG   GGT   GCT   CAG   GGC   ACT   TTC     624
```

-continued

```
Cys Ser Val Asn His Pro Ile Phe Gln Gly Gly Ala Gln Gly Thr Phe
        195                 200                 205

GTA GTC AAG TTC GAT GTC TCC TCC AAG GCC AGC CTG GGT GAC AGG TTG    672
Val Val Lys Phe Asp Val Ser Ser Lys Ala Ser Leu Gly Asp Arg Leu
    210                 215                 220

CTC ATG GGG GCC AGT GCC AGC AGT GAG AAT AAT AAG CCT GCG AGC AAC    720
Leu Met Gly Ala Ser Ala Ser Ser Glu Asn Asn Lys Pro Ala Ser Asn
225                 230                 235                 240

AAG ACC TCC TTT GAG CTG GAA CTG CCA GTG AAA TAC GCT GTC TAC ATG    768
Lys Thr Ser Phe Glu Leu Glu Leu Pro Val Lys Tyr Ala Val Tyr Met
                245                 250                 255

ATG ATC ACA AGG CAC GAA GGC TCC ACC AGG TTC TTC AAC TTT TCC ACT    816
Met Ile Thr Arg His Glu Gly Ser Thr Arg Phe Phe Asn Phe Ser Thr
            260                 265                 270

TCC GCT GAG AAG AGC AGC AAA GAG GCC GAG CAC CGC TAT CGG GTG AAC    864
Ser Ala Glu Lys Ser Ser Lys Glu Ala Glu His Arg Tyr Arg Val Asn
        275                 280                 285

AAC CTG AGT CTG CGA GAT GTG GCC GTC AGC GTG GAC TTC TGG GCC CCC    912
Asn Leu Ser Leu Arg Asp Val Ala Val Ser Val Asp Phe Trp Ala Pro
    290                 295                 300

GTG CAG CTG AAC GGA GCA GCT GTG TGG GAC GTG GCG GTG GAG GCC CCT    960
Val Gln Leu Asn Gly Ala Ala Val Trp Asp Val Ala Val Glu Ala Pro
305                 310                 315                 320

GCC CAG AGC CTG CCC TGT GCG CGG GAG AGG GAA CCT CCG AGG ACC TCT    1008
Ala Gln Ser Leu Pro Cys Ala Arg Glu Arg Glu Pro Pro Arg Thr Ser
                325                 330                 335

GAC CTG AGC CGG GTC CCG GGG AGT CCC GTG CTG GAC TGC AGC GTT GCG    1056
Asp Leu Ser Arg Val Pro Gly Ser Pro Val Leu Asp Cys Ser Val Ala
            340                 345                 350

CAC TGC CTG AGG TTC CGC TGC CAC ATC CCC TCC TTC AGC GCC AAG GAG    1104
His Cys Leu Arg Phe Arg Cys His Ile Pro Ser Phe Ser Ala Lys Glu
        355                 360                 365

GAG CTC CAC TTC ACC CTG AAG GGC AAC CTC AGC TTC GCC TGG GTC AGC    1152
Glu Leu His Phe Thr Leu Lys Gly Asn Leu Ser Phe Ala Trp Val Ser
    370                 375                 380

CAG ATG CTG CAA AAG AAG GTG TCG GTG GTG AGT GTG GCC GAG ATC ACC    1200
Gln Met Leu Gln Lys Lys Val Ser Val Val Ser Val Ala Glu Ile Thr
385                 390                 395                 400

TTC AAC AGG GCC GTG TAC TCC CAA GTT CCG GGC GAG GAG CCC TTT ATG    1248
Phe Asn Arg Ala Val Tyr Ser Gln Val Pro Gly Glu Glu Pro Phe Met
                405                 410                 415

AGA GCC CAG GTG GAG ACG GTG CTG GAG GAG TAT GAG GAG CAC GAC CCC    1296
Arg Ala Gln Val Glu Thr Val Leu Glu Glu Tyr Glu Glu His Asp Pro
            420                 425                 430

GTC CCC CTG GTG GTG GGC AGC TGT GTG GGC GGC CTG CTG CTG CTG GCT    1344
Val Pro Leu Val Val Gly Ser Cys Val Gly Gly Leu Leu Leu Leu Ala
        435                 440                 445

CTC ATC TCA GCC ACC CTG TAC AAG CTT GGC TTC TTC AAG CGC CGG TAC    1392
Leu Ile Ser Ala Thr Leu Tyr Lys Leu Gly Phe Phe Lys Arg Arg Tyr
    450                 455                 460

AAG GAG ATG CTG GGC GAG AAA CCG GGA GAC GCG GCC ACC TTC CCC GGG    1440
Lys Glu Met Leu Gly Glu Lys Pro Gly Asp Ala Ala Thr Phe Pro Gly
465                 470                 475                 480

GAG GAC GCC AGC TGC GGG GCT TCA GAT TTG CCT TTG TCC CAG              1482
Glu Asp Ala Ser Cys Gly Ala Ser Asp Leu Pro Leu Ser Gln
                485                 490

TG                                                                   1484
```

( 2 ) INFORMATION FOR SEQ ID NO:103:

( i ) SEQUENCE CHARACTERISTICS:
  ( A ) LENGTH: 494 amino acids
  ( B ) TYPE: amino acid
  ( D ) TOPOLOGY: linear ( i i ) MOLECULE TYPE: protein ( x i ) SEQUENCE DESCRIPTION: SEQ ID NO:103:

```
Asp Val Gln Ser Ser Ile Ser Tyr Asp Leu Ala Leu Asp Pro Gly Arg
 1               5                  10                  15

Leu Val Ser Arg Ala Ile Phe Gln Glu Thr Gln Asn Gln Thr Leu Thr
                 20                  25                  30

Arg Arg Lys Thr Leu Gly Leu Gly Arg His Cys Glu Thr Met Arg Leu
             35                  40                  45

Leu Leu Pro Asp Cys Val Glu Asp Val Val Asn Pro Ile Val Leu His
         50                  55                  60

Leu Asn Phe Ser Leu Glu Gly Gln Pro Ile Leu Ser Ser Gln Asn Leu
 65                  70                  75                  80

Arg Pro Val Leu Ala Thr Gly Ser Gln Asp His Phe Ile Ala Ser Leu
                 85                  90                  95

Pro Phe Glu Lys Asn Cys Gly Gln Arg Leu Cys Glu Gly Asp Leu
            100                 105                 110

Ser Ile Ser Phe Asn Phe Ser Gly Leu Asn Thr Leu Leu Val Gly Leu
            115                 120                 125

Ser Leu Glu Leu Thr Val Thr Val Thr Val Arg Asn Glu Gly Glu Asp
    130                 135                 140

Ser Tyr Gly Thr Ala Ile Thr Leu Tyr Tyr Pro Ala Gly Leu Ser Tyr
145                     150                 155                 160

Arg Arg Val Ser Gly Gln Thr Gln Pro Trp Gln Arg Pro Leu His Leu
                165                 170                 175

Ala Cys Glu Ala Val Pro Thr Glu Ser Glu Gly Leu Arg Ser Thr Ser
                180                 185                 190

Cys Ser Val Asn His Pro Ile Phe Gln Gly Gly Ala Gln Gly Thr Phe
        195                 200                 205

Val Val Lys Phe Asp Val Ser Ser Lys Ala Ser Leu Gly Asp Arg Leu
    210                 215                 220

Leu Met Gly Ala Ser Ala Ser Ser Glu Asn Asn Lys Pro Ala Ser Asn
225                     230                 235                 240

Lys Thr Ser Phe Glu Leu Glu Leu Pro Val Lys Tyr Ala Val Tyr Met
                245                 250                 255

Met Ile Thr Arg His Glu Gly Ser Thr Arg Phe Phe Asn Phe Ser Thr
                260                 265                 270

Ser Ala Glu Lys Ser Ser Lys Glu Ala Glu His Arg Tyr Arg Val Asn
            275                 280                 285

Asn Leu Ser Leu Arg Asp Val Ala Val Ser Val Asp Phe Trp Ala Pro
290                 295                 300

Val Gln Leu Asn Gly Ala Ala Val Trp Asp Val Ala Val Glu Ala Pro
305                 310                 315                 320

Ala Gln Ser Leu Pro Cys Ala Arg Glu Arg Glu Pro Pro Arg Thr Ser
                325                 330                 335

Asp Leu Ser Arg Val Pro Gly Ser Pro Val Leu Asp Cys Ser Val Ala
            340                 345                 350

His Cys Leu Arg Phe Arg Cys His Ile Pro Ser Phe Ser Ala Lys Glu
        355                 360                 365

Glu Leu His Phe Thr Leu Lys Gly Asn Leu Ser Phe Ala Trp Val Ser
    370                 375                 380
```

| Gln | Met | Leu | Gln | Lys | Lys | Val | Ser | Val | Val | Ser | Val | Ala | Glu | Ile | Thr |
| 385 | | | | | 390 | | | | | 395 | | | | | 400 |

| Phe | Asn | Arg | Ala | Val | Tyr | Ser | Gln | Val | Pro | Gly | Glu | Glu | Pro | Phe | Met |
| | | | | 405 | | | | | 410 | | | | | 415 | |

| Arg | Ala | Gln | Val | Glu | Thr | Val | Leu | Glu | Glu | Tyr | Glu | Glu | His | Asp | Pro |
| | | | 420 | | | | | 425 | | | | | 430 | | |

| Val | Pro | Leu | Val | Val | Gly | Ser | Cys | Val | Gly | Gly | Leu | Leu | Leu | Leu | Ala |
| | | 435 | | | | | 440 | | | | | 445 | | | |

| Leu | Ile | Ser | Ala | Thr | Leu | Tyr | Lys | Leu | Gly | Phe | Phe | Lys | Arg | Arg | Tyr |
| | 450 | | | | | 455 | | | | | 460 | | | | |

| Lys | Glu | Met | Leu | Gly | Glu | Lys | Pro | Gly | Asp | Ala | Ala | Thr | Phe | Pro | Gly |
| 465 | | | | | 470 | | | | 475 | | | | | | 480 |

| Glu | Asp | Ala | Ser | Cys | Gly | Ala | Ser | Asp | Leu | Pro | Leu | Ser | Gln |
| | | | | 485 | | | | | 490 | | | | |

( 2 ) INFORMATION FOR SEQ ID NO:104:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:104:

TGTCCAGGAC AAGAGATGGA CATTGC          26

( 2 ) INFORMATION FOR SEQ ID NO:105:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:105:

GAGCTATTTC ATAGCAAGAA TGGG            24

( 2 ) INFORMATION FOR SEQ ID NO:106:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:106:

TATAGCATAG CGAATGATCC                 20

( 2 ) INFORMATION FOR SEQ ID NO:107:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:107:

```
ATGGTCCGTG GAGTTGTGAT C                                                                    21
```

(2) INFORMATION FOR SEQ ID NO:108:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:108:

```
TCGAGATCCA CCAAACTGCA C                                                                    21
```

(2) INFORMATION FOR SEQ ID NO:109:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:109:

```
Asn Leu Asp Val Glu Glu Pro Thr Ile Phe Gln Glu Asp Ala
 1               5                  10
```

(2) INFORMATION FOR SEQ ID NO:110:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:110:

```
Asn Leu Asp Val Glu Glu Pro Thr Ile Phe Xaa Glu Asp Ala
 1               5                  10
```

(2) INFORMATION FOR SEQ ID NO:111:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:111:

```
Phe Asn Leu Asp Val Glu Glu Pro Thr Ile Phe Gln Glu Asp Ala
 1               5                  10                  15
```

(2) INFORMATION FOR SEQ ID NO:112:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:112:

```
Phe Asn Leu Asp Val Glu Glu Pro Thr Ile Phe Gln Glu Asp Ala Gly
 1               5                  10                  15
Gly
```

(2) INFORMATION FOR SEQ ID NO:113:

(i) SEQUENCE CHARACTERISTICS:
(A) LENGTH: 16 amino acids
(B) TYPE: amino acid
(D) TOPOLOGY: linear (ii) MOLECULE TYPE: protein (xi) SEQUENCE DESCRIPTION: SEQ ID NO:113:

Phe Asn Leu Asp Thr Glu Glu Leu Thr Ala Phe Val Asp Ser Ala Gly
1               5                   10                  15

(2) INFORMATION FOR SEQ ID NO:114:

(i) SEQUENCE CHARACTERISTICS:
(A) LENGTH: 17 amino acids
(B) TYPE: amino acid
(D) TOPOLOGY: linear (ii) MOLECULE TYPE: protein (xi) SEQUENCE DESCRIPTION: SEQ ID NO:114:

Phe Asn Leu Asp Thr Glu Asn Ala Met Thr Phe Gln Glu Asn Ala Arg
1               5                   10                  15
Gly

METHOD OF IDENTIFYING MODULATORS OF BINDING BETWEEN AND VCAM-1

This application is a continuation-in-part of U.S. Pat. application Ser. No. 08/605,672, filed Feb. 22, 1996, which is now abandoned, which is a continuation-in-part of U.S. application Ser. No. 08/362,652, filed Dec. 21, 1994, now U.S. Pat. No. 5,766,850, which is a continuation-in-part of U.S. application Ser. No. 08/286,889, filed Aug. 5, 1994, which issued as U.S. Pat. No. 5,470,953 on Nov. 28, 1995, which in turn is a continuation-in-part of U.S. application Ser. No. 08/173,497, filed Dec. 23, 1993, which issued as U.S. Pat. No. 5,437,958 on Aug. 1, 1995.

FIELD OF THE INVENTION

The present invention relates to the cloning and expression of polynucleotides encoding a novel human $\beta_2$ integrin $\alpha$ subunit, designated $\alpha_d$, which is structurally related to the known human $\beta_2$ integrin $\alpha$ subunits, CD11a, CD11b and CD11c. The present invention also relates to polynucleotides isolated from other species which show homology to human $\alpha_d$ encoding sequences.

BACKGROUND OF THE INVENTION

The integrins are a class of membrane-associated molecules which actively participate in cellular adhesion. Integrins are transmembrane heterodimers comprising an $\alpha$ subunit in noncovalent association with a $\beta$ subunit. To date, at least fourteen a subunits and eight $\beta$ subunits have been identified [reviewed in Springer, Nature 346:425–434 (1990)]. The $\beta$ subunits are generally capable of association with more than one $\alpha$ subunit and the heterodimers sharing a common $\beta$ subunit have been classified as subfamilies within the integrin population.

One class of human integrins, restricted to expression in white blood cells, is characterized by a common $\beta_2$ subunit. As a result of this cell-specific expression, these integrins are commonly referred to as the leukocyte integrins, Leu-CAMs or leukointegrins. Because of the common $\beta_2$ subunit, an alternative designation of this class is the $\beta_2$ integrins. The $\beta_2$ subunit (CD18) has previously been isolated in association with one of three distinct $\alpha$ subunits, CD11a, CD11b or CD11c. The isolation of a cDNA encoding human CD18 is described in Kishimoto, et al., Cell 48:681–690 (1987). In official WHO nomenclature, the heterodimeric proteins are referred to as CD11a/CD18, CD11b/CD18, and CD11c/CD18; in common nomenclature they are referred to as LFA-1, Mac-1 or Mo1 and p150,95 or LeuM5, respectively [Cobbold, et al., in Leukocyte Typing III, McMichael (ed), Oxford Press, p.788 (1987)]. The human $\beta_2$ integrin $\alpha$ subunits CD11a, CD11b and CD11c have been demonstrated to migrate under reducing condition in electrophoresis with apparent molecular weights of approximately 180 kD, 155 kD and 150 kD, respectively, and DNAs encoding these subunits have been cloned [CD11a, Larson, et al., J. Cell Biol. 108:703–712 (1989); CD11b, Corbi, et al., J. Biol. Chem. 263:12403–12411 (1988) and CD11c, Corbi, et al. EMBO J. 6:4023–4028 (1987)]. Putative homologs of the human $\beta_2$ integrin $\alpha$ and $\beta$ chains, defined by approximate similarity in molecular weight, have been variously identified in other species including monkeys and other primates [Letvin, et al., Blood 61:408–410 (1983)], mice [Sanchez-Madrid, et al., J. Exp. Med. 154:1517 (1981)], and dogs [Moore, et al., Tissue Antigens 36:211–220 (1990)].

The absolute molecular weights of presumed homologs from other species have been shown to vary significantly [see, e.g., Danilenko et al., Tissue Antigens 40:13–21 (1992)], and in the absence of sequence information, a definitive correlation between human integrin subunits and those identified in other species has not been possible. Moreover, variation in the number of members in a protein family has been observed between different species. Consider, for example, that more IgA isotypes have been isolated in rabbits than in humans [Burnett, et al., EMBO J. 8:4041–4047 (1989) and Schneiderman, et al., Proc. Natl. Acad. Sci. (USA) 86:7561–7565 (1989)]. Similarly, in humans, at least six variants of the metallothionine protein have been previously identified [Karin and Richards, Nature 299:797–802 (1982) and Varshney, et al., Mol. Cell. Biol. 6:26–37, (1986)], whereas in the mouse, only two such variants are in evidence [Searle, et al., Mol. Cell. Biol. 4:1221–1230 (1984)]. Therefore, existence of multiple members of a protein family in one species does not necessarily imply that corresponding family members exist in another species.

In the specific context of $\beta_2$ integrins, in dogs it has been observed that the presumed canine $\beta_2$ counterpart to the human CD18 is capable of dimer formation with as many as four potentially distinct $\alpha$ subunits [Danilenko, et al., supra]. Antibodies generated by immunizing mice with canine splenocytes resulted in monoclonal antibodies which immunoprecipitated proteins tentatively designated as canine homologs to human CD18, CD11a, CD11b and CD11c based mainly on similar, but not identical, molecular weights. Another anti-canine splenocyte antibody, Ca11.8H2, recognized and immunoprecipitated a fourth $\alpha$-like canine subunit also capable of association with the $\beta_2$ subunit, but having a unique molecular weight and restricted in expression to a subset of differentiated tissue macrophages.

Antibodies generated by immunization of hamsters with murine dendritic cells resulted in two anti-integrin antibodies [Metlay, et al., J. Exp. Med. 171:1753–1771 (1990)]. One antibody, 2E6, immunoprecipitated a predominant heterodimer with subunits having approximate molecular weights of 180 kD and 90 kD in addition to minor bands in the molecular weight range of 150–160 kD. The second antibody, N418, precipitated another apparent heterodimer with subunits having approximate molecular weights of 150 kD and 90 Kd. Based on cellular adhesion blocking studies, it was hypothesized that antibody 2E6 recognized a murine counterpart to human CD18. While the molecular weight of the N418 antigen suggested recognition of a murine homolog to human CD11c/CD18, further analysis indicated that the murine antigen exhibited a tissue distribution pattern which was inconsistent with that observed for human CD11c/CD18.

The antigens recognized by the canine Ca 11.8H2 antibody and the murine N418 antibody could represent a variant species (e.g., a glycosylation or splice variant) of a previously identified canine or murine $\alpha$ subunit. Alternatively, these antigens may represent unique canine and murine integrin $\alpha$ subunits. In the absence of specific information regarding primary structure, these alternatives cannot be distinguished.

In humans, CD11a/CD18 is expressed on all leukocytes. CD11b/CD18 and CD11c/CD18 are essentially restricted to expression on monocytes, granulocytes, macrophages and natural killer (NK) cells, but CD11c/CD18 is also detected on some B-cell types. In general, CD11a/CD18 predominates on lymphocytes, CD11b/CD18 on granulocytes and CD11c/CD18 on macrophages [see review, Arnaout, Blood 75:1037–1050 (1990)]. Expression of the $\alpha$ chains, however, is variable with regard to the state of activation and differentiation of the individual cell types [See review, Larson and Springer, *Immunol. Rev.* 114:181–217 (1990).]

The involvement of the $\beta_2$ integrins in human immune and inflammatory responses has been demonstrated using monoclonal antibodies which are capable of blocking $\beta_2$ integrin-associated cell adhesion. For example, CD11a/ CD18, CD11b/CD18 and CD11c/CD18 actively participate in natural killer (NK) cell binding to lymphoma and adenocarcinoma cells [Patarroyo, et al., *Immunol. Rev.* 114:67–108 (1990)], granulocyte accumulation [Nourshargh, et al., *J. Immunol.* 142:3193–3198 (1989)], granulocyte-independent plasma leakage [Arfors, et al., *Blood* 69:338–340 (1987)], chemotactic response of stimulated leukocytes [Arfors, et al., supra] and leukocyte adhesion to vascular endothelium [Price, et al., *J. Immunol.* 139:4174–4177 (1987) and Smith, et al., *J. Clin. Invest.* 83:2008–2017 (1989)]. The fundamental role of $\beta_2$ integrins in immune and inflammatory responses is made apparent in the clinical syndrome referred to as leukocyte adhesion deficiency (LAD), wherein clinical manifestations include recurrent and often life threatening bacterial infections. LAD results from heterogeneous mutations in the $\beta_2$ subunit [Kishimoto, et al., *Cell* 50:193–202 (1987)] and the severity of the disease state is proportional to the degree of the deficiency in $\beta_2$ subunit expression. Formation of the complete integrin heterodimer is impaired by the $\beta_2$ mutation [Kishimoto, et al., supra].

Interestingly, at least one antibody specific for CD18 has been shown to inhibit human immunodeficiency virus type-1 (HIV-1) syncytia formation in vitro, albeit the exact mechanism of this inhibition is unclear [Hildreth and Orentas, *Science* 244:1075–1078 (1989)]. This observation is consistent with the discovery that a principal counter-receptor of CD11a/CD18, ICAM-1, is also a surface receptor for the major group of rhinovirus serotypes [Greve, et al., *Cell* 56:839 (1989)].

The significance of $\beta_2$ integrin binding activity in human immune and inflammatory responses underscores the necessity to develop a more complete understanding of this class of surface proteins. Identification of yet unknown members of this subfamily, as well as their counterreceptors, and the generation of monoclonal antibodies or other soluble factors which can alter biological activity of the $\beta_2$ integrins will provide practical means for therapeutic intervention in $\beta_2$ integrin-related immune and inflammatory responses.

BRIEF DESCRIPTION OF THE INVENTION

In one aspect, the present invention provides novel purified and isolated polynucleotides (e.g., DNA and RNA transcripts, both sense and anti-sense strands) encoding a novel human $\beta_2$ integrin $\alpha$ subunit, $\alpha_d$, and variants thereof (i.e., deletion, addition or substitution analogs) which possess binding and/or immunological properties inherent to $\alpha_d$. Preferred DNA molecules of the invention include cDNA, genomic DNA and wholly or partially chemically synthesized DNA molecules. A presently preferred polynucleotide is the DNA as set forth in SEQ ID NO: 1, encoding the polypeptide of SEQ ID NO: 2. Also provided are recombinant plasmid and viral DNA constructions (expression constructs) which include $\alpha_d$ encoding sequences, wherein the $\alpha_d$ encoding sequence is operatively linked to a homologous or heterologous transcriptional regulatory element or elements.

Also provided by the present invention are isolated and purified mouse and rat polynucleotides which exhibit homology to polynucleotides encoding human $\alpha_d$. A preferred mouse polynucleotide is set forth in SEQ ID NO: 52; a preferred rat polynucleotide is set forth in SEQ ID NO: 54.

As another aspect of the invention, prokaryotic or eukaryotic host cells transformed or transfected with DNA sequences of the invention are provided which express $\alpha_d$ polypeptide or variants thereof. Host cells of the invention are particularly useful for large scale production of $\alpha_d$ polypeptide, which can be isolated from either the host cell itself or from the medium in which the host cell is grown. Host cells which express $\alpha_d$ polypeptide on their extracellular membrane surface are also useful as immunogens in the production of $\alpha_d$-specific antibodies. Preferably, host cells transfected with $\alpha_d$ will be co-transfected to express a $\beta_2$ integrin subunit in order to allow surface expression of the heterodimer.

Also provided by the present invention are purified and isolated $\alpha_d$ polypeptides, fragments and variants thereof. Preferred $\alpha_d$ polypeptides are as set forth in SEQ ID NO: 2. Novel $\alpha_d$ products of the invention may be obtained as isolates from natural sources, but, along with $\alpha_d$ variant products, are preferably produced by recombinant procedures involving host cells of the invention. Completely glycosylated, partially glycosylated and wholly de-glycosylated forms of the $\alpha_d$ polypeptide may be generated by varying the host cell selected for recombinant production and/or post-isolation processing. Variant $\alpha_d$ polypeptides of the invention may comprise water soluble and insoluble $\alpha_d$ polypeptides including analogs wherein one or more of the amino acids are deleted or replaced: (1) without loss, and preferably with enhancement, of one or more biological activities or immunological characteristics specific for $\alpha_d$; or (2) with specific disablement of a particular ligand/receptor binding or signalling function. Fusion polypeptides are also provided, wherein $\alpha_d$ amino acid sequences are expressed contiguously with amino acid sequences from other polypeptides. Such fusion polypeptides may possess modified biological, biochemical, and/or immunological properties in comparison to wild-type $\alpha_d$. Analog polypeptides including additional amino acid (e.g., lysine or cysteine) residues that facilitate multimer formation are contemplated.

Also comprehended by the present invention are polypeptides and other non-peptide molecules which specifically bind to $\alpha_d$. Preferred binding molecules include antibodies (e.g., monoclonal and polyclonal antibodies), counterreceptors (e.g., membrane-associated and soluble forms) and other ligands (e.g., naturally occurring or synthetic molecules), including those which competitively bind $\alpha_d$ in the presence of $\alpha_d$ monoclonal antibodies and/or specific counterreceptors. Binding molecules are useful for purification of $\alpha_d$ polypeptides and identifying cell types which express $\alpha_d$. Binding molecules are also useful for modulating (i.e., inhibiting, blocking or stimulating) of in vivo binding and/or signal transduction activities of $\alpha_d$.

Assays to identify $\alpha_d$ binding molecules are also provided, including in vitro assays such as immobilized ligand binding assays, solution binding assays, and scintillation proximity assays, as well as cell based assays such as di-hybrid screening assays, split hybrid screening assays, and the like. Cell based assays provide for a phenotypic change in a host cell as a result of specific binding interaction or disruption of a specific binding interaction, thereby permitting indirect quantitation or measurement of some specific binding interaction.

In vitro assays for identifying antibodies or other compounds that modulate the activity of $\alpha_d$ may involve, for example, immobilizing $\beta_d$ or a natural ligand to which $\alpha_d$ binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of $\alpha_d$ binding.

Another type of in vitro assay for identifying compounds that modulate the interaction between $\alpha_d$ and a ligand involves immobilizing $\alpha_d$ or a fragment thereof on a solid support coated (or impregnated with) a fluorescent agent, labelling the ligand with a compound capable of exciting the fluorescent agent, contacting the immobilized $\alpha_d$ with the labelled ligand in the presence and absence of a putative modulator compound, detecting light emission by the fluorescent agent, and identifying modulating compounds as those compounds that affect the emission of light by the fluorescent agent in comparison to the emission of light by the fluorescent agent in the absence of a modulating compound. Alternatively, the $\alpha_d$ ligand may be immobilized and $\alpha_d$ may be labelled in the assay.

A cell based assay method contemplated by the invention for identifying compounds that modulate the interaction between $\alpha_d$ and a ligand involves transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a second hybrid DNA sequence encoding part or all of the ligand and the DNA binding domain or activating domain of the transcription factor which is not incorporated in the first fusion, evaluating the effect of a putative modulating compound on the interaction between $\alpha_d$ and the ligand by detecting binding of the ligand to $\alpha_d$ in a particular host cell by measuring the production of reporter gene product in the host cell in the presence or absence of the putative modulator, and identifying modulating compounds as those compounds altering production of the reported gene product in comparison to production of the reporter gene product in the absence of the modulating compound. Presently preferred for use in the assay are the lexA promoter, the lexA DNA binding domain, the GAL4 transactivation domain, the lacZ reporter gene, and a yeast host cell.

A modified version of the foregoing assay may be used in isolating a polynucleotide encoding a protein that binds to $\alpha_d$ by transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a library of second hybrid DNA sequences encoding second fusions of part or all of putative $\alpha_d$ binding proteins and the DNA binding domain or activating domain of the transcription factor which is not incorporated in the first fusion, detecting binding of an $\alpha_d$ binding protein to $\alpha_d$ in a particular host cell by detecting the production of reporter gene product in the host cell, and isolating second hybrid DNA sequences encoding $\alpha_d$ binding protein from the particular host cell.

In a preferred embodiment utilizing the split hybrid assay, the invention provides a method to identify an inhibitor of binding between an $\alpha_d$ protein or fragment thereof and an $\alpha_d$ binding protein or binding fragment thereof comprising the steps of: (a) transforming or transfecting a host cell with a first DNA expression construct comprising a first selectable marker gene encoding a first selectable marker protein and a repressor gene encoding a repressor protein, said repressor gene under transcriptional control of a promoter; (b) transforming or transfecting said host cell with a second DNA expression construct comprising a second selectable marker gene encoding a second selectable marker protein and a third selectable marker gene encoding a third selectable marker protein, said third selectable marker gene tinder transcriptional control of an operator, said operator specifically acted upon by said repressor protein such that interaction of said repressor protein with said operator decreases expression of said third selectable marker protein; (c) transforming or transfecting said host cell with a third DNA expression construct comprising a fourth selectable marker gene encoding a fourth selectable marker protein and an $\alpha_d$ fusion protein gene encoding an $\alpha_d$ protein or fragment thereof in frame with either a DNA binding domain of a transcriptional activation protein or a transactivating domain of said transcriptional activation protein; (d) transforming or transfecting said host cell with a fourth DNA expression construct comprising a fifth selectable marker gene encoding a fifth selectable marker protein and a second fusion protein gene encoding an $\alpha_d$ binding protein or binding fragment thereof in frame with either the DNA binding domain of said transcriptional activation protein or the transactivating domain of said transcriptional activation protein, whichever is not included in first fusion protein gene; (e) growing said host cell under conditions which permit expression of said $\alpha_d$ protein or fragment thereof and said $\alpha_d$ binding protein or fragment thereof such that said $\alpha_d$ protein or fragment thereof and $\alpha_d$ binding protein or binding fragment thereof interact bringing into proximity said DNA binding domain and said transactivating domain reconstituting said transcriptional activating protein; said transcriptional activating protein acting on said promoter to increase expression of said repressor protein; said repressor protein interacting with said operator such that said third selectable marker protein is not expressed; (f) detecting absence of expression of said selectable gene; (g) growing said host cell in the presence of a test inhibitor of binding between said $\alpha_d$ protein or fragment thereof and said $\alpha_d$ binding protein or fragment thereof; and (h) comparing expression of said selectable marker protein in the presence and absence of said test inhibitor wherein decreased expression of said selectable marker protein is indicative of an ability of the test inhibitor to inhibit binding between said $\alpha_d$ protein or fragment thereof and said $\alpha_d$ binding protein or binding fragment thereof such that said transcriptional activating protein is not reconstituted, expression of said repressor protein is not increased, and said operator increases expression of said selectable marker protein.

The invention comprehends host cells wherein the various genes and regulatory sequences are encoded on a single DNA molecule as well as host cells wherein one or more of the repressor gene, the selectable marker gene, the $\alpha_d$ fusion protein gene, and the $\alpha_d$ binding protein gene are encoded on distinct DNA expression constructs. In a preferred embodiment, the host cells are transformed or transfected with DNA encoding the repressor gene, the selectable marker gene, the $\alpha_d$ fusion protein gene, and the $_d$ fusion binding protein gene, each encoded on a distinct expression construct. Regardless of the number of DNA expression constructs introduced, each transformed or transfected DNA expression construct further comprises a selectable marker gene sequence, the expression of which is used to confirm that transfection or transformation was, in fact, accomplished. Selectable marker genes encoded on individually transformed or transfected DNA expression constructs are distinguishable from the selectable marker under transcriptional regulation of the tet operator in that expression of the selectable marker gene regulated by the tet operator is central to the preferred embodiment; i.e., regulated expression of the selectable marker gene by the tet operator provides a measurable phenotypic change in the host cell that is used to identify a binding protein inhibitor. Selectable marker genes encoded on individually transformed or transfected DNA expression constructs are provided as determinants of successful transfection or transformation of the individual DNA expression constructs. Preferred host cells of the invention include transformed S. cerevisiae strains designated YI596 and YI584 which were deposited Aug. 13, 1996 with the American Type Culture Collection (ATCC), 12301 Parklawn Drive, Rockville, Md. 20852, and assigned Accession Numbers ATCC 74384 and ATCC 74385, respectively.

The host cells of the invention include any cell type capable of expressing the $\alpha_d$ and $\alpha_d$ binding proteins required as described above and which are capable of being transformed or transfected with functional promoter and operator sequences which regulate expression of the heterologous proteins also as described. In a preferred embodiment, the host cells are of either mammal, insect or yeast origin. Presently, the most preferred host cell is a yeast cell. The preferred yeast cells of the invention can be selected from various strains, including the S. cerevisiae yeast transformants described in Table 1. Alternative yeast specimens include S. pombe, K. lactis, P. pastoris, S. carlsbergensis and C. albicans. Preferred mammalian host cells of the invention include Chinese hamster ovary (CHO), COS, HeLa, 3T3, CV1, LTK, 293T3, Rat1, PC12 or any other transfectable cell line of human or rodent origin. Preferred insect cell lines include SF9 cells.

In a preferred embodiment, the selectable marker gene is regulated by an operator and encodes an enzyme in a pathway for synthesis of a nutritional requirement for said host cell such that expression of said selectable marker protein is required for growth of said host cell on media lacking said nutritional requirement. Thus, as in a preferred embodiment where a repressor protein interacts with the operator, transcription of the selectable marker gene is down-regulated and the host cells are identified by an inability to grow on media lacking the nutritional requirement and an ability to grow on media containing the nutritional requirement. In a most preferred embodiment, the selectable marker gene encodes the HIS3 protein, and host cells transformed or transfected with a HIS3-encoding DNA expression construct are selected following growth on media in the presence and absence of histidine. The invention, however, comprehends any of a number of alternative selectable marker genes regulated by an operator. Gene alternatives include, for example, URA3, LEU2, LYS2 or those encoding any of the multitude of enzymes required in various pathways for production of a nutritional requirement which can be definitively excluded from the media of growth. In addition, conventional reporter genes such as chloramphenicol acetyltransferase (CAT), firefly luciferase, β-galactosidase (β-gal), secreted alkaline phosphatase (SEAP), green fluorescent protein (GFP), human growth hormone (hGH), β-glucuronidase, neomycin, hygromycin, thymidine kinase (TK) and the like may be utilized in the invention.

In the preferred embodiment, the host cells include a repressor protein gene encoding the tetracycline resistance protein which acts on the tet operator to decrease expression of the selectable marker gene. The invention, however, also encompasses alternatives to the tet repressor and operator, for example, E. coli trp repressor and operator, his repressor and operator, and lac operon repressor and operator.

The DNA binding domain and transactivating domain components of the fusion proteins may be derived from the same transcription factor or from different transcription factors as long as bringing the two domains into proximity through binding between $\alpha_d$ and the $\alpha_d$ binding protein permits formation of a functional transcriptional activating protein that increases expression of the repressor protein with high efficiency. A high efficiency transcriptional activating protein is defined as having both a DNA binding domain exhibiting high affinity binding for the recognized promoter sequence and a transactivating domain having high affinity binding for transcriptional machinery proteins required to express repressor gene mRNA. The DNA binding domain component of a fusion protein of the invention can be derived from any of a number of different proteins including, for example, LexA or Gal4. Similarly, the transactivating component of the invention's fusion proteins can be derived from a number of different transcriptional activating proteins, including for example, Gal4 or VP16.

The promoter sequence of the invention which regulates transcription of the repressor protein can be any sequence capable of driving transcription in the chosen host cell. The promoter may be a DNA sequence specifically recognized by the chosen DNA binding domain of the invention, or any other DNA sequence with which the DNA binding domain of the fusion protein is capable of high affinity interaction. In a preferred embodiment of the invention, the promoter sequence of the invention is either a HIS3 or alcohol dehydrogenase (ADH) promoter. In a presently most preferred embodiment, the ADH promotor is employed in the invention. The invention, however, encompasses numerous alternative promoters, including, for example, those derived from genes encoding HIS3, ADH, URA3, LEU2 and the like.

The methods of the invention encompass any and all of the variations in host cells as described above. In particular, the invention encompasses a method wherein: the host cell is a yeast cell; the selectable marker gene encodes HIS3; transcription of the selectable marker gene is regulated by the tet operator; the repressor protein gene encodes the tetracycline resistance protein; transcription of the tetracycline resistance protein is regulated by the HIS3 promoter; the DNA binding domain is derived from LexA; and the transactivating domain is derived from VP16. In another embodiment, the invention encompasses a method wherein: the host cell is a yeast cell; the selectable marker gene encodes HIS3; transcription of the selectable marker gene is regulated by the tet operator; the repressor protein gene encodes the tetracycline resistance protein; transcription of the tetracycline resistance protein is regulated by the alcohol dehydrogenase promoter; the DNA binding domain is derived from LexA; and the transactivating domain is derived from VP16.

In alternative embodiments of the invention wherein the host cell is a mammalian cell, variations include the use of mammalian DNA expression constructs to encode the $\alpha_d$ and $\alpha_d$ binding fusion genes, the repressor gene, and the selectable marker gene, and use of selectable marker genes encoding antibiotic or drug resistance markers (i.e., neomycin, hygromycin, thymidine kinase).

There are at least three different types of libraries used for the identification of small molecule modulators. These include: (1) chemical libraries, (2) natural product libraries, and (3) combinatorial libraries comprised of random peptides, oligonucleotides or organic molecules.

Chemical libraries consist of structural analogs of known compounds or compounds that are identified as "hits" via natural product screening. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Combinatorial libraries are composed of large numbers of peptides, oligonucleotides or organic compounds as a mixture. They are relatively easy to prepare by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries.

Hybridoma cell lines which produce antibodies specific for $\alpha_d$ are also comprehended by the invention. Techniques for producing hybridomas which secrete monoclonal antibodies are well known in the art. Hybridoma cell lines may be generated after immunizing an animal with purified $\alpha_d$, variants of $\alpha_d$ or cells which express $\alpha_d$ or a variant thereof on the extracellular membrane surface. Immunogen cell types include cells which express $\alpha_d$ in vivo, or transfected prokaryotic or eukaryotic cell lines which normally do not normally express $\alpha_d$ in vivo. Presently preferred antibodies of the invention are secreted by hybridomas designated 169A, 169B, 170D, 170F, 170E, 170X, 170H, 188A, 188B, 188C, 188E, 188F, 188G, 188I, 188J, 188K, 188L, 188M, 188N, 188P, 188R, 188T, 195A, 195C, 195D, 195E, 195H, 197A-1, 197A-2, 197A-3, 197A -4, 199A, 199H, 199M, 205A, 205C, 205E, 212A, 212D, 217G, 217H, 217I, 217K, 217L, 217M, 226A, 226B, 226C, 226D, 226E, 226F, 226G, 226H, 226I, 236A, 236B, 236C, 236F, 236G, 236H, 236I, 236K, 237L, 236M, 240F, 240G, and 240H.

The value of the information contributed through the disclosure of the DNA and amino acid sequences of $\alpha_d$ is manifest. In one series of examples, the disclosed $\alpha_d$ cDNA sequence makes possible the isolation of the human $\alpha_d$ genomic DNA sequence, including transcriptional control elements for the genomic sequence. Identification of $\alpha_d$ allelic variants and heterologous species (e.g., rat or mouse) DNAs is also comprehended. Isolation of the human $\alpha_d$ genomic DNA and heterologous species DNAs can be accomplished by standard DNA/DNA hybridization techniques, under appropriately stringent conditions, using all or part of the $\alpha_d$ cDNA sequence as a probe to screen an appropriate library. Alternatively, polymerase chain reaction (PCR) using oligonucleotide primers that are designed based on the known cDNA sequence can be used to amplify and identify genomic $\alpha_d$ DNA sequences. Synthetic DNAs encoding the $\alpha_d$ polypeptide, including fragments and other variants thereof, may be produced by conventional synthesis methods.

DNA sequence information of the invention also makes possible the development, by homologous recombination or "knockout" strategies [see, e.g., Kapecchi, *Science* 244:1288–1292 (1989)], to produce rodents that fail to express a functional $\alpha_d$ polypeptide or that express a variant $\alpha_d$ polypeptide. Such rodents are useful as models for studying the activities of $\alpha_d$ and $\alpha_d$ modulators in vivo.

DNA and amino acid sequences of the invention also make possible the analysis of $\alpha_d$ epitopes which actively participate in counterreceptor binding as well as epitopes which may regulate, rather than actively participate in, binding. Identification of epitopes which may participate in transmembrane signal transduction is also comprehended by the invention.

DNA of the invention is also useful for the detection of cell types which express $\alpha_d$ polypeptide. Standard DNA/RNA hybridization techniques which utilize $\alpha_d$ DNA to detect $\alpha_d$ RNA may be used to determine the constitutive level of $\alpha_d$ transcription within a cell, as well as changes in the level of transcription in response to internal or external agents. Identification of agents which modify transcription and/or translation of $\alpha_d$ can, in turn, be assessed for potential therapeutic or prophylactic value. DNA of the invention also makes possible in situ hybridization of $\alpha_d$ DNA to cellular RNA to determine the cellular localization of $\alpha_d$ specific messages within complex cell populations and tissues.

DNA of the invention is also useful for identification of non-human polynucleotide sequences which display homology to human $\alpha_d$ sequences. Possession of non-human $\alpha_d$ DNA sequences permits development of animal models (including, for example, transgenic models) of the human system.

As another aspect of the invention, monoclonal or polyclonal antibodies specific for $\alpha_d$ may be employed in immunohistochemical analysis to localize $\alpha_d$ to subcellular compartments or individual cells within tissues. Immunohistochemical analyses of this type are particularly useful when used in combination with in situ hybridization to localize both $\beta_d$ mRNA and polypeptide products of the $\beta_d$ gene.

Identification of cell types which express $\beta_d$ may have significant ramifications for development of therapeutic and prophylactic agents. It is anticipated that the products of the invention related to $\beta_d$ can be employed in the treatment of diseases wherein macrophages are an essential element of the disease process. Animal models for many pathological conditions associated with macrophage activity have been described in the art. For example, in mice, macrophage recruitment to sites of both chronic and acute inflammation is reported by Jutila, et al., *J. Leukocyte Biol.* 54:30–39 (1993). In rats, Adams, et al., [*Transplantation* 53:1115–1119 (1992) and *Transplantation* 56:794–799 (1993)] describe a model for graft arteriosclerosis following heterotropic abdominal cardiac allograft transplantation. Rosenfeld, et al., [*Arteriosclerosis* 7:9–23 (1987) and *Arteriosclerosis* 7:24–34 (1987)] describe induced atherosclerosis in rabbits fed a cholesterol supplemented diet. Hanenberg, et al., [*Diabetologia* 32:126–134 (1989)] report the spontaneous development of insulin-dependent diabetes in BB rats. Yamada et al., [*Gastroenterology* 104:759–771 (1993)] describe an induced inflammatory bowel disease, chronic granulomatous colitis, in rats following injections of streptococcal peptidoglycan-polysaccharide polymers. Cromartie, et al., [*J. Exp. Med.* 146:1585–1602 (1977)] and Schwab, et al., [*Infection and Immunity* 59:4436–4442 (1991)] report that injection of streptococcal cell wall protein into rats results in an arthritic condition characterized by inflammation of peripheral joints and subsequent joint destruction. Finally, Huitinga, et al., [*Eur. J. Immunol* 23:709–715 (1993) describe experimental allergic encephalomyelitis, a model for multiple sclerosis, in Lewis rats. In each of these models, $\alpha_d$ antibodies, other $\alpha_d$ binding proteins, or soluble forms of $\alpha_d$ are utilized to attenuate the disease state, presumably through inactivation of macrophage activity.

Pharmaceutical compositions for treatment of these and other disease states are provided by the invention. Pharmaceutical compositions are designed for the purpose of inhibiting interaction between $\alpha_d$ and its ligand(s) and include various soluble and membrane-associated forms of $\alpha_d$ (comprising the entire $\alpha_d$ polypeptide, or fragments thereof which actively participate in $\alpha_d$ binding), soluble and membrane-associated forms of $\alpha_d$ binding proteins (including antibodies, ligands, and the like), intracellular or extracellular modulators of $\alpha_d$ binding activity, and/or modulators of $\alpha_d$ and/or $\alpha_d$-ligand polypeptide expression, including modulators of transcription, translation, post-translational processing and/or intracellular transport.

The invention also comprehends methods for treatment of disease states in which $\alpha_d$ binding, or localized accumulation of cells which express $\alpha_d$, is implicated, wherein a patient suffering from said disease state is provided an amount of a pharmaceutical composition of the invention sufficient to modulate levels of $\alpha_d$ binding or to modulate accumulation of cell types which express $\alpha_d$. The method of treatment of the invention is applicable to disease states such as, but not limited to, Type 1 diabetes, atherosclerosis, multiple sclerosis, asthma, psoriasis, lung inflammation, acute respiratory distress syndrome and rheumatoid arthritis.

BRIEF DESCRIPTION OF THE DRAWING

Numerous other aspects and advantages of the present invention will be apparent upon consideration of the following description thereof, reference being made to the drawing wherein:

FIG. 1A through 1D comprises an alignment of the human amino acid sequences of CD11b (SEQ ID NO: 3), CD11c (SEQ ID NO: 4) and $\alpha_d$ (SEQ ID NO: 2).

DETAILED DESCRIPTION OF THE INVENTION

The present invention is illustrated by the following examples relating to the isolation of a cDNA clone encoding $\alpha_d$ from a human spleen cDNA library. More particularly, Example 1 illustrates the use of anti-canine $\alpha_{TM1}$ antibody in an attempt to detect a homologous human protein. Example 2 details purification of canine $\alpha_{TM1}$ and N-terminal sequencing of the polypeptide to design oligonucleotide primers for PCR amplification of the canine $\alpha_{TM1}$ gene. Example 3 addresses large scale purification of canine $\alpha_{TM1}$ for internal sequencing in order to design additional PCR primers. Example 4 describes use of the PCR and internal sequence primers to amplify a fragment of the canine $\alpha_{TM1}$ gene. Example 5 addresses cloning of the human $\alpha_d$-encoding cDNA sequence. Example 6 describes Northern blot hybridization analysis of human tissues and cells for expression of $\alpha_d$ mRNA. Example 7 details the construction of human $\alpha_d$ expression plasmids and transfection of COS cells with the resulting plasmids. Example 8 addresses ELISA analysis of $\alpha_d$ expression in transfected COS cells. Example 9 describes FACS analysis of COS cells transfected with human $\alpha_d$ expression plasmids. Example 10 addresses immunoprecipitation of CD18 in association with $\alpha_d$ in co-transfected COS cells. Example 11 relates to stable transfection of $\alpha_d$ expression constructs in Chinese hamster ovary cells. Example 12 addresses CD18-dependent binding of $\alpha_d$ to the intercellular adhesion molecule ICAM-R, an ICAM-R mutant protein, and complement fact iC3b. Example 13 describes scintillation proximity screening assays to identify inhibitors or enhancers (i.e., modulators) of $\alpha_d$ ligand/anti-ligand binding interactions. Example 14 addresses construction of expression plasmids which encode soluble forms of $\alpha_d$, and binding analyses of the expression products. Example 15 relates to production of $\alpha_d$-specific polyclonal sera and monoclonal antibodies. Example 16 describes flow cytometry analysis using $\alpha_d$ monoclonal antibodies. Example 17 addresses expression of $\alpha_d$ on human monocytes. Example 18 describes analysis of $\alpha_d$ tissue distribution, expression of $\alpha_d$ on peripheral blood leukocytes, expression in inflammatory and non-inflammatory synovium using anti-$\alpha_d$ polyclonal serum, expression in disease lung and liver, human bone marrow, and PBMC from breast cancer patients. Example 19 addresses unregulation of $\alpha_d$ expression in vitro and in vivo. Example 20 describes isolation of rat cDNA sequences which show homology to human $\alpha_d$ gene sequences. Example 21 addresses tissue specific expression of rat $\alpha_d$ mRNA. Example 22 relates to construction of full length rat $\alpha_d$ expression plasmids, rat $\alpha_d$ I domain expression plasmids, including I domain/IgG fusion proteins, production of monoclonal antibodies to full length and I domain fusion proteins, and production of polyclonal antisera to rat $\alpha_d$ I domain sequences fused to human IgG4. Example 23 describes specificity of monoclonal antibody 199M. Example 24 presents results from a T cell proliferation assay using rat $\alpha_d$ expressing macrophages. Example 25 describes immunoprecipitation of rat $\alpha_d$ from bone marrow. Example 26 describes rat $\alpha_d$ expression in various animal models. Example 27 relates to an assay for inhibition of NK-tumor cell-induced target cell lysis using $\alpha_d$ monoclonal antibodies. Example 28 addresses isolation of mouse cDNA sequences which show homology to human $\alpha_d$ gene sequences. Example 29 describes isolation of additional mouse $\alpha_d$ cDNA clones used to confirm sequence analysis. Example 30 relates to in situ hybridization analysis of various mouse tissues to determine tissue and cell specific expression of the putative mouse homolog to human $\alpha_d$. Example 31 describes generation of expression constructs which encode the putative mouse homolog of human $\alpha_d$. Example 32 addresses design of a "knock-out" mouse wherein the gene encoding the putative mouse homolog of human $\alpha_d$ is disrupted. Example 33 describes isolation of rabbit cDNA clones which show homology to human $\alpha_d$ encoding sequences. Example 34 describes isolation of monkey $\alpha_d$. Example 35 relates to characterization of the antigen recognized by monoclonal antibody 217L. Example 36 describes animal models of human disease states wherein modulation of $\alpha_d$ is assayed for therapeutic capabilities. Example 37 describes expression of $\alpha_d$ in animal model disease states.

EXAMPLE 1

Attempt to Detect a Human Homolog of Canine $\alpha_{TM1}$

The monoclonal antibody Ca11.8H2 [Moore, et al., supra] specific for canine $\alpha_{TM1}$ was tested for cross-reactivity on human peripheral blood leukocytes in an attempt to identify a human homolog of canine $\alpha_{TM1}$. Cell preparations (typically 1×10⁶ cells) were incubated with undiluted hybridoma supernatant or a purified mouse IgG-negative control antibody (10 µg/ml) on ice in the presence of 0.1% sodium azide. Monoclonal antibody binding was detected by subsequent incubation with FITC-conjugated horse anti-mouse IgG (Vector Laboratories, Burlingame, Calif.) at 6 µg/ml. Stained cells were fixed with 2% w/v paraformaldehyde in phosphate buffered saline (PBS) and were analyzed with a Facstar Plus fluorescence-activated cell sorter (Becton Dickinson, Mountain View, Calif.). Typically, 10,000 cells were analyzed using logarithmic amplification for fluorescence intensity.

The results indicated that Ca11.8H2 did not cross-react with surface proteins expressed on human peripheral blood leukocytes, while the control cells, neoplastic canine peripheral blood lymphocytes, were essentially all positive for $\alpha_{TM1}$.

Because the monoclonal antibody Ca11.8H2 specific for the canine α subunit did not cross react with a human homolog, isolation of canine $\alpha_{TM1}$ DNA was deemed a necessary prerequisite to isolate a counterpart human gene if one existed.

EXAMPLE 2

Affinity Purification of Canine $\alpha_{TM1}$ for N-Terminal Sequencing

Canine $\alpha_{TM1}$ was affinity purified in order to determine N-terminal amino acid sequences for oligonucleotide probe/primer design. Briefly, anti-$\alpha_{TM1}$ monoclonal antibody Ca11.8H2 was coupled to Affigel 10 chromatographic resin (BioRad, Hercules, Calif.) and protein was isolated by specific antibody-protein interaction. Antibody was conjugated to the resin, according to the BioRad suggested protocol, at a concentration of approximately 5 mg antibody per ml of resin. Following the conjugation reaction, excess antibody was removed and the resin blocked with three volumes of 0.1M ethanolamine. The resin was then washed with thirty column volumes of phosphate buffered saline (PBS).

Twenty-five grains of a single dog spleen were homogenized in 250 ml of buffer containing 0.32M sucrose in 25 mM Tris-HCl, Ph 8.0, with protease inhibitors. Nuclei and cellular debris were pelleted with centrifugation at 1000 g for 15 minutes. Membranes were pelleted from the supernatant with centrifugation at 100,000 g for 30 minutes. The membrane pellet was resuspended in 200 ml lysis buffer (50 mM NaCl, 50 mM borate, pH 8.0, with 2% NP-40) and incubated for 1 hour on ice. Insoluble material was then pelleted by centrifugation at 100,000 g for 60 minutes. Ten milliliters of the cleared lysate were transferred to a 15 ml polypropylene tube with 0.5 ml Ca11.8H2-conjugated Affigel 10 resin described above. The tube was incubated overnight at 4° C. with rotation and the resin subsequently washed with 50 column volumes D-PBS. The resin was then transferred to a microfuge tube and boiled for ten minutes in 1 ml Laemmli (non-reducing) sample buffer containing 0.1M Tris-HCl, pH 6.8, 2% SDS, 20% glycerol and 0.002% bromophenol blue. The resin was pelleted by centrifugation and discarded; the supernatant was treated with ⅕ volume α-mercaptoethanol (Sigma, St. Louis, Mo.) and run on a 7% polyacrylamide gel. The separated proteins were transferred to Immobilon PVDF membrane (Millipore, Bedford, Mass.) as follows.

The gels were washed once in deionized, Millipore-filtered water and equilibrated for 15–45 minutes in 10 mM 3-[cyclohexylamino]-1-propanesulfonic acid (CAPS) transfer buffer, pH 10.5, with 10% methanol. Immobilon membranes were moistened with methanol, rinsed with filtered water, and equilibrated for 15–30 minutes in CAPS transfer buffer. The initial transfer was carried out using a Biorad transfer apparatus at 70 volts for 3 hours. The Immobilon membrane was removed after transfer and stained in filtered 0.1% R250 Coomassie stain for 10 minutes. Membranes were destained in 50% methanol/10% acetic acid three times, ten minutes each time. After destaining, the membranes were washed in filtered water and air-dried.

Protein bands of approximately 150 kD, 95 kD, 50 kD and 30 kD were detected. Presumably the 50 kD and 30 kD bands resulted from antibody contamination. N-terminal sequencing was then attempted on both the 150 kD and 95 kD bands, but the 95 kD protein was blocked, preventing sequencing. The protein band of 150 kD was excised from the membrane and directly sequenced with an Applied Biosystems (Foster City, Calif.) Model 473A protein sequencer according to the manufacturer's instructions. The resulting amino acid sequence is set in SEQ ID NO: 5 using single letter amino acid designations.

FNLDVEEPMVFQ (SEQ ID NO: 5)

The identified sequence included the FNLD sequence characteristic of α subunits of the integrin family [Tamura, et al., *J. Cell. Biol.* 111:1593–1604 (1990)].

Primer Design and Attempt to Amplify Canine $\alpha_{TM1}$ Sequences

From the N-terminal sequence information, three oligonucleotide probes were designed for hybridization: a) "Tommer," a fully degenerate oligonucleotide; b) "Patmer," a partially degenerate oligonucleotide; and c) "Guessmer," a nondegenerate oligonucleotide based on mammalian codon usage. These probes are set out below as SEQ ID NOS: 6, 7 and 8, respectively. Nucleic acid symbols are in accordance with 37 C.F.R. §1.882 for these and all other nucleotide sequences herein.

5'-TTYAAYYTGGAYGTNGARGARCCNATGGTN-TTYCA-3' (SEQ ID NO: 6)

5'-TTCAACCTGGACGTGGAGGAGCCCATGGTG-TTCCAA-3' (SEQ ID NO: 7)

5'-TTCAACCTGGACGTNGAASANCCCATGGTC-TTCCAA-3' (SEQ ID NO: 8)

Based on sequencing data, no relevant clones were detected using these oligonucleotides in several low stringency hybridizations to a canine spleen/peripheral blood macrophage cDNA library cloned into λλZAP (Stratagene, La Jolla, Calif.).

Four other oligonucleotide primers, designated 5'Deg, 5'Spec, 3'Deg and 3'Spec (as set out in SEQ ID NOS: 9, 10, 11 and 12, respectively, wherein Deg indicates degenerate and Spec indicates non-degenerate) were subsequently designed based on the deduced N-terminal sequence for attempts to amplify canine $\alpha_{TM1}$ sequences by PCR from phage library DNA purified from plate lysates of the Stratagene library described above.

5'-TTYAAYYTNGAYGTNGARGARCC-3' (SEQ ID NO: 9)

5'-TTYAAYYTGGACGTNGAAGA-3' (SEQ ID NO: 10)

5'-TGRAANACCATNGGYTC-3' (SEQ ID NO: 11)

5'-TTGGAAGACCATNGGYTC-3' (SEQ ID NO: 12)

The $\alpha_{TM1}$ oligonucleotide primers were paired with T3 or T7 vector primers, as set out in SEQ ID NOS: 13 and 14, respectively, which hybridize to sequences flanking the polylinker region in the Bluescript phagemid found in λZAP.

5'-ATTAACCCTCACTAAAG-3' (SEQ ID NO: 13)

5'-AATACGACTCACTATAG-3' (SEQ ID NO: 14)

The PCR amplification was carried out in Taq buffer (Boehringer Mannheim, Indianapolis, Ind.) containing magnesium with 150 ng of library DNA, 1 μg of each primer, 200 μM dNTPs and 2.5 units Taq polymerase (Boehringer Mannheim) and the products were separated by electrophoresis on a 1% agarose gel in Tris-Acetate-EDTA (TAE) buffer with 0.25 μg/ml ethidium bromide. DNA was transferred to a Hybond (Amersham, Arlington Heights, Ill.) membrane by wicking overnight in 10×SSPE. After transfer, the immobilized DNA was denatured with 0.5M NaOH with 0.6M NaCl, neutralized with 1.0M Tris-HCl, pH 8.0, in 1.5M NaCl, and washed with 2×SSPE before UV crosslinking with a Stratalinker (Stratagene) crosslinking apparatus. The membrane was incubated in prehybridization buffer (5×SSPE, 4×Denhardts, 0.8% SDS, 30% formamide) for 2 hr at 50° C. with agitation.

Oligonucleotide probes 5'Deg, 5'Spec, 3'Deg and 3'Spec (SEQ ID NOS: 9, 10, 11 and 12, respectively) were labeled using a Boehringer Mannheim kinase buffer with 100–300 $\mu$Ci $\lambda P^{32}$-dATP and 1–3 units of polynucleotide kinase for 1–3 hr at 37° C. Unincorporated label was removed with Sephadex G-25 fine (Pharmacia, Piscataway, N.J.) chromatography using 10 mM Tris-HCl, pH 8.0, 1 mM EDTA (TE) buffer and the flow-through added directly to the prehybridization solution. Membranes were probed for 16 hr at 42° C. with agitation and washed repeatedly, with a final stringency wash of 1×SSPE/0.1% SDS at 50° for 15 min. The blot was then exposed to Kodak X-Omat AR film for 1–4 hours at −80° C.

The oligonucleotides 5'Deg, 5'Spec, 3'Deg and 3'Spec only hybridized to PCR products from the reactions in which they were used as primers and failed to hybridize as expected to PCR products from the reactions in which they were not used as primers. Thus, it was concluded that none of the PCR products were specific for $\alpha_{TM1}$ because no product hybridized with all of the appropriate probes.

EXAMPLE 3

Large Scale Affinity Purification of Canine $\alpha_{Tm1}$ for Internal Seguencing In order to provide additional amino acid sequence for primer design, canine $\alpha_{TM1}$ was purified for internal sequencing. Three sections of frozen spleen (approximately 50 g each) and frozen cells from two partial spleens from adult dogs were used to generate protein for internal sequencing. Fifty grains of spleen were homogenized in 200–300 ml borate buffer with a Waring blender. The homogenized material was diluted with 1 volume of buffer containing 4% NP-40, and the mixture then gently agitated for at least one hour. The resulting lysate was cleared of large debris by centrifugation at 2000 g for 20 min, and then filtered through either a Corning (Corning, N.Y.) prefilter or a Corning 0.8 micron filter. The lysate was further clarified by filtration through the Corning 0.4 micron filter system.

Splenic lysate and the antibody-conjugated Affigel 10 resin described in Example 2 were combined at a 150:1 volume ratio in 100 ml aliquots and incubated overnight at 4° C. with rocking. The lysate was removed after centrifugation at 1000 g for 5 minutes, combined with more antibody-conjugated Affigel 10 resin and incubated overnight as above. The absorbed resin aliquots were then combined and washed with 50 volumes D-PBS/0.1% Tween 20 and the resin transferred to a 50 ml Biorad column. Adsorbed protein was eluted from the resin with 3–5 volumes of 0.1M glycine (pH 2.5); fractions of approximately 900 $\mu$l were collected and neutralized with 100 $\mu$l 1M Tris buffer, pH 8.0. Aliquots of 15 $\mu$l were removed from each fraction and boiled in an equal volume of 2×Laemmli sample buffer with $\frac{1}{15}$ volume 1M dithiothreitol (DTT). These samples were electrophoresed on 8% Novex (San Diego, Calif.) polyacrylamide gels and visualized either by Coomassie stain or by silver stain using a Daiichi kit (Enprotech, Natick, Mass.) according to the manufacturer's suggested protocol. Fractions which contained the largest amounts of protein were combined and concentrated by vacuum. The remaining solution was diluted by 50% with reducing Laeminli sample buffer and run on 1.5 mm 7% polyacrylamide gels in Tris-glycine/SDS buffer. Protein was transferred from the gels to Immobilon membrane by the procedure described in Example 2 using the Hoefer transfer apparatus.

The protein bands corresponding to canine $\alpha_{TM1}$ were excised from 10 PVDF membranes and resulted in approximately 47 $\mu$g total protein. The bands were destained in 4 ml 50% methanol for 5 minutes, air dried and cut into 1×2 mm pieces. The membrane pieces were submerged in 2 ml 95% acetone at 4° C. for 30 minutes with occasional vortexing and then air dried.

Prior to proteolytic cleavage of the membrane bound protein, 3 mg of cyanogen bromide (CNBr) (Pierce, Rockford, Ill.) were dissolved in 1.25 ml 70% formic acid. This solution was then added to a tube containing the PVDF membrane pieces and the tube incubated in the dark at room temperature for 24 hours. The supernatant (S1) was then removed to another tube and the membrane pieces washed with 0.25 ml 70% formic acid. This supernatant (S2) was removed and added to the previous supernatant (S1). Two milliliters of Milli Q water were added to the combined supernatants (S1 and S2) and the solution lyophilized. The PVDF membrane pieces were dried under nitrogen and extracted again with 1.25 ml 60% acetonitrile, 0.1% tetrafluoroacetic acid (TFA) at 42° C. for 17 hours. This supernatant (S3) was removed and the membrane pieces extracted again with 1.0 ml 80% acetonitrile with 0.08% TFA at 42° C. for 1 hour. This supernatant (S4) was combined with the previous supernatants (S1, S2 and S3) and vacuum dried.

The dried CNBr fragments were then dissolved in 63 $\mu$l 8M urea, 0.4M NH$_4$HCO$_3$. The fragments were reduced in 5 $\mu$l 45 mM dithiothreitol (DTT) and subsequently incubated at 50° C. for 15 minutes. The solution was then cooled to room temperature and the fragments alkylated by adding 5 $\mu$l 100 mM iodoacetamide (Sigma, St. Louis, Mo.). Following a 15 minute incubation at room temperature, the sample was diluted with 187 $\mu$l Milli Q water to a final urea concentration of 2.0M. Trypsin (Worthington, Freehold, N.J.) was then added at a ratio of 1:25 (w:w) of enzyme to protein and the protein digested for 24 hours at 37° C. Digestion was terminated with addition of 30 $\mu$l TFA.

The protein fragments were then separated with high performance liquid chromatography (HPLC) on a Waters 625 LC system (Millipore, Milford, Mass.) using a 2.1×250 mm, 5 micron Vydac C-18 column (Vydac, Hesperia, Calif.) equilibrated in 0.05% TFA and HPLC water (buffer A). The peptides were eluted with increasing concentration of 80% acetonitrile in 0.04% TFA (buffer B) with a gradient of 38–75% buffer B for 65–95 minutes and 75–98% buffer B for 95–105 minutes. Peptides were fractionated at a flow rate of 0.2 ml/minute and detected at 210 nm.

Following fractionation, the amino acid sequence of the peptides was analyzed by automated Edman degradation performed on an Applied Biosystems Model 437A protein sequencer using the manufacturer's standard cycles and the Model 610A Data Analysis software program, Version 1.2.1. All sequencing reagents were supplied by Applied Biosystems. The amino acid sequences of seven of the eight internal fragments are set out below wherein "X" indicates the identity of the amino acid was not certain.

VFQEXGAGFGQ (SEQ ID NO: 15)
LYDXVAATGLXQPI (SEQ ID NO: 16)
PLEYXDVIPQAE (SEQ ID NO: 17)
FQEGFSXVLX (SEQ ID NO: 18)
TSPTFIXMSQENVD (SEQ ID NO: 19)

LVVGAPLEVVAVXQTGR (SEQ ID NO: 20)

LDXKPXDTA (SEQ ID NO: 21)

Primer Design

One internal amino acid sequence (set out in SEQ ID NO: 22) obtained was then used to design a fully degenerate oligonucleotide primer, designated p4(R) as set out in SEQ ID NO: 23.

FGEQFSE (SEQ ID NO: 22)

5'-RAANCCYTCYTGRAAACTYTC-3' (SEQ ID NO: 23)

EXAMPLE 4

PCR Cloning of a Canine $\alpha_{TM1}$ Fragment

The 5' portion of the canine $\alpha_{TM1}$ gene was amplified from double-stranded canine splenic cDNA by PCR.

Generation of Double Stranded Canine Spleen cDNA

One gram of frozen material from a juvenile dog spleen was ground in liquid nitrogen on dry ice and homogenized in 20 ml RNA-Stat 60 buffer (Tel-Test B, Inc, Friendswood, Tex.). Four ml chloroform were added, and the solution extracted by centrifugation at 12,000 g for 15 minutes. RNA was precipitated from the aqueous layer with 10 ml ethanol. Poly A$^+$ RNA was then selected on Dynal Oligo dT Dynabeads (Dynal, Oslo, Norway). Five aliquots of 100 µg total RNA were combined and diluted with an equal volume of 2×binding buffer (20 mM Tris-HCl, pH 7.5, 1.0M LiCl, 1 mM EDTA, 0.1% SDS). RNA was then incubated 5 minutes with the Oligo dT Dynabeads (1.0 ml or 5 mg beads for all the samples). Beads were washed with buffer containing 10 mM Tris-HCl, pH 7.5, 0.15M LiCl, 1 mM EDTA and 0.1% SDS, according to the manufacturer's suggested protocol prior to elution of poly A$^+$ mRNA with 2 mM EDTA, pH 7.5. Double-stranded cDNA was then generated using the eluted poly A$^+$ mRNA and the Boehringer Mannheim cDNA Synthesis Kit according to the manufacturer's suggested protocol.

Isolation of a Partial Canine $\alpha_{TM1}$ cDNA

Oligonucleotide primers 5'Deg (SEQ ID NO: 9) and p4(R) (SEQ ID NO: 23) were employed in a standard PCR reaction using 150 ng double-stranded cDNA, 500 ng of each primer, 200 µM dNTPs and 1.5 units Taq polymerase (Boehringer Mannheim) in Taq buffer (Boehringer Mannheim) with magnesium. The resulting products (1 µl of the original reaction) were subjected to a second round of PCR with the same primers to increase product yield. This band was eluted from a 1% agarose gel onto Schleicher & Schuell (Keene, N.H.) NA45 paper in a buffer containing 10 mM Tris-HCl, pH 8, 1 mM EDTA, 1.5M NaCl at 65° C., precipitated, and ligated into the pCR $^{tm}$II vector (Invitrogen, San Diego, Calif.) using the TA cloning kit (Invitrogen) and the manufacturer's suggested protocol. The ligation mixture was transformed by electroporation into XL-1 Blue bacteria (Stratagene). One clone, 2.7, was determined to contain sequences corresponding to $\alpha_{TM1}$ peptide sequences which were not utilized in design of the primers.

Sequencing was performed with an Applied Biosystems 373A DNA sequencer (Foster City, Calif.) with a Dye-deoxy terminator cycle sequence kit (ABI) in which fluorescent-labeled dNTPs were incorporated in an asymmetric PCR reaction [McCabe, "Production of Single Stranded DNA by Asymmetric PCR," in *PCR Protocols: A Guide to Methods and Applications*, Innis, et al. (eds.) pp. 76–83 Academic Press: New York (1990)] as follows. Samples were held at 96° C. for 4 minutes and subjected to 25 cycles of the step sequence: 96° C., for 15 seconds; 50° C. for 1 second; 60° C. for 4 minutes. Sequence data was automatically downloaded into sample files on the computer that included chromatogram and text files. The sequence of the entire insert of clone 2.7 is set out in SEQ ID NO: 24.

Attempts to isolate the full length canine $\alpha_{TM1}$ cDNA from the Stratagene library (as described in Example 2) were unsuccessful. Approximately 1×106 phage plaques were screened by hybridization under low stringency conditions using 30% formamide with clone 2.7 as a probe, but no positive clones resulted. Attempts to amplify relevant sequences downstream from those represented in clone 2.7 using specific oligonucleotides derived from clone 2.7 or degenerate primers based on amino acid sequence from other peptide fragments paired with a degenerate oligonucleotide based on the conserved α subunit amino acid motif GFFKR [Tamura, et al., supra] were also unsuccessful.

EXAMPLE 5

Cloning of a Putative Human Homolog of Canine $\alpha_{TM1}$

To attempt the isolation of a human sequence homologous to canine $\alpha_{TM1}$ the approximately 1 kb canine $\alpha_{TM1}$ fragment from clone 2.7 was used as a probe. The probe was generated by PCR under conditions described in Example 2 using NT2 (as set out in SEQ ID NO: 25) and p4(R) (SEQ ID NO: 23) primers.

5'-GTNTTYCARGARGAYGG-3' (SEQ ID NO: 25)

The PCR product was purified using the Qiagen (Chatsworth, Ga.) Quick Spin kit and the manufacturer's suggested protocol. The purified DNA (200 ng) was labeled with 200 µCi $\alpha^{32}$PdCTP using the Boehringer Mannheim Random Prime Labelling kit and the manufacturer's suggested protocol. Unincorporated isotope was removed with Sephadex G25 (fine) gravity chromatography. The probe was denatured with 0.2N NaOH and neutralized with 0.4M Tris-HCl, pH 8.0, before use.

Colony lifts on Hybond filters (Amersham) of a human spleen cDNA library in pCDNA/Amp (Invitrogen, San Diego, Calif.) were prepared. The filters were initially denatured and neutralized as described in Example 2 and subsequently incubated in a prehybridization solution (8 ml/filter) with 30% formamide at 50° C. with gentle agitation for 2 hours. Labeled probe as described above was added to this solution and incubated with the filters for 14 hours at 42° C. The filters were washed twice in 2×SSC/0.1% SDS at 37° C. and twice in 2×SSC/0.1% SDS at 50° C. Final stringency washes were 1×SSC/0.1% SDS, twice at 65° C. (1×SSC is 150 mM NaCl, 15 mM sodium citrate, pH 7.0). Filters were exposed to Kodak X-Omat AR film for six hours with an intensifying screen. Colonies giving signals on duplicate lifts were streaked on LB medium with magnesium (LBM)/carbenicillin plates and incubated overnight at 37° C. Resulting streaked colonies were lifted with Hybond filters and these filters were treated as above. The filters were hybridized under more stringent conditions with the 1 kb probe from clone 2.7, labeled as previously described, in a 50% formamide hybridization solution at 50° C. for 3 hours. Probed filters were washed with a final stringency of 0.1×SSC/0.1% SDS at 65° C. and exposed to Kodak X-Omat AR film for 2.5 hours at −80° C. with an intensifying screen. Positive colonies were identified and cultured in LBM/carbenicillin medium overnight. DNA from the cultures was prepared using the Promega Wizard miniprep kit according to the manufacturer's suggested protocol and the resulting DNA was sequenced.

The initial screening resulted in 18 positive clones, while the secondary screening under more stringent hybridization conditions produced one positive clone which was designated 19A2. The DNA and deduced amino acid sequences of the human $\alpha_d$ clone 19A2 are set out in SEQ ID NOS: 1 and 2, respectively.

Characteristics Of The Human $\alpha_d$ cDNA and Predicted Polypeptide

Clone 19A2 encompasses the entire coding region for the mature protein, plus 48 bases (16 amino acid residues) of the 5' upstream signal sequence and 241 bases of 3' untranslated sequence which do not terminate in a polyadenylation sequence. The core molecular weight of the mature protein is predicted to be around 125 kD. The extracellular domain is predicted to encompass approximately amino acid residues 17 through 1108 of SEQ ID NO: 2. This extracellular region is contiguous with about a 20 amino acid region homologous to the human CD11c transmembrane region (residues 1109 through 1128 of SEQ ID NO: 2). The cytoplasmic domain comprises approximately 30 amino acids (about residues 1129 through 1161 of SEQ ID NO: 2). The protein also contains a region (around residues 150 through 352) of approximately 202 amino acids homologous to the 1 (insertion) domain common to CD11a, CD11b and CD11c [Larson and Springer, supra], $\alpha_E$ [Shaw, et al., *J. Biol. Chem.* 269:6016–6025 (1994)] and in VLA-1 and VLA-2, [Tamura, et al., supra]. The I domain in other integrins has been shown to participate in ICAM binding [Landis, et al., *J. Cell. Biol.* 120:1519–1527 (1993); Diamond, et al., *J. Cell. Biol.* 120:1031–1043 (1993)], suggesting that $\alpha_d$ may also bind members of the ICAM family of surface molecules. This region has not been demonstrated to exist in any other integrin subunits.

The deduced amino acid sequence of $\alpha_d$ shows approximately 36% identity to that of CD11a, approximately 60% identity to CD11b and approximately 66% identity to CD11c. An alignment of amino acid sequences for (CD11b SEQ ID NO: 3), CD11c (SEQ ID NO: 4) and $\alpha_d$ (SEQ ID NO: 2) is presented in FIG. 1.

The cytoplasmic domains of $\alpha$ subunits in $\beta_2$ integrins are typically distinct from one another within the same species, while individual $\alpha$ subunits show high degrees of homology across species boundaries. Consistent with these observations, the cytoplasmic region of $\alpha_d$ differs markedly from CD11a, CD11b, and CD11c except for a membrane proximal GFFKR amino acid sequence which has been shown to be conserved among all $\alpha$ integrins [Rojiani, et al., *Biochemistry* 30:9859–9866 (1991)]. Since the cytoplasmic tail region of integrins has been implicated in "inside out" signaling and in avidity regulation [Landis et al., supra], it is possible that $\alpha_d$ interacts with cytosolic molecules distinct from those interacting with CD11a, CD11b, and CD11c, and, as a result, participates in signaling pathways distinct from those involving other $\beta_2$ integrins.

The extracellular domain of $\alpha_d$ contains a conserved DGSGS amino acid sequence adjacent the I-domain; in CD11b, the DGSGS sequence is a metal-binding region required for ligand interaction [Michishita, et al. *Cell* 72:857–867 (1993)]. Three additional putative cation binding sites in CD11b and CD11c are conserved in the $\alpha_d$ sequence at amino acids 465–474, 518–527, and 592–600 in clone 19A2 (SEQ ID NO: 1). The $\alpha_d$ I-domain is 36%, 62%, and 57% identical to the corresponding regions in CD11a, CD11b, and CD11c, respectively, and the relatively low sequence homology in this region suggests that $\alpha_d$ may interact with a set of extracellular proteins distinct from proteins with which other known $\beta_2$ integrins interact. Alternatively, the affinity of $\alpha_d$ for known $\beta_2$ integrin ligands, for example, ICAM-1, ICAM-2 and/or ICAM-R, may be distinct from that demonstrated for the other $\beta_2$ integrin/ICAM interactions. [See Example 12.]

Isolation of Additional Human $\alpha_d$ cDNA Clones for Sequence Verification

In order to confirm the DNA sequence encoding human $\alpha_d$, additional human cDNAs were isolated by hybridization from a human splenic oligo dt-primed cDNA library (Invitrogen) in pcDNA/Amp (described in Example 5) which was size selected by agarose gel electrophoresis for cDNA greater than 3 kb in length. The probe for hybridization was derived from a 5' region of $\alpha_d$ as described below. Hybridization conditions were the same as described above for the isolation of the initial human $\alpha_d$ clone, except that following hybridization, filters were washed twice in 2×SSC/0.1% SDS at room temperature and once in 2×SSC/0.1% SDS at 42° C. Filters were exposed to Kodak X-Omat AR film overnight.

The 5' $\alpha_d$ hybridization probe was generated by PCR from the 19A2 clone using primers CD11c 5' For (SEQ ID NO: 94) and CD11c 5' Rev (SEQ ID NO: 95) under the following conditions. Samples were held at 94° C. for four minutes and subjected to 30 cycles of the temperature step sequence i) 94° C., for 15 seconds; ii) 5° C., for 30 seconds; and iii) 72° C., for 1 minute in a Perkin-Elmer 9600 thermocycler.

CD11c 5' For: (5')CTGGTCTGGAGGTGCCTTCCTG (3') (SEQ ID NO: 94)

$CD_{11}c$ 5' Rev: (5')CCTGAGCAGGAGCACCTGGCC(3') (SEQ ID NO: 95)

The amplification product was purified using the BioRad (Hercules, Calif.) Prep-A-Gene kit according to manufacturer's suggested protocol. The resulting 5' $\alpha_d$ probe was approximately 720 bases long, corresponding to the region from nucleotide 1121 to nucleotide 1839 in SEQ ID NO: 1. The purified DNA (approximately 50 ng) was labeled with $^{32}$P-dCTP using a Boehringer Mannheim (Indianapolis, Ind.) Random Prime Labeling kit according to manufacturer's suggested protocol. Unincorporated isotope was removed using Centrisep Spin Columns (Princeton Separations, Adelphia, N.J.) according to manufacturer's suggested protocol. Labeled probe was added to the filters in a prehybridization solution containing 45% formamide and incubation allowed to proceed overnight at 50° C. Following incubation, the filters were washed as described above.

Thirteen colonies gave signals on duplicate lifts. Positive colonies were picked from master plates, diluted in LBM and carbenicillin (100 $\mu$g/ml) and plated at varying dilutions onto Hybond (Amersham) filters. Duplicate filters were hybridized with the same solution from the primary hybridization and following hybridization, the filters were washed at a final stringency of 2×SSC/0.1% SDS at 42° C. and exposed to film.

Ten of the originally identified thirteen positive colonies were confirmed in the secondary screen. Of these ten clones, two (designated A7.Q and A8.Q) were sequenced and determined to encode human $\alpha_d$. Clone A7.Q was found to be approximately 2.5 kb in length, including a 5' leader, part of a coding region, and an additional 60 bases of 5' untranslated sequence. The incomplete coding region was determined to have resulted from an aberrantly spliced intron region at corresponding nucleotide 2152 of SEQ ID NO: 1. Clone A8.Q was determined to be approximately 4 kb in length, spanning the entire $\alpha_d$ coding region and also including an intron sequence at corresponding base 305 of SEQ ID NO: 1. In comparison to the originally isolated $\alpha_d$ clone (SEQ ID NO: 1), one difference was observed in that both A7.Q and A8.Q clones were determined to have a three base CAG codon insertion occurring at base 1495. Sequences for clones A7.Q AND A8.Q are set out in SEQ ID NOs: 96 and 97, respectively, and a composite human sequence derived from clones A7.Q and A8.Q, and its corresponding deduced amino acid sequence, are set out in SEQ ID NOs: 98 and 99, respectively.

EXAMPLE 6

Northern Analysis of Human $\alpha_d$ Expression in Tissues

In order to determine the relative level of expression and tissue specificity of $\alpha_d$, Northern analysis was performed using fragments from clone 19A2 as probes. Approximately 10 βg of total RNA from each of several human tissues or cultured cell lines were loaded on a formaldehyde agarose gel in the presence of 1 μg of ethidium bromide. After electrophoresis at 100 V for 4 hr, the RNA was transferred to a nitrocellulose membrane (Schleicher & Schuell) by wicking in 10×SSC overnight. The membrane was baked 1.5 hr at 80° C. under vacuum. Prehybridization solution containing 50% formamide in 3-(N-morpholino)propane sulfonic acid (MOPS) buffer was used to block the membrane for 3 hr at 42° C. Fragments of clone 19A2 were labeled with the Boehringer Mannheim Random Prime kit according to the manufacturer's instructions including both $\alpha P^{32}dCTP$ and $\alpha P^{32}dTTP$. Unincorporated label was removed on a Sephadex G25 column in TE buffer. The membrane was probed with $1.5 \times 10^6$ counts per ml of prehybridization buffer. The blot was then washed successively with 2×SSC/ 0.1% SDS at room temperature, 2×SSC/0.1% SDS at 42° C., 2×SSC/0.1% SDS at 50° C., 1×SSC/0.1% SDS at 5° C., 0.5×SSC/0.1% SDS at 50° C. and 0.1×SSC/0.1% SDS at 50° C. The blot was then exposed to film for 19 hr.

Hybridization using a BstXI fragment from clone 1 9A2 (corresponding to nucleotides 2011 to 3388 in SEQ ID NO: 1) revealed a weak signal in the approximately 5 kb range in liver, placenta, thymus, and tonsil total RNA. No signal was detected in kidney, brain or heart samples. The amount of RNA present in the kidney lane was minimal, as determined with ethidium bromide staining.

When using a second fragment of clone 19A2 (encompassing the region from bases 500 to 2100 in SEQ ID NO: 1), RNA transcripts of two different sizes were detected in a human multi-tissue Northern (MTN) blot using polyA+ RNA (Clontech). An approximately 6.5 kb band was observed in spleen and skeletal muscle, while a 4.5 kb band was detected in lung and peripheral blood leukocytes. The variation in sizes observed could be caused by tissue specific polyadenylation, cross reactivity of the probe with other integrin family members, or hybridization with alternatively spliced mRNAs.

Northern analysis using a third fragment from clone 19A2, spanning nucleotides 2000 to 3100 in SEQ ID NO: 1, gave results consistent with those using the other clone 19A2 fragments.

RNA from three myeloid lineage cell lines was also probed using the fragments corresponding to nucleotides 500 to 2100 and 2000 to 3100 in SEQ ID NO: 1. A THP-1 cell line, previously stimulated with PMA, gave a diffuse signal in the same size range (approximately 5.0 kb), with a slightly stronger intensity than the tissue signals. RNA from unstimulated and DMSO-stimulated HL-60 cells hybridized with the $\alpha_d$ probe at the same intensity as the tissue samples, however, PMA treatment seemed to increase the signal intensity. Since PMA and DMSO drive HL-60 cell differentiation toward monocyte/macrophage and granulocyte pathways, respectively, this result suggests enhanced $\alpha_d$ expression in monocyte/macrophage cell types. U937 cells expressed the $\alpha_d$ message and this signal did not increase with PMA stimulation. No band was detected in Molt, Daudi, H9, JY, or Jurkat cells.

EXAMPLE 7

Transient Expression of Human $\alpha_d$ Constructs

The human clone 19A2 lacks an initiating methionine codon and possibly some of the 5' signal sequence. Therefore, in order to generate a human expression plasmid containing 19A2 sequences, two different strategies were used. In the first, two plasmids were constructed in which signal peptide sequences derived from genes encoding either CD11b or CD11c were spliced into clone 19A2 to generate a chimeric $\alpha_d$ sequence. In the second approach, a third plasmid was constructed in which an adenosine base was added at position 0 in clone 19A2 to encode an initiating methionine.

The three plasmids contained different regions which encoded the 5' portion of the $\alpha_d$ sequence or the chimeric $\alpha_d$ sequence. The $\alpha_d$ region was PCR amplified (see conditions in Example 2) with a specific 3' primer BamRev (set out below in SEQ ID NO: 26) and one of three 5' primers. The three 5' primers contained in sequence: (1) identical non-specific bases at positions 1–6 allowing for digestion, an EcoRI site from positions 7–12 and a consensus Kozak sequence from positions 13–18; (2) a portion of the CD11b (primer ER1B) or CD11c (primer ER1C) signal sequence, or an adenosine (primer ER1D); and (3) an additional 15–17 bases specifically overlapping 5' sequences from clone 19A2 to allow primer annealing. Primers ER1B, ER1C or ER1D are set out in SEQ ID NOS: 27, 28 or 29, respectively, where the initiating methionine codon is underlined and the EcoRI site is double underlined.

5'-CCACTGTCAGGATGCCCGTG-3' (SEQ ID NO: 26)

5'-AGTTACGAATTCGCCACC ATGGCTCTACGGGTGCTTCTTCTG-3' (SEQ ID NO: 27)

5'-AGTTACGAATTCGCCACC ATGACTCGGACTGTGCTTCTTCTG-3' (SEQ ID NO: 28)

5'-AGTTACGAATTCGCCACC ATGACCTTCGGCACTGTG-3' (SEQ ID NO: 29)

The resulting PCR product was digested with EcoRI and BamHI.

All three plasmids contained a common second $\alpha_d$ region (to be inserted immediately downstream from the 5' region described in the previous paragraph) including the 3' end of the $\alpha_d$ clone. The second $\alpha_d$ region, which extended from nucleotide 625 into the XbaI site in the vector 3' polylinker region of clone 19A2, was isolated by digestion of clone 19A2 with BamHI and XbaI.

Three ligation reactions were prepared in which the 3' $\alpha_d$ BamHI/XbaI fragment was ligated to one of the three 5' $\alpha_d$ EcoRI/BamHI fragments using Boehringer Mannheim ligase buffer and T4 ligase (1 unit per reaction). After a 4 hour incubation at 14° C., an appropriate amount of vector pcDNA.3 (Invitrogen) digested with EcoRI and XbaI was added to each reaction with an additional unit of ligase. Reactions were allowed to continue for another 14 hours. One tenth of the reaction mixture was then transformed into competent XL-1 Blue cells. The resulting colonies were cultured and the DNA isolated as in Example 5. Digestion with EcoRI identified three clones which were positive for that restriction site, and thus, the engineered signal sequences. The clones were designated pATM.B1 (CD11b/$\alpha_d$, from primer ER1B), pATM.C10 (CD11c/$\alpha_d$, from primer ER1C) and pATM.D12 (adenosine/$\alpha_d$ from primer ER1d). The presence of the appropriate signal sequences in each clone was verified by nucleic acid sequencing.

Expression from the $\alpha_d$ plasmids discussed above was effected by cotransfection of COS cells with the individual plasmids and a CD18 expression plasmid, pRC.CD18. As a positive control, COS cells were also co-transfected with the plasmid pRC.CD18 and a CD11a expression plasmid, pDC.CD11A.

Cells were passaged in culture medium (DMEM/ 10%FBS/pen-strep) into 10 cm Corning tissue culture-treated petri dishes at 50% confluency 16 hours prior to transfection. Cells were removed from the plates with Versene buffer (0.5 mM NaEDTA in PBS) without trypsin for all procedures. Before transfection, the plates were washed once with serum-free DMEM. Fifteen micrograms of each plasmid were added to 5 ml transfection buffer (DMEM with 20 µg/ml DEAE-Dextran and 0.5 mM chloroquine) on each plate. After 1.5 hours incubation at 37° C., the cells were shocked for 1 minute with 5 ml DMEM/ 10% DMSO. This DMSO solution was then replaced with 10 ml/plate culture medium.

Resulting transfectants were analyzed by ELISA, FACS, and immunoprecipitation as described in Examples 8, 9, and 10.

EXAMPLE 8

ELISA Analysis of COS Transfectants

In order to determine if the COS cells co-transfected with CD18 expression plasmid pRC.CD18 and an $\alpha_d$ plasmid expressed $\alpha_d$ on the cell surface in association with CD18, ELISAs were performed using primary antibodies raised against CD18 (e.g., TS1/18 purified from ATCC HB203). As a positive control, ELISAs were also performed on cells co-transfected with the CD18 expression plasmid and a CD11a expression plasmid, pDC.CD11A. The primary antibodies in this control included CD18 antibodies and anti-CD11a antibodies (e.g., TS1/22 purified from ATCC HB202).

For ELISA, cells from each plate were removed with Versene buffer and transferred to a single 96-well flat-bottomed Corning tissue culture plate. Cells were allowed to incubate in culture media 2 days prior to assay. The plates were then washed twice with 150 µl/well D-PBS/0.5% teleost skin gelatin (Sigma) solution. This buffer was used in all steps except during the development. All washes and incubations were performed at room temperature. The wells were blocked with gelatin solution for 1 hour. Primary antibodies were diluted to 10 µg/ml in gelatin solution and 50 µl were then added to each well. Triplicate wells were set up for each primary antibody. After 1 hour incubation, plates were washed 3× with 150 µl/well gelatin solution. Secondary antibody (goat anti-mouse Ig/HRP-Fc specific [Jackson, West Grove, Pa.]) at a 1:3500 dilution was added at 50 µl/well and plates were incubated for 1 hour. After three washes, plates were developed for 20 minutes with 100 µl/well o-phenyldiamine (OPD) (Sigma) solution (1 mg/ml OPD in citrate buffer) before addition of 50 µl/well 15% sulfuric acid.

Analysis of transfectants in the ELISA format with anti-CD18 specific antibodies revealed no significant expression above background in cells transfected only with the plasmid encoding CD18. Cells co-transfected with plasmid containing CD11a and CD18 showed an increase in expression over background when analyzed with CD18 specific antibodies or with reagents specific for CD11a. Further analysis of cells co-transfected with plasmids encoding CD18 and one of the $\alpha_d$ expression constructs (pATM.C10 or pATM.D12) revealed that cell surface expression of CD18 was rescued by concomitant expression of $\alpha_d$. The increase in detectable CD18 expression in COS cells transfected with pATM.C10 or pATM.D12 was comparable to that observed in co-transfected CD11a/CD18 positive control cells.

EXAMPLE 9

FACS Analysis of COS Transfectants

For FACS analysis, cells in petri dishes were fed with fresh culture medium the day after transfection and allowed to incubate 2 days prior to the assay. Transfectant cells were removed from the plates with 3 ml Versene, washed once with 5 ml FACS buffer (DMEM/2% FBS/0.2% sodium azide) and diluted to 500,000 cells/sample in 0.1 ml FACS buffer. Ten microliters of either 1 mg/ml FITC-conjugated CD18, CD11a, or CD11b specific antibodies (Becton Dickinson) or 800 µg/ml CFSE-conjugated murine 23F2G (anti-CD18) (ATCC HB11081) were added to each sample. Samples were then incubated on ice for 45 minutes, washed 3×with 5 ml/wash FACS buffer and resuspended in 0.2 ml FACS buffer. Samples were processed on a Becton Dickinson FACscan and the data analyzed using Lysys II software (Becton Dickinson).

COS cells transfected with CD18 sequences only did not stain for CD18, CD11a or CD11b. When co-transfected with CD11a/CD18, about 15% of the cells stained with antibodies to CD11a or CD18. All cells transfected with CD18 and any $\alpha_d$construct resulted in no detectable staining for CD11a and CD11b. The pATM.B1, pATM.C10 and pATM.D12 groups stained 4%, 13% and 8% positive for CD18, respectively. Fluorescence of the positive population in the CD11a/CD18 group was 4-fold higher than background. In comparison, the co-transfection of $\alpha_d$constructs with the CD18 construct produced a positive population that showed a 4- to 7-fold increase in fluorescence intensity over background.

EXAMPLE 10

Biotin-Labeled Immunoprecipitation of Human $\alpha_D$/CD18 Complexes from Co-Transfected COS Cells Immunoprecipitation was attempted on cells co-transfected with CD18 and each of the $\alpha_d$expression plasmids separately described in Example 7 in order to determine if $\alpha_d$could be isolated as part of the αβ heterodimer complex characteristic of integrins.

Transfected cells (1–3×10$^8$ cells/group) were removed from petri dishes with Versene buffer and washed 3 times in 50 ml/group D-PBS. Each sample was labeled with 2 mg Sulpho-NHS Biotin (Pierce, Rockford, Ill.) for 15 minutes at room temperature. The reaction was quenched by washing 3 times in 50 ml/sample cold D-PBS. Washed cells were resuspended in 1 ml lysis buffer (1% NP40, 50 mM Tris-HCl, pH 8.0, 0.2M NaCl, 2 mM Ca$^{++}$, 2 mM Mg$^{++}$, and protease inhibitors) and incubated 15 minutes on ice. Insoluble material was pelleted by centrifugation at 10,000 g for 5 minutes, and the supernatant removed to fresh tubes. In order to remove material non-specifically reactive with mouse immunoglobulin, a pre-clearance step was initially performed. Twenty-five micrograms of mouse immunoglobulin (Cappel, West Chester, Pa.) was incubated with supernatants at 4° C. After 2.5 hr, 100 μl (25 μg) rabbit anti-mouse Ig conjugated Sepharose (prepared from Protein A Sepharose 4B and rabbit anti-mouse IgG, both from Zymed, San Francisco, Calif.) was added to each sample; incubation was continued at 4° C. with rocking for 16 hours. Sepharose beads were removed from the supernatants by centrifugation. After pre-clearance, the supernatants were then treated with 20 μg anti-CD18 antibody (TS1.18) for 2 hours at 4° C. Antibody/antigen complexes were isolated from supernatants by incubation with 100 μl/sample rabbit anti-mouse/Protein A-sepharose preparation described above. Beads were washed 4 times with 10 mM HEPES, 0.2M NaCl, and 1% Triton-X 100. Washed beads were pelleted and boiled for 10 minutes in 20 μl 2×Laemmli sample buffer with 2% β-mercaptoethanol. Samples were centrifuged and run on an 8% prepoured Novex polyacrylamide gel (Novex) at 100 V for 30 minutes. Protein was transferred to nitrocellulose membranes (Schleicher & Schuell) in TBS-T buffer at 200 mAmps for 1 hour. Membranes were blocked for 2 hr with 3% BSA in TBS-T. Membranes were treated with 1:6000 dilution of Strep-avidin horse radish peroxidase (POD) (Boehringer Mannheim) for 1 hour, followed by 3 washes in TBS-T. The Amersham Enhanced Chemiluminescence kit was then used according to the manufacturer's instructions to develop the blot. The membrane was exposed to Hyperfilm MP (Amersham) for 0.5 to 2 minutes.

Immunoprecipitation of CD18 complexes from cells transfected with pRC.CD18 and either pATM.B1, pATM.C10 or pATM.D12 revealed surface expression of a heterodimeric species consisting of approximately 100 kD β chain, consistent with the predicted size of CD18, and an α chain of approximately 150 kD, corresponding to $\alpha_d$.

EXAMPLE 11

Stable Transfection of Human $\alpha_d$ in Chinese Hamster Ovary Cells

To determine whether $\alpha_d$ is expressed on the cell surface as a heterodimer in association with CD18, cDNAs encoding each chain were both transiently and stably transfected into a cell line lacking both $\alpha_d$ and CD18.

For these experiments, $\alpha_d$ cDNA was augmented with additional leader sequences and a Kozak consensus sequence, as described in Example 7, and subcloned into expression vector pcDNA3. The final construct, designated pATM.D12, was co-transfected with a modified commercial vector, pDC1.CD18 encoding human CD18 into dihydrofolate reductase (DHFR)⁻Chinese hamster ovary (CHO) cells. The plasmid pDC1.CD18 encodes a DHFR⁺ marker and transfectants can be selected using an appropriate nucleoside-deficient medium. The modifications which resulted in pDC1.CD18 are as follows.

The plasmid pRC/CMV (Invitrogen) is a mammalian expression vector with a cytomegalovirus promoter and ampicillin resistance marker gene. A DHFR gene from the plasmid pSC 1190-DHFR was inserted into pRC/CMV 5' of the SV40 origin of replication. In addition, a polylinker from the 5' region of the plasmid pHF2G-DHF was ligated into the pRC/CMV/DHFR construct, 3' to the DHFR gene. CD18 encoding sequences are subsequently cloned into the resulting plasmid between the 5' flanking polylinker region and the bovine growth hormone poly A encoding region.

Surface expression of CD18 was analyzed by flow cytometry using the monoclonal antibody TS1/18. Heterodimer formation detected between $\alpha_d$ and CD18 in this cell line was consistent with the immunoprecipitation described in Example 10 with transient expression in COS cells.

EXAMPLE 12

Human $\alpha_D$ Binds to ICAM-R in a CD18-Dependent Fashion

In view of reports that demonstrate interactions between the leukocyte integrins and intercellular adhesion molecules (ICAMs) which mediate cell-cell contact [Hynes, *Cell* 69:11–25 (1992)], the ability of CHO cells expressing $\alpha_d$/CD18 to bind ICAM-1, ICAM-R, or VCAM-1 was assessed by two methods.

In replicate assays, soluble ICAM-1, ICAM-R, or VCAM-1 IgG1 fusion proteins were immobilized on plastic and the ability of $\alpha_d$/CD18 CHO transfected cells to bind the immobilized ligand was determined. Transfected cells were labeled internally with calcein, washed in binding buffer (RPMI with 1% BSA), and incubated in either buffer only (with or without 10 ng/ml PMA) or buffer with anti-CD18 monoclonal antibodies at 10 μg/ml. Transfected cells were added to 96-well Immulon 4 microtiter plates previously coated with soluble ICAM-1/IgG1, ICAM-R/IgG1 or VCAM-1/IgG1 fusion protein, or bovine serum albumin (BSA) as a negative control. Design of the soluble forms of these adhesion molecules is described and fully disclosed in co-pending and co-owned U.S. Pat. application Ser. No. 08/102,852, filed Aug. 5, 1993. Wells were blocked with 1% BSA in PBS prior to addition of labeled cells. After washing the plates by immersion in PBS with 0.1% BSA for 20 minutes, total fluorescence remaining in each well was measured using a Cytofluor 2300 (Millipore, Milford, Mass.).

In experiments with immobilized ICAMs, $\alpha_d$/CD18 co-transfectants consistently showed a 3–5 fold increase in binding to ICAM-R/IgG1 wells over BSA coated wells. The specificity and CD18-dependence of this binding was demonstrated by the inhibitory effects of anti-CD18 antibody TS1/18. The binding of cells transfected with CD11a/CD18 to ICAM-1/IgG1 wells was comparable to the binding observed with BSA coated wells. CD11a/CD18 transfected cells showed a 2–3 fold increase in binding to ICAM-1IgG1 wells only following pretreatment with PMA. PMA treatment of $\alpha_d$/CD18 transfectants did not affect binding to ICAM-1/IgG1 or ICAM-R/IgG1 wells. No detectable binding of $\alpha_d$/CD18 transfectants to VCAM-1/IgG1 wells was observed.

Binding of $\alpha_d$/CD18-transfected cells to soluble ICAM-1/IgG1, ICAM-R/IgG1, or VCAM-1/IgG1 fusion proteins was determined by flow cytometry. Approximately one million $\alpha_d$/CD18-transfected CHO cells (grown in spinner flasks for higher expression) per measurement were suspended in 100 μl binding buffer (RPMI and 1% BSA) with or without 10 μg/ml anti-CD18 antibody. After a 20 minute incubation at room temperature, the cells were washed in binding buffer and soluble ICAM-1/IgG1 or ICAM-R/IgG1 fusion protein was added to a final concentration of 5 μg/ml. Binding was allowed to proceed for 30 minute at 37° C., after which the cells were washed three times and resuspended in 100 μl binding buffer containing FITC-conjugated sheep anti-human IgG1 at a 1:100 dilution. After a 30 minute incubation, samples were washed three times and suspended in 200 μl binding buffer for analysis with a Becton Dickinson FACScan.

Approximately 40–50% of the $\alpha_d$/CD18 transfectants indicated binding to ICAM-R/IgG1, but no binding to ICAM-1/IgG1 or VCAM-1/IgG1 proteins. Pretreatment of transfected cells with PMA has no effect on $\alpha_d$/CD18 binding to either ICAM-1/IgG1, ICAM-R/IgG1 or VCAM-1IgG1, which was consistent with the immobilized adhesion assay. Binding by ICAM-R was reduced to background levels after treatment of $\alpha_d$/CD18 transfectants with anti-CD18 antibody TS1/18.

The collective data from these two binding assays illustrate that $\alpha_d$/CD18 binds to ICAM-R and does so preferentially as compared to ICAM-1 and VCAM-1. The $\alpha_d$/CD18 binding preference for ICAM-R over ICAM-1 is opposite that observed with CD11a/CD18 and CD11b/CD18. Thus modulation of $\alpha_d$/CD18 binding may be expected to selectively affect normal and pathologic immune function where ICAM-R plays a prominent role. Moreover, results of similar assays, in which antibodies immunospecific for various extracellular domains of ICAM-R were tested for their ability to inhibit binding of ICAM-R to $\alpha_d$/CD18 transfectants, indicated that $\alpha_d$/CD18 and CD11a/CD18 interact with different domains of ICAM-R.

The failure of CD11a/CD18 to bind ICAM-1/IgG1 or ICAM-R/IgG1 in solution suggests that the affinity of binding between CD11a/CD18 and ICAM-1 or ICAM-R is too low to permit binding in solution. Detection of $\alpha_d$/CD18 binding to ICAM-R/IgG1, however, suggests an unusually high binding affinity.

In the assays described above, the VCAM-1/Ig fusion protein comprised the seven extracellular immunoglobulin-like domains. The fusion protein was produced in transfected CHO cells and protein yield determined by sandwich ELISA. The seven domain VCAM-1 fusion protein from CHO cell supernatant was employed without purification and protein yield was found to be extremely low. Because of the low protein yield in the VCAM-1 preparations, $\alpha_d$/CD18 binding to VCAM-1 was re-examined using a commercial VCAM-1 preparation (R & D Systems, Minneapolis, Minn.) in order to determine if the low VCAM-1 concentration resulted in undetectable $\alpha_d$ binding.

As before, CHO cells expressing $\alpha_d$ and CD18 were utilized in adhesion assays employing immobilized recombinant adhesion molecules. Using flow cytometry, it was shown that $\alpha_d$-transfected CHO cells expressed both $\alpha_d$ and CD18 and none of the other $\beta_2$ integrins. The transfected CHO cells were also shown to express neither of the two known VCAM-1 binding partner proteins, $\alpha_4\beta_1$ and $\alpha_4\beta_7$. The parental CHO cell line was shown to express no $\alpha_4$ or $\beta_2$ integrins. Binding experiments were carried out essentially as described above.

Results indicated that $\alpha_d$-transfected CHO cells bound immobilized VCAM-1 at a rate of approximately 14.2% as compared to binding to immobilized BSA at a rate of 7.5% and to immobilized E-selection at a rate of 2.8%. In addition, binding to immobilized VCAM-1 was essentially blocked (3.0% binding) in the presence of a monoclonal antibody specific for the first domain of VCAM-1. The parental CHO cells did not bind either VCAM-1, E-selection or BSA (all binding rates were less than 2%). Binding of the transfected CHO cells also decreased with serial passage of the cells which was consistent with the observed decrease in $\alpha_d$ surface expression over the same time period.

In order to determine if cells which naturally express $\alpha_d$/CD18 utilize VCAM-1 as a binding partner, peripheral blood eosinophils were isolated and cultured five to seven days in the presence of 10 ng/ml IL-5 in order to increase $\alpha_d$ expression. Flow cytometry indicated that IL-5 incubation increased $\alpha_d$ expression two- to four-fold, but had no effect on $\alpha_4$ expression.

Results indicated that the cultured eosinophils bound immobilized VCAM-1 at a rate of approximately 28.8% and that the binding was partially inhibited by both an anti-CD18 monoclonal antibody (binding rate 17.1%) and a monoclonal antibody against $\alpha_4$ (binding rate 18.1%). Contrary to the preliminary results above with low levels and/or impure VCAM-1, these data suggest that $\alpha_d \beta_2$ is a ligand for VCAM-1.

The FACS adhesion assay described above was used to test the binding of an ICAM-R mutant E37A/Ig to CHO cells expressing $\alpha_d$/CD18. E37A/Ig has been shown to obviate binding to an LFA-1/Ig chimera [Sadhu, et al., *Cell Adhesion and Communication* 2:429–440 (1994)]. The mutant protein was expressed in a soluble form from stably transfected CHO cell line and purified over a ProsepA column as described by Sadhu, et al., supra.

E37A/Ig binding with the $\alpha_d$/CD18 transfectants was not detected in repeated assays. The mean fluorescence intensity (MFI) of the E37A/Ig chimera detected by FITC-conjugated anti-human antibody was identical to the MFI of the detecting antibody alone, indicating there was no detectable signal above background using the E37A/Ig mutant protein in the assay. Similarly, in an ELISA, carried out as described in Example 14, the E37A/Ig mutant did not appear to bind immobilized $\alpha_d$/CD18.

$\alpha_d$ Binding to iC3b

Complement component C3 can be proteolytically cleaved to form the complex iC3b, which initiates the alternative pathway of complement activation and leads ultimately to cell-mediated destruction of a target. Both CD11b and CD11c have been implicated in iC3b binding and subsequent phagocytosis of iC3b-coated particles. A peptide fragment in the CD11I domain has recently been identified as the site of iC3b interaction [Ueda, et al., *Proc. Natl. Acad. Sci. (USA)* 91:10680–10684 (1994)]. The region of iC3b binding is highly conserved in CD11b, CD11c, and $\alpha_d$, suggesting an $\alpha_d$/iC3b binding interaction.

Binding of $\alpha_d$ to iC3b is performed using transfectants or cell lines naturally expressing $\alpha_d$ (for example, PMA-stimulated HL60 cells) and iC3b-coated sheep red blood cells (sRBC) in a rosette assay [Dana, et al., *J. Clin. Invest.* 73:153–159 (1984)]. The abilities of $\alpha_d$/CD18 CHO transfectants, VLA4-CHO transfectants (negative control) and PMA-stimulated HL60 cells (positive control) to form rosettes are compared in the presence and absence of an anti-CD18 monoclonal antibody (for example TS1/18.1).

EXAMPLE 13

Screening by Scintillation Proximity Assay ID of Modulators of $\alpha_D$ Binding Specific inhibitors of binding between the $\alpha_d$ ligands of the present invention and their binding partners ($\alpha_d$ ligand/anti-ligand pair) may be determined by a variety of means, such as scintillation proximity assay techniques as generally described in U.S. Pat. No. 4,271,139, Hart and Greenwald, *Mol. Inmunol.* 12:265–267 (1979), and Hart and Greenwald, *J. Nuc. Med.* 20:1062–1065 (1979), each of which is incorporated herein by reference.

Briefly, one member of the $\alpha_d$ ligand/anti-ligand pair is bound to a solid support either directly or indirectly. Indirect capture would involve a monoclonal antibody, directly bound to the support, which recognizes a specific epitope at the C-terminus of the soluble integrin $\beta$ chain protein. This epitope would be either the hemagglutinin protein or the mycobacterial IIIE9 epitope [Anderson, et al., *J. Immunol.*

141:607–613 (1988). A fluorescent agent is also bound to the support. Alternatively, the fluorescent agent may be integrated into the solid support as described in U.S. Pat. No. 4,568,649, incorporated herein by reference. The non-support bound member of the $\alpha_d$ ligand/anti-ligand pair is labeled with a radioactive compound that emits radiation capable of exciting the fluorescent agent. When the ligand binds the radiolabeled anti-ligand, the label is brought sufficiently close to the support-bound fluorescer to excite the fluorescer and cause emission of light. When not bound, the label is generally too distant from the solid support to excite the fluorescent agent, and light emissions are low. The emitted light is measured and correlated with binding between the ligand and the anti-ligand. Addition of a binding inhibitor to the sample will decrease the fluorescent emission by keeping the radioactive label from being captured in the proximity of the solid support. Therefore, binding inhibitors may be identified by their effect on fluorescent emissions from the samples. Potential anti-ligands to $\alpha_d$ may also be identified by similar means.

The soluble recombinant $\alpha_d$/CD18 leucine zipper construct (see Example 14) is used in a scintillation proximity assay to screen for modulators of CAM binding by the following method. The recombinant integrin is immobilized with a nonblocking anti-$\alpha$ subunit or anti-$\beta$ subunit antibody previously coated on a scintillant-embedded plate. Chemical library compounds and a specific biotinylated CAM/Ig chimera are added to the plate simultaneously. Binding of the CAM/Ig chimera is detected by labeled strepavidin. In the assay, ICAM-1Ig and ICAM-R/Ig are biotinylated with NHS-Sulfo-biotin LC (long chain, Pierce) according to manufacturer's suggested protocol. Labeled proteins are still reactive with CAM specific antibodies and can be shown to react with immobilized LFA-1 by ELISA, with detection by Strepavidin-HRP and subsequent development with OPD.

Alternatively, the recombinant leucine zipper protein is purified, or partially purified, and coated directly on the scintillant embedded plate. Unlabelled CAM/Ig chimera and chemical library compounds are added simultaneously. Bound CAM/Ig is detected with $^{125}$I-labeled anti-human Ig.

As yet another alternative, purified CAM/Ig protein is immobilized on the scintillant plate. Chemical library compounds and concentrated supernatant from cells expressing recombinant leucine zipper integrin are added to the plate. Binding of the recombinant integrin is detected with a labeled, non-blocking $\alpha$ or $\beta$ subunit antibody.

Screening for Small Molecule Modulators

As an alternative to scintillation proximity assays, $\alpha_d$ binding partners and inhibitors of the same can be identified using ELISA-like assays as described below.

Soluble $\alpha_d$/CD18 leucine zipper (LZ) construct (see Example 14) was captured from tissue culture supernatants using the anti-$\alpha_d$ antibody 212D (see Example 15). The 212D antibody was immobilized on 96-well Immulon IV plates (Costar) in bicarbonate coating buffer (pH 9.5) overnight at 4° C. The same protocol was used to immobilize the anti-CD11a antibody TS2/4.1 for immobilization of a LFA-1 leucine zipper (LFA-1LZ) fusion protein; LFA-1 was used as a negative control for VCAM-1 binding and a positive control for ICAM-1 binding. The plates were blocked with 300 μl/well 3% bovine serum albumin for one hour and washed in D-PBS. Tissue culture supernatants from stable CHO transfectants expressing either $\alpha_d$/CD18LZ or LFA-1LZ were added at 100 μl/well and allowed to incubate for 6 to 8 hours at 4° C. The plates were washed twice with Tris-buffered saline with Tween 20 (TBS-T), followed by one wash with TBS (no Tween) containing 2 mM each calcium chloride, magnesium chloride, and manganese chloride. The latter served as assay and wash buffer during the remainder of the assay.

After integrin capture, the plates were washed three times with 250 μl/well TBS. Purified CAM/Ig (see Example 12) was added to each well following serial 2:3 dilutions starting at a concentration of 10 to 20 μg/ml. CAM/Igs were allowed to bind for two hours at room temperature before plates were washed as above. Bound fusion protein was detected with horseradish peroxidase-conjugated goat anti-human Ig antibody (Jackson Labs) followed by development with o-phenyldiamine (OPD).

Results indicated that while ICAM-1/Ig caused a 5- to 7-fold increase in signal when bound to LFA-1LZ, it failed to bind $\alpha_d$/CD18LZ. In contrast, VCAM-1/Ig exhibited a 5-fold increase in signal above background in wells containing $\alpha_d$/CD18LZ, but not in wells with LFA-1LZ. An ICAM-R mutant E37A/1g (see Example 12) did not bind either integrin.

The $\alpha_d$ specific monoclonal antibodies 212D, 217L, 217I, 217H, 217G, 217K, and 217M were tested for the ability to inhibit VCAM-1 binding to immobilized $\alpha_d$/CD18. In addition, anti-VCAM-1 monoclonal antibodies 130 K, 130 P and IG11B1 (Caltag) were used to determine reaction specificity. The anti-$\alpha_d$ monoclonal antibodies were used at 5 μg/ml and the anti-VCAM-1 antibodies at 25 μg/ml; the higher anti-VCAM-1 antibody concentration was used in view of the fact that VCAM-1 is in solution in the assay system.

Partial blocking (50%) resulted in the wells treated with either 217I or 130 K and 130 P used together. The combination of 130 K/130 P also completely inhibits the interaction of VLA-4 and VCAM-1 which suggested that $\alpha_d$ and VLA-4 bind to distinct sites on VCAM-1 and the possibility of developing antagonists which selectively interfere with $\alpha_d$/VCAM-1 binding.

This assay can be adapted as follows to perform high throughput screening assays for inhibitors Of $\alpha_d$ binding. VCAM-1/Ig is biotinylated and used as above in the presence of pooled chemical compounds previously solubilized in DMSO; bound VCAM-1/Ig is then detected with a strepavidin-europium (Eu) complex. The strepavidin-Eu complex is activated by chelation resulting in measurable light emission. Changes, or more particularly a decrease, in emission is indicative of inhibition of VCAM-1/$\alpha_d$ binding, presumably as a result of action by one or more compounds in the pool of small molecules, which are then assayed individually or in smaller groupings.

EXAMPLE 14

Soluble Human $\alpha_d$ Expression Constructs

The expression of full-length, soluble human $\alpha_d$/CD18 heterodimeric protein provides easily purified material for immunization and binding assays. The advantage of generating soluble protein is that it can be purified from supernatants rather than from cell lysates (as with full-length membrane-bound $\alpha_d$/CD18); recovery in therefore improved and impurities reduced.

The soluble $\alpha_d$ expression plasmid was constructed as follows. A nucleotide fragment corresponding to the region from bases 0 to 3161 in SEQ ID NO: 1, cloned into plasmid pATM.D12, was isolated by digestion with HindIII and AatII. A PCR fragment corresponding to bases 3130 to 3390 in SEQ ID NO: 1, overlapping the HindIII/AatII fragment and containing an addition MluI restriction site at the 3' terminus, was amplified from pATM.D12 with primers sHAD.5 and sHAD.3 set out in SEQ ID NOS: 30 and 31, respectively.

5'-TTGCTGACTGCCTGCAGTTC-3' (SEQ ID NO: 30)
5'-GTTCTGACGCGTAATGGCATTGTAGACCTCGTCTTC-3' (SEQ ID NO: 31)

The PCR amplification product was digested with AatII and MluI and ligated to the HindIII/AatII fragment. The resulting product was ligated into HindIII/MluI-digested plasmid pDC1.s.

This construct is co-expressed with soluble CD18 in stably transfected CHO cells, and expression is detected by autoradiographic visualization of immunoprecipitated CD18 complexes derived from $^{35}$S-methionine labeled cells. The construct is also co-expressed with CD18 in 293 cells [Berman, et al., *J. Cell. Biochem.* 52:183–195 (1993)].

Soluble Full-Length $\alpha_d$ Construct

Alternative $\alpha_d$ expression constructs are also contemplated by the invention. In order to facilitate expression and purification of an intact $\alpha_d$/CD18 heterodimer, soluble $\alpha_d$ and CD18 expression plasmids will be constructed to include a "leucine zipper" fusion sequence which should stabilize the heterodimer during purification [Chang, et al., *Proc. Natl. Acad. Sci. (USA)*, 91:11408–11412 (1994)]. Briefly, DNA encoding the acidic and basic amino acid strands of the zipper have been generated by primer annealing using oligonucleotides described in Chang, et al. The DNA sequences have been further modified to include additional Mlu1 and Xba1 restriction sites at the 5' and 3' ends, respectively, of the DNA to facilitate subcloning into $\alpha_d$ or CD18 expression constructs previously described. In addition, sequences representing either hemagglutinin protein or a polyhistidine sequence have been added, as well as a stop codon inserted after the Xba1 site. The hemagglutinin or polyhistidine sequences are incorporated to facilitate affinity purification of the expressed protein. Sequences encoding the basic strand of the zipper are incorporated on the plasmid vector expressing CD18; the acidic strand is inserted on the a chain construct. Upon expression of 5 the modified $\alpha_d$ and CD18 proteins in a host cell, it is presumed that interaction between the acidic and basic strands of the zipper structure will stabilize the heterodimer and permit isolation of the intact $\alpha_d$/CD18 molecule by affinity purification as described above.

Plasmids were constructed for expression of soluble $\alpha_d$ and CD18 with acidic and basic "leucine zipper" sequences and transfected into COS cells by the DEAE/Dextran method described in Example 7. The resulting protein was referred to as $\alpha_d$/CD18LZ. Hemagglutinin and polyhistidine tags were not incorporated into $\alpha_d$/CD18LZ. Transfected cells were grown for 14 days in reduced serum (2%) conditions. Supernatants harvested every five days from transfected cells were assayed for protein production by ELISA as described in Example 8. Briefly, the $\alpha_d$/CD18LZ heterodimer was immobilized on plates coated with anti-$\alpha_d$ monoclonal antibody 169B (see Example 15). The $\alpha_d$/CD18LZ complex was detected by addition of a biotinylated anti-CD18 monoclonal antibody, TS1/18.1 (see Example 8), followed by addition of strepavidin/horse radish peroxidase (HRP) conjugate and o-phenyldiamine (OPD). Protein was clearly detectable in the supernatants.

Binding Assays Using Soluble Full Length $\alpha_d$ Expression Products

Functional binding assays using the soluble full length $\alpha_d$/CD18LZ heterodimer described above were performed by immobilizing the heterodimer on plates coated with monoclonal antibody 169B or a non-blocking anti-CD18 monoclonal antibody (see Example 15). Wells were blocked with fish skin gelatin to prevent non-specific binding before addition of CAM/Ig chimeras (see Example 12) at a starting concentration of 10 μg/ml. Binding of the chimeras to $\alpha_d$/CD18 was detected with a goat-anti-human Ig HRP conjugate (Jackson Labs) and subsequent development with OPD.

VCAM-1/Ig was observed to bind to captured $\alpha_d$/CD18LZ at a 3–5 fold higher level than to captured CD11a/CD18. ICAM-1/Ig and ICAM-2/Ig bound soluble CD11a/CD18 heterodimer approximately 15 and 10 fold above background, respectively, but did not bind $\alpha_d$/CD18. VCAM-1 binding was reduced approximately 50% in the presence of the VCAM-1 specific antibodies 130K and 130P used in combination.

The binding assay was also performed with the ICAM/Ig protein immobilized on 96-well plates followed by addition of recombinant soluble integrin in cellular supernatant. Binding of the soluble integrins were detected with an unlabeled non-blocking α or β subunit specific murine antibody, followed by incubation with HRP-conjugated goat anti-mouse antibody and development with OPD.

Results indicated that a non-blocking antibody detected $\alpha_d$/CD18LZ binding to ICAM-R/Ig 10 fold greater than binding detected in control well containing no antibody. Soluble $\alpha_d$/CD18 binding was not detected with immobilized ICAM-1/Ig, however binding was detected between $\alpha_d$/CD18 and immobilized CD11b/CD18 and CD11a/CD18 15 and 5 fold, respectively, greater than background binding.

Because previous studies have demonstrated that CD11b and CD11c bind lipopolysaccharide (LPS) [Wright, *Curr. Opin. Immunol.* 3:83–90 (1991); Ingalls and Golenbock, *J. Exp. Med.* 181:1473–1479 (1995)], LPS binding to $\alpha_d$/CD18 was also assessed using flow cytometry and plate-based assays. Results indicated that FITC-labelled LPS isolated from *S. Minnesota* and *S. typhosa* (both obtained from Sigma) at 20 μg/ml were able to weakly bind $\alpha_d$/CD18 transfected CHO cells. No binding was observed with un-transfected control CHO cells. In ELISA format assays, biotinylated LPS [Luk, et al., *Alan. Biochem.* 232:217–224 (1995)] at 0.5–3.0 μg bound immobilized $\alpha_d$/CD18LZ with a signal four fold greater that the capture antibody and blocking reagent alone. Apparent binding of LPS to CD11a/CD18 was discounted by subtracting from each experimental value background binding to anti-CD11a antibody TS2/4.

In order to identify other ligands for $\alpha_d$/CD18, the recombinant $\alpha_d$/CD18LZ protein is used in a two tier study. Binding of various cell types to immobilized protein is used to determine which cells express $\alpha_d$ ligands on the cell surface. Antibody inhibition is then used to determine if the observed cell binding results from interaction with known surface adhesion molecules. If no inhibition results, co-immunoprecipitation with $\alpha_d$/CD18LZ bound to proteins from lysates of cells which will bind $\alpha_d$ is used to attempt to identify the ligand.

Soluble Human $\alpha_d$ I Domain Expression Constructs

It has previously been reported that the I domain in CD11a can be expressed as an independent structural unit that maintains ligand binding capabilities and antibody recognition [Randi and Hogg, *J. Biol. Chem.* 269:12395–12398 (1994); Zhout, et al., *J. Biol. Chem.* 269:17075–17079 (1994); Michishita, et al., *Cell* 72:857–867 (1993)]. To generate a soluble fusion protein comprising the $\alpha_d$ I domain and human IgG4, the $\alpha_d$ I domain is amplified by PCR using primers designed to add flanking BamHI and XhoI restriction sites to facilitate subcloning. These primers are set out in SEQ ID NOS: 32 and 33 with restriction sites underlined.

5'-ACGTATGCA<u>GGATCCC</u>ATCAAGAGATGGA-

CATCGCT-3' (SEQ ID NO: 32)

5'-ACTGCATGT<u>CTCGAG</u>GCTGAAGCCTTCTT-
GGGACATC-3' (SEQ ID NO: 33)

The C nucleotide immediately 3' to the BamHI site in SEQ ID NO: 32 corresponds to nucleotide 435 in SEQ ID NO: 1; the G nucleotide 3' to the XhoI site in SEQ ID NO: 33 is complementary to nucleotide 1067 in SEQ ID NO: 1. The amplified I domain is digested with the appropriate enzymes, the purified fragment ligated into the mammalian expression vector pDCs and the prokaryotic expression vector pGEX-4T-3 (Phanmacia) and the I domain fragment sequenced. The fusion protein is then expressed in COS, CHO or *E. coli* cells transfected or transformed with an appropriate expression construct.

Given the affinity of $\alpha_d$ for ICAM-R, expression of the $\alpha_d$ I domain may be of sufficient affinity to be a useful inhibitor of cell adhesion in which $\alpha_d$ participates.

Analysis of Human $\alpha_d$ I Domain/IgG4 Fusion Proteins

Protein was resolved by SDS-PAGE under reducing and non-reducing conditions and visualized by either silver staining or Coomassie staining. Protein was then transferred to Immobilon PVDF membranes and subjected to Western blot analysis using anti-human IgG monoclonal antibodies or anti-bovine Ig monoclonal antibodies.

Protein detected was determined to migrate at about 120 kD under non-reducing conditions and at about 45 kD under reducing conditions. Minor bands were also detected on non-reducing gels at approximately 40–50 kD which were reactive with the anti-human, but not anti-bovine, antibodies. A 200 kD minor band was determined to be bovine Ig by Western blot.

Binding Assays Using I Domain Expression Products

The ability of the I domain to specifically recognize ICAM-R/IgG chimeric protein was tested in an ELISA format. Serial dilutions of $\alpha_d$ I domain IgG4 fusion protein (I $\alpha_d$/IgG4) in TBS were incubated with ICAM-1/IgG, ICAM-R/IgG, VCAM-1/IgG, or an irrelevant IgG1 myeloma protein immobilized on Immulon IV RIA/EIA plates. CD11a I domain/IgG chimeric protein and human IgG4 kappa myeloma protein were used as negative controls. Bound IgG4 was detected with the biotinylated anti-IgG4 monoclonal antibody HP6023 followed by addition of strepavidin-peroxidase conjugate and development with substrate o-phenyldiamine.

In repeated assays, no binding of the CD11a/IgG4 protein or the IgG4 myeloma protein was detected with any of the immobilized proteins. The I $\alpha_d$/IgG4 protein did not bind to fish skin gelatin or bovine serum albumin blocking agents, human IgG1, or ICAM-1/IgG. A two to three fold increase in binding signal over background was detected in ICAM-R/IgG protein coated wells using 1–5 µg/ml concentrations of I $\alpha_d$/IgG4 protein. The signal in VCAM-1/IgG protein coated wells was 7–10 fold higher than background. In previous assays, $\alpha_d$/CD18 transfected CHO cells did not bind VCAM-1/IgG protein, suggesting that VCAM-1 binding may be characteristic of isolated I domain amino acid sequences.

Additional $\alpha_d$ I Domain Constructs

Additional $\alpha_d$ I domain constructs are generated in the same fashion as the previous construct, but incorporating more amino acids around the $\alpha_d$ I domain. Specific constructs include: i) sequences from exon 5 (amino acids 127–353 in SEQ ID NO: 2), preceding the current construct, ii) the EF-hand repeats (amino acids 17–603 in SEQ ID NO: 2) following the I domain, and iii) the alpha chain truncated at the transmembrane region (amino acids 17–1029 in SEQ ID NO: 2), with an IgG4 tail for purification and detection purposes. These constructs are ligated into either the mammalian expression vector pDCS1 or the prokaryotic expression vector pGEX-4T-3 (Pharmacia) and the I domain sequenced. The fusion proteins are then be expressed in COS, CHO, or *E. coli* cells transformed or transfected with an appropriate expression construct. Protein are purified on a ProSepA column (Bioprocessing Limited, Durham, England), tested for reactivity with the anti-IgG4 monoclonal antibody HP6023 and visualized on polyacrylamide gels with Coomassie staining.

In order to construct an expression plasmid for the entire $\alpha_d$ polypeptide, pATM.D12, described supra, is modified to express an $\alpha_d$-IgG4 fusion protein by the following method. IgG4 encoding DNA is isolated from the vector pDCS1 by PCR using primers which individually incorporate a 5' AatII restriction site (SEQ ID NO: 89) and a 3 ' Xba1 restriction site (SEQ ID NO: 90).

5'-CGCTGTGACGTCAGAGTTGAGTCCAAA-
TATGG-3' (SEQ ID NO: 89)

5'-GGTGACACTATAGAATAGGGC-3' (SEQ ID NO: 90)

Plasmid pATM.D12 is digested with AatII and Xba1, and the appropriately digested and purified IgG4 PCR product ligated into the linear vector.

EXAMPLE 15

Production of Human $\alpha_d$-Specific Monoclonal Antibodies

1. Transiently transfected cells from Example 7 were washed three times in Dulbecco's phosphate buffered saline (D-PBS) and injected at 5×10⁶ cells/mouse into Balb/c mice with 50 µg/mouse muramyl dipeptidase (Sigma) in PBS. Mice were injected two more tines in the same fashion at two week intervals. The pre-bleed and immunized serum from the mice were screened by FACS analysis as outlined in Example 9 and the spleen from the mouse with the highest reactivity to cells transfected with $\alpha_d$/CD18 was fused. Hybridoma culture supernatants were then screened separately for lack of reactivity against COS cells transfected with CD11a/CD18 and for reactivity with cells co-transfected with an $\alpha_d$ expression plasmid and CD18.

This method resulted in no monoclonal antibodies.

2. As an alternative for production of monoclonal antibodies, soluble $\alpha_d$ I domain/IgG4 fusion protein was affinity purified from supernatant of stably transfected CHO cells and used to immunize Balb/c mice as described above. Hybridomas were established and supernatants from these hybridomas were screened by ELISA for reactivity against $\alpha_d$ I domain fusion protein. Positive cultures were then analyzed for reactivity with full length $\alpha_d$/CD18 complexes expressed on CHO transfectants.

Mouse 1908 received three initial immunizations of $\alpha_d$/CD18 transfected CHO cells and two subsequent boosts with soluble $\alpha_d$/CD18 heterodimer. Two final immunizations included 50 µg/mouse $\alpha_d$ I domain/IgG4 fusion protein. The fusion produced 270 IgG-producing wells. Supernatant from 45 wells showed at least 7-fold higher binding to I $\alpha_d$/IgG4 fusion protein than to human IgG4 by ELISA. None of the supernatants reacted to $\alpha_d$/CD18 transfected CHO cells as determined by FACS analysis.

To determine whether the supernatants were able to recognize integrin alpha subunit proteins in another context, fresh frozen splenic sections were stained with supernatants from 24 of the 45 wells. Three supernatants were determined to be positive: one stained large cells in the red pulp, while two others stained scattered cells in the red pulp and also trabeculae.

These supernatants were further analyzed by their ability to immunoprecipitate biotinylated CD18 complexes from either $\alpha_d$/CD18 transfected CHO cells or PMA-stimulated HL60 cells. Fusion wells with supernatants that recognized protein in detergent lysates (which should not be as conformationally constrained as protein expressed as heterodimers) were selected for further subcloning. Monoclonal antibodies which recognize protein in detergent may be more useful in immunoprecipitation of heterodimeric complexes from transfectants, tissues, and cell lines.

3. As another alternative to monoclonal antibody production, CD18 complexes were immunoprecipitated from human spleen lysates with the anti-CD18 monoclonal antibody 23F2G after preclearance of CD11a/CD18 (using monoclonal antibody TS2/4) and CD11b/CD18 (using monoclonal antibody Mo-1). Five Balb/c mice, ten to twelve weeks old, were immunized by subcutaneous injection with approximately 30 µg of resulting protein in complete Freund's adjuvant on day 0, followed by two boosts of 30 µg immunogen/mouse on days 28 and 43 in incomplete Freund's adjuvant. Test sera were drawn ten days following the final boost and reactivity was assessed by using 1:500 dilution of each serum to detect 1 µg/lane immunogen in a Western blot. Sera from three mice detected bands of approximately 95 and 150 kD; no signal was seen in lanes treated with a 1:50 dilution of preimmune sera. The 150 kD band was presumed to represent $\alpha_d$ in an in vivo glycosylation state. In addition, all post immune sera immunoprecipitated protein from lysates of biotinylated $\alpha_d$/CD18 CHO cells that migrated at appropriate molecular weights on SDS-PAGE to represent the heterodimer. From these results, mouse #2212 was selected and was further immunized by intraperitoneal injection on day 64 with 30 µg immunogen in PBS. The mouse was sacrificed four days later, and the spleen was sterilely removed.

A single-cell suspension was formed by grinding the spleen between the frosted ends of two glass microscope slides submerged in serum-free RPMI 1640 supplemented with 2 mM L-glutamine, 1 mM sodium pyruvate, 100 units/ml penicillin, and 100 µg/ml streptomycin (RPMI) (Gibco, Canada). The cell suspension was filtered through a sterile 70-mesh Nitex cell strainer (Becton Dickinson, Parsippany, N.J.), and the filtrate washed twice by centrifugation at 200×g for 5 minutes. The resulting pellet was resuspended in 20 ml serum-free RPMI. Thymocytes taken from three naive Balb/c mice were prepared in a similar manner.

Prior to fusion, NS-1 myeloma cells, kept in log phase in RPMI with 10% Fetalclone serum (FCS) (Hyclone Laboratories, Inc., Logan, Utah) for three days prior to fusion, were pelleted by centrifugation at 200×g for 5 minutes, washed twice as described in the foregoing paragraph, and counted. Approximately $2 \times 10^8$ spleen cells were combined with $4 \times 10^7$ NS-1 cells, and the resulting mixture pelleted by centrifugation at 200×g. The supernatant was discarded. The cell pellet dislodged by tapping the tube and 2 ml of 50% PEG 1500 in 75 mM Hepes (pH 8.0, 37° C.) (Boehringer Mannheim) was added over the course of one minute with stirring. An additional 14 ml of serum-free RPMI was subsequently added over the next seven minutes, followed by immediate addition of 16 ml RPMI. The resulting mixture was centrifuged at 200×g for 10 minutes and the supernatant was discarded. The pellet was resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and 1.5×106 thymocytes/ml, and dispensed into ten 96-well flat bottom tissue culture plates (Corning, United Kingdom) at 200 µl/well. Cells were fed on days 2, 4, and 6 days post-fusion by aspirating approximately 100 µl from each well with an 18 G needle (Becton Dickinson), and adding 100 µl/well plating medium described above, except containing 10 units/ml IL-6 and lacking thymocytes.

On day 7–10 post-fusion, supernatant from each well was screened by antibody capture ELISA, testing for the presence of mouse IgG. Immulon 4 plates (Dynatech, Cambridge, Mass.) were coated with 50 µl/well goat anti-mouse IgA, IgG, or IgM (Organon Teknika) diluted 1:5000 in 50 mM carbonate buffer, pH 9.6, at 4° C. Plates were washed 3× with PBS containing 0.5% Tween 20 (PBST) and 50 µl culture supernatant from each well was added. After incubation at 37° C. for 30 minutes, wells were washed with PBST as above, and 50 µl of horseradish peroxidase conjugated goat anti-mouse IgG(fc) (Jackson ImmunoResearch, West Grove, Pa.) diluted 1:3500 in PBST was added to each well. Plates were incubated as above, washed 4× with PBST and 100 µl substrate, consisting of 1 mg/ml o-phenylene diamine (Sigma) and 0.1 µl/ml 30% $H_2O_2$ in 100 mM Citrate, pH 4.5, was added. The color reaction was stopped after five minutes with addition of 50 µl 15% $H_2SO_4$. Absorbance at 490nm was determined for each well using a plate reader (Dynatech).

Hybridomas were further characterized as follows. Supernatants from IgG-producing cultures were analyzed by flow cytometry for reactivity to $\alpha_d$/CD18-transformed CHO cells but not to JY cells (a B-cell line positive for LFA-1, but not other $\beta_2$ integrins as observed in previous in-house staining experiments). Briefly, $5 \times 10^5$ $\alpha_d$/CD18-transformed CHO or $\alpha_d$/CD18 JY cells were suspended in 50 µl RPMI containing 2% FBS and 10 mM $NaN_3$ (FACS buffer). Individual cell suspensions were added to 50 µl IgG positive hybridoma culture supernatant in wells of 96-well round bottomed plates (Corning). After a 30 minute incubation on ice, cells were washed twice by pelleting in a clinical centrifuge, supernatant from each well was discarded, and pellets resuspended in 200–300 µl FACS buffer. The last wash was replaced with 50 µl/well of a 1:100 dilution of a F(ab')$_2$ fragment of sheep anti-mouse IgG (H +L)-FITC conjugate (Sigma, St. Louis, Mo.) prepared in FACS Buffer. After incubation as described above, cells were washed twice with Dulbecco's PBS (D-PBS) supplemented with 10 mM $NaN_3$, and finally resuspended in D-PBS containing 1% paraformaldehyde. Samples were then transferred to polystyrene tubes for flow cytometric analysis (FACS) with a Becton Dickinson FACsan analyzer.

The fusion yielded four cultures deemed positive by both criteria. When the secondary screen was repeated on expanded supernatants approximately four days later, three of the four cultures remained positive. The three wells, designated 169A, 169B, 169D were cloned two to three times, successively, by doubling dilution in RPMI, 15% FBS, 100 mM sodium hypoxanthine, 16 mM thymidine, and 10 units/ml IL-6. Wells of clone plates were scored visually after four days and the number of colonies in the least dense wells were recorded. Selected wells of the each cloning were assayed by FACS after 7–10 days. Activity was found in two of the cultures, 169A and 169B. In the final cloning, positive wells containing single colonies were expanded in RPMI with 11% FBS. Antibody from clonal supernatants of 169A and 169B were isotyped using IsoStrip kit (Boehringer Mannheim) according to manufacturer instructions and found to be of the IgG1 isotype.

Immunoprecipitation of $\alpha_d$/CD18 complexes from CHO transfectants and PMA-stimulated HL60 cells was used as a tertiary screen for specificity. Hybridomas 169A and 169B precipitated appropriate bands from CHO lines, and a single α chain species of 150–160 kD from HL60 cells as determined by SDS-PAGE. Hybridomas 169A and 169B were deposited May 31, 1995 with the American Type Culture Collection, 12301 Parklawn Drive, Rockville, Md. 20852 and assigned Accession Numbers HB11907 and HB11906, respectively.

In order to more fully characterize binding properties of 169A and 169B, the ability of each antibody to inhibit binding of the other or the anti-CD18 antibody TS1/18.1 to soluble $\alpha_d$/CD18 was tested. Soluble full length $\alpha_d$/CD18 was immobilized by each unlabeled antibody separately in a 96-well plate format, and biotinylated antibodies were used to detect protein bound by the same or different unlabeled antibodies. Binding was detected using a goat anti-mouse Ig/HRP conjugate followed by addition of OPD substrate. Results indicated that antibody 169A was able to block binding of biotinylated 169A and TS1/18.1, while the antibody 169B blocked binding only of itself.

4. Another mouse (#2214), immunized by the same protocol as mouse #2212, was selected and further immunized by a pre-fusion boost on day 70 with 30 μg purified $\alpha_d$ from spleen lysates in PBS. The mouse was sacrificed four days later, and the spleen was sterilely removed.

The fusion and cloning of positive cells were carried out as described above. The fusion produced five anti-$\alpha_d$ monoclonal hybridomas designated 170D, 170F, 170E, 170X, and 170H which were isotyped as IgG1 using the IsoStrip kit (Boehringer Mannheim) according to the manufacturer's instructions.

5. Still another mouse, #2211, immunized by the same initial protocol as mouse #2212 and mouse #2214, was selected and further immunized on day 88 with 30 μg immunogen and a pre-fusion boost of 30 μg immunogen on day 203. The mouse was sacrificed four days later, and the spleen was removed and fusion carried out as described above. Hybridoma supernatant was screened by antibody capture ELISA and by flow cytometry as detailed in the above paragraphs.

Fifteen positive hybridomas were identified, designated 188A, 188B, 188C, 188E, 188F, 188G, 188I, 188J, 188K, 188L, 188M, 188N, 188P, 188R and 188T, and isotyped in an ELISA assay. Briefly, Immulon 4 plates (Dynatech, Cambridge, Mass.) were coated at 4° C. with 50 μl/well goat anti-mouse IgA,G,M (Organon Teknika) diluted 1:5000 in 50 mM carbonate buffer, pH 9.6. Plates were blocked for 30 minutes at 37° C. with 1% BSA in PBS, washed three times with PBS/0.05% Tween 20 (PBST) and 50 μl culture supernatant (diluted 1:10 in PBST) added. After incubation and washing as above, 50 μl of horseradish peroxidase conjugated rabbit anti-mouse $IgG_1$, $G_{2a}$, or $G_3$ (Zymed, San Francisco, Calif.), diluted 1:1000 in PBST with 1% normal goat serum, was added. Plates were incubated as above, washed four times with PBST, after which 100 μl substrate, consisting of 1 mg/ml o-phenylene diamine (Sigma) and 0.1 μl/ml 30% $H_2O_2$ in 100 mM citrate, pH 4.5, was added. The color reaction was stopped in 5 minutes with the addition of 50 μl of 15% $H_2SO_4$. $A_{490}$ was read on a plate reader (Dynatech) and all fifteen antibodies were determined to be IgG1.

The excess spleen cells from mouse #2211 were frozen in a cryovial and stored in liquid nitrogen. The cryovial was thawed quickly by placing into a 37° C. water bath, and moving it in a circular motion just until contents were melted. Cells were transferred to a 15 ml centrifuge tube where warm RPMI containing 11% FBS was added slowly 1 ml at a time, allowing three to five minutes between additions. Another 5 ml warm RPMI was added and after a five minute wait, the tube was centrifuged at 200× g for five minutes and supernatant aspirated. Cells were resuspended in RPMI and a fusion carried out as described above. Hybridoma supernatant was screened by antibody capture and flow cytometry as described above.

The fusion yielded five clones designated 195A, 195C, 195D, 195E and 195H. The clones were isotyped by the ELISA procedure as described above; monoclonal antibodies 195A, 195C, 195D and 195E were determined to be $IgG_1$ and 195H was determined to be $IgG_{2a}$.

6. In another attempt to generate anti-ad monoclonal antibodies, mouse #2213 was immunized using the same protocol as mice 2214, 2211, and 2212, but also further immunized on day 414 and 441 with 30 μg of human $\alpha_d$/CD18 leucine zipper (LZ) bound to sepharose beads. The immunogen for mouse #2213 was prepared by immunoprecipitating human $\alpha_d$/CD18LZ (Example 14) with an anti-CD18 monoclonal antibody and protein A sepharose. The precipitated complex was resuspended as a slurry at a 1:1 ratio with PBS prior to injection. The mouse was sacrificed four days after the booster immunization. The spleen was removed and a fusion carried out as previously described above.

Positive hydridomas were identified by ELISA using human $\alpha_d$/CD18LZ immobilized with the F(ab)'$_2$ fragment of a non-blocking anti-CD18 antibody. Briefly, the F(ab)'$_2$ fragments were coated at 100 μg/well onto Immulon 4 ELISA plates overnight at 4° C. After the buffer was aspirated, the wells were blocked for 30 minutes at 37° C. with 0.5% fish skin gelatin (Sigma). After washing three times in PBST, 50 μl/well of supernatant from CHO cells, previously transformed with a plasmid encoding soluble $\alpha_d$/CD18LZ, was added and the plates incubated at 37° C. for 30 minutes. The washing steps were repeated and 50 μl/well hybridoma supernatant was added. Detection of monoclonal antibody was carried out as described above. Positive wells were assayed by flow cytometry using CHO cells transformed with $\alpha_d$/CD18-encoding DNA as described above and two positive hybridomas designated 212A and 212D were identified. Antibodies secreted by the hybridomas were isotyped as IgG1 using the isotype ELISA procedure described above.

7. In yet another method to generate anti-human $\alpha_d$ monoclonal antibodies, mice were immunized with $\alpha_d$/CD18LZ sepharose beads, prepared as described above, and each mouse receiving 30 μg immunogen on day 0, day 36, and day 66. Mouse #2477 was selected for fusion after screening the mouse sera by the recombinant protein ELISA format as described above. The fusion, selection, and cloning procedures were carried out using the methods described above for fusion 212. Seven positive hybridomas, 217F, 217G, 217H, 217I, 217K, 217L, and 217M were identified, but hybridoma 217F lost reactivity as determined by flow cytometry during the last round of cloning. Antibodies from the six remaining hybridoma lines were isotyped as previously described and all were found to be IgG1.

8. In another method to generate $\alpha_d$ monoclonal antibodies, mouse #2480 was immunized by the same protocol as mouse #2477 but further immunized by interperitoneal injection on days 217 and 218 with 30 μg $\alpha_d$/CD18LZ. The mouse was sacrificed on day 221, the spleen removed and fusion carried out as described above. Hybridoma supernatant was screened by ELISA as described and flow cytometry to determine reactivity to JY cells previously transfected with DNA encoding $\alpha_d$/CD18. The screening procedures were carried out as described above. The fusion produced three positive hybridomas 240F, 240G, and 240H, which secreted antibodies isotyped by the ELISA method to all be IgG1.

9. In order to identify antibodies capable of inhibiting functional ad binding, soluble $\alpha_d$/CD18LZ (see Example 14) is used for immunization. The protein is isolated on an affinity chromatography resin from supernatant of transiently transfected COS cells and the resin-bound $\alpha_d$ used as an immunogen. A selected mouse is immunized as described above and given a final boost two weeks after the initial immunization. Immunization by this technique prevents possible changes in protein conformation often associated with detergent lysis of cells. Additional mice are immunized with recombinant protein, also resin-bound, but were not initially immunized with protein purified from cell lysate.

Hybridomas, prepared as described above, which result from the immunization are screened by ELISA on the recombinant protein immobilized from a cell supernatant using the Fab fragment of a non-blocking antibody. Alternatively, flow cytomotry is used to assay for reactivity to JY cells previously transfected with $\alpha_d$ cDNA.

10. As another alternative, monoclonal antibodies are generated as follows. Affinity purified $\alpha_d$/CD18 heterodimeric protein from detergent lysates of stably transfected CHO cells is used with 50 μg/ml muramyl dipeptidase to immunize Balb/c mice as described above. Mice receive three immunizations before serum reactivity against $\alpha_d$/CD18 is determined by immunoprecipitation of biotinylated complexes in the CHO transfectants. Hybridomas from positive animals are established according to standard protocols, after which hybridoma cultures are selected by flow cytometry using $\alpha_d$/CD18 transfectants. CD11a/CD18 transfectants are utilized to control for CD18-only reactivity.

11. As another alternative for monoclonal antibody production, Balb/c mice undergo an immunization/ immunosuppression protocol designed to reduce reactivity to CHO cell determinants on transfectants used for immunization. This protocol involves immunization with untransfected CHO cells and subsequent killing of CHO-reactive B-cell blasts with cyclophosphamide treatment. After three rounds of immunization and cyclophosphamide treatment are performed, the mice are immunized with $\alpha_d$/CD18 CHO transfected cells as described above.

12. As another alternative, CD18 complexes from detergent lysates of PMA stimulated HL60 cells are enriched by preclearance as described above. Other β32 integrins are cleared on the same columns. Immunization with the resulting complexes, hybridoma production, and screening protocols are performed as described supra.

Production of Polyclonal Sera

Purified $\alpha_d$ I domain/IgG4 chimera (Example 14) was used to generate polyclonal anti-serum in rabbits. The $\alpha_d$ I domain/IgG4 antigen was injected at 100 μg/rabbit initially in complete Freund's adjuvant, followed by three boosts with the same amount of protein in incomplete Freund's adjuvant. Test bleeds were assayed after the third and fourth injections. Rabbit immunoglobulin (Ig) was purified from the serum on a protein A-sepharose column and precleared of anti-human IgG reactivity on a human IgG/Affigel 10 column. Reactivity by ELISA to the I domain chimera, but not to human IgG, was used to confirm complete preclearance.

The precleared polyclonal sera was used to immunoprecipitate protein from detergent lysates of surface-biotinylated CHO cells previously transfected with $\alpha_d$ and CD18 expression vectors. Immunoprecipitation was carried out by the method previously described in Example 10. The precleared sera recognized a protein complex of the same molecular weight as that precipitated by anti-CD18 monoclonal antibody TS1.18. In addition, the sera recognized a single band of appropriate size in a Western blot of CD18 complexes from $\alpha_d$/CD18 transfected CHO cells. Affinity purified integrins CD11a/CD18, CD11b/CD18, and VLA4 from human spleen were not recognized by the rabbit polyclonal sera. The sera failed to react with $\alpha_d$-transfected CHO cells in solution, as determined by flow cytometry. It was therefore concluded that the polyclonal rabbit sera was only capable of recognizing denatured $\alpha_d$ I domain/IgG4 proteins.

In an attempt to produce polyclonal antisera against $\alpha_d$/CD18, a mouse was immunized 3 times with $\alpha_d$ transfected CHO cells (D6.CHO, $\alpha_d$/CD18) with adjuvant peptide and once with purified $\alpha_d$/CD18 heterodimer. A final boost included only $\alpha_d$/CD18 heterodimer. Approximately 100 μl immunized serum was precleared by addition of approximately 108 LFA-1-transfected CHO cells for 2 hours at 4° C. The resulting serum was assayed for $\alpha_d$ reactivity at dilutions of 1/5000, 1/10000, 1/20000 and 1/40000 on normal human spleen. The polyclonal antibody was reactive at a dilution of 1/20000, while a 1/40000 dilution stained very weakly.

EXAMPLE 16

Flow Cytometric Analysis Using Anti-$\alpha_d$ Monoclonal Antibodies

Several primary and immortalized cell lines were used in a survey with the anti-ad monoclonal antibodies 212D, 217K, and 217L. Cell staining was performed and analyzed according to the methods described in Example 17. Primary CD8$^+$/CD56$^-$ and CD4$^-$/CD8$^-$/CD56$^+$ cell lines specific for MAGE-3 (melanoma associated proteins) peptides were strongly positive for CD11b and CD11c, but were not stained by any of the $\alpha_d$ antibodies. MAGE-3 peptide-specific cells are expanded from peripheral blood mononuclear cell populations using peptide-loaded antigen presenting cells (APCs, either dendritic cells or monocytes). Repeated stimulations under limiting dilution conditions, combined with phenotypic selection, result in clonal cytolytic lines which will specifically kill target cells bearing the native protein from which the peptides were derived.

Dendritic cells from peripheral blood, cultured for seven days in the presence of cytokines IL-4 and GM-CSF, were stained strongly by antibodies to CD11a, CD11b, and CD11c, as well as the 217L anti-old antibody. The antibodies 212D, 217K, 217I, 217H, and 217M did not react with these cells nor with dendritic cells, obtained from a variety of donors, in repeated experiments. By day 14 of culture, the surface expression of the 217L antigen had waned and the staining disappeared completely by day 21. During the culture period, CD11b and CD11c expression remained at a high level (2 to 3 logs over background staining).

EXAMPLE 17

Human Monocyte Expression of $\alpha_d$ Purification of Human Monocytes from Peripheral Blood Approximately 300 ml of blood was drawn from a volunteer donor into 3.8% sodium citrate buffer (Sigma). The blood was diluted to 480 ml with endotoxin-free PBS (Sigma), and 30 ml of diluted blood was carefully layered onto 17 ml of Histopaque in a 50 ml centrifuge tube. The gradients were spun for 30 minutes at 1500 rpm in a Beckman Tabletop Centrifuge. The cellular layer, representing mononuclear cells, was collected from each gradient and transferred to a new 50 ml tube. The volume was increased to 50 ml with endotoxin-free PBS, 0.1% BSA (endotoxin free), and the tubes centrifuged for 15 minutes at 1500 rpm in a Beckman Tabletop Centrifuge. The supernatant was discarded and the cells resuspended in a small volume of PBS/BSA and subsequently pooled.

A second gradient (which uses Percoll [Denholm and Wolber, *J. Immunol. Meth.* 144:247–251 (1991)]) was required to purify monocytes from the mixed population of cells obtained as described above. Briefly, 10 ml of 10× Hanks buffer (Gibco) was mixed with 600 μl of 1.0N HCL. To this mixture, 60 ml of Percoll (Pharmacia, Piscataway N.J.) was added and the mixture stirred slowly until all Percoll was in solution. The pH of the Percoll solution was adjusted to 7.0, after which 8.0 ml of gradient mixture was added to six 15 ml round-bottomed polystyrene tubes. Exactly 4.0 ml of cell suspension was added to each gradient and the tubes inverted several times to mix thoroughly. The gradients were centrifuged for 25 minutes in a fixed-angle rotor at 1690 rpm at room temperature. The monocyte fraction, which appeared as a thin white band in the gradients, was collected and transferred to new 50 ml centrifuge tubes. The volume was adjusted to 50 ml with PBS/0.1% BSA and the cells pelleted by centrifugation. The cell pellets were resuspended in a small volume and pooled and cell number determined using a hemacytometer. Cells were resuspended in FACS buffer (RPI 1640, 2.0% FBS, 0.2% sodium azide) and adjusted to one million cells/condition, i.e., one million cells were used for each FACS staining condition to assay for various cellular markers.

FACS Staining and Analysis

Single antibody cell staining was carried out using antibodies immunospecific for $\alpha_d$ or cell markers directly conjugated with a fluorescent tag detectable marker. The mouse anti-human $\alpha_d$ antibodies 212D or 217L were added to cells at 10 μg/ml after which the mixture was incubated on ice for 30 minutes and washed three times. Ten microliters of directly conjugated cell markers, CD3-FITC (Becton-Dickinson) (specific for T cells) or CD33 -FITC (Becton-Dickinson) (specific for monocytes) were added to additional cell samples, while 10 μl of a secondary antibody, anti-mouse FITC (Sigma), was added to the 212D and 217L stained cells. All samples were incubated on ice for 30 minutes in the dark, washed three times, and resuspended in 300 μl of 2.0% paraformaldehyde. Samples were processed on a Becton Dickinson FACScan and the data analyzed using Lysys II software (Becton Dickinson).

In the first experiment, monocytes represented 68% and T-cells 18% of the total cells purified using the double-gradient method. There was a significant amount of staining of both cell types cells for $\alpha_d$ by both 212D and 217L, 55% and 65% of the cells respectively. Based on later experiments, there appeared to be some donor-to-donor variation in the relative amount of $\alpha_d$ staining on freshly isolated human monocytes, although the isolated monocytes always stained positive. When human IgG (used at 1 mg/ml for 10 minutes on ice prior to addition of primary antibody) was added to the cells to block any potential Fc receptor binding problems, there was no change in the $\alpha_d$ staining. When these cells were cultured in suspension using Hydron coated dishes (Interferon Sciences) in 10% FBS/RPM-1640 and analyzed for $\alpha_d$ expression, there was loss of surface expression within 24 hours which continued to diminish over a seven day time course. Relative to expression of other integrins on freshly isolated human monocytes, including CD11a, CD11b, and CD11c, the $\alpha_d$ staining was lower.

2-Color FACS Staining of Human Monocytes for $\alpha_d$

For 2-color FACS staining, both 212D and 217L antibodies were biotinylated using NHS-LC-biotin (Pierce) according to manufacturer's instruction. In a separate experiment, cells were isolated as described above and stained using biotinylated 212D and 217L antibodies and a biotinylated control IgG1 antibody at 10 μg/ml on ice for 30 minutes. The cells were washed three times in FACS buffer (modified to include D-PBS, 2% FBS, and 0.2% sodium azide), and resuspended in 1.0 ml FACS buffer. Both 10 μl FITC-conjugated CD33 (specific for monocytes) and 5 μl streptavidin PE (PharMingen) were added to cell suspensions. Samples were incubated on ice for 30 minutes in the dark, washed 3 times in FACS buffer, and resuspended in 300 μl 1 % paraformaldehyde. Samples were processed by FACS as described above.

Of the two antibodies, 217L showed significant staining on CD33+ cells compared to the control. Antibody 212D also stained this cell type, but the number of CD33$^+$ cells staining was significantly less than observed with antibody 217L. This result was consistent in two separate experiments. In related experiments using biotinylated antibodies 212D and 217L, 217L-biotin consistently stained more cells than 212D-biotin.

Mononuclear cells representing a mixture of lymphocytes and monocytes obtained before Percoll gradient separation were also examined by 2-color analysis as above, and double-stained for 212D and 217L-biotin in combination with FITC-conjugated antibodies immunospecific for CD3 (T cells), CD4 (helper T cells), CD5 (thymocytes, mature T cells, sub-populations of B cells), CD8 (cytotoxic/suppressor T cells), CD14 (monocytes, neutrophils, follicular dendritic reticulum cells), CD20 (B cells), and CD56 (NK cells, subsets of T cells) (Becton Dickinson). No discernible $\alpha_d$ positive populations of cells co-expressed with these cellular markers.

EXAMPLE 18

Analysis of $\alpha_d$ Distribution

Tissue distribution of $\alpha_d$/CD18 was determined using polyclonal anti-serum generated as described in Example 15.

Purified rabbit polyclonal antibody was used at concentrations ranging between 120 ng/mil and 60 μg/ml for immunocytochemical analysis of frozen human spleen sections. Sections of 6 micron thickness were layered onto Superfrost Plus Slides (VWR) and stored at −70° C. Prior to use, slides were removed from −70° C. and placed at 55° C. for 5 minutes. Sections were then fixed in cold acetone for 2 minutes and air dried. Sections were blocked in a solution containing 1% BSA, 30% normal human sera and 5% normal rabbit sera for 30 minutes at room temperature. Primary antibody was applied to each section for 1 hour at room temperature. Unbound antibody was removed by washing the slides 3 times in TBS buffer for 5 minutes per wash. Next, a rabbit anti-mouse IgG link antibody was applied to each section in the same TBS buffer. A mouse alkaline phosphatase anti-alkaline phosphatase (APAAP) antibody, incubated for 30 minutes at room temperature, was used to detect the second antibody. Slides were then washed 3 times in TBS buffer. Fast Blue substrate (Vector Labs) was applied and color development stopped by immersion in water. Slides were counterstained in Nuclear Fast Red (Sigma) and rinsed in water before mounting with Aqua Mount (Baxter). Staining was detected in the splenic red pulp with this reagent, but not with an irrelevant rabbit polyclonal Ig preparation or the unpurified preimmune serum from the same animal.

Once mouse serum was determined to have specific $\alpha_d$ reactivity, it was used to stain various lymphoid and non-lymphoid tissues. Monoclonal antibodies recognizing CD18, CD11a, CD11b, and CD11c were used in the same experiment as controls. Staining of normal spleen sections with $\alpha_d$ polyclonal sera, and monoclonal antibodies to CD11a, CD11b, CD11c, and CD18 revealed the following results. The pattern observed with $\alpha_d$ polyclonal sera did not display the same pattern of labeling as CD11a, CD11b, CD11c, or CD18. There is a distinct pattern of labeling with some cells located in the marginal zone of the white pulp and a distinct labeling of cells peripheral to the marginal zone. This pattern was not observed with the other antibodies. Individual cells scattered throughout the red pulp were also labeled which may or may not be the same population or subset seen with CD11a and CD18.

Labeling with CD11c did display some cells staining in the marginal zone, but the antibody did not show the distinct ring pattern around the white pulp when compared to $\alpha_d$ polyclonal sera, nor did labeling in the red pulp give the same pattern of staining as $\alpha_d$ polyclonal sera.

Therefore, the labeling pattern seen with $\alpha_d$ polyclonal serum was unique compared to that seen using antibodies to the other $\beta_2$ integrins (CD11a, CD11b, CD11c, and CD18), and suggests that the in vivo distribution of $\alpha_d$ in man is distinct from that of other $\beta_2$ integrins.

Characterization of Human $\alpha_d$ Expression with Monoclonal Antibodies

Antibodies secreted by hybridomas 169A and 169B were used to analyze human $\alpha_d$ expression in frozen tissue sections by immunocytochemistry and on cell lines and peripheral blood leukocytes by flow cytometry. Hybridoma supernatants used in both sets of experiments were undiluted.

Tissue Staining

All stains were carried out as described above, except for liver sections which were stained in the following manner. After acetone fixation, sections were quenched in 1% $H_2O_2$ and 1% sodium azide in TBS for 15 minutes at room temperature. After primary antibody staining, a rabbit anti-mouse antibody directly conjugated to peroxidase was applied for 30 minutes at room temperature. Slides were washed 3 times in TBS buffer. A swine anti-rabbit antibody, directly conjugated to peroxidase, was incubated for 30 minutes at room temperature to detect the second antibody. Slides were then washed 3 times in TBS buffer and AEC substrate (Vector Labs) was applied and to allow color development. Slides were counterstained with Hematoxylin Gill's No. 2 (Sigma), and subsequently rinsed in water before dehydration and mounting.

In spleen sections, the majority of expression was localized to the splenic red pulp on cells identified by morphology as granulocytes and macrophages. A large number of granulocytes were stained, while only a subset of macrophages gave signal. A small number of follicular dendritic cells in the white pulp also were weakly stained by the $\alpha_d$ antibodies. CD11a and CD18 staining was detected throughout the red and white pulp. CD11c staining was more pronounced in large cells presumed to be macrophages in the splenic white pulp and in the marginal zone surrounding the white pulp; diffuse staining in the red pulp was also noted. CD11b appeared to have distribution overlapping with but not identical t $\alpha_d$ in the red pulp, with no white pulp involvement.

Integrin expression in normal and (rheumatoid) arthritic synovial tissue was compared. Minimal staining with all anti-integrin antibodies (including antibodies specifically immunoreactive with CD11a, CD11b, CD11c, CD18, as well as ad) was noted in normal tissue, with a widespread distribution on resident cells, presumably macrophages. In the inflamed synovium, expression of all integrins was more localized to cells clustered around lymphatic vessels. While $\alpha_d$ and CD11b expression patterns were similar, CD11c did not appear to be as strongly expressed and was restricted to a subset of leukocytes.

In the dog, CD11b, but not $\alpha_d$, expression was observed on liver macrophages, or Kuppfer cells. Staining of normal human liver sections (as previously described for staining of dog liver section, supra) confirmed the conservation of this staining pattern in humans. In addition, CD11c was detected at low levels. In sections from a hepatitis patient, all leukointegrin staining was higher than observed on normal liver, while $\alpha_d$ expression was detected on macrophages and granulocytes in these samples.

Minimal staining of normal human colon sections was observed with anti-$\alpha_d$ antibodies; faint smooth muscle staining and leukocyte staining was observed. All leukointegrins were detected at higher levels in sections from patients with Crohn's disease.

Normal lung showed a limited number of weakly $\alpha_d$-positive cells; these were determined by morphology to be macrophages and neutrophils. In lung tissue from a patent with emphysema, $\alpha_d$ staining was observed on neutrophils and on macrophages containing hemosiderin, an iron-containing pigment, indicating red cell engulfment by these cells.

Sections of normal brain and plaque lesions from patients with multiple sclerosis (MS) were examined for integrin expression. In normal brain, $\alpha_d$ staining was less intense than that of CD11a, CD11b, and CD11c, and restricted to cells typed as microglial cells by morphology and CD68 staining. CD11b positive cells were located surrounding vessels and throughout the tissue. CD11c$^+$ cells appeared to be located within vessels, whereas $\alpha_d^+$ cells surrounded the vessels. In MS tissue sections, $\alpha_d$ expression was found on both microglial cells and on a non-macrophage leukocyte subset; $\alpha_d^+$ cells were located within plaque lesions, as well as throughout the cortex. The $\alpha_d$ signal was equivalent in intensity to CD11c, but lower than that of CD11b.

Both thoracic aorta and abdominal aorta sections from PDAY (Pathobiological Determinants of Atherosclerosis in Youth, LSU Medical Center) tissue samples were analyzed with anti-leukointegrin and anti-CAM antibodies. The lesions examined were consistent with aortic fatty streaks which consisted of subintimal aggregates of large foam cells (mostly macrophages with ingested lipid) and infiltrates of smaller leukocytes. Single label studies with monoclonal antibodies specific for $\alpha_d$ and the other $\beta_2$ integrin $\alpha$ chains (CD11a, CD11b, and CD11c), plus a macrophage marker (CD68) revealed that the majority of lipid-laden macrophages expressed a moderate level of $\alpha_d$ and CD18, while expressing CD11a and CD11c at weak or weak to moderate levels, respectively. CD11b was faintly expressed, and then by only a subset of macrophages.

Double label studies were conducted to determine the relative localization of $\alpha_d$ and ICAM-R antigens in the aortic sections. Since foam cells in these sections stained with the antibody Ham 56, specific for a macrophage marker, but not with antibodies to smooth muscle actin, it was determined that the foam cells were not derived from subintimal smooth muscle cells. CD68 positive macrophages expressing $\alpha_d$ were surrounded by and interspersed with small ICAM-R positive leukocytes. There appeared to be a limited number of small leukocytes which were CD68 negative but stained with both $\alpha_d$ and ICAM-R antibodies.

Distribution of $\alpha_d$ in normal tissues appeared to be on resident leukocytes in a pattern overlapping with but not identical to that of CD11b and CD11c, two other leukointegrin $\alpha$ chains which have previously been characterized as having restricted leukocyte distribution. Cellular morphology indicated that $\alpha_d$ staining is largely confined to macrophages and granulocytes, with limited lymphocyte staining. Generally, tissue inflammation appeared to increase the number and types of leukocytes observed in a particular tissue, along with increased staining of leukointegrins, including $\alpha_d$. Since the cellular and spatial distribution of the leukointegrins was not identical in pathologic tissues, it was inferred that distinct functions and ligands exist for each family member, including $\alpha_d$, in specific contexts.

Interestingly, $\alpha_d$ expression in early atherosclerotic lesions appeared to be more pronounced than that of CD11a, CD11b, and CD11c, suggesting that $\alpha_d$ may play a central role in the establishment of these lesions. The apposed distribution of $\alpha_d$ and ICAM-R positive cells, supported by evidence suggesting an interaction between $\alpha_d$ and ICAM-R, suggests that $\alpha_d$ may be involved in leukocyte recruitment or activation at early stages in these lesions.

Cell Line and Peripheral Blood Leukocyte Staining

The antibodies 169A and 169B stained a promyeolmonocytic cell line, HL60, by FACS. Surface expression of $\alpha_d$ in these cells is negatively affected by PMA stimulation, which is reported to induce differentiation along a macrophage pathway, but is unaffected by DMSO, which induces granulocyte differentiation [Collins, et al., Blood 70:1233–1244 (1987)]. The FACS profiles of 169A and 169B were antithetical with PMA stimulation to those observed with anti-CD11b and anti-CD11c monoclonal antibodies. A monocyte cell line, THP-1, also exhibited weak staining with 169A and 169B. In addition, a subset of cells in the lymphocyte and monocyte gates of peripheral blood leukocytes appeared to be weakly positive by FACS. A subset of peripheral blood monocytes stained weakly with 169A and 169B, while B lymphocytes were found to have no surface expression of $\alpha_d$. The CD8$^+$ subset of T lymphocytes was $\alpha_d^+$. In addition, antibodies 169A and 169B failed to detect antigen on the B cell lines, JY, Ramos, a basophilic line, KU812, and T cell lines, Jurkat, SKW, and Molt 16.

In light of the results with HL60 cells, granulocytes were isolated from peripheral blood by ficoll/hypaque gradient centrifugation and subsequent red blood cells lysis. All preparations were found to be >90% PMNs by visualization of nuclear morphology in acetic acid. Separate populations were stimulated for 30 minutes with 50 ng/ml PMA or 10–8M formyl peptide (fMLP) to release potential intracellular integrin stores. Unstimulated populations exhibited low, but significant expression of 169A and 169B antigens over an IgG1 control, with a detectable increase observed upon stimulation. On PMNs, levels of $\alpha_d$ and CD11c surface expression were more similar than that observed on HL60 cells. The antibody 169B was used subsequently to precipitate a heterodimeric molecule from a detergent lysate of biotinylated PMNs with subunit sizes of approximately 150 and 95 kD appropriate t $\alpha_d$ and CD18, respectively.

The presence of $\alpha_d$ on PMNs could not be anticipated from the information known about canine $\alpha_d$ expression. Canine neutrophils, unlike their human counterparts, express the T helper cell marker CD4, and also integrin VLA-4, and therefore may have different ligands and functions in the dog than in the human.

Staining of PBL Subgroups

The present study was undertaken to determine the distribution of this $\beta_2$ integrin in human peripheral blood leukocytes. In addition, the cell surface density of $\alpha_d$ relative to other $\beta_2$ integrins was compared. Finally, the acute regulation of $\alpha_d$ expression in purified human eosinophils was also evaluated.

Human peripheral blood leukocytes were separated by density gradient centrifugation into a mononuclear cell fraction (containing monocytes, lymphocytes, and basophils) and granulocytes (neutrophils and eosinophils) [Warner, et al., J. Immunol. Meth. 105:107–110 (1987)]. For some experiments, eosinophils were purified using CD16 immunomagnetic selection to purities greater than 95% [Hansel, et al., J. Immunol. Meth. 122:97–103 (1989)]. Skin mast cells were enzymatically dispersed from human skin and enriched as previously described [Lawrence, et al., J. Immunol. 139:3062–3069 (1987)].

Cells were labelled with appropriate dilutions of monoclonal antibody specific for either CD11a (MHM24), CD11b (H5A4), CD11c (BU-15), or $\alpha_d$ (169A). A murine control IgG$_1$ was also employed. Cells were washed and then incubated with phycoerythrin-conjugated goat-anti-mouse IgG. In some experiments, cells were incubated with excess murine IgG and FITC-labelled murine monoclonal antibody or goat polyclonal antibody specific for a particular cell (e.g., CD3, CD4, or CD8 for T-cells; CD16+ lymphocytes for NK cells; anti-IgE for basophils [Bochner, et al., J. Immunol. Meth. 125:265–271 (1989)]. The samples were then examined by flow cytometry (Coulter EPICS Profile) using appropriate gating to identify cell subsets.

For studies with human eosinophils in which acute upregulation of ad expression was examined, cells were stimulated for 15 minutes at 37° C. with phorbol ester (10 ng/ml), RANTES (100 ng/ml) [Schall, Cytokine 3:165–183 (1991)], or IL-5 (10 ng/ml) prior to labeling with the various monoclonal antibodies as described above.

Results showed that $\alpha_d$ was present on all peripheral blood eosinophils, basophils, neutrophils, monocytes, and NK cells. A small subset (approximately 30%) of CD8$^+$ lymphocytes was also found to express $\alpha_d$. Skin mast cells and CD4$^+$ lymphocytes did not express $\alpha_d$ d. In general, CD11a and CD11b are present at a higher density on leukocytes then $\alpha_d$, the latter being expressed at relatively low levels similar to CD11c. Among leukocytes, monocytes and CD8$^+$ cells have the highest density of $\alpha_d$, while eosinophils have the lowest level of $\alpha_d$ expression. Expression on neutrophils, basophils, and NK cells was intermediate.

Stimulation of peripheral eosinophils with the CC chemokine RANTES caused no change in the expression of any of the $\beta_2$ integrins. Treatment with phorbol ester, however, produced a two to three fold increase in expression of both CD11b and $\alpha_d$, but did not effect expression of CD11a or CD11c. IL-5 treatment resulted in the selective upregulation of CD11b expression without affecting levels of the other integrin subunits.

Combined, these results indicate that in peripheral blood leukocytes, $\alpha_d$ is generally expressed at a level comparable to CD11 c. Highest levels are found on monocytes and a subset of CD8$^+$ lymphocytes. Human skin mast cells do not express $\alpha_d$. Purified eosinophils appear to have pre-formed intracytoplasmic storage pools of CD11b and $\alpha_d$. However, the differential upregulation shown by IL-5 versus PMA suggests that these storage pools are separate from each other.

Staining patterns for peripheral blood leukocyte (PBL) subgroups were also determined by flow cytometry using a combination of gating and surface markers, as described above, in an attempt to more precisely define the 169 A/B negative lymphocyte group. PBL were isolated on Ficoll as previously described and stained separately with 169A, 169B and monoclonal antibodies to CD14 (monocyte/macrophage marker), CD20 (B cell), CD56 (NK cell), T cell receptor α/β (T cell), CD16 (neutrophils, NKs), and α4 (a negative marker for neutrophils). Gates were defined by size and marker distribution.

Results indicated that cells in the CD14+ monocyte gate exhibited low levels of 169A and 169B staining. A bimodal expression pattern observed in earlier experiments in the lymphocyte gate was resolved by increasing forward scatter. The mixed TCR+/CD20+ population appeared to have low, but homogenous levels of 169A/B expression, whereas a population mapped at slightly higher side scatter (cellular complexity), which stained 50% positive for CD56, appeared to have a distinctly 169A/B negative population. The negative population was also not recognized by TCR, CD20, CD14, or CD16 antibodies.

Synovial Distribution of $\alpha_d$

In order to determine cellular distribution of $\alpha_d$, other $\beta_2$ integrins and their counterreceptors in inflammatory and non-inflammatory synovium, monoclonal antibodies to the various $\beta_2$ integrin and immunoglobulin supergene families were used in immunohistological studies. Protein expression was determined in normal, osteoarthritic and rheumatoid synovial tissue samples.

Results indicated that the synovial lining cell layer expressed high levels of VCAM-1, CD11b/CD18 and $\alpha_d$/CD18. In these cells, CD11c/CD18 expression is restricted and CD11a/CD18 is generally not detected. In rheumatoid arthritis synovitis, expression of $\beta_2$ integrins in the synovial cell layer increases in proportion to the degree of hyperplasia. The ratio of cells which express CD11c increases significantly, approaching that of CD11b and $\alpha_d$, but there is no increase in CD11a expression.

In the sublining areas of the tissue, aggregates and diffuse infiltrates of CD3/CD11a/ICAM-R+ lymphocytes are interspersed among CD68/CD11b/$\alpha_d$+ macrophages. A significant number of aggregates demonstrate intense $\alpha_d$ staining, particularly in T cell rich areas.

The synovial endothelium variably expressed ICAM-1 and ICAM-2 with minimal evidence of ICAM-R expression.

Combined, these results indicate that synovial macrophages and macrophage-like synovial cells constitutively express high levels of the $\beta_2$ integrins CD11b and $\alpha_d$. In synovitis, there is an expansion of this subset of cells in both the lining and sublining areas, along with an apparent increase in expression of CD11c. Specific populations of rheumatoid synovial T lymphocytes, in addition to expressing CD11a and ICAM-R, also express high levels of $\alpha_d$, the latter molecule having been shown above to be expressed at low levels by peripheral blood lymphocytes.

$\alpha_d$ Expression in Disease Lung and Liver Tissue

Lung tissue from an individual with sarcoidosis and liver tissue from two individuals with cirrhosis were sectioned at 6 μm thickness and air dried on Superfrost Plus (VWR Scientific) slides for 15 minutes at room temperature. Prior to use, slides were incubated at 50° C. for approximately 5 minutes. Sections were fixed in cold (4° C.) acetone (EM Science) for 2 minutes at room temperature and allowed to air dry at room temperature. Sections were placed in a solution of 100 ml 1×TBS, 1.1 ml 30% $H_2O_2$ (Sigma), 1.0 ml 10% $NaN_3$ (Sigma), for 15 minutes at room temperature to remove endogenous peroxidase activity. Each section was blocked with 150 μl of a solution containing 20% normal human serum (Boston Biomedica), 5% normal rat serum (Harlan), and 2% BSA (Sigma) in 1×TBS for 30 minutes at room temperature. After incubation, the solution was gently blotted from the sections. Primary monoclonal antibody was prepared at a protein concentration of 10 μg/ml in blocking solution and 75 μl applied to each tissue section for 1 hour at room temperature. After incubation, sections were washed three times in 1×TBS for 5 minutes each wash to remove unbound antibody. Excess TBS was removed by aspirating around the tissue following the final wash. Biotinylated rat anti-mouse antibody (Jackson Laboratories) was diluted 1:400 in blocking solution and 75 μl was applied to each section for 30 minutes at room temperature. Slides were washed two times with 1×TBS for 5 minutes each wash. Peroxidase conjugated goat anti-biotin antibody (Vector Laboratories) was diluted 1:200 in blocking solution and 75 μl was applied to each section for 30 minutes at room temperature. Slides were washed two times in 1×TBS for 5 minutes each wash. Substrate 3-amino-9-ethylcarbazole (AEC) (Vector Laboratories) or 3,3 '-diaminobenzidine (DAB) substrate (Vector Laboratories) was applied and color development stopped by immersion in water. Slides were counterstained in Gill's hematoxylin #2 (Sigma) and rinsed in water before mounting with either Aquamount (Baxter) or Cytoseal (VWR).

In the sarcoidosis lung, only the 217L monoclonal antibody stained cells and the majority of 217L epitope expression was localized to granulomas. Giant cells within the granulomas appeared to be negative for the 217L antigen. Expression of the 217L epitope was localized to cells that morphologically appeared to be epithelioid histiocytes, highly differentiated phagocytic cells of macrophage lineage. Distribution of other integrins was observed to overlap with that of the 217L epitope in the sarcoidosis lung, but the expression patterns were not identical. For example, antibodies immunospecific for all other integrins labeled cells in the granulomas as well as the giant cells which were negative for 217L staining.

Sections from a second patient diagnosed with sarcoidosis were negative for expression of the 217L epitope, however it is unclear from pathology reports whether this patient had received steroidal immunosuppressants, the most common form of treatment.

In sections from the cirrhotic liver tissue, anti-$\alpha_d$ antibodies labeled foam cells in the connective tissue between hepatic nodules as well as a subset of lymphocytes. Distribution of CD11c overlapped with $\alpha_d$ expression but was not identical; anti-CD11c antibody also labeled a subset of foam cells but labeled more macrophages and lymphocytes than anti-$\alpha_d$ antibody. There was no apparent overlap in the distribution of CD11 a and CD11b expression with $\alpha_d$ expression.

Antibody 217L also stained phagocytic-type cells which were clustered and isolated from the populations identified by both 212D and 217L. Antibodies to CD11b and CD11c stained the 217L+ clusters in a dissimilar fashion.

In related experiments, antibodies 212D and 217L were used to stain human splenic tissue sections as well as serial sections from spleens of the non-human primate *M. nemestrina*. Splenocytes isolated from fresh human and monkey splenic tissue were also evaluated by flow cytometry for $\alpha_d$ expression. Both antibodies 212D and 217L recognized human and monkey splenocytes. By both ICC and FACS, the $\alpha_d$+population represented about 20% of total cells, unlike in rodents which exhibit a greater percentage of $\alpha_d^+$ cells. The positive population appeared to be morphologically identical to macrophages.

Human Bone Marrow Staining

Human bone marrow samples were obtained from the iliac bone of healthy bone marrow donors according to standard techniques. The original sample was diluted 1:3 in Iscove's medium and centrifuged for 20 minutes at 2000 RPM. The buffy coat layer was carefully collected, washed once, and hemolyzed using hemolytic buffer (0.83% ammonium chloride, 0.1% sodium bicarbonate, EDTA free). Cells were resuspended in PBS with 15 % FBS, aliquoted at 100,000 cells/tube in 100 μl, and put on ice. Immunostaining was performed as previously described. Briefly, monoclonal mouse anti-human $\alpha_d$ antibody 212D or 217L or mouse anti-human CD18 or mouse anti-human CD50 (ICAM-R specific) antibody was individually added to each cell sample at a final concentration of 10 μg/ml and the mixture incubated on ice for 20 minutes. The cells were washed twice and incubated for an additional 20 minutes with goat anti-mouse FITC. Cells were washed twice and resuspended in 1% paraformaldehyde. Fluorescence was measured using a Fluorescence Activated Cell Sorter FACSCAN (Becton Dickinson).

Results from four experiments indicated that $\alpha_d$ expression as determined using antibody 212D was found on 13 to 43% of the cells (median 27%) and on 6 to 55% of cells (median 21%) using antibody 217L. CD18 expression was observed on 60–96% of cells (median 71%) and CD50 on 86–99% of cells (median 94%).

Expression of $\alpha_d$ on Peripheral Blood Mononuclear Cells From Patients with Breast Cancer Peripheral blood mononuclear cells were isolated using Ficoll separation of blood samples from patients with high risk breast cancer, i.e., those patients having breast cancer with poor prognosis features, who had undergone bone marrow transplantation. Cells were screened by immunostaining for the expression of $\alpha_d$ as described above.

Results indicated that $\alpha_d$ expression as determined using antibody 212D was found on 20% of cells and on 13% of the cells using antibody 217L. Antibody 212D also stained a subpopulation of small cells which appeared most likely to be lymphocytes. The percentage of cells expressing $\alpha_d$ were comparable to that generally observed in a normal blood donor.

In addition, antibody 212D appeared to stain not only large cells that were CD14+, but also much smaller cells which were tentatively identified as CD3+. This result was observed both in blood and in bone marrow.

The variation of the number of cells expressing $\alpha_d$ might be explained by a variation in the cell composition of the bone marrow aspirate from donor to donor (e.g., the amount of bone marrow in comparison to the amount of circulating blood).

EXAMPLE 19

Upregulation of $\alpha_d$ Expression

Because leukocyte integrins are generally upregulated during hemodialysis and contribute to the immune alterations observed in chronic renal failure [Rabb, et al., *J. Am. Soc. Nephrol.* 6:1445–1450 (1995) and Rabb, et al., *Am. J. Kidnet Dis.* 23:155–166 (1994)], $\alpha_d$/CD18 surface expression was examined during hemodialysis and chronic renal failure. In addition, expression of $\alpha_d$/CD18 in vitro following PKC stimulation was also investigated.

Whole blood samples were obtained from five randomly chosen hospital patients with non-renal conditions. Blood samples were incubated with PMA at 50 ng/ml for 30 minutes at 37° C. prior to surface staining and flow cytometry. Blood samples were also collected from patients with chronic renal failure. Patients were stable, non-diabetics who were undergoing dialysis three times a week. Baseline samples were obtained prior to beginning dialysis, and subsequent samples were drawn at 15 minutes and 180 minutes during dialysis with a cuprophane membrane. Blood samples from normal subjects having no known diseases were used as negative controls.

For cell staining, 5 μg of antibodies 169A and 169B (and a negative control 1B7) were incubated with 100 μl whole blood in the dark for 15 minutes. Becton Dickinson lysing reagent (2 ml) was added to each mixture and incubation continued for 10 minutes in the dark. Cells were then pelleted and suspended in PBS. The cells were again pelleted by centrifugation and mixed with a secondary FITC-conjugated antibody and incubated for 30 minutes in the dark. Cells were then washed with PBS, centrifuged, aspirated, and resuspended in 1.0% formalin.

Flow cytometry was carried out using the procedure of Rabb, et al. [*J. Am. Soc. Nephrol.* 6:1445–450 (1995)]. Samples were analyzed using Simulset Software (Becton Dickinson) on a FACScan flow cytometer (Becton Dickinson). A minimum of 22,000 cells was analyzed for each sample. Granulocyte, monocyte, and lymphocyte subsets were gated by forward light scatter and side light scatter. Cell subset purity was assessed by CD45 staining and CD14 staining.

Results indicated that $\alpha_d$/CD18 expression can be detected in samples drawn from normal human subjects; expression was greatest on monocytes and lowest on lymphocytes. Expression on neutrophils was intermediate between monocytes and lymphocytes. Staining with antibody 169B was weaker than with antibody 169A. PMA treatment upregulated $\alpha_d$/CD18 expression, particularly on neutrophils and monocytes.

In samples from the renal failure patients, $\alpha_d$/CD18 expression was detectable on neutrophils, monocytes, and lymphocytes prior to the onset of dialysis. After 15 minutes of dialysis using the leukocyte activating membrane, a minor increase in $\alpha_d$/CD18 expression was detected. Expression on monocytes and lymphocytes actually decreased by the end of treatment. This result indicates that $\alpha_d$/CD18 expression is distinct from that observed for CD11a/CD18, CD 11b/CD18, and L-selection expression following dialysis.

EXAMPLE 20

Isolation of Rat cDNA Clones

In view of the existence of both canine and human $\alpha_d$ subunits, attempts were made to isolate homologous genes in other species, including rat (this example) and mouse (Example 20, infra).

A partial sequence of a rat cDNA showing homology to the human $\alpha_d$ gene was obtained from a rat splenic λgt10 library (Clontech). The library was plated at 2×10⁴ pfu/plate onto 150 mm LBM/agar plates. The library was lifted onto Hybond membranes (Amersham), denatured 3 minutes, neutralized 3 minutes and washed 5 minutes with buffers as described in standard protocols [Sambrook, et al., *Molecular Cloning: a laboratory manual*, p.2.110]. The membranes were placed immediately into a Stratalinker (Stratagene) and the DNA crosslinked using the autocrosslinking setting. The membranes were prehybridized and hybridized in 30% or 50% formamide, for low and high stringency conditions, respectively. Membranes were initially screened with a $^{32}$P-labeled probe generated from the human $\alpha_d$ cDNA, corresponding to bases 500 to 2100 in clone 19A2 (SEQ ID NO: 1). The probe was labeled using Boehringer Mannheim's Random Prime Kit according to manufacturer's suggested protocol. Filters were washed with 2×SSC at 55° C.

Two clones, designated 684.3 and 705.1, were identified which showed sequence homology to human $\alpha_d$, human CD11b, and human CD11c. Both clones aligned to the human $\alpha_d$ gene in the 3' region of the gene, starting at base 1871 and extending to base 3012 for clone 684.3, and bases 1551 to 3367 for clone 705.1.

In order to isolate a more complete rat sequence which included the 5' region, the same library was rescreened using the same protocol as employed for the initial screening, but using a mouse probe generated from clone A 1160 (See Example 20, infra). Single, isolated plaques were selected from the second screening and maintained as single clones on LBM/agar plates. Sequencing primers 434FL and 434FR (SEQ ID NOS: 34 and 35, respectively) were used in a standard PCR protocol to generate DNA for sequencing.

5'-TATAGACTGCTGGGTAGTCCCCAC-3' (SEQ ID NO: 34)

5'-TGAAGATTGGGGGTAAATAACAGA-3' (SEQ ID NO: 35)

DNA from the PCR was purified using a Quick Spin Column (Qiagen) according to manufacturer's suggested protocol.

Two clones, designated 741.4 and 741.11, were identified which overlapped clones 684.3 and 705.1; in the overlapping regions, clones 741.1 and 741.11 were 100% homologous to clones 684.3 and 705.1. A composite rat cDNA having homology to the human $\alpha_d$ gene is set out in SEQ ID NO: 36; the predicted amino acid sequence is set forth in SEQ ID NO: 37.

Cloning of the 5' end of Rat $\alpha_d$

A 5' cDNA fragment for the rat $\alpha_d$ gene was obtained using a Clonetech rat spleen RACE cloning kit according to manufacturer's suggested protocol. The gene specific oligonucleotides used were designated 741.11#2R and 741.2#1R (SEQ ID NOS: 59 and 58, respectively).

5'-CCAAAGCTGGCTGCATCCTCTC-3' (SEQ ID NO: 59)

5'-GGCCTTGCAGCTGGACAATG-3' (SEQ ID NO: 58)

Oligo 741.11#2R encompasses base pairs 131–152 in SEQ ID NO: 36, in the reverse orientation and 741.2#1R encompasses bases pairs 696–715 in SEQ ID NO: 36, also in the reverse orientation. A primary PCR was carried out using the 3'-most oligo, 741.2#1R. A second PCR followed using oligo 741.11#2R and DNA generated from the primary reaction. A band of approximately 300 base pairs was detected on a 1% agarose gel.

The secondary PCR product was ligated into plasmid pCRTAII (Invitrogen) according to manufacturer's suggested protocol. White (positive) colonies were picked and added to 100 µl LBM containing 1 µl of a 50 mg/ml carbenicillin stock solution and 1 µl M13 K07 phage culture in individual wells in a round bottom 96 well tissue culture plate. The mixture was incubated at 37° C. for 30 minutes to one hour. Following the initial incubation period, 100 µl of LBM (containing 1 µl of 50 mg/ml carbenicillin and a 1:250 dilution of a 10 mg/ml kanamycin stock solution) were added and the incubation was continued overnight at 37° C.

Using a sterile 96 well metal transfer prong, supernatant from the 96 well plate was transferred to four Amersham Hybond nylon filters. The filters were denatured, neutralized and cross linked by standard protocols. The filters were prehybridized in 20 mls of prehybridization buffer (5×SSPE; 5×Denhardts; 1% SDS; 50 ugs/ml denatured salmon sperm DNA) at 50° C. for several hours while shaking.

Oligo probes 741.11#1 and 741.11#1R (SEQ ID NOS: 56 and 57, respectively), encompassing base pairs 86–105 (SEQ ID NO: 36) in the forward and reverse orientation respectively, were labeled as follows.

5'-CCTGTCATGGGTCTAACCTG-3' (SEQ ID NO: 56)

5'-AGGTTAGACCCATGACAGG-3' (SEQ ID NO: 57)

Approximately 65 WP oligo DNA in 12 µl dH$_2$O was heated to 65° C. for two minutes. Three µl of 10 mCi/ml $\lambda$-$^{32}$P-ATP were added to the tube along with 4 µl 5×Kinase Buffer (Gibco) and 1 µl T4 DNA Kinase (Gibco). The mixture was incubated at 37° C. for 30 minutes. Following incubation, 16 µl of each labeled oligo probe were added to the prehybridization buffer and filters and hybridization was continued overnight at 42° C. The filters were washed three times in 5×SSPE; 0.1% SDS for 5 minutes per wash at room temperature, and autoradiographed for 6 hours. Positive clones were expanded and DNA purified using the Magic Mini Prep Kit (Promega) according to manufacturer's suggested protocol. Clone 2F7 was selected for sequencing and showed 100% homology to clone 741.11 in the overlapping region. The complete rat $\alpha_d$ nucleic acid sequence is set out in SEQ ID NO: 54; the amino acid sequence is set out in SEQ ID NO: 55.

Characteristics of the Rat cDNA and Amino Acid Sequences

Neither nucleic acid nor amino acid sequences have previously been reported for rat α subunits in β$_2$ integrins. However sequence comparisons to reported human β$_2$ integrin α subunits suggests that the isolated rat clone and its predicted amino acid sequence are most closely related t $\alpha_d$ nucleotide and amino acid sequences.

At the nucleic acid level, the isolated rat cDNA clone shows 80% identity in comparison to the human $\alpha_d$ cDNA; 68% identity in comparison to human CD11b; 70% identity in comparison to human CD11c; and 65% identity in comparison to mouse CD11b. No significant identity is found in comparison to human CD11a and to mouse CD11a.

At the amino acid level, the predicted rat polypeptide encoded by the isolated cDNA shows 70% identity in comparison to human $\alpha_d$ polypeptide; 28% identity in comparison to human CD11a; 58% identity in comparison to human CD11b; 61% identity in comparison to human CD11c; 28% identity in comparison to mouse CD11a; and 55% identity in comparison to mouse CD11b.

EXAMPLE 21

Northern Analysis of Rat Tissue for $\alpha_d$ Expression

RNA was obtained from a panel of Lewis rat tissues in order to perform Northern analysis using a rat $\alpha_d$ probe. Samples included total RNA from normal spleen, kidney, liver, lung, and bone marrow, in addition to poly(A$^+$) RNA from normal spleen, brain, spinal cord, thymus, skin, small intestine, and rat antigen activated T cells and diseased EAE (experimental allergic encephalomyelitis) spleen and lymph node. The experiments were carried out using the techniques described in Example 6.

The $\alpha_d$ probe was selected from a region of the rat cDNA encompassing nucleotides 1184 to 3008 in SEQ ID NO: 54 which represents the area having the lowest degree of homology with rat CD11c and rat CD11b. The 1124 bp probe was generated by a restriction enzyme digestion with EcoR1 of 10 μg rat $\alpha_d$ cDNA clone 684.3. The fragment was gel purified and used in a random primed labelling reaction as described in Example 6. The Northern blot was prehybridized, hybridized and washed as described in Example 6 except the probe was added to the hybridization buffer at 5.5×10⁵ cpm/ml.

After autoradiography for five days, bands were detected in lanes containing total spleen RNA as well as poly(A⁺) RNA from a normal rat as well as a spleen from a rat with active EAE, where the amount of RNA was significantly greater than that from normal spleen. The transcript size detected was consistent with the size of the full length rat cDNA clone.

EXAMPLE 22

Production And Characterization Of Rodent $\alpha_d$-Specific Antibodies—Antibodies Against Rat $\alpha_d$ I Domain/Hu IgG4 Fusion Proteins In view of the fact that the I domain of human $\beta_2$ integrins has been demonstrated to participate in ligand binding, it was assumed that the same would be true for rat $\alpha_d$ protein. Monoclonal antibodies immunospecific for the rat $\alpha_d$ I domain may therefore be useful in rat models of human disease states wherein $\alpha_d$ binding is implicated.

Oligos "rat alpha-DI5" (SEQ ID NO: 87) and "rat alpha-DI3" (SEQ ID NO: 88) were generated from the rat $\alpha_d$ sequence corresponding to base pairs 469–493 and base pairs 1101–1125 (in the reverse orientation), respectively, in SEQ ID NO: 54. The oligos were used in a standard PCR reaction to generate a rat $\alpha_d$ DNA fragment containing the I domain spanning base pairs 459–1125 in SEQ ID NO: 54. The PCR product was ligated into vector pCRTAII (Invitrogen) according to manufacturer's suggested protocol. A positive colony was selected and expanded for DNA purification using a Qiagen (Chatsworth, Ga.) Midi Prep kit according to manufacturer's protocol. The DNA was digested with XhoI and BglII in a standard restriction enzyme digest and a 600 base pair band was gel purified which was subsequently ligated into pDCS1 /HuIgG4 expression vector. A positive colony was selected, expanded and DNA purified with a Quiagen Maxi Prep Kit.

COS cells were plated at half confluence on 100 mm culture dishes and grown overnight at 37° C. in 7% CO₂. Cells were rinsed once with 5 ml DMEM. To 5 ml DMEM, 50 μl DEAE-Dextran, 2 μl chloroquine and 15 μg rat $\alpha_d$ I domain/HuIgG4 DNA described above was added. The mixture was added to the COS cells and incubated at 37° C. for 3 hours. Media was then removed and 5 ml 10% DMSO in CMF-PBS was added for exactly one minute. The cells were gently rinsed once with DMEM. Ten ml DMEM containing 10% FBS was added to the cells and incubation continued overnight at 37° C. in 7% CO₂. The next day, media was replaced with fresh media and incubation continued for three additional days. The media was harvested and fresh media was added to the plate. After three days, the media was collected again and the plates discarded. The procedure was repeated until 2 liters of culture supernatant were collected.

Supernatant collected as described above was loaded onto a Prosep-A column (Bioprocessing Limited) and protein purified as described below.

The column was initially washed with 15 column volumes of Wash Buffer containing 35 mM Tris and 150 mM NaCl, pH 7.5. Supernatant was loaded at a slow rate of less than approximately 60 column volumes per hour. After loading, the column was washed with 15 column volumes of Wash Buffer, 15 column volumes of 0.55M diethanolamine, pH 8.5, and 15 column volumes 50 mM citric acid, pH 5.0. Protein was eluted with 50 mM citric acid, pH 3.0. Protein was neutralized with 1.0M Tris, pH 8.0, and dialyzed in sterile PBS.

The rat $\alpha_d$ I domain protein was analyzed as described in Example 14. The detected protein migrated in the same manner as observed with human I domain protein.

Production of Monoclonal Antibodies to Rat $\alpha_d$ I Domain/HuIgG4 Fusion Proteins Mice were individually immunized with 50 μg purified rat $\alpha_d$ I domain/HuIgG4 fusion protein previously emulsified in an equal volume of Freunds Complete Adjuvant (FCA) (Sigma). Approximately 200 μl of the antigen/adjuvant preparation was injected at 4 sites in the back and flanks of each of the mice. Two weeks later the mice were boosted with an injection of 100 μl rat $\alpha_d$ I domain/HuIgG4 antigen (50 μg/mouse) previously emulsified in an equal volume of Freunds Incomplete Adjuvant (FIA). After two additional weeks, the mice were boosted with 50 μg antigen in 200 μl PBS injected intravenously.

To evaluate serum titers in the immunized mice, retroorbital bleeds were performed on the animals ten days following the third immunization. The blood was allowed to clot and serum isolated by centrifugation. The serum was used in an immunoprecipitation on biotinylated (BIP) rat splenocytes. Serum from each mouse immunoprecipitated protein bands of expected molecular weight for rat $\alpha_d$ and rat CD18. One mouse was selected for the fusion and was boosted a fourth time as described above for the third boost.

The hybridoma supernatants were screened by antibody capture, described as follows. Immulon 4 plates (Dynatech, Cambridge, Mass.) were coated at 4° C. with 50 μl/well goat anti-mouse IgA, IgG or IgM (Organon Teknika) diluted 1:5000 in 50 mM carbonate buffer, pH 9.6. Plates were washed 3x with PBS containing 0.05% Tween 20 (PBST) and 50 μl culture supernatant was added. After incubation at 37° C. for 30 minutes, and washing as described above, 50 μl horseradish peroxidase-conjugated goat anti-mouse IgG9 (Fc) (Jackson ImmunoResearch, West Grove, Pa.) diluted 1:3500 in PBST was added. Plates were incubated as described above and washed 4x with PBST. Immediately thereafter, 100 μl substrate, containing 1 mg/ml o-phenylene diamine (Sigma) and 0.1 μl/ml 30% $H_2O_2$ in 100 mM citrate, pH4.5, was added. The color reaction was stopped after 5 minutes with the addition of 50 μl 15% $H_2SO_4$. Absorbance at 490 nm was read on a Dynatech plate reader.

Supernatant from antibody-containing wells was also analyzed by ELISA with immobilized rat $\alpha_d$ I domain/HuIgG4 fusion protein. An ELISA with HuIgG4 antibody coated plates served as a control for reactivity against the IgG fusion partner. Positive wells were selected for further screening by BIP on rat splenocyte lysates using techniques described below.

Production of Polyclonal Sera To Rat $\alpha_d$ I Domain/HuIgG4 Fusion Protein

Two rabbits were prebled prior to immunization with 100 μg purified rat $\alpha_d$ I domain/HuIgG4 fusion protein in complete Freund's adjuvant. Injections were repeated at the same dose every three weeks in incomplete Freunds adjuvant (IFA). After three injections the rabbits were test bled and the collected sera used in a standard immunoprecipitation on rat splenocyte lysates. It was determined that sera from both rabbits were immunoreactive with rat $\alpha_d$. The rabbits were boosted again with 100 ug antigen in IFA, and the collected sera assayed for increased immunoreactivity with rat $\alpha_d$ by immunoprecipitation. The animals were given a final boost and 10 days later, bled out and sera collected.

Rat $\alpha_d$ Histology

Rabbit polyclonal sera generated against rat $\alpha_d$ "I" domain was used in immunohistochemical staining of rat tissue sections by the technique described in Example 18. The staining pattern detected on frozen and on paraffin embedded rat spleen sections was essentially identical to that observed with the antibodies against human $\alpha_d$, with staining individual cells throughout the red pulp. The staining pattern differed from that observed with monoclonal antibodies against rat CD11a, CD11b and CD18. In addition, a positive staining pattern was seen in the thymus on individual cells throughout the cortex. Neither of these tissue gave any signal when stained with the rabbit preimmune sera.

Analysis of Antibody Specificity

Rats were sacrificed by asphyxiation with $CO_2$ and spleens were removed using standard surgical techniques. Splenocytes were harvested by gently pushing the spleen through a wire mesh with a 3 cc syringe plunger in 20 mls RPMI. Cells were collected into a 50 ml conical tube and washed in the appropriate buffer.

Cells were washed three times in cold D-PBS and resuspended at a density of $10^8$ to $10^9$ cells in 40 ml PBS. Four mg of NHS-Biotin (Pierce) was added to the cell suspension and the reaction was allowed to continue for exactly 15 minutes at room temperature. The cells were pelleted and washed three times in cold D-PBS.

Cells were resuspended at a density of $10^8$ cells/ml in cold lysis Buffer (1% NP40; 50 mM Tris-HCl, pH 8.0; 150 mM NaCl; 2 mM CaCl; 2 mM MgCl; 1:100 solution of pepstain, leupeptine, and aprotinin, added just before adding to cells; and 0.0001 g PMSF crystals, added just before adding to cells). Lysates were vortexed for approximately 30 seconds, incubated for 5 minute at room temperature, and further incubated for 15 minutes on ice. Lysates were centrifuged for 10 minutes at 10,000×g to pellet the insoluble material. Supernatant was collected into a new tube and stored at between 4° C. and −20° C.

One ml cell lysate was precleared by incubation with 200 μl of a protein A sepharose slurry (Zymed) overnight at 4° C. Precleared lysate was aliquoted into Eppendorf tubes at 50 μl/tube for each antibody to be tested. Twenty-five μl of polyclonal serum or 100 to 500 μl of monoclonal antibody supernatant were added to the precleared lysates and the resulting mixture incubated for 2 hours at 4° C. with rotation. One hundred μl rabbit anti-mouse IgG (Jackson) bound to protein A sepharose beads in a PBS slurry was then added and incubation continued for 30 minutes at room temperature with rotation. Beads were pelleted with gentle centrifugation, and washed three times with cold Wash Buffer (10 mM HEPES; 0.2M NaCl; 1% Trition X-100). Supernatant was removed by aspiration, and 20 μl 2×SDS sample buffer containing 10% β-mercaptoethanol was added. The sample was boiled for 2 minutes in a water bath, and the sample loaded onto a 5% SDS PAGE gel. Following separation, the proteins were transferred to nitrocellulose at constant current overnight. The nitrocellulose filters were blocked with 3% BSA in TBS-T for 1 hour at room temperature and the blocking buffer was removed. A 1:6000 dilution of Strepavidin-HRP conjugate (Jackson) in 0.1% BSA TBS-T was added and incubation continued for 30 minutes at room temperature. Filters were washed three times for 15 minutes each with TBS-T and autoradiographed using Amersham's ECL kit according to manufacturer's suggested protocol.

Production of Monoclonal Antibodies To Full Length Rat $\alpha_d$ Protein

Rat $\alpha_d$ was purified from rat splenocytes to prepare an immunogen for generating anti-rat $\alpha_d$ monoclonal antibodies. Spleens from approximately 50 normal female Lewis rats, 12–20 weeks of age, were collected and a single cell suspension was made from the tissue by forcing it through a fine wire screen. Red blood cells were removed by lysis in buffer containing 150 mM $NH_4Cl$, 10 mM $KHCO_3$, 0.1 mM EDTA, pH 7.4, and remaining leukocytes were washed two times with phosphate buffered saline (PBS). The splenocytes were pelleted by centrifugation and lysed in buffer containing 50 mM Tris, 150 mM NaCl, 2 mM CaCl2, 2 mM MgC12, 10 mM PMSF, leupeptin, pepstatin and 1% Triton X-100. Splenocyte lysis was carried out on ice for 30 minutes with one ml of lysis buffer per 5×108 splenocytes. Insoluble material was removed by centrifugation.

CD11a, CD11b and CD11c were removed from the spleen lysate by immunoprecipitation as follows. A 750 μl volume of a Protein A-Sepharose slurry was incubated with 2 mg rabbit anti-mouse immunoglobulin at 4° C. for 30 minutes. The rabbit anti-mouse-Protein A-Sepharose was washed three times with lysis buffer and suspended in a final volume of 1.5 ml of lysis buffer. Approximately 200 μg each of rat $β_2$ integrin specific monoclonal antibodies, 515F (specific for rat CD11a), OX-42 (specific for rat CD11b) and 100 g (specific for rat CD11c) were each added to 50 ml of the rat spleen lysate. Following a 30 minute incubation at 4° C., 500 μl of the rabbit anti-mouse-Protein A-Sepharose was added to the spleen lysates and mixed with end-over-end rotation for 30 minutes at 4° C. The lysate was centrifuged at 2500×g for 10 minutes to pellet the CD11a, CD11b, and CD11c bound to the rabbit anti-mouse-Protein A-Sepharose, and the supernatant transferred to a clean 50 ml centrifuge tube. Immunoprecipitation with the antibodies 515F, OX-42, and 100 g was repeated two additional times to insure complete removal of CD11a, CD11b, and CD11c.

$β_2$ integrins remaining in the lysate were isolated using affinity purification. Approximately 250 μl of a slurry of anti-rat CD18 monoclonal antibody 20C5B conjugated to CNBr-Sepharose was added to the lysates and mixed with end-over-end rotation for 30 minutes at 4° C. Antibody/antigen complexes were pelleted by centrifugation at 2500×g for ten minutes and the pellet washed three times with lysis buffer before being stored at 4° C.

Immunization of Armenian Hamsters

1. Armenian hamsters, six to eight weeks old, were initially immunized with approximately 50 μg of a recombinant protein consisting of the I domain of rat $α_d$ fused to the human IgG4 heavy chain emulsified in complete Freund's adjuvant. Primary immunization was followed by subsequent immunizations with rat $α_d$ I domain/HuIgG4 emulsified in incomplete Freund's adjuvant on Days 14, 33, and 95. Two separate fusions, designated 197 and 199, were subsequently performed.

Four days prior to fusion 197 (day 306), one hamster was administered a combination of rat $α_d$ protein purified from splenocytes and CHO cells transfected with rat $α_d$. The fusion boost was given three days prior to the fusion (day 307) with purified rat $α_d$ protein and $α_d$ transfected CHO cells. Rat $α_d$ transfected CHO cells were prepared as described below.

A gene segment encoding full length rat $α_d$ protein was inserted into the pDC1 vector and transfected by electroporation into CHO cells together with a human CD18-pRC construct. Transfected cells were grown in the presence of hypoxanthine to select for cells successfully transfected with the pRC construct and in the presence of g418 to select for cells transfected with the pDC1 construct. After 3 weeks, the cells were stained with the rat $\alpha_d$ specific rabbit polyclonal sera and sorted by FACS. A small percentage of the cells which expressed the highest levels of surface $\alpha_d$ (approximately 3% of the total population) were collected and further expanded. FACS selection was repeated several times to provide a population cells with high levels of $\alpha_d$ surface expression.

The $\alpha_d$ transfected cells were also characterized by flow cytometry using a rat $\alpha_d$ specific polyclonal sera and a human CD18 specific monoclonal antibody, TS1.18.1. Results confirmed that the transfected CHO cells expressed high levels of both rat $\alpha_d$ and human CD18.

Finally, $\alpha_d$ and CD18 expression in the cells was evaluated by immunoprecipitation. A rat $\alpha_d$ specific rabbit polyclonal sera was found to immunoprecipitate proteins with two distinct molecular weights: the higher molecular weight protein(s) being approximately 170 kD, and the lower molecular weight protein(s) 95 kD. These findings were consistent with expression of a rat $\alpha_d$/human CD18 heterodimeric complex on the surface of the transfected CHO cells.

On the day of the fusion, the spleen was removed and a single-cell suspension was formed by grinding the tissue between frosted ends of two glass microscope slides submerged in serum free RPMI 1640 supplemented with 2 mM L-glutamine, 1 mM sodium pyruvate, 100 units/ml penicillin, and 100 µg/ml streptomycin (RPM1) (Gibco, Canada). The cell suspension was filtered through sterile 70-mesh Nitex cell strainer (Becton Dickinson, Parsippany, N.J.), and washed twice by centrifuging at 200×g for five minutes and resuspending the pellet in 20 ml serum free RPMI. Thymocytes taken from three naive Balb/c mice were prepared in a similar manner. NS-1 myeloma cells, kept in log phase in RPM1 with 10% Fetaclone serum (FBS) (Hyclone Laboratories, Inc. Logan, Utah) for three days prior to fusion, were centrifuged at 200 ×g for five minutes, and the pellet was washed twice as previously described.

Approximately 1.15×108 spleen cells were combined with 5.8×10⁷ NS-1 cells, centrifuged and the supernatant removed by aspiration. The cell pellet was dislodged by tapping the tube and seven ml of 37° C. PEG 1500 (50% in 75 mM Hepes, pH 8.0) (Boehringer Mannheim) was added with stirring over the course of one minute, followed by adding 14 ml of serum free RPM1 over seven minutes. An additional eight ml RPMI was added and the cells were centrifuged at 200×g for 10 minutes. The supernatant was removed and the pellet resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and 1.5×106 thymocytes/ml. The suspension was dispensed into ten 96-well flat bottom tissue culture plates (Corning, United Kingdom) at 200 µl/well and the cells were fed on days 4, 5, 6, and 7 days post fusion by aspirating approximately 100 µl from each well with an 18 G needle (Becton Dickinson) and adding 100 µl plating medium described above except lacking thymocytes.

On day 10, supernatants from the fusion wells were screened by flow cytometry for reactivity to rat $\alpha_d$/human CD18 transfected CHO cells. Approximately 5×105 rat $\alpha_d$ transfected CHO cells were suspended in 50 µl RPMI containing 2.0% FBS and 0.05% sodium azide and added to approximately 100 µl of hybridoma culture supernatant in 96-well, round-bottomed plates. Positive controls for staining included rabbit anti-$\alpha_d$ polyclonal sera and TS1/18 (anti-human CD18). Cells were incubated for 30 minutes on ice, washed three times in FACS buffer (RPM1, 2.0% FBS, 0.05% NaAzide), and incubated for 30 minutes on ice with a FITC-conjugated goat anti-hamster antibody (Jackson Immunol Research Labs) at a final dilution of 1:200 in FACS buffer. Cells were washed three times in FACS buffer and resuspended in 200 ml of FACS buffer. Samples were analyzed with a Becton Dickinson FACscan analyzer. To insure that positive clone wells were specific for rat $\alpha_d$, the screen was repeated with non-transfected CHO cells. Wells which met the criteria of reacting with rat $\alpha_d$ CHO transfectants and not the untransfected CHO cells were cloned.

Following primary screening, cells from positive wells were cloned initially by doubling dilution and subsequently by limiting dilution in RPM1, 15% FBS 100 mM sodium hypoxanthine, 16 mM thymidine, and 10 units/ml IL-6. In the limiting dilution step, the percentage of wells showing growth was determined and clonality was predicted using a Poisson distribution analysis. Wells showing growth were analyzed by FACS after 10–12 days. After final cloning, positive wells were expanded in RPMI and 11% FBS. Cloning yielded one culture deemed positive by these criteria, from which four separate subclones designated 197A-1, 197A-2, 197A-3, and 197A-4 were expanded.

Prior to fusion 199, a second hamster was boosted on day 307 with 2.3×106 rat $\alpha_d$ (RAD)-transfected CHO cells. Two final immunizations were administered four days prior to the fusion (day 334) and again three days prior to the fusion (day 335). The boost on day 334 consisted of 2×106 rat $\alpha_d$ S transfected CHO cells and 200 µl of purified rat $\alpha_d$ bound to Sepharose (described previously) administered by intraperitoneal injection. The day 335 boost consisted of 5×106 rat $\alpha_d$ transfected CHO cells, also administered by intraperitoneal injection. The fusion and screening protocols for fusion 199 were identical to fusion 197, and three hybridomas, designated 199A, 199H, and 199M, with supernatant reactive with rat $\alpha_d$ were identified and cloned.

2. A second immunization was carried out using the same protocols which led up to fusions 197 and 199. After the day 334 boost, there were no further immunizations until days 394 and 395. Prior to the fusion, the hamsters were administered 2×106 RAD-transfected CHO cells along with 300 µl of purified rat $\alpha_d$-Sepharose which was administered interpertoneally. The fusion and screening protocols for the subsequent fusion 205 were identical to those of fusions 199 and 197, except that during cloning, Armenian hamster ELISA reagents, e.g. goat anti-Armenian hamster antibodies (Jackson ImmunolResearch Labs), were used as an initial screen. Positive wells identified by this method were subsequently screened by FACS as described. Fusion 205 yielded three separate positive clones named 205A, 205C, 205E.

3. In another method to generate anti-rat $\alpha_d$ monoclonal antibodies, 6 to 12 week old BALB/c mice were immunized on day 1 with purified rat $\alpha_d$-Sepharose administered subcutaneously in complete Fruend's adjuvant. A second boost was administered by the same route on day 25 with the same immunogen in incomplete Fruend's adjuvant. A third boost identical to the second was performed on day 42. No further boosts were carried out until the pre-fusion boosts which consisted of 400 µl (for fusion 226) and 250 µl (for fusion 236) purified rat $\alpha_d$-Sepharose injected intraperitoneally. Each volume contained approximately 10 to 15 µg antigen as determined by Coomassie staining. The prefusion boosts for fusion 226 occurred on days 62 and 63 and the fusion was performed on day 66. For fusion 236, the prefusion boosts were performed on days 132 and 133 and the fusion was performed on day 136. Both fusion protocols differed from that used for the Armenian hamster fusions described above in that a 5:1 ratio of splenocytes to NS-1 cells was used as compared to a ratio of 2:1 in the Armenian hamster fusions. The fusion protocol was otherwise identical to the Armenian hamster protocol.

The screening and cloning protocols for fusions 226 and 236 were identical to those used in fusions 197, 199, and 205, except that an initial screen by ELISA was performed. In the ELISA, a goat anti-mouse whole molecule was employed to capture the mouse antibody from hybridoma supernatant and a goat anti-mouse horse radish peroxidase conjugate was used to detect mouse antibody. Positive supernatants were subsequently screened by FACS as described for fusions 197 through 205.

Fusion 226 yielded nine positive clones designated 226A, 226B, 226C, 226D, 226E, 226F, 226G, 226H, and 226I. Fusion 236 yielded ten positive clones designated 236A, 236B, 236C, 236F, 236G, 236H, 236I, 236K, 236L, and 236M. Monoclonal antibodies generated from these clones were isotyped by ELISA as described in Example 15. All antibodies were found to be of the IgG1 isotype.

Characterization of Monoclonal Antibodies to Rat $\alpha_d$

In order to characterize the anti-rat $\alpha_d$ antibodies, biotin labeled spleens lysates were prepared as described in Example 22, section D, above. Lysates were precleared prior to use in immunoprecipitations. Initially, 50 μg/ml of normal murine immunoglobulin was added to the lysate and the resulting solution mixed with end-over-end rotation for 30 minutes at 4° C. A 75 μl slurry of a protein A-Sepharose coated with rabbit anti-mouse immunoglobulin was added and mixing was continued with end-over-end rotation for 30 minutes. The rabbit anti-mouse coated protein A beads were pelleted by centrifugation at 15,000 rpm in a table-top microfuge for five minutes at 4° C. and the supernatant collected. The pelleted material was discarded.

For each cloned hybridoma, approximately 300 μl of supernatant was placed into a Eppendorf microfuge tube, to which was added 30 μl 10% Triton X-100, 30 μl of a 100×stock solution of pepstatin, leupeptin and aprotinin, 100 μg PMSF crystals, and 50 μl of precleared biotinylated rat spleen lysate. Samples were vortexed gently and placed onto an end-over-end rotator at 4° C. for 30 minutes. A control sample was prepared by adding 10 mg/ml of a rabbit anti-rat $\alpha_d$ specific polyclonal antibody to 50 μl of rat spleen lysate.

Following a 30 minute incubation, 75 μl of protein A-Sepharose beads in a PBS slurry was added to each sample and incubated with end-over-end rotation at 4° C. for 30 minutes. The protein A-coupled beads were pelleted by centrifugation at 15,000 rpm in a table-top microfuge for 5 minutes at 4° C. and the supernatant was collected. The pelleted beads were washed sequentially with a series of 1 ml detergent washes as follows: buffer #1 containing 10 mM Tris, 400 mM NaCl, 1.0% Triton X-100, pH 8.0; buffer #2 containing 10 mM Tris, 400 mM NaCl, 0.5% Triton X-100, pH 8.0; buffer #3 containing 10 mM Tris, 400 mM NaCl, 1.0% Triton X-100, 0.1% deoxycholate, pH 8.0; and buffer #4 containing 10 mM Tris, 400 mM NaCl, 0.5M LiCl$_2$, pH 8.0. A final washed was carried out with wash buffer #1. Beads were vortexed gently between each wash and pelleted using a tabletop microfuge. Supernatants were removed by transfer pipette, and after the final wash, all remaining buffer was removed from the beads by Hamilton syringe. A 50 μl aliquot of SDS sample buffer containing Bromphenol Blue and Pyronine Y dyes and β-mercaptoethanol at a final concentration of 10% was added to each pellet. The mixture was vortexed vigorously for 1–2 minutes and incubated at room temperature for 5–10 minutes. Samples were centrifuged for 5 minutes at 15,000 rpm in a table-top microfuge at 4° C. and released protein was collected and transferred to a new microfuge tube. Aliquots from each sample were boiled for four minutes in a water bath before loading onto 7.5% SDS-PAGE gels. Following separation by PAGE, proteins were transferred to nitrocellulose filters for one hour at 200 mAmps, and the filters were blocked in a solution of 3.0% BSA/TBS-T overnight at 4° C. A solution of 0.1% BSA-TBS-T containing a 1:6000 dilution of streptavidin-OPD was added to each filter and incubation allowed to continue for one hour at room temperature. The filters were washed five times for ten minutes each in TBS-T, and developed using Amersham's ECL kit according to the manufacturer's suggested protocol.

Clone 199M was found to immunoprecipitate a heterodimeric protein. The larger protein subunit had an approximate molecular weight of 170–175 kD which was consistent with the size of the protein immunoprecipitated by the rabbit anti-rat $\alpha_d$ polyclonal control. A second protein was also precipitated with an approximate molecular weight of 95 kD, consistent with the weight of CD18.

EXAMPLE 23

Specificity of Monoclonal Antibody 199M

A CNBr-Sepharose affinity column with conjugated 199M monoclonal antibody was used to affinity purify rat $\alpha_d$ from spleen cell lysates. Briefly, approximately 1.3×10$^{10}$ rat spleen cells were lysed in buffer consisting of 150 mM NaCl, 10 mM PMSF, 10 mM Tris, 1% Triton X-100, pH 8.0. Cells in the buffer were incubated for 30 minutes on ice and centrifuged at approximately 10,000×g for 30 minutes at 4° C.

Antibody 199M was conjugated to CNBr-activated Sepharose 4B (Pharmacia) by the following method. One gram of the activated resin was suspended in 1 mM HCl for 15 minutes and washed three times with 15 ml of 1 mM HCl and once with 15 ml coupling buffer containing 0.1 mM HCO$_3$, 0.5 M NaCl, pH 8.0. Antibody 199M in coupling buffer was added to resin suspension at a final concentration of approximately 10–20 mg/ml and the mixture incubated overnight at 4° C. The following day the conjugated resin was pelleted by centrifugation and the supernatant removed. Unreacted groups on the resin were blocked by incubation in 0.1M Tris, pH 8.0 for one hour at room temperature. The conjugated resin was washed with 0.1M citric acid, pH 3.0, and stored in lysis buffer as a 1:2 slurry containing 0.1% sodium azide.

For affinity purification, spleen cells were incubated with end-over-end mixing overnight with 0.4 ml of the 199M-conjugated Sepharose resin. The resin was then pelleted by centrifugation and washed four times with 15 ml lysis buffer. Aliquots of approximately 100 μl of each gel were boiled briefly in reducing sample buffer containing 0.1M Tris-HCl, pH 6.8, 2.0% SDS, 20% glycerol, 0.0002% bromophenol blue, 10% β-mercaptoethanol (final concentration 5%) and loaded onto and proteins resolved using a 6.0% polyacrylamide SDS gel (SDS-PAGE).

The affinity purified material was found to contain two major and one minor protein species when separated on SDS-PAGE. A prominent protein band with a molecular weight of 90 kD was consistent with the known size of CD18 and this band was not sequenced. A second prominent band of 160 kD was detected which was consistent with the predicted molecular weight for $\alpha_d$. In addition, a minor band with an apparent molecular weight of 200 kD was also detected. Both the 160 kD and 200 kD species were further analyzed by amino terminal protein sequencing with the results compared to the amino acid sequence predicted by the rat $\alpha_d$ cDNA, as well as to the known amino acid sequences for CD11c and CD11b. The sequence of both the 160 and 200 kD bands were found to be consistent with the amino acid sequence predicted by cloned rat $\alpha_d$, suggesting that there may be two forms of $\alpha_d$, perhaps resulting from splice variants or glycosylation differences.

EXAMPLE 24

T Cell Proliferation Assay Using Rat $\alpha_d$-Expressing Macrophages

Macrophages expressing $\alpha_d$ isolated from rat spleens were used as antigen presenting cells (APC) to stimulate a myelin basic protein specific T cell line designated LR-21. Briefly, rats were injected intravenously with a 100 μl volume of iron particles (BioMag, Cambridge, Mass.). The following day a single cell suspension was prepared from the spleens and $\alpha_d^+$ macrophages which had phagocytosed iron particles were collected using a magnet. Flow cytomotery and immunoprecipitation indicated that 50 to 80% of the cells which phagocytose iron are $\alpha_d^+$.

The results indicated that spleen macrophages expressing $\alpha_d$ were very poor APC's compared to other APC such as thymic macrophages. The monoclonal antibody designated 205C was also tested in the proliferation assay with the $\alpha_d$ positive macrophages and the LR-21 cell line. Proliferation assays were then carried out as follows.

Spleen macrophages positive for $\alpha_d$ expression were suspended at a density of $6 \times 10^6$ cells/ml in RPMI containing 5% normal rat serum and 100 μl of the macrophage suspension was added to each well. Cells from the LR-21 line were suspended at 1×106 cell/ml in RPMI with 5% normal rat serum and 50 μl of the suspension was added to each well. Monoclonal antibody 205C was added to each well in a volume of 50 μl to a final concentration of 50, 10 and 2 μg/ml. Plates were incubated at 37° C. for 72 hours and 1 μCi $^3$H-thymidine was added for the final 24 hours of incubation. Cells were harvested onto glass fiber mats and $^3$H incorporation determined using a Direct Beta Counter (Packard Matrix 96).

Results from the experiments indicate that high concentrations of antibody 205C (10 and 50 μg/ml) are able to reduce T cell proliferation in a dose dependent manner.

EXAMPLE 25

Immunoprecipitation of $\alpha_d$ from Rat Bone Marrow

Bone marrow cells were harvested from a Lewis rat by flushing the femur bone with PBS. The cells were washed, biotinylated, and immunoprecipitated, essentially as described in Example 18, using 20 μg purified monoclonal antibodies to immunoprecipitate protein from 100 μl of precleared cell lysates. Detection of immunoprecipitated protein was carried out in the manner as previously described.

The rat $\alpha_d$ monoclonal antibody 205C immunoprecipitated two bands which migrated at 160 kD and 95 kD. Bands of this size were consistent with the size for the α and β chains in $\alpha_d$/CD18 as observed in immunoprecipitation of proteins from spleen cell lysates using the same antibody. Antibodies against rat CD11a, CD11b, or CD11c immuno- precipitated alpha chains distinct from $\alpha_d$ and all antibodies co-immunoprecipitated a protein having a molecular weight consistent with that known for CD18.

EXAMPLE 26

Expression of $\alpha_d$ in Animal Models

Preliminary results indicated that rat $\alpha_d$ is selectively expressed by subpopulations of macrophages, including cortical macrophages in the thymus, Kupffer cells in the liver, perivascular cells in the central nervous system, a subset of peritoneal macrophages, and resident bone marrow macrophages. In addition, a subset of thioglycolate macrophages showed upregulation of $\alpha_d$ expression following stimulation with dexamethasone. The observed macrophage-restricted expression of rat $\alpha_d$ suggested further analysis of expression in various animal models.

Expression of Rat $\alpha_d$ in Phenylhydrazine Model

The administration of phenylhydrazine to animals results in massive red blood cell (rbc) damage which leads to a transient anemia. Damaged rbcs are cleared from circulation by red pulp macrophages, resulting in significant splenomegaly. It is proposed that macrophages which express $\alpha_d$ may be involved in the clearance of damaged rbcs and other foreign material from circulation.

To test this hypothesis, groups of rats were treated with saline alone or phenylhydrazine dissolved in saline and administrated by intraperitoneal injection at a dosage of 100 mg/kg body weight. In some experiments rats were treated with a polyclonal antiserum generated to the "I domain" of rat $\alpha_d$.

At various time points following phenylhydrazine administration, animals were sacrificed. Spleen weight and hematocrit were used as parameters of rbcs clearance. In addition, kidney, spleen and liver were collected for histopathologic evaluation, which included immunostaining for CD11a, CD11b, CD11c and $\alpha_d$.

Gross findings indicated that four days following treatment with phenylhydrazine (saline controls and $\alpha_d$ treatment) rats developed a dramatic splenomegaly, while hematocrit levels dropped. Treatment with the $\alpha_d$ polyclonal serum had no effect on spleen weight or the drop in hematocrit induced with phenylhydrazine.

Tissue from saline and day 4 phenylhydrazine treated rats were sectioned at 4 μm thickness and air dried on Superfrost Plus (VWR Scientific) slides at room temperature for 15 minutes. Prior to use, slides were incubated at 50° C. for approximately 5 minutes. Sections were fixed in cold (4° C.) acetone (EM Science) for 2 minutes at room temperature and allowed to dry at room temperature. Sections were placed in 100 ml 1×TBS, 1.1 ml 30% $H_2O_2$ (Sigma), 1 ml 10% $NaN_3$ (Sigma) for 15 minutes at room temperature to remove endogenous peroxidase activity. Each section was blocked using 150 μl of a solution containing 30% normal rat serum (Harlan Bioproducts), 2% BSA (Sigma) in 1×TBS for 30 minutes at room temperature, after which the solution was gently blotted from the sections. Each section received 75 μl of biotinylated hamster anti-rat $\alpha_d$ antibody 205C at a protein concentration of 13.3 μg/ml diluted in blocking solution, for 1 hour at room temperature. After incubation, the sections were washed three times in 1×TBS for 5 minutes each to remove any unbound antibody. Excess TBS was removed by aspirating around the tissue following the final wash. Peroxidase-conjugated goat anti-biotin antibody (Vector Laboratories) was diluted 1:200 in blocking solution and 75 μl was applied to each section for 30 minutes at room temperature. After incubation, slides were washed two times in 1×TBS for 5 minutes each wash. AEC substrate (Vector Laboratories) was applied and color development stopped by immersion in water. Slides were counterstained in Gill's hematoxylin #2 (Sigma) and rinsed in water, after which they were successively dehydrated in 70%, 95%, 100% EtOH, and Xylene. Sections were then mounted with cytoseal (VWR).

In the saline-treated rat spleen sections, the majority of $\alpha_d$ expression was localized in the splenic red pulp on cells identified morphologically as macrophages, granulocytes, and a subpopulation of lymphocytes. In the phenylhydrazine-treated rat spleens, however, the splenic red pulp had undergone morphological changes such that the only cell type identified was a population of large macrophages which had engulfed damaged red blood cells. The majority of these large macrophages were observed to expressed $\alpha_d$. Also in the phenylhydrazine-treated rat, there appeared to be an increase in the number of macrophages in the splenic white pulp that expressed $\alpha_d$.

A double label experiment to determine expression of $\alpha_d$ and CD11c was also performed on a phenylhydrazine-treated rat spleen. As previously described, $\alpha_d$ expression was detected on large macrophages in the splenic red pulp that appeared to have engulfed damaged red blood cells. CD11c expression was also detected on large macrophages in the splenic red pulp and there appeared to be more CD11c positive cells in the red pulp than $\alpha_d$ positive cells. The majority of macrophages expressing $\alpha_d$ also expressed CD11c even though a small subset of $\alpha_d$ positive macrophages were observed that did not express CD11c. There was also a population of CD11c positive macrophages that did not express $\alpha_d$.

Immunohistology analysis therefore indicates that there appears to be an upregulation of CD11c expression in the spleen of phenylhydrazine treated animals compared to the saline controls on day 4. Expression of the other integrins, CD11a, CD11b and $\alpha_d$, however, appears to be unaffected by the phenylhydrazine treatment. Treatment with polyclonal "I" domain $\alpha_d$ antibody also showed no effect on the uptake of rbcs by the red pulp macrophages, but the majority of macrophages that are engulfing rbcs are $\alpha_d$ positive. The $\alpha_d$ positive macrophages which had engulfed damaged rbcs were not present in spleens collected 7 days after phenylhydrazine administration.

A double label experiment was then performed on the day 4 phenylhydrazine-treated rat spleens using an apoptosis assay and ICC with biotin-conjugated antibody 205C. Tissue from normal rat and day four phenylhydrazine-treated rats were sectioned at 4 microns thickness and air dried on Superfrost Plus slides (VWR Scientific) at room temperature for 15 minutes and stored at −20° C. Prior to use, slides were warmed to 50° C. Warmed slides were placed in buffer containing 100 ml 1×TBS, 1.1 ml 30% $H_2O_2$ (Sigma), 1 ml 10% $NaN_3$ (Sigma) for 15 minutes at room temperature to remove endogenous peroxidase activity. Each section was blocked using 150 µl of a solution containing 20% normal rat serum (Harlan Bioproducts), 2% BSA (Sigma) in 1×TBS for 10 minutes at 37° C., after which the solution was gently blotted from the sections. Each section was incubated for 30 minutes at 37 ° C. with 75 µl biotinylated hamster anti-rat $\alpha_d$ antibody 205C at a protein concentration of 26.6 µg/ml diluted in blocking solution. Sections were then washed three times for five minutes each in 1×TBS to remove unbound antibody. Excess TBS was removed by aspirating around the tissue following the final wash. Alkaline phosphatase-conjugated avidin/biotin complex (Vector Laboratories) prepared according to the manufacturer's instructions was applied to each section for 20 minutes at 37° C. After incubation, slides were washed two times for five minutes each in 1×TBS. Sections were fixed for five minutes with 4% paraformaldehyde (Sigma) at 4° C. Sections were then rinsed in 1×PBS and placed in CSK buffer (100 mM NaCl, 300 mM sucrose, 10 mM pipes pH 6.8, 3 mM $MgCl_2$, 0.5% Triton-X-100) for two minutes at 4° C. Sections were rinsed in 1×PBS for two minutes at room temperature after which the sections were washed three times for five minutes each with 1×PBS. TUNEL reaction mixture (Boehringer Mannheim) was applied to each section for 60 minutes at 37° C. After incubation, the sections were washed three times in 1×PBS for 5 minutes each wash. The apoptosis kit methodology is similar to in situ hybridization; the TUNEL reagent (which is FITC conjugated) hybridizes to "nicked" DNA. Converter-POD (a peroxidase conjugated antibody which recognizes the FITC tag on the TUNEL reagent) was applied to each section for 30 minutes at 37 ° C. and the sections were washed three times for five minutes each with 1×PBS. AEC (Vector Laboratories) was applied and color development stopped by immersion in water. Sections were mounted with Aquamount (VWR).

In the model, numerous cells in both the red and white pulp regions of the spleen were undergoing apoptosis, but large macrophages in the red pulp (which expressed $\alpha_d$ and disappeared on day 7 of the model) that had engulfed RBCs were not found to be undergoing apoptosis.

Cell Type Analysis of Rat $\alpha_d$ Expression on Normal Rat Spleen

In order to determine which rat cell types express $\alpha_d$, a double label staining was performed on normal rat spleen. Sections of normal rat spleen were prepared as described above through the rat serum blocking step. After the addition of primary cell marker antibodies, alkaline phosphatase-conjugated goat anti-mouse antibody (Jackson Laboratories) was diluted 1:500, in the same diluent used for the primary antibodies, and 75 µl was applied to each section for 30 minutes at room temperature. Slides were washed two times in 1×TBS for five minutes each wash. Alkaline phosphatase conjugated donkey anti-goat antibody (Jackson Laboratories) was diluted 1:300, in antibody diluent, and 75 µl was applied to each section for 30 minutes at room temperature. After washing and blocking as above, each section received 75 µl of biotinylated hamster anti-rat $\alpha_d$ antibody (205C), at a protein concentration of 20 µg/ml, for 1 hour 45 minutes each and then washed to remove unbound antibody. Excess TBS was removed by aspirating around the tissue following the final wash. Peroxidase conjugated goat anti-biotin (Vector Laboratories) was diluted 1:200, in antibody diluent, and 75 µl was applied to each section for 45 minutes at room temperature. Slides were washed two times 1×TBS for five minutes each wash. AEC substrate (Vector Laboratories) was applied and color development was stopped by immersion in water. Fast Blue substrate (Vector Laboratories) was then applied and color development was stopped by immersion in water. Slides were then mounted with Aquamount (Baxter).

Dual antibody immunocytochemistry was performed using antibodies to CD5, CD2, CD4, CD8, NK marker, or HIS 45 (a T cell marker) in conjunction with anti-$\alpha_d$ antibody in an attempt to determine the phenotype of cells expressing $\alpha_d$. No double labeled cells were detected with CD2/$\alpha_d$ or HIS 45/$\alpha_d$. In the splenic red pulp of a normal rat $\alpha_d$ labeled clusters of small cells which were found to also express CD5. It was not determined if the CD5 positive cells were T cells or B cells. A small population of $\alpha_d$ expressing cells in the red pulp were also determined to express CD4.

In addition, a subset of NK cells and CD8 positive cells were also identified that expressed $\alpha_d$. Therefore, $\alpha_d$ expression in the spleen was found on a subset of T cells, possibly a subset of B cells, a subset of NK cells, and subset of macrophages.

Expression of $\alpha_d$ on Large Granulocytic Leukocytes (LGL) Tumor Cells from the F344 Rat Model A rat model for LGL-leukemia was designed in the F344 rat using tumor cells received from the National Cancer Institute which were injected intravenously into 3 male F344 rats (1 million cells each). The disease took three months to manifest, at which time several of the animals were sacrificed and tissues examined by FACS and histochemical analysis.

For FACS analysis, a portion of the spleen was removed and a single-cell suspension prepared as described in example below. Briefly, the splenic tissue was minced into smaller pieces with scissors and passed through a wire mesh screen in the presence of D-PBS. The cells were pelleted by centrifugation and resuspended in 30 ml D-PBS. Histopaque gradients (Sigma) were prepared by layering 5.0 ml of the cell suspension over 5.0 ml of Histopaque within a 15 ml centrifuge tube. The gradients were centrifuged for 30 minutes at 1500 rpm using a Beckman Tabletop Centrifuge and the cellular layer collected, washed once in D-PBS, and counted by hemacytometer. The cells were resuspended in FACS buffer (RPMI-1640/2% FBS, 0.2% sodium azide) to a density of 1×106 cells/sample.

The cells were two-color stained by incubation with the hamster anti-rat $\alpha_d$ antibody 205C conjugated to biotin (10 $\mu$g/ml) and one of a series of antibodies against rat cellular markers that were FITC conjugated. These second antibodies included anti-macrophage-FITC, anti-CD3-FITC, and anti-IgM (B-cell)-FITC antibodies (all from PharMingen), in addition to a FITC-conjugated antibody with NK cell specificity (Harlan). The FITC conjugated antibodies were each used at 10 $\mu$l/sample.

The samples were first incubated on ice for 30 minutes with 205C-biotin antibody, washed three times in FACS buffer, and resuspended in 1.0 ml FACS buffer. The FITC conjugates were added along with 5 $\mu$l streptavidin-PE (Pharmigen) and the samples placed on ice for 30 minutes. After incubation, the samples were washed three times in FACS buffer and resuspended in 200 $\mu$l FACS buffer. Samples were examined using a Becton Dickinson FACscan and the data analyzed using Lysis II software (Becton Dickinson).

The results overwhelmingly demonstrated expression of $\alpha_d$ on the surface of NK, or LGL, cells. Cells which stained positive for B-cell and T-cell markers did not reveal $\alpha_d$ expression and cells which stained using the macrophage marker showed only a slight degree of $\alpha_d$ expression. It is believed that, at this point in the disease, the spleen is composed predominantly of NK tumor cells, consistent with the observation that a large population of spleen cells stained for expression of both the NK marker and $\alpha_d$.

These observations were also consistent with results from a parallel experiment using peripheral blood cells also collected from the same animals and processed as above for FACS. Results using peripheral blood cells indicated that circulating NK cells also express $\alpha_d$, while cells expressing other cellular markers in the blood did not show $\alpha_d$ expression. Results using peripheral blood cells, however, were not as dramatic as the splenic cell results presumably due to a difference in the percentage of different cell types present in the spleen and peripheral blood.

In subsequent FACS analysis of rat spleen cells from these model animals, identical results were obtained. Upon further analysis using the above method of cell preparation, the LGL tumor cells have also shown staining for expression of CD18 as well as CD11a, CD11b, and CD11c.

Histochemical analysis was carried out on both normal and NK F344 diseased tissue using the ICC procedure described above. Preliminary data indicated that $\alpha_d$ was expressed in NK F344 tumor lung and liver tissue, but was either not detected or was expressed in very low levels in normal respective tissue. Diseased lung tissue showed expression of $\alpha_d$ on small and large clusters of cells, as well as individual cells throughout the lung. The NK F344 liver showed weak labeling around vessels and other cells throughout the tissue. Antibodies to the other $\beta_2$ integrins indicated these molecules are expressed at similar levels in both normal and diseased tissue although labeling patterns did vary.

In parallel analyses, the normal rat thymus showed slight $\alpha_d$ expression in scattered cells in the cortex, while the F344 NK thymus showed an increased level of $\alpha_d$ expression. While the normal spleen showed expression in the red pulp, the NK spleen had cluster labeling throughout the tissue.

The NK spleen was then tested at weekly intervals from onset of the disease which indicated t hat the level of expression of $\alpha_d$ increased up until the third week and then dropped off at the fourth week.

EXAMPLE 27

Assay for Inhibition of NK-Tumor Cell-Induced Target Cell Lysis Using Anti-$\alpha_d$ Monoclonal Antibodies A specific function of NK cells is to target and kill virally-infected and foreign cells. To assay the ability of NK cells to lyse a specific target cell, target cells are labeled with $^{51}$chromium and as lysis occurs, increasing radioactivity is detected in the medium. It was postulated that $\alpha_d$, previously shown to be expressed on NK cells , might participate in NK targeted cell killing. To test this hypothesis, tumor cells were pre-incubated with $\alpha_d$ antibodies in order to assess the role of $\alpha_d$ in a functional assay.

Preparation of $\alpha_d$ Positive NK-tumor Effector Cells

F344 rats were injected with NK tumor cells, originally obtained from the National Cancer Institute and passaged through animals three to four weeks prior to removal of the spleen. The spleen was removed and was minced into small pieces which were passed through a wire-mesh screen in the presence of D-PBS. The resultant cell suspension was centrifuged at 1500 rpm in a Beckman tabletop centrifuge for 10 minutes at room temperature. The supernatant was aspirated and the cell pellet resuspended in 30 ml D-PBS.

Histopaque separation of mononuclear cells from blood was then carried out as follows. Five ml Histopaque (Sigma) was added to six 15 ml centrifuge tubes on top of which was layered 5.0 ml of the cell suspension described above. The cells were centrifuged at 1500 rpm for 30 minutes in a Beckman Tabletop centrifuge at room temperature. The cellular layer was collected, pooled and counted by hemacytometer. Several dilutions of the isolated tumor cells were prepared in D-PBS buffer and subsequently incubated in the presence or absence of anti-rat $\alpha_d$ antibodies at a concentration of 50 $\mu$g/ml. Control antibodies included an anti-rat CD18 antibody and an anti-rat ICAM-1 antibody which were also incubated with the cells at 50 $\mu$g/ml concentration. Tumor cells were pre-incubated with antibodies at 37° C. for approximately 30 minutes prior to the assay.

Chromium Labeling of Yak-i Target Cells

Yak-1 cells (ATCC), a mouse lymphoma cell line, were cultured in 10% FBS/RPMI 1640. Cells were harvested by centrifugation and resuspended at a density of approximately 1 ×10⁷ cells in 1.5 to 4.0 ml of RPMI "test media" made from 500 ml RPMI 1640, 5 ml Pen-Strep antibiotic solution, and 10 ml FBS. Approximately 200 to 300 µCi of $^{51}$chromium was added to the Yak-1 cell suspension which were then incubated at 37° C. for 45 to 60 minutes with gentle mixing. Following incubation, the volume was increased to 50 ml with test media and the cells pelleted by centrifugation. The supernatant was discarded and cells were suspended in 1 to 3 ml test media and adjusted to a density of 5×10⁴ cells/ml. Non-labeled Yak-1 cells were also prepared at a concentration of 1×10⁷ cell/ml to use as autologous controls.

The activity of labeled cells was determined by assaying 100 µl of the labeled cell suspension in triplicate using a gamma counter.

Short-Term Chromium Release Assay

NK effector cells of each dilution were plated in triplicate in a volume of 100 µl test media in a 96-well microtiter plate and 100 µl labeled Yak-1 cells were added to each well. Autologous, i.e., spontaneous or background, release was obtained by incubating 100 µl of labeled cells with non-labeled Yak cells at each of the effector dilutions. Total $^{51}$chromium release was obtained by adding 1.0% Triton to target cells in one set of wells. Spontaneous release was measured by the amount of $^{51}$chromium found in wells with only target cells. Incubation of effector/target cells was carried out for four hours at 37° C. after which the plates were centrifuged and 100 µl supernatant collected from each well and radioactivity measured.

Cytolytic activity was calculated by using the following formula:

$$\% \text{ cytolytic activity} = \frac{cmp \text{ of sample} - \text{spontaneous release } cpm}{100\% \text{ release } cmp - \text{spontaneous release } cmp} \times 100$$

Results indicated that neither hamster anti-rat $\alpha_d$ antibodies (including 199M and 205C) nor mouse anti-rat $\alpha_d$ antibodies (226A, 226B, 226C, 226D, 226F, 226G, 226H, and 226I) effected the ability of NK tumor cells to kill or lyse the labeled target cells.

EXAMPLE 28

Isolation of Mouse cDNA Clones

Isolation of a Mouse $\alpha_d$ Homolog was Attempted

Cross-species hybridization was performed using two PCR-generated probes: a 1.5 kb fragment corresponding to bases 522 to 2047 from human clone 19A2 (SEQ ID NO: 1), and a 1.0 kb rat fragment which corresponds to bases 1900 to 2900 in human clone 19A2 (SEQ ID NO: 1). The human probe was generated by PCR using primer pairs designated ATM-2 and 9–10.1 set out in SEQ ID NOS: 38 and 39, respectively; the rat probe was generated using primer pairs 434L and 434R, set out in SEQ ID NOS: 34 and 35, respectively. Samples were incubated at 94° C. for 4 minutes and subjected to 30 cycles of the temperature step sequence: 94° C.; 50° C. 2 minutes; 72° C., 4 minutes.

5'-GTCCAAGCTGTCATGGGCCAG-3' (SEQ ID NO: 38)

5'-GTCCAGCAGACTGAAGAGCACGG-3 (SEQ ID NO: 39)

The PCR products were purified using the Qiagen Quick Spin kit according to manufacturer's suggested protocol, and approximately 180 in DNA was labeled with 200 µCi [$^{32}$P]-dCTP using a Boehringer Mannheim Random Primer Labeling kit according to manufacturer's suggested protocol. Unincorporated isotope was removed using a Centri-sep Spin Column (Princeton Separations, Adelphia, N.J.) according to manufacturer's suggested protocol. The probes were denatured with 0.2N NaOH and neutralized with 0.4M Tris-HCl, pH 8.0, before use.

A mouse thymic oligo dT-primed cDNA library in lambda ZAP II (Stratagene) was plated at approximately 30,000 plaques per 15 cm plate. Plaque lifts on nitrocellulose filters (Schleicher & Schuell, Keene, N.H.) were incubated at 50° C. with agitation for 1 hour in a prehybridization solution (8 ml/lift) containing 30% formamide. Labeled human and rat probes were added to the prehybridization solution and incubation continued overnight at 50° C. Filters were washed twice in 2×SSC/0.1% at room temperature, once in 2×SSC/0.1% SDS at 37° C., and once in 2×SSC/0.1% SDS at 42° C. Filters were exposed on Kodak X-Omat AR film at −80° C. for 27 hours with an intensifying screen.

Four plaques giving positive signals on duplicate lifts were restreaked on LB medium with magnesium (LBM)/carbenicillin (100 mg/ml) plates and incubated overnight at 37° C. The phage plaques were lifted with Hybond filters (Amersham), probed as in the initial screen, and exposed on Kodak X-Omat AR film for 24 hours at −80° C. with an intensifying screen.

Twelve plaques giving positive signals were transferred into low Mg⁺⁺ phage diluent containing 10 mM Tris-HCl and 1 mM MgCl₂. Insert size was determined by PCR amplification using T3 and T7 primers (SEQ ID NOS: 13 and 14, respectively) and the following reaction conditions. Samples were incubated at 94° C. for 4 minutes and subjected to 30 cycles of the temperature step sequence: 94° C., for 15 seconds; 50° C., for 30 seconds; and 72° C. for 1 minute.

Six samples produced distinct bands that ranged in size from 300 bases to 1 kb. Phagemids were released via co-infection with helper phage and recircularized to generate Bluescript SK (Stratagene). The resulting colonies were cultured in LBM/carbenicillin (100 mg/ml) overnight. DNA was isolated with a Promega Wizard miniprep kit (Madison, Wis.) according to manufacturer's suggested protocol. EcoRI restriction analysis of purified DNA confirmed the molecular weights which were detected using PCR. Insert DNA was sequenced with M13 and M13 reverse.1 primers set out in SEQ ID NOS: 40 and 41, respectively.

5'-TGTAAAACGACGGCCAGT-3' (SEQ ID NO: 40)

5'-GGAAACAGCTATGACCATG-3' (SEQ ID NO: 41)

Sequencing was performed as described in Example 4.

Of the six clones, only two, designated 10.3–1 and 10.5–2, provided sequence information and were identical 600 bp fragments. The 600 bp sequence was 68% identical to a corresponding region of human $\alpha_d$, 40% identical to human CD11a, 58% identical to human CD11c, and 54% identical to mouse CD11b. This 600 bp fragment was then utilized to isolate a more complete cDNA encoding a putative mouse $\alpha_d$ homolog.

A mouse splenic cDNA library (oligo dT⁻ and random-primed) in lambda Zap II (Stratagene) was plated at 2.5×10⁴ phage/15 cm LBM plate. Plaques were lifted on Hybond nylon transfer membranes (Amersham), denatured with 0.5M NaOH/1.5M NaCl, neutralized with 0.5M Tris Base/1.5M NaCl/11.6 HCl, and washed in 2×SSC. The DNA was cross-linked to filters by ultraviolet irradiation.

Approximately 500,000 plaques were screened using probes 10.3–1 and 10.5–2 previously labeled as described supra. Probes were added to a prehybridization solution and incubated overnight at 50° C. The filters were washed twice in 2×SSC/0.1% SDS at room temperature, once in 2×SSC/ 0.1% SDS at 37° C., and once in 2×SSC/0.1% SDS at 42° C. Filters were exposed on Kodak X-Omat AR film for 24 hours at −80° C. with an intensifying screen. Fourteen plaques giving positive signals on duplicate lifts were subjected to a secondary screen identical to that for the initial screen except for additional final high stringency washes in 2×SSC/0.1% SDS at 50° C., in 0.5×SSC/0.1% SDS at 50° C., and at 55° C. in 0.2×SSC/0.1% SDS. The filters were exposed on Kodak X-Omat AR film at −80° C. for 13 hours with an intensifying screen.

Eighteen positive plaques were transferred into low $Mg^{++}$ phage diluent and insert size determined by PCR amplification as described above. Seven of the samples gave single bands that ranged in size from 600 bp to 4 kb. EcoRI restriction analysis of purified DNA confirmed the sizes observed from PCR and the DNA was sequenced with primers M13 and M13 reverse.1 (SEQ ID NOS: 40 and 41, respectively).

One clone designated B3800 contained a 4 kb insert which corresponded to a region 200 bases downstream of the 5' end of the human $\alpha_d$ 19A2 clone and includes 553 bases of a 3' untranslated region. Clone B3800 showed 77% identity to a corresponding region of human $\alpha_d$, 44% identity to a corresponding region of human CD11a, 59% identity to a corresponding region of human CD11c, and 51% identity to a corresponding region of mouse CD11b. The second clone A 1160 was a 1.2 kb insert which aligned to the 5' end of the coding region of human $\alpha_d$ approximately 12 nucleic acids downstream of the initiating methionine. Clone A1160 showed 75% identity to a corresponding region of human $\alpha_d$, 46% identity to a corresponding region of human CD11a, 62% identity to a corresponding region of human CD11c, and 66% identity to a corresponding region of mouse CD11b.

Clone A 1160, the fragment closer to the 5' end of human clone 19A2, is 1160 bases in length, and shares a region of overlap with clone B3800 starting at base 205 and continuing to base 1134. Clone A 1160 has a 110-base insertion (bases 704–814 of clone A 1160) not present in the overlapping region of clone B3800. This insertion occurs at a probable exon-intron boundary [Fleming, et al., *J. Immunol.* 150:480–490 (1993)] and was removed before subsequent ligation of clones A 1160 and B3800.

Rapid Amplification of 5' cDNA end of the Putative Mouse $\alpha_d$ Clone

RACE PCR [Frohman, "RACE: Rapid Amplification of cDNA Ends," in PCR Protocols: A Guide to Methods and Applications, Innis, et al. (eds.) pp. 28–38, Academic Press: New York (1990)] was used to obtain missing 5' sequences of the putative mouse $\alpha_d$ clone, including 5' untranslated sequence and initiating methionine. A mouse splenic RACE-Ready kit (Clontech, Palo Alto, Calif.) was used according to the manufacturer's suggested protocol. Two antisense, gene-specific primers, A1160 RACE1-primary and A1160 RACE2-nested (SEQ ID NOS: 42 and 43), were designed to perform primary and nested PCR.

5'-GGACATGTTCACTGCCTCTAGG-3' (SEQ ID NO: 42)

5'-GGCGGACAGTCAGACGACTGTCCTG-3' (SEQ ID NO: 43)

The primers, SEQ ID NOS: 42 and 43, correspond to regions starting 302 and 247 bases from the 5' end, respectively. PCR was performed as described, supra, using the 5' anchor primer (SEQ ID NO: 44) and mouse spleen cDNA supplied with the kit.

5'-CTGGTTCGGCCCACCTCTGAAGGTTCCAGAA-TCGATAG-3' (SEQ ID NO: 44)

Electrophoresis of the PCR product revealed a band approximately 280 bases in size, which was subcloned using a TA cloning kit (Invitrogen) according to manufacturer's suggested protocol. Ten resulting colonies were cultured, and the DNA isolated and sequenced. An additional 60 bases of 5' sequence were identified by this method, which correspond to bases 1 to 60 in SEQ ID NO: 45.

Characteristics of the Mouse cDNA and Predicted Amino Acid Sequence

A composite sequence of the mouse cDNA encoding a putative homolog of human $\alpha_d$ is set out in SEQ ID NO: 45. Although homology between the external domains of the human and mouse clones is high, homology between the cytoplasmic domains is only 30%. The observed variation may indicate C-terminal functional differences between the human and mouse proteins. Alternatively, the variation in the cytoplasmic domains may result from splice variation, or may indicate the existence of an additional $\beta_2$ integrin gene(s).

At the amino acid level, the mouse cDNA predicts a protein (SEQ ID NO: 46) with 28% identity to mouse CD11a, 53% identity to mouse CD11b, 28% identity to human CD11a, 55% identity to human CD11b, 59% identity to human CD11c, and 70% identity to human $\alpha_d$. Comparison of the amino acid sequences of the cytoplasmic domains of human $\alpha_d$ and the putative mouse homolog indicates regions of the same length, but having divergent primary structure. Similar sequence length in these regions suggests species variation rather than splice variant forms. When compared to the predicted rat polypeptide, Example 20, supra, mouse and rat cytoplasmic domains show greater than 60% identity.

EXAMPLE 29

Isolation of Additional Mouse $\alpha_d$ cDNA Clones for Sequence Verification

In order to verify the nucleic and amino acids sequences describe in Example 28 for mouse $\alpha_d$, additional mouse sequences were isolated for the purposes of confirmation.

Isolation of mouse cDNA by hybridization with two homologous $\alpha_d$ probes (3' and 5') was performed using both a mouse splenic random primed library and an oligo dT-primed cDNA library in lambda ZAP II (Strategene). The library was plated at 5×105 phage per 15 cm LBM plate. Plaques were lifted on Hybond nylon membranes (Amersham), and the membranes were denatured (0.5M NaOH/1.5M NaCl), neutralized (0.5M Tris Base/1.5M NaCl /11.6M HCl) and washed (2×SSC salt solution). DNA was cross-lined to filters by ultraviolet irradiation.

Probes were generated using primers described below in a PCR reaction under the following conditions. Samples were held at 94° C. for 4 minutes and then run through 30 cycles of the temperature step sequence (94° C. for 15 seconds; 50° C. for 30 seconds; 72° C. for 1 minute in a Perkin-Elmer 9600 thermocycler).

The 3' probe was approximately 900 bases long and spanned a region from nucleotides 2752 to 3651 (in SEQ ID NO: 1) (5'→3') and was produced with primers 11.b-1/ 2FOR11and 11.b-1/2REV2 as shown in SEQ ID NOS: 69 and 74, respectively. This probe was used in a first set of lifts.

The 5' probe was approximately 800 bases long and spanned a region from nucleotides 149 to 946 (in SEQ ID NO: 1) (5'→3') and was produced with primers 11.b-1/ 2FOR1 and 11.a-1/1REV1 as shown in SEQ ID NOS: 50 and 85, respectively). This probe was used in a second set of lifts.

In a third set of lifts, both probes described above were used together on the same plates.

completely sequenced using the appropriate primers (listed below) for that particular region.

| | | |
|---|---|---|
| 11.b-1/2FOR1 | 5'-GCAGCCAGCTTCGGACAGAC-3' | (SEQ ID NO: 50) |
| 11.a-1/1FOR2 | 5'-CCGCCTGCCACTGGCGTGTGC-3' | (SEQ ID NO: 60) |
| 11.a-1/1FOR3 | 5'-CCCAGATGAAGGACTTCGTCAA-3' | (SEQ ID NO: 61) |
| 11.b-1/2FOR4 | 5'-GCTGGGATCATTCGCTATGC-3' | (SEQ ID NO: 62) |
| 11.b-1/2FOR5 | 5'-CAATGGATGGACCAGTTCTGG-3' | (SEQ ID NO: 63) |
| 11.b-1/2FOR6 | 5'-CAGATCGGCTCCTACTTTGG-3' | (SEQ ID NO: 64) |
| 11.b-1/2FOR7 | 5'-CATGGAGCCTCGAGACAGG-3' | (SEQ ID NO: 65) |
| 11.b-1/2FOR8 | 5'-CCACTGTCCTCGAAGCTGGAG-3' | (SEQ ID NO: 66) |
| 11.b-1/2FOR9 | 5'-CTTCGTCCTGTGCTGGCTGTGGGCTC-3' | (SEQ ID NO: 67) |
| 11.b-1/2FOR10 | 5'-CGCCTGGCATGTGAGGCTGAG-3' | (SEQ ID NO: 68) |
| 11.b-1/2FOR11 | 5'-CCGTGATCAGTAGGCAGGAAG-3' | (SEQ ID NO: 69) |
| 11.b-1/2FOR12 | 5'-GTCACAGAGGGAACCTCC-3' | (SEQ ID NO: 70) |
| 11.b-1/2FOR13 | 5'-GCTCCTGAGTGAGGCTGAAATCA-3' | (SEQ ID NO: 71) |
| 11.b-1/2FOR14 | 5'-GAGATGCTGGATCTACCATCTGC-3' | (SEQ ID NO: 72) |
| 11.b-1/2FOR15 | 5'-CTGAGCTGGGAGATTTTTATGG-3' | (SEQ ID NO: 73) |
| 11.b-1/2REV2 | 5'-GTGGIJCAGCACTGAAATCTG-3' | (SEQ ID NO: 74) |
| 11.b-1/2REV3 | 5'-CGTTTGAAGAAGCCAAGCTTG-3' | (SEQ ID NO: 75) |
| 1l.b-1/2REV4 | 5'-CACAGCGGAGGTGCAGGCAG-3' | (SEQ ID NO: 76) |
| 11.b-1/2REV5 | 5'-CTCACTGCTTGCGCTGGC-3' | (SEQ ID NO: 77) |
| 11.b-1/2REV6 | 5'-CGGTAAGATAGCTCTGCTGG-3' | (SEQ ID NO: 78) |
| 11.b-1/2REV7 | 5'-GAGCCCACAGCCAGCACAGG-3' | (SEQ ID NO: 79) |
| 11.b-1/2REV8 | 5'-GATCCAACGCCAGATCATACC-3' | (SEQ ID NO: 80) |
| 11.b-1/2REV9 | 5'-CACGGCCAGGTCCACCAGGC-3' | (SEQ ID NO: 81) |
| 11.b-1/2REV10 | 5'-CACGTCCCCTAGCACTGTCAG-3' | (SEQ ID NO: 82) |
| 11.b-1/2REV11 | 5'-CCATGTCCACAGAACAGAGAG-3' | (SEQ ID NO: 51) |
| 11.b-1/2REV12 | 5'-TTGACGAAGTCCTTCATCTGGG-3' | (SEQ ID NO: 83) |
| 11.b-1/2REV13 | 5'-GAACTGCAAGCTGGAGCCCAG-3' | (SEQ ID NO: 84) |
| 11.a-1/1REV1 | 5'-CTGGATGCTGCGAAGTGCTAC-3' | (SEQ ID NO: 85) |
| 11.a-1/1REV2 | 5'-GCCTTGGAGCTGGACGATGGC-3' | (SEQ ID NO: 86) |

Approximately 500,000 plaques were screened using the two probes from above which were labeled in the same way as described in Example 20. Labeled probes were added to a prehybridization solution, containing 45% formamide, and incubated overnight at 50° C. Filters were washed twice in 2×SSC/0.1% SDS at room temperature (22° C.). A final wash was carried out in 2×SSC/0.1% SDS at 50° C. Autoradiography was for 19 hours at −80° C. on Kodak X-Omat AR film with an intensifying screen.

Thirteen plaques giving positive signals on at least duplicate lifts were subjected to a secondary screen performed as described for the initial screen except that both the 3' and 5' labeled probes were used for hybridization and an additional final wash was incorporated using 2×SSC/0.1 % SDS at 65' C. Autoradiography was performed as described above for 2.5 hours.

Thirteen plaques (designated MS2P1 through MS2P13) giving positive signals were transferred into low $Mg^{++}$ phage diluent. Insert size was determined by PCR amplification (Perkin-Elmer 9600 thermocycler) using T3 and T7 primers which anneal to Bluescript phagemid in ZAP II (sequence previously described) under the same conditions shown above. Band sizes ranged from 500 bases to 4 Kb. Phagemids were isolated, prepared, and sequenced with M13 and M13 reverse.1 primers (SEQ ID NOS: 40 and 41, respectively). Five of the thirteen clones; MS2P-3, MS2P-6, MS2P-9, MS2P-12, and MS2P-13, were sequenced, and together, represented a region from approximately base 200 at the 5' end to about 300 bases past a first stop codon at the 3' end.

Automated sequencing was performed as described in Example 4 by first using M13 and M13 reverse.1 primers (SEQ ID NOS: 40 and 41, respectively) to sequence the ends of each clone and to determine its position relative to construct #17 (SEQ ID NO: 45). Each clone was then completely sequenced using the appropriate primers (listed below) for that particular region.

Sequences were edited, aligned, and compared to a previously isolated mouse $\alpha_d$ sequence (construct #17, SEQ ID NO: 45).

Alignment of the new sequences revealed an 18 base deletion in construct #17 beginning at nucleotide 2308; the deletion did not cause a shift in the reading frame. Clone MS2P-9, sequenced as described above, also revealed the same 18 base deletion. The deletion has been observed to occur in 50% of mouse clones that include the region but has not been detected in rat or human $\alpha_d$ clones. The eighteen base deletion is characterized by a 12 base palindromic sequence AAGCAGGAGCTCCTGTGT (SEQ ID NO: 91). This inverted repeat in the nucleic acid sequence is self-complementary and may form a loop out, causing cleavage during reverse transcription. The mouse $\alpha_d$ sequence which includes the additional 18 bases is set forth in SEQ ID NO: 52; the deduced amino acid sequence is set forth in SEQ ID NO: 53.

EXAMPLE 30

In Situ Hybridizations in Mouse

Tissue distribution was then determined for mouse $\alpha_d$ in order to provide a comparison to that in humans, described in Example 6.

A single stranded 200 bp mRNA probe was generated from a DNA template, corresponding to nucleotides 3460 to 3707 in the cytoplasmic tail region of the murine cDNA, by in vitro RNA transcription incorporating $^{35}$S-UTP (Amersham).

Whole mouse embryos (harvested at days 11–18 after fertilization) and various mouse tissues, including spleen, kidney, liver, intestine, and thymus, were hybridized in situ with the radiolabeled single-stranded mRNA probe.

Tissues were sectioned at 6 μm thickness, adhered to Vectabond (Vector Laboratories, Inc., Burlingame, Calif.)

coated slides, and stored at −70° C. Prior to use, slides were removed from −70° C. and placed at 50° C. for approximately 5 minutes. Sections were fixed in 4% paraformaldehyde for 20 minutes at 4° C., dehydrated with an increasing ethanol gradient (70–95–100%) for 1 minute at 4° C. at each concentration, and air dried for 30 minutes at room temperature. Sections were denatured for 2 minutes at 70° C. in 70% formamide/2×SSC, rinsed twice in 2×SSC, dehydrated with the ethanol gradient described supra and air dried for 30 minutes. Hybridization was carried out overnight (12–16 hours) at 55° C. in a solution containing $^{35}$S-labeled riboprobes at 6×10$^5$ cpm/section and diethylpyrocarbonate (DEPC)-treated water to give a final concentration of 50% formamide, 0.3M NaCl, 20 mM Tris-HCl, pH 7.5, 10% dextran sulfate, 1×Denhardt's solution, 100 mM dithiothreitol (DTT) and 5 mM EDTA. After hybridization, sections were washed for 1 hour at room temperature in 4×SSC/10 mM DTT, 40 minutes at 60° C. in 50% formamide/2×SSC/10 mM DTT, 30 minutes at room temperature in 2×SSC, and 30 minutes at room temperature in 0.1×SSC. The sections were dehydrated, air dried for 2 hours, coated with Kodak NTB2 photographic emulsion, air dried for 2 hours, developed (after storage at 4° C. in complete darkness) and counterstained with hematoxylin/eosin.

Spleen tissue showed a strong signal primarily in the red pulp. This pattern is consistent with that of tissue macrophage distribution in the spleen, but does not exclude other cell types.

EXAMPLE 31

Generation of Mouse Expression Constructs

In order to construct an expression plasmid including mouse cDNA sequences exhibiting homology to human $\alpha_d$, inserts from clones A 1160 and B3800 were ligated. Prior to this ligation, however, a 5' leader sequence, including an initiating methionine, was added to clone A1160. A primer designated "5' PCR leader" (SEQ ID NO: 47) was designed to contain: (1) identical nonspecific bases at positions 1–6 allowing for digestion; (2) a BamHI site (underlined in SEQ ID NO: 47) from positions 7–12 to facilitate subcloning into an expression vector; (3) a consensus Kozak sequence from positions 13–18, (4) a signal sequence including a codon for an initiating methionine (bold in SEQ ID NO: 47), and (5) an additional 31 bases of specifically overlapping 5' sequence from clone A 1160 to allow primer annealing. A second primer designated "3' end frag" (SEQ ID NO: 48) was used with primer "5' PCR leader" to amplify the insert from clone A1160.

```
5'-AGTTACGGATCCGGCACCATGAC-      (SEQ ID NO: 47)
   -CTTCGGCACTGTGATCCTCCTGTGTG-3'

5'-GCTGGACGATGGCATCCAC-3'        (SEQ ID NO: 48)
```

The resulting PCR product did not digest with BamHI, suggesting that an insufficient number of bases preceded the restriction site, prohibiting recognition by the enzyme. The length of the "tail" sequence preceding the BamHI site in the 5' primer (SEQ ID NO: 47) was increased and PCR was repeated on the amplification product from the first PCR. A 5' primer, designated mAD.5'.2(SEQ ID NO: 49), was designed with additional nonspecific bases at positions 1–4 and an additional 20 bases specifically overlapping the previously employed "5'PCR leader" primer sequences.

5'-GTAGAGTTACGGATCCGGCACCAT-3' (SEQ ID NO: 49)

Primers "mAD.5'.2"" and "3' end frag" were used together in PCR with the product from the first amplification as template. A resulting secondary PCR product was subcloned into plasmid pCRtmII (Invitrogen) according to manufacturer's suggested protocol and transformed into competent One shot cells (Invitrogen). One clone containing the PCR product was identified by restriction enzyme analysis using BamHI and EcoRI and sequenced. After the sequence was verified, the insert was isolated by digestion with BamHI and EcoRI and gel purified.

The insert from clone B3800 was isolated by digestion with EcoRI and NotI, gel purified, and added to a ligation reaction which included the augmented A 1160 BamHI/EcoRI fragment. Ligation was allowed to proceed for 14 hours at 14° C. Vector pcDNA.3 (Invitrogen), digested with BamHI and NotI, was added to the ligation reaction with additional ligase and the reaction was continued for another 12 hours. An aliquot of the reaction mixture was transformed into competent E. coli cells, the resulting colonies cultured, and one positive clone identified by PCR analysis with the primers 11.b-1/2FOR1 and 11.b-1/2REV11 (SEQ ID NOS: 50 and 51, respectively). These primers bridge the A 1160 and B3800 fragments, therefore detection of an amplification product indicates the two fragments were ligated. The sequence of the positive clone was verified with the primers set out in SEQ ID NOS: 50 and 51, which amplify from base 100 to 1405 after the initiating methionine.

EXAMPLE 32

Construction of a Knock-Out Mouse

In order to more accurately assess the immunological role of the protein encoded by the putative mouse $\alpha_d$ cDNA, a "knock-out" mouse is designed wherein the genomic DNA sequence encoding the putative $\alpha_d$ homolog is disrupted by homologous recombination. The significance of the protein encoded by the disrupted gene is thereby assessed by the absence of the encoded protein. Generation of "knock-out" mice is described in Deng, et al., Mol. Cell. Biol. 13:2134–2140 (1993).

Design of such a mouse begins with construction of a plasmid containing sequences to be "knocked out" by homologous recombination events. A 750 base pair fragment of the mouse cDNA (corresponding to nucleotides 1985 to 2733 in SEQ ID NO: 45) was used to identify a mouse genomic sequence encoding the putative mouse $\alpha_d$ homolog from a λFIXII genomic library. Primary screening resulted in 14 positive plaques, seven of which were confirmed by secondary screening. Liquid lysates were obtained from two of the plaques giving the strongest signal and the λ DNA was isolated by conventional methods. Restriction mapping and Southern analysis confirmed the authenticity of one clone, designated 14–1, and the insert DNA was isolated by digestion with NotI. This fragment was cloned into Bluescript SKII$^+$.

In order to identify a restriction fragment of approximately 9 to 14 kb, a length reported to optimize the probability of homologous recombination events, Southern hybridization was performed with the 750 bp cDNA probe. Prior to hybridization, a restriction map was constructed for clone 14–1. A 12 kb fragment was identified as a possible candidate and this fragment was subcloned into pBluescript SKII$^+$ in a position wherein the mouse DNA is flanked by thymidine kinase encoding cassettes. Further analysis of this clone with an I domain probe (corresponding to nucleotides 454–1064 in SEQ ID NO: 45) indicated that the clone did not contain I domain encoding sequences.

Using the same I domain probe, the λFIXII genomic library was rescreened. Initially, six positive clones were detected, one of which remained positive upon secondary screening. DNA isolated from this clone reacted strongly in Southern analysis with an I domain probe. No reactivity was detected using the original 750 bp probe, however, indicating that this clone included regions 5' to nulcleotides 1985–2773 of SEQ ID NO: 45.

Alternatively, the lack of hybridization to the 750 bp probe may have suggested that the clone was another member of the integrin family of proteins. To determine if this explanation was plausible, the 13 kb insert was subcloned into pBluescript SKII+. Purified DNA was sequenced using primers corresponding to $\alpha_d$ I domain nucleic acid sequences 441–461, 591–612, 717–739, and reverse 898–918 in SEQ ID NO: 52. Sequence information was obtained using only the first 4441–4461 primer, and only the 5'-most exon of the I domain was efficiently amplified. The remainder of the I domain was not amplified. The resulting clone therefore comprised exon 6 of the mouse $\alpha_d$ gene, and intronic sequences to the 3' and 5' end of the exon. Exon 7 was not represented in the clone. After sequencing, a construct is generated containing neomycin resistance and thymidine kinase genes.

The neomycin resistance (neo$^r$) gene is inserted into the resulting plasmid in a manner that interrupts the protein coding sequence of the genomic mouse DNA. The resulting plasmid therefore contains a neo$^r$ gene within the mouse genomic DNA sequences, all of which are positioned within a thymidine kinase encoding region. Plasmid construction in this manner is required to favor homologous recombination over random recombination [Chisaka, et al., Nature 355:516–520 (1992)].

An alternative strategy was used to generate constructs useful for production of $\alpha_d$ knock out mice. Two sets of oligonucleotide primers were submitted to Genome Systems, Inc. (St. Louis, Mo.) for high stringency PCR analysis of a large-insert library made from genomic DNA of embryonic stem cells. The primers corresponded to the first and last exons of the I domain in $\alpha_d$. Three clones were identified, two of which, designated 1117 and 1118, were reactive with both primers and one, designated 1119, which only the primers from the last exon could amplify.

Identification of a Mouse Genomic $\alpha_d$ DNA

Plasmid DNA was prepared from bacterial lysates of clones 1117 and 1118 according to manufacturer's instructions (Genome Systems, Inc.) The $\alpha_d$ inserts were verified by PCR using the oligonucleotides madk.f1 (SEQ ID NO: 104) and madk.r1 (SEQ ID NO: 105) and madk.r2 (SEQ ID NO: 106).

madk.f1    SEQ ID NO: 104
TGT CCA GGA CAA GAG ATG GAC ATT GC madk.r1    SEQ ID NO: 105
GAG CTA TTT CAT AGC AAG AAT GGG madk.r2    SEQ ID NO: 106
TAT AGC ATA GCG AAT GAT CC Aliquots of both plasmids were digested with restriction enzymes BamHI, PstI, SacI, SalI, SmaI, XbaI, and XhoI (Boehringer Mannheim). Each digest sample was resolved on 0.8% agarose gel and the polynucleotides transferred onto Hybond-N+ nucleic acid transfer membrane (Amersham) for analysis. The blot was probed with $^{32}$P-random primed DNA generated using a 1.6 kb template obtained by PCR using oligos madfor 1 (SEQ ID NO: 107) and madrev 1 (SEQ ID NO: 108).

madfor 1    SEQ ID NO: 107
ATG GTC CGT GGA GTT GTG ATC madrev 1    SEQ ID NO: 108
TCG AGA TCC ACC AAA CTG CAC Hybridization was carried out at 42° C. overnight in SSPE buffer with 50% formamide. The labeled blot was washed five times in 2×SSPE at room temperature. Radiolabeled bands were visualized by exposure of the blot to Kodak X-Omat autoradiography film at −70° C. for two hours.

Two fragments of interest were identified from clone 1118: a SacI fragment of 4.1 kb and an XbaI fragment of 8.3 kb. The entire sample contents from the SacI and XbaI digests of clone 1118 were ligated into the vector pBluescript KS+ without further purification, and following ligation, the entire reaction contents were transformed into calcium-competent preparations of the E. coli strain TG1/lambda SmR. Resulting colonies were isolated and cultured overnight in 200 μl selective medium containing M13KO7 helper virus to replicate single stranded DNA. A 10 μl aliquot of supernatant from each well was then blotted onto Hybond-N+ transfer membrane and hybridized with the same probe and protocol as described above. Cultures were expanded from nine positive clones and plasmid DNA was isolated from each culture using a Wizard Plus Miniprep DNA Purification System (Promega). Restriction digests and PCR were used to confirm presence and size of inserts in the isolated plasmids.

Three clones were subjected to sequence analysis using the vector primers T3 and T7 and oligonucleotide primers corresponding to murine $\alpha_d$ sequences. Sequence comparison of these three clones with the murine cDNA using Geneworks software indicated that all three contained both exons 1 and 2 of murine $\alpha_d$. The longest clone, referred to as A, was an XbaI clone of 8280 kb length, and the two shorter clones, referred to as E and H, were identical SacI clones of 4112 kb length. The 8280 kb XbaI clone was selected for further development.

EXAMPLE 33

Cloning of Rabbit $\alpha_d$

Construction and Screening of the Rabbit cDNA Library

Identification of human $\alpha_d$ homologs in rats and mice led to the investigation of the existence of a rabbit homolog which would be useful in rabbit models of human disease states described infra.

Poly A+ RNA was prepared from a whole rabbit spleen using an Invitrogen FastTrack kit (San Diego, Calif.) according to manufacturer's suggested protocol and reagents supplied with the kit. From 1.65 g tissue, 73 μg poly A+RNA were isolated. The rabbit spleen RNA was used to construct a ZAP Express cDNA library using a kit from Stratagene (La Jolla, Calif.). Resulting cDNA was directionally cloned into EcoRI and XhoI sites in the lambda arms of a pBK-CMV phagemid vector. Gigapack II Gold (Stratagene) was used to package the lambda arms into phage particles. The resulting library titer was estimated to be approximately 8×105 particles, with an average insert size of 1.2 kb.

The library was amplified once by plating for confluent plaque growth and cell lysate was collected. The amplified library was plated at approximately 30,000 plaque forming units (pfu) per 150 mm plate with E. coli and the resulting mixture incubated for 12–16 hrs at 37° C. to allow plaque formation. Phage DNA was transferred onto Hybond N+nylon membranes (Amersham, Arlington Heights, Ill.).

The membranes were hybridized with a mixture of two random primed radiolabeled mouse $\alpha_d$ PCR DNA probes. The first probe was generated from a PCR product spanning nucleotides 149–946 in SEQ ID NO: 52. The second probe was from a PCR product spanning nucleotides 2752–3651 in SEQ ID NO: 52. Probes were labeled by random priming (Boehringer Mannheim Random Primed DNA Labeling Kit) and the reaction mixture was passed over a Sephadex G-50 column to remove unincorporated nucleotides. The hybridization solution was composed of 5×SSPE, 5×Denhardts, 1% SDS, 40% Formamide and the labeled probes at 1 ×10$^6$ dpm/ml. Hybridization was carried out at 42° C. for 16–18 hours. Filters were washed extensively in 2×SSPE/0.1% SDS at room temperature and exposed to X-ray film to visualize any hybridizing plaques.

Two clones with significant sequence homology to human $\alpha_d$ were identified. Clone #2 was approximately 800 bp in length and mapped to the 5' end of human $\alpha_d$ Clone #2 includes an initiating methionine and complete leader sequence. Clone #7 was approximately 1.5 kb and includes an initiating methionine. The 5' end of clone #7 overlapped that of clone #2, while the 3' sequences terminated at a point beyond the I domain sequences. Clone #7 was completely sequenced by the primer walking method. The nucleotide and deduced amino acid sequences for clone #7 are set out in SEQ ID NOs: 100 and 101, respectively.

The predicted N terminal amino acid sequence for rabbit $\alpha_d$ as determined from clones #2 and #7 indicated a protein with 73% identity with human $\alpha_d$, 65% identity with mouse $\alpha_d$, and 58% identity with mouse CD11b, human CD11b, and human CD11c. The nucleic acid sequence for clone #2 is set out in SEQ ID NO: 92; the predicted amino acid sequence is set out in SEQ ID NO: 93

Isolation of a full length rabbit $\alpha_d$ cDNA was attempted using labeled rabbit clone # 7 and rescreening the cDNA library from which the fragment was derived. Twenty-five additional clones were identified with one, designated clone 49, determined to be the largest. Clone 49 was completely sequenced using the nested deletions technique. The nucleotide and amino acid sequences for clone 49 are set out in SEQ ID NOs: 102 and 103, respectively. Since clones #7 and #49 did not overlap, oligonucleotides were designed to be used as primers in a PCR with first strand rabbit spleen cDNA to isolate the missing sequence.

The relationship of the putative amino acid sequence of these two partial clones with that of other leukointegrins is described in Table 1.

TABLE 1

Percent identity of $\beta_2$ integrin family members on the amino acid level.

|  | Human $\alpha_d$ | Rabbit #7 | Rabbit #49 |
|---|---|---|---|
| Human $\alpha_d$ | 100 | 74 | 80 |
| Mouse $\alpha_d$ | 70 | 67 | 74 |
| Rat $\alpha_d$ | 70 | 66 | 73 |
| Mouse CD11a | random* | 28 | 28 |
| Mouse CD11b | 55 | 59 | 53 |
| Human CD11a | 36 | 28 | 28 |
| Human CD11b | 60 | 58 | 55 |
| Human CD11c | 66 | 59 | 62 |

*If <25% identity, it is just random alignment and not significant.

Isolation of a rabbit $\alpha_d$ clone allows expression of the protein, either on the surface of transfectants or as a soluble full length or truncated form. This protein is then used as an immunogen for the production of monoclonal antibodies for use in rabbit models of human disease states.

EXAMPLE 34

Isolation of Monkey $\alpha_d$
Preparation of Affinity Columns

In order to prepare an affinity column resin to isolate $\alpha_d$ from monkey spleen, 10 mg each of the anti-human $\alpha_d$ antibodies 212D and 217L were dialyzed overnight against coupling buffer containing 0.1M NaHCO$_3$, 0.5M NaCl, pH 8.3. Approximately 1.0 g of CNBr Sepharose 4B (Pharmacia, Piscataway N.J.) was prepared according to the manufacturer's recommended protocol and 1.0 ml of the resin combined with each of the dialyzed antibodies. The resulting slurry was mixed by rotation overnight at 4° C. and coupled resin obtained by centrifugation for 5 minutes at 1000 rpm in a Beckman tabletop centrifuge. The nonabsorbed supernatant fraction was collected and assayed for the presence of uncoupled protein by spectrophotometer. Results indicated that all available antibody had bound to the gel matrix. Uncoupled active groups on the resins were blocked with 1M ethanolamine for 2 hours at room temperature and the resins washed in a series of alternating high and low pH changes in Coupling buffer followed by a final wash using acetate buffer containing 0.1M NaC$_2$H$_3$O$_2$·3H$_2$O and 0.5M NaCl, pH 4.0. Both resins were stored at 4° C. in Coupling buffer.

Preparation of Monkey Spleen

Female macaque spleens were obtained from the University of Washington's Regional Primate Center. Spleen tissue was injected with 100 U/ml collagenase D (Sigma) and minced into small pieces. Tissue pieces were then suspended in a small volume of Lysis Buffer containing 50 mM Tris, 150 mM NaCl, 2 mM CaCl$_2$, 2 mM MgCl$_2$, pH 8.0, with 1.0% Triton-X100 detergent and stored at –70° C. Protease inhibitors PLA (a mixture of Pepstatin A, leupeptin, and aprotinin, each from Sigma) and 4-(2-aminoethyl) benzene sulfonyl fluoride-HCl (AEBSF) (Nova Biochem, La Jolla, Calif.) were added to prevent proteolysis of protein during storage. Tissue was stored until a total of six macaque spleens was obtained.

Spleen tissue from the six monkeys was pooled and homogenized in a Waring blender, three cycles of ten seconds each, in TSA Lysis Buffer containing 25 mM Tris, 0.15M NaCl, 0.02% NaN$_3$, 1.0% Triton, 1×PLA and 0.1 mM AEBSF. Lysate was collected and placed on a rocking platform for one hour at 4° C., and then centrifuged for 15 minutes at 3000 rpm in a Beckman tabletop centrifuge. Supernatant was collected and the pelleted cellular debris discarded. A total volume of 550 ml of lysate was collected and precleared by incubating the lysate for 2 hours at 4° C. with CNBr Sepharose previously treated in 1M ethanolamine in order to block reactive sites. Following incubation, the resin was removed by centrifugation and the supernatant collected.

Affinity Purification and Sequencing

The spleen lysate prepared as described above was divided in half and combined individually with the 212D- and 217L-prepared CNBr Sepharose gels. The resulting slurries were mixed with rotation for three days at 4° C., after which the nonabsorbed fraction was collected by centrifugation at 10 minutes 1500 rpm in a Beckman tabletop centrifuge and saved. The gels were transferred to 15 ml centrifuge tubes and washed sequentially in several volumes of D-PBS. Aliquots of approximately 100 1μl of each gel were boiled briefly in reducing sample buffer containing 0.1M Tris-HCl, pH 6.8, 2.0% SDS, 20% glycerol, 0.0002% bromophenol blue, 10% β-mercaptoethanol (final concentration 5%) and loaded onto and proteins resolved using a 6.0% polyacrylamide SDS gel (SDS-PAGE). The gel was Coomasie stained and proteins having molecular weights consistent with $\alpha_d$ and CD18 were detected along with a number of background proteins.

In an attempt to improve purification of the protein having the molecular weight similar to $\alpha_d$, two 100 μl aliquots of each gel with bound protein were washed by different means. In one method, gels were washed several times in buffer containing 150 mM NaCl, 10 mM Tris, 1.0% Triton-X100, pH 8.0, and in a second method, gels were washed identically, but bound protein was eluted in a final wash with 0.05M glycine, pH 2.4. As before, the eluted protein was boiled briefly in reducing sample buffer and resolved on a 6.0% SDS-PAGE gel. Coomasie staining detected only proteins consistent with $\alpha_d$ and CD18 from the resin washed in low pH glycine buffer, thus this isolation method was chosen. In order to isolate protein for sequencing, the remaining CNBr Sepharose resin was washed four times as described above and approximately three quarters of the resin suspended in 2.0 ml 0.05M glycine, pH 2.4, and vortexed vigorously. The resin was pelleted by centrifugation for 3 minutes and the nonabsorbed fraction collected. The gel was then washed once more in glycine buffer and this wash pooled with the previous nonabsorbed fraction. The pooled fractions were dialyzed against D-PBS overnight at 4° C. with two changes. After dialysis, the samples were dried down to reduce volumes to 1.0 ml.

For sequencing, the eluates were separated on 7.0% resolving gels and proteins transferred to Immobilon (PVDF) membranes (Millipore, Bedford Mass.) as described in Example 2. Briefly, the gels were washed once in deionized water and equilibrated for 15 to 45 minutes in 10 mM cyclohexylamino-propanesulfoic acid buffer (CAPS), pH 10.5, with 10% methanol. PVDF membranes were rinsed in both methanol and distilled water, then equilibrated in CAPS transfer buffer for 15 to 30 minutes. Proteins were transferred to PVDF membranes for 3 hours at 70 volts after which they were stained in filtered 0.1% R250 Coomasie stain for 10 minutes. Membranes were washed to destained in 50% methanol/10% acetic acid three times, 10 minutes each wash, washed once more in filtered water, and dried.

Two predominant protein bands of approximately 150 kD and 95 kD were detected from both the 212D- and 217L-coupled resins which were consistent with proteins detected on the previously run analytical scale gels. A less distinct band was observed on the membrane derived from 217L-coupled resin located directly beneath the protein at 150 kD, but the band was not detected after the membrane was dried. The 150 kD band from each membrane was excised from the membrane and directly sequenced with an Applied Biosystems (Foster City, Calif.) Model 473A protein sequencer according to the manufacturer's suggested method.

Results indicated that the amino terminal sequence of the monkey protein isolated using 212D-coupled resin had the amino acid sequence as set out in SEQ ID NO: 109, and the amino terminus of the protein isolated using 217L-coupled resin had the sequence shown in SEQ ID NO: 110. The "X" in SEQ ID NO: 110 indicates an indeterminable residue.

| 212D-Couple Protein | SEQ ID NO: 109 |
|---|---|
| NLDVEEPTIFQEDA | |
| 217L-Coupled Protein | SEQ ID NO: 110 |
| NLDVEEPTIFXEDA | |

A comparison of the monkey sequences with the amino terminal sequences of human $\alpha_d$ and other α chains in the $\beta_2$ integrin family is shown in Table 2.

TABLE 2

Comparison of Monkey αd Amino Terminal Sequence With Human $\beta_2$ α Subunits

| PROTEIN | SEQ ID NO: | AMINO TERMINAL SEQUENCE |
|---|---|---|
| Monkey $\alpha_d$ | 111 | F N L D V E E P T I F Q E D A |
| Human | 112 | F N L D V E E P T I F Q E D A G G |
| Human CD11c | 113 | F N L D T E E L T A F V D S A G |
| Human CD11b | 114 | F N L D T E N A M T F Q E N A R G |

Based on the sequence identify, it can be concluded that both 212D and 217L recognize $\alpha_d$ in both macaque and human.

EXAMPLE 35

Characterization of 217L Antigen

Based on the N-terminal sequence of protein precipitated from monkey spleen in the previous example, it can be concluded that antibodies 217L and 212D recognize $\alpha_d$ protein in both monkey and human. Immunocytochemical (ICC) analysis and immunoprecipitation experiments, however, indicate that 217L has additional reactivity unshared by 212D. FACS and ICC experiments using antibodies to all α chains ruled out cross-reactivity of 217L with CD11c, the most closely related leukointegrin α chain, and CD11b. Therefore, it may be that the 217L antibody also recognizes either a conformational, glycosylation, or splice variant of $\alpha_d$ or a novel α chain which shares sequence homology with $\alpha_d$.

The unique distribution of the antigen recognized by antibody 217L in sarcoid lung tissue (see Example 18), with a non-overlapping staining pattern in relationship to CD11c, suggests that the antigen may have biological significance. Therefore, in order to more fully understand the significance of the 217L antigen, analysis of the protein and underlying DNA encoding the protein are required and various approaches are contemplated.

Immunoprecipitation of a protein complex from human dendritic cells or peripheral blood is carried out using the antibody 217L, followed by N-terminal sequence of the precipitated proteins. Sequence analysis will reveal whether the protein recognized on peripheral blood cells shares amino terminal identity with $\alpha_d$. The protein precipitated from dendritic cells or peripheral blood cells is then treated with deglycosylating enzymes and compared to CD11c and $\alpha_d$ precipitated from other sources to provide a comparison of molecular weight of the primary amino acid sequence.

Additionally, a cDNA library generated from dendritic cell RNA is probed with the entire $\alpha_d$ cDNA under low stringency. Reactive clones are analyzed by nucleic acid sequencing over the entire length of the clone in order to determine if non-$\alpha_d$ sequences exist in the clones.

EXAMPLE 36

Animal Models for Determining $\alpha_d$ Therapeutic Utility

Immunohistologic data in dog and in situ hybridization in rats and mice has determined that in spleen $\alpha_d$ is expressed primarily by macrophages present in red pulp and in lymph nodes, $\alpha_d$ is found in medullary cords and sinuses. The expression pattern is remarkably similar to what has been reported for two murine antigens defined by the monoclonal antibodies F4/80 and SK39. While biochemical characterization of these murine antigens has demonstrated that they are distinct from $\alpha_d$, it is highly probably that $\alpha_d$ defines the same macrophage subset as the murine F4/80 and SK39 antigens.

In mouse, SK39-positive macrophages have been identified in splenic red pulp where they may participate in the clearance of foreign materials from circulation, and in medulla of lymph nodes [Jutila, et al., *J. Leukocyte Biol.* 54:30–39 (1993)]. SK39-positive macrophages have also been reported at sites of both acute and chronic inflammation. Furthermore, monocytes recruited to thioglycolate-inflamed peritoneal cavities also express the SK39 antigen. Collectively, these findings suggest that, if SK39$^+$ cells are also $\alpha_d^+$, then these cells are responsible for the clearance of foreign materials in the spleen and participate in inflammation where macrophages play a significant role.

While the function of $\alpha_d$ remains unclear, other more well characterized $\beta_2$ integrins have been shown to participate in a wide variety of adhesion events that facilitate cell migration, enhance phagocytosis, and promote cell-cell interactions, events which all lead to upregulation of inflammatory processes. Therefore, it is highly plausible that interfering with the normal $\alpha_d$ function may also interfere with inflammation where macrophages play a significant role. Such an anti-inflammatory effect could result from: i) blocking macrophage recruitment to sites of inflammation, ii) preventing macrophage activation at the site of inflammation or iii) interfering with macrophage effector functions which damage normal host tissue through either specific autoimmune responses or as a result of bystander cell damage.

Disease states in which there is evidence of macrophages playing a significant role in the disease process include multiple sclerosis, arthritis, graft atherosclerosis, some forms of diabetes and inflammatory bowel disease. Animal models, discussed below, have been shown to reproduce many of the aspects of these human disorders. Inhibitors of $\alpha_d$ function are tested in these model systems to determine if the potential exists for treating the corresponding human diseases.

Graft Arteriosclerosis

Cardiac transplantation is now the accepted form of therapeutic intervention for some types of end-state heart disease. As the use of cyclosporin A has increased one year survival rates to 80%, the development of progressive graft arteriosclerosis has emerged as the leading cause of death in cardiac transplants surviving beyond the first year. Recent studies have found that the incidence of significant graft arteriosclerosis 3 years following a cardiac transplant is in the range of 36–44% [Adams, et al., *Transplantation* 53:1115–1119 (1992); Adams, et al., *Transplantation* 56:794–799 (1993)].

Graft arteriosclerosis typically consists of diffuse, occlusive, intimal lesions which affect the entire coronary vessel wall, and are often accompanied by lipid deposition. While the pathogenesis of graft arteriosclerosis remains unknown, it is presumably linked to histocompatibility differences between donor and recipient, and is immunologic in nature. Histologically, the areas of intimal thickening are composed primarily of macrophages, although T cells are occasionally seen. It is therefore possible that macrophages expressing $\alpha_d$ may play a significant role in the induction and/or development of graft arteriosclerosis. In such a case, monoclonal antibodies or small molecule inhibitors (for example, soluble ICAM-R) of $\alpha_d$ function could be given prophylactically to individuals who received heart transplants and are at risk of developing graft arteriosclerosis.

Although atherosclerosis in heart transplants presents the greatest threat to life, graft arteriosclerosis is also seen in other solid organ transplants, including kidneys and livers. Therapeutic use of $\alpha_d$ blocking agents could prevent graft arteriosclerosis in other organ transplants and reduce complications resulting from graft failure.

One model for graft arteriosclerosis in the rat involves heterotopic cardiac allografts transplanted across minor histocompatibility barriers. When Lewis cardiac allografts are transplanted into MHC class I and II compatible F-344 recipients, 80% of the allografts survive at least 3 weeks, while 25% of the grafts survive indefinitely. During this low-grade graft rejection, arteriosclerosis lesions form in the donor heart. Arterial lesions in 120 day old allografts typically have diffuse fibrotic intimal thickening indistinguishable in appearance from graft arteriosclerosis lesions found in rejecting human cardiac allografts.

Rats are transplanted with hearts mismatched at minor histocompatibility antigens, for example Lewis into F-344. Monoclonal antibodies specific for rat $\alpha_d$ or small molecule inhibitors of $\alpha_d$ are given periodically to transplant recipients. Treatment is expected to reduce the incidence of graft arteriosclerosis in non-rejecting donor hearts. Treatment of rats with $\alpha_d$ monoclonal antibodies or small molecule inhibitors may not be limited to prophylactic treatments. Blocking $\alpha_d$ function is also be expected to reduce macrophage mediated inflammation and allow reversal of arterial damage in the graft.

Atherosclerosis in Rabbits fed Cholesterol

Rabbits fed an atherogenic diet containing a cholesterol supplement for approximately 12–16 weeks develop intimal lesions that cover most of the lumenal surface of the ascending aorta [Rosenfeld, et al., *Arteriosclerosis* 7:9–23 (1987); Rosenfeld, et al., *Arteriosclerosis* 7:24–34 (1987)]. The atherosclerotic lesions seen in these rabbits are simmer to those in humans. Lesions contain large numbers of T cells, most of which express CD45RO, a marker associated with memory T cells. Approximately half of the infiltrating T cells also express MHC class II antigen and some express the IL-2 receptor suggesting that many of the cells are in an activated state.

One feature of the atherosclerotic lesions found in cholesterol fed rabbits, but apparently absent in rodent models, is the accumulation of foam cell-rich lesions. Foam cell macrophages are believed to result from the uptake of oxidized low-density lipoprotein (LDL) by specific receptors. Oxidized LDL particles have been found to be toxic for some cell types including endothelial cells and smooth muscle cells. The uptake of potentially toxic, oxidized LDL particles by macrophages serves as an irritant and drives macrophage activation, contributing to the inflammation associated with atherosclerotic lesions.

Once monoclonal antibodies have been generated to rabbit $\alpha_d$, cholesterol fed rabbits are treated. Treatments include prophylactic administration of $\alpha_d$ monoclonal antibodies or small molecule inhibitors, to demonstrate that $\alpha_d$ $^+$ macrophages are involved in the disease process. Additional studies would demonstrate that monoclonal antibodies to $\alpha_d$ or small molecule inhibitors are capable of reversing vessel damage detected in rabbits fed an atherogenic diet.

Insulin-Dependent Diabetes

BB rats spontaneously develop insulin-dependent diabetes at 70–150 days of age. Using immunohistochemistry, MHC class II$^+$, ED1 $^+$ macrophages can be detected infiltrating the islets early in the disease. Many of the macrophages appear to be engaged in phagocytosis of cell debris or normal cells. As the disease progresses, larger numbers of macrophages are found infiltrating the islets, although significant numbers of T cells, and later B cells, also appear to be recruited to the site [Hanenberg, et al., *Diabetologia* 32:126–134 (1989)].

Development of diabetes in BB rats appears to depend on both early macrophage infiltration and subsequent T cells recruitment. Treatment of BB rats with silica particles, which are toxic to macrophages, has been effective in blocking the early macrophage infiltration of the islets. In the absence of early macrophage infiltration, subsequent tissue damage by an autoaggressive lymphocyte population fails to occur. Administration of monoclonal antibody OX-19 (specific for rat CD5) or monoclonal antibody OX-8 (specific for rat CD8), which block the T cell-associated phase of the disease, is also effective in suppressing the development of diabetes.

The central role of macrophages in the pathology of this model makes it attractive for testing inhibitors of $\alpha_d$ function. Rats genetically predisposed to the development of insulin-dependent diabetes are treated with monoclonal antibodies to $\alpha_d$ or small molecule inhibitors and evaluated for the development of the disease. Preventing or delaying clinical onset is evidence that $\alpha_d$ plays a pivotal role in macrophage damage to the islet cells.

Inflammatory Bowel Disease (Crohn's Disease Ulcerative Colitis)

Animal models used in the study of inflammatory bowel disease (IBD) are generally elicited by intrarectal administration of noxious irritants (e.g. acetic acid or trinitrobenzene sulfonic acid/ethanol). Colonic inflammation induced by these agents is the result of chemical or metabolic injury and lacks the chronic and spontaneously relapsing inflammation associated with human IBD. However, a recently described model using subserosal injections of purified peptidoglycan-polysaccharide (PG-PS) polymers from either group A or group D streptococci appears to be a more physiologically relevant model for human IBD [Yamada, et al., *Gastroenterology* 104:759–771 (1993)].

In this model PG-PS is injected into the subserosal layer of the distal colon. The resulting inflammatory response is biphasic with an initial acute episode three days after injection, which is followed by a spontaneous chronic phase three to four weeks later. The late phase response is granulomatous in nature, and results in colonic thickening, adhesions, colonic nodules and mucosal lesions. In addition to mucosal injury, PG-PS colitis frequently leads to arthritis anemia and granulomatous hepatitis. The extraintestinal manifestations of the disease make the model attractive for studying Crohn's colitis in that a significant number of patients with active Crohn's disease suffer from arthritic joint disease and hepatobillary inflammation.

Granulomatous lesions are the result of chronic inflammation which leads to the recruitment and subsequent activation of cells of the monocyte/macrophage lineage. Presence of granulomatous lesions in Crohn's disease and the above animal model make this an attractive clinical target for $\alpha_d$ monoclonal antibodies or other inhibitors of $\alpha_d$ function. Inhibitors of $\alpha_d$ function are expected to block the formation of lesions associated with IBD or even reverse tissue damage seen in the disease.

Arthritis

Arthritis appears to be a multi-factorial disease process involving a variety of inflammatory cell types including neutrophils, T lymphocytes and phagocytic macrophages. Although a variety of arthritis models exist, preparations of streptococcal cell wall proteoglycan produce a disorder most similar to the human disease.

In rats, streptococcal cell wall induces inflammation of peripheral joints characterized by repeated episodes of disease progression followed by remission and eventually resulting in joint destruction over a period of several months [Cromartie, et al., *J. Exp. Med.* 146:1585–1602 (1977); Schwab et al., *Infection and Immunity* 59:4436–4442 (1991)]. During the chronic phase of the disease, mononuclear phagocytes or macrophages are believed to play a major role in destruction of the synovium. Furthermore, agents which suppress the recruitment of macrophages into the synovium effectively reduce the inflammation and pathology characteristic of arthritis.

A central role for the macrophage in synovium destruction that leads to arthritis predicts that monoclonal antibodies to $\alpha_d$ or inhibitors of $\alpha_d$ function may have therapeutic potential in the treatment of this disease. As in other models previously described, $\alpha_d$ monoclonal antibodies or small molecule inhibitors administered prophylactically are expected to block or moderate joint inflammation and prevent destruction of the synovium. Agents that interfere with $\alpha_d$ function may also moderate ongoing inflammation by preventing the recruitment of additional macrophages to the joint or blocking macrophage activation. The net result would be to reverse ongoing destruction of the joint and facilitate tissue repair.

Multiple Sclerosis

Although pathogenesis of multiple sclerosis (MS) remains unclear, it is generally accepted that the disease is mediated by $CD4^+$ T cells which recognize autoantigens in the central nervous system and initiate an inflammatory cascade. The resulting immune response results in the recruitment of additional inflammatory cells, including activated macrophages which contribute to the disease. Experimental autoimmune encephalomyelitis (EAE) is an animal model which reproduces some aspects of MS. Recently, monoclonal antibodies reactive with CD11b/CD18 [Huitinga, et al., *Eur. J. Immunol.* 23:709–715 (1993)] present on inflammatory macrophages have been shown to block both clinical and histologic disease. The results suggest that monoclonal antibodies or small molecule inhibitors to $\alpha_d$ are likely to be effective in blocking the inflammatory response in EAE. Such agents also have important therapeutic applications in the treatment of MS.

Immune Complex Alveolitis

Alveolar macrophages located in the alveolar ducts, airways, connective tissue, and pleural spaces of the lung represent the lung's first line of defense against inhaled environmental agents. In response to stimulation by agents, including bacterial-derived LPS, IFN-γ and immune complexes, alveolar macrophages release a variety of potent inflammatory mediators, including highly reactive oxygen radicals and nitrogen intermediates. While superoxide anions, hydrogen peroxide and nitric oxide (NO ·) have important functions in eradicating pathogens and lysing tumor targets, these agents can have injurious effects on normal tissues.

In a rat model of immune complex alveolitis, NO· release from alveolar macrophages has been shown to mediate much of the lung damage [Mulligan, et al., *Proc. Natl. Acad. Sci. (USA)* 88:638–6342 (1991)]. NO· has also been implicated as a mediator in other immune complex mediated injuries including dermal vasculitis [Mulligan, et al., supra] and could potentially play a role in diseases such as glomerulonephritis.

NO· mediated tissue damage is not limited to inflammation involving immune complexes. For example, microglial cell stimulated, by agents such as PMA, LPS or IFN-γ, produce NO· at levels capable of killing oligodendrocytes [Merrill, et al., *Immunol.* 151:2132 (1993)]. Pancreatic islet cells have also been found to be sensitive to NO·, and macrophage release of this mediator has been implicated in the tissue damage which leads to diabetes [Kroncke, et al., *BBRC* 175:752–758 (1991)]. More recently, it was conclusively demonstrated that NO· release plays a role in endotoxic shock [MacMicking, et al., *Cell* 81:641–650 (1995)]. When administered lipopolysaccharide (LPS), normal wild-type mice experience a severe, progressive decline in arterial pressure resulting in death. Mice deficient in inducible nitric oxide, however, experience a much less severe decline in arterial pressure in response to LPS, and all survive the treatment.

In vitro assays indicate that blockage of $\alpha_d$ is effective at blocking some aspects of macrophage (or leukocyte which express $\alpha_d$, in general) activation, including NO· release. Alveolar macrophages stimulated with IFN-γ in the presence of anti-$\alpha_d$ polyclonal anti-serum (generated in rabbits against a rat $\alpha_d$ I domain polypeptide) were found to produce significantly less nitrite/nitrate-breakdown products of NO· than macrophages treated with control anti-serum. This finding indicates that monoclonal antibodies to $\alpha_d$, particularly to the I-domain, may be potent anti-inflammatory agents with potential uses in MS, diabetes, lung inflammation and endotoxic shock. Furthermore, in contrast to CD18, which effects the function of a wide variety of leukocyte types, the limited distribution of $\alpha_d$ may make this a more attractive target than CD18 for preventing macrophage (or leukocyte which express $\alpha_d$, in general) activation.

Rat IgG immune complex-induced alveolitis is a widely used experimental model important in understanding acute lung injury. The injury is elicited by instilling anti-bovine serum albumin (BSA) antibodies into lungs via tracheal cannulation, followed by an intravenous injection of BSA. The formation of immune complexes in the microvasculature of the lung leads to complement activation and the recruitment of neutrophils into the lung. Presumably, formation of immune complexes in the lung following extravasation of leukocytes from the blood and subsequent leukocyte movement across lung epithelium. The subsequent release of mediators, including radicals, TNF-α and nitric oxide (NO·), from activated endothelial cells, neutrophils and macrophages which participate in progression of the disease. Pathologic features of the disease include increased vascular permeability leading to edema and the presence of large numbers of erythrocytes and PMNs present in the alveolar spaces.

Polyclonal anti-serum specific for the I domain Of $\alpha_d$ was tested in a rat model of immune complex-induced alveolitis. The anti-$\alpha_d$ polyclonal serum was administered via tracheal cannulation at the same time anti-BSA was introduced into the lungs. Lung injury was subsequently elicited by intravenous administration of BSA along with a trace amount of $^{125}$I-labeled BSA (approximately 800,000 cpm) to quantitate edema resulting from lung injury. Lung injury was allowed to proceed for four hours and damage was assessed using a lung permeability value, is defined as the ratio of $^{125}$I-labeled BSA in the lung compared to the amount of label present in the 1.0 ml of blood. Typically lung permeability values for positive control rates range between 0.6 and 0.8, while negative controls (rats not receiving BSA) have permeability index values in the range of 0.1–0.2.

Initial studies indicated that treatment with anti-$\alpha_d$ polyclonal anti-serum reduced lung permeability values by greater that 50%, representing a dramatic moderation of lung injury. Historically, treatments with anti-CD18 have reduced permeability values by 60%. These findings indicate that $\alpha_d$ may be the most important $\beta_2$ integrin during acute lung injury, however it cannot be precisely determined if the effect of the anti-sera prohibits leukocyte extravasation from the blood, or movement across lung epithelia.

As additional proof that $\alpha_d$ moderates lung injury, TNF-alpha levels in the bronchoalveolar lavage fluid were evaluated. Treatment with the anti-$\alpha_d$ anti-serum was found to reduce TNF-alpha levels approximately four-fold. TNF-alpha has long been viewed as an important mediator in acute lung inflammation, and responsible for the recruitment of inflammatory cells into sites of inflammation, cell activation and tissue damage. Presumably, anti-$\alpha_d$ anti-serum blocks activation of resident alveolar macrophages during the formation of immune complex alveolitis, and thereby moderates the release of TNF-α and NO·, and reduces subsequent tissue damage caused by these agents and the recruitment of neutrophils.

F344 Rat Model of LGL Leukemia

LGL leukemia in the F344 rat was first described in the early to mid 1980's as a transplantable leukemia with stable NK cell activity. This leukemia has been suggested as a possible model for human T gamma lymphoma and T-cell Chronic Lymphocytic Leukemia [Ward and Reynolds, *Am. J. Pathol.* 111:1–10 (1982); Stromberg, *Am. J. Pathol.* 119:517–519 (1985); Reynolds, et al. *J. Immunol.* 132:534–540 (1984)]. This model provides abundant cells for studies of LGL and NK cell function. Of particular interest is the presence of $\alpha_d$ on the surface of these cells as detected using hamster anti-rat antibody 205C through FACS analysis described in Example 26. In view of this observation, the roles of $\alpha_d$ in vitro (for example, using the cytolytic assays previously described) and in vivo were examined.

The pathologic features of LGL leukemia include severe splenomegaly, a pale mottled liver, enlargement of peripheral lymph nodes and petechial hemorrhages in lung, brain, and lymph node. Because $\alpha_d$ is present in the red pulp of normal rat spleen (on splenic macrophages), and the hallmark of LGL leukemia is severe splenomegaly, it was hypothesized that the $\alpha_d$ positive NK tumor cells may also "home" or tether to a yet defined ligand and proliferate here. To test this hypothesis, tumor cells were radiolabeled and injected with and without $\alpha_d$ antibody treatment into recipient rats. Spleens from these animals were removed after three hours and the presence of NK tumor cells determined. A more complete description of the methods used and experimental results are as follows.

Tumor cells, obtained from the spleens of rats with LGL leukemia and prepared as described below, were adoptively transferred to recipient rats 2 to 4 weeks prior to each experiment. From previous studies by histology and FACS analysis, it was known that a rapid proliferation of the tumor and resulting splenomegaly occurs about three to four weeks after adoptive transfer. In the first experiment, a spleen was removed from an animal that had been exposed to tumor cells for four weeks. A single-cell suspension was made by mincing up the spleen into smaller pieces with scissors and passing these pieces through a mesh screen in the presence of D-PBS. The cell suspension was collected in a 50 ml tube and centrifuged for 10 minutes at 1500 rpm in a Beckman tabletop centrifuge at room temperature. The supernatant was discarded, and the cells resuspended in 30 ml of D-PBS. Approximately 5.0 ml of this cell suspension was layered onto 5.0 ml of Histopaque, and the gradients centrifuged for 30 minutes at 1500 rpm. The cellular layer from these gradients was collected, pooled, and counted by hemacytometer. The cell number was adjusted so that each recipient rat received 1.0×107 cells, with a slight overestimation to account for cell loss during washes and preparing syringes. The cells were suspended in NK "test media" (RPMI-1640 plus antibiotics, plus 2% FBS) and labeled with 10 mCi of $^{51}$chromium for one hour at 37° C. After incubation, the volume of the cell suspension was increased to 50 ml with test media and the cells pelleted by centrifugation for 10 minutes, 1200 rpm. The supernatant was discarded and the cells washed two more times as described. The labeled cells were suspended at a final concentration of 1×107 cells/ml and preincubated in the presence or absence of anti-rat $\alpha_d$ antibodies as well as a control IgG1 antibody prior to injection into recipient rats. The final concentration of antibody used per animal was adjusted to 5.5 mg/kg, or approximately 1 mg/animal. A minimum of four animals was used for each condition.

Recipient rats were weighed and injected subcutaneously with 150 to 200 µl ACE solution (containing 0.25 ml Ketamine, 0.2 ml Ace and 0.8 ml Rompin) to anesthetize. From each antibody treatment, 1.0×10$^7$ cells were injected intravenously into animals. Approximately 300 µl of each cell suspension was examined using a gamma counter to determine the total cpm injected/rat. The labeled NK cells were allowed to circulate in the rats for three hours after which the animals were sacrificed and 1.0 ml of peripheral blood drawn by aortic puncture. Spleens were removed from each animal, weighed, and counted using a gamma counter. To determine the percentage of cells returning to the spleen, the counts per minute (cpm)/spleen were divided by the total known cpm injected into the rat. To determine the cpm in peripheral blood, an assumption was made that blood represents about 6.0% of the total rat's weight. The cpm in 1.0 ml blood was multiplied by 6.0% of the animal's total weight to determine total cpm in blood. This number was then divided by the total number of cpm's injected into each animal to obtain the percentage of cpm remaining in blood.

In the first experiment, antibodies 226B, 226G, 226H, 226I, 20C5B (a non-blocking CD18 antibody) and a control antibody were used. Antibodies 226B and 226G appeared to significantly reduce the number of cells returning to the spleen as compared to the control antibody and the other two 226 antibodies; approximately 7 to 8% of the labeled cells returned to the spleen after incubation with the control antibodies, while approximately 6% of the cells returned to the 5 spleen after incubation with 226B and 226G antibodies. The percentage of total cpm in blood, between 0.9 and 1.4%, did not show a marked difference between treatment groups with the exception of 226B, which had lower values than all other groups.

In a second experiment, several adjustments were made to the protocol defined above. First, an increase to four animals per condition was made, and second, the spleen from a tumor-bearing rat was removed at 2.5 weeks post-adoptive transfer rather than four weeks as above. The NK cells were prepared in exactly the same manner and injected into recipient animals following incubation with either antibody 226B or 226G or a control antibody at the doses defined above. Again, the labeled cells were allowed to circulate for three hours after which the animals were sacrificed and blood and spleens collected as above. In addition, the tissues from two of the animals/condition were removed to determine other locations of the tumor cells. These tissues included liver, brain, thymus, lung, long bone (for bone marrow) and kidney.

The results indicated that, in the control IgG1, approximately 32% of tumor cells were in the spleen, whereas both 226B and 226G showed reduced numbers, 28% and 29%, respectively, of labeled cells in the spleen. The percentage of cells in the blood were similar for each antibody, approximately 3 to 4% of the total cpm's were found in blood, with 226G antibody treatment slightly less than the other two groups.

The tissue distribution was similar between treatment groups with liver showing 27% of total cpm, brain 0.05%, thymus 0.10%, lung 15%, kidney 0.80%, and long bone 1.3%.

In a third experiment, an increase in the number of animal per condition (n=6 or 7) was made in an attempt to detect statistical differences between the three treatment groups above. Again, the spleen from an animal injected with tumor cells two weeks prior to the experiment was used and prepared by the same method described above. The cells were labeled in the same manner and injected into the animals and allowed to circulate for three hours. In this experiment, only blood samples and spleens were collected from animals due to the large number of animals used.

The results were consistent with the second experiment in that approximately 30% of labeled cells were observed to have returned to the spleen in the control group, while only 25% in 226B antibody-treated cells and 27% in 226G antibody-treated cells were found in the spleen. The blood values again did not show major differences between groups, with approximately 17% of the total cpm's found in blood in the control group and 15.8% and 14.75%, respectively. were found for 226B and 226G treated groups.

To determine if three hours was an optimum time point to examine differences between treatment groups, a small adjustment was made in a fourth experiment. Again, cells were isolated and prepared in the same way for injection into recipient animals, except that an additional anti-CD18 antibody 20C5B was added to the panel of test antibodies. In addition, only four animal were used for each condition. In this experiment, the cells were allowed to circulate for only 30 minutes after injection, at which point blood samples were drawn and spleen removed from the animals.

At the 30 minute time point, the total cpm in the spleen was reduced from values observed in the second and third experiments to 12 to 13%. There were no apparent differences between all treatment groups in the spleen samples, although two of the four animal in the group treated with antibody 226B did have slightly lower values. The blood values were again similar between all groups, with approximately 6 to 7% of the total cpm found in blood. The only marked difference between blood groups was a larger spread in data points from 226B and 226G antibody-treated animals. These findings suggest that $\alpha_d$ plays a role in the homing of leukemia cells to the spleen. Experiments indicate that homing requires several hours and maximum inhibition with the $\alpha_d$ specific monoclonal antibodies occurs at 3 hours.

Macaque Models for Multiple Sclerosis and Atherosclerosis

Monoclonal antibodies 212D and 217L were shown by immunocytochemical staining and immunoprecipitation to cross-react with macaque splenocytes. The specificity of recognition was confirmed by immunoprecipitation and amino terminal sequencing of an $\alpha_d$ species homolog from macaque spleen (Example 34). In view of these previous observations, the two antibodies were used to stain tissues obtained from macaques in either experimental autoimmune encephalitis (EAE) or atherosclerosis studies. Both of these diseases are marked by infiltration into lesions of phagocytotic macrophages which take up myelin basic protein (MBP) in the EAE or low density lipoprotein in atherosclerosis. MBP or lipid-laden macrophages can be identified morphorologically or by staining with Oil Red O (ORO) or antibody Ham 56 (Dako, Carpinteria, Calif.). The protocol employed in these studies is as described in Example 18 to characterize $\alpha_d$ expression in human tissues.

Sections from macaque brains with EAE were marked by infiltration of lymphocytes and macrophages. Expression of $\alpha_d$ was localized to a subset of macrophages in lesions which stained with ORO indicating previous uptake of MBP. Lesions which were negative for ORO staining were also negative for $\alpha_d$ expression. This result suggested a direct correlation between ORO staining and $\alpha_d$. Similar results were observed using antibodies 217K, 217I, and 217H.

Atherosclerosis lesions were obtained from either thoracic or abdominal arteries of macaques on high fat diets. Lesions occur in both locations in humans, but those which progress pathologically are more often located in the abdominal aorta. The lesions tested in this study were separated into five different stages (I through V) and normal. Stage (IV/V) lesions were derived from the abdominal aorta and the remainder were derived from the thoracic aorta.

Early stage lesions (I/II) showed little macrophage infiltration and low or even absent levels of $\alpha_d$ expression. In later stage lesions, foam cell infiltration was greater and $\alpha_d$ expression was detectable.

Staining patterns for other leukointegrin $\alpha_d$ chain subunits were overlapping with, but not identical to, $\alpha_d$ expression in both tissues. Most notably, expression of $\alpha_d$ subunits of non-$\alpha_d$ leukointegrins was detected on lymphocytes that did not stain with anti-$\alpha_d$ antibodies.

These results suggest that $\alpha_d$ expression may be characteristic of phagocytotic macrophages in both animal models. It is unclear, however, whether $\alpha_d$ is directly involved in phagocytosis or some downstream process such as antigen presentation.

EXAMPLE 37

Expression of $\alpha_d$ in Preclinical Models

In order to assess differential expression of $\alpha_d$ in various disease states, tissue sections from animal disease models were stained with anti-$\alpha_d$ polyclonal serum produced as described above (see Example 22). Tissue from normal and diseased rats was sectioned at 6 μm thickness and air dried on Superfrost Plus (VWR Scientific) slides at room temperature overnight. After drying, sections were stored at −70° C. until use. Prior to use, slides were removed from −70° C. and placed at 50° C. for approximately 5 minutes. Sections were fixed in cold (4° C.) acetone (Stephens Scientific) for 10 minutes at room temperature and allowed to dry at room temperature. Each section was blocked with 150 μl of a solution containing 30% normal rat serum (Harlan Bioproducts), 5% normal goat serum (Vector Laboratories) and 1% bovine serum (BSA) (Sigma Chemical Company) in 1×TBS for 30 minutes at room temperature, after which the solution was gently blotted from the sections. Rabbit polyclonal serum, at a protein concentration of 34 μg/ml, and preimmune serum from the same rabbit, at a protein concentration of 38.5 μg/ml, were diluted in the blocking solution and 100 μl separately applied to each tissue section for 30 minutes 37° C. The serum solution was blotted from the sections and unbound antibody removed by washing three times in 1×TBS for 5 minutes. Excess TBS was removed by blotting following the final wash. Biotinylated goat anti-rabbit antibody from a Elite Rabbit IgG Vectastain ABC kit (Vector) was prepared according to manufacturer's suggested protocol and 100 μl of the resulting solution was applied to each section for 15 minutes at 37° C. Slides were washed two times in 1×TBS for five minutes in each wash, after which 100 μl of streptavidin-gold conjugate (Goldmark Biologicals), diluted 1:100 in 5% normal rat serum and 1% BSA, was applied to each section for one hour at room temperature. Slides were washed three times with TBS for five minutes each wash, and 100 μl of 1% glutaraldehyde (Sigma) in TBS buffer was applied for five minutes at room temperature. Slides were again washed three times in TBS for five minutes each wash, and five times in sterile deionized water for three minutes each wash. Excess liquid was blotted from each slide and two drops each of silver enhancing and initiating solution (Goldmark Biologicals) were applied to each section. The reaction was allowed to proceed for 20–30 minutes at room temperature, after which the sections were rinsed thoroughly in sterile deionized water, air dried overnight at room temperature and mounted with Cytoseal 60 (VWR). As controls, tissue sections were labeled with monoclonal antibodies recognizing CD11a, CD11b, CD11c and CD18 in the same experiments by identical protocols.

Labeling with $\alpha_d$ polyclonal sera and monoclonal antibodies to CD11a, CD11b, CD11c, and CD18 revealed a staining pattern for $\alpha_d$ different from than observed for the other α subunits.

In normal lung tissue, $\alpha_d$ expression was detected on respiratory epithelium of the bronchi (but not the epithelium in the alveolar spaces) and on individual cells which appear to be alveolar macrophages within the airspaces. The signal observed with the polyclonal serum was significantly higher than the background signal level with the pre-immune serum control. In pulmonary granuloma tissue, 24 and 96 hours after administration of glycan, a different signal was detected with the $\alpha_d$ staining respiratory epithelium throughout the alveolar area and a stronger signal detected on what appear to be alveolar macrophages throughout the airways. In the lung tissue from animals which had presumably recovered from the disease (sacrificed 16 days after administration of glycan), no signal was observed with the $\alpha_d$ antibody. Very little background was observed with the pre-immunization serum in each of these tissues.

Using rat lung tissue from an antigen-induced asthma model, a very strong signal was detected with $\alpha_d$ antibody in the respiratory epithelium of both the bronchi and the alveolar spaces. The signal was significantly higher than the background signal level in the pre-immunization serum control.

Preclinical Model—L. Monocytogenes

Evidence suggests that $\alpha_d$ positive macrophages in the spleen red pulp are involved in the clearance of damaged rbcs and other particles from circulation. It is hypothesized that bacterial agents are also cleared from circulation by the $\alpha_d$ positive macrophages in the spleen red pulp. Non-infectious agents which would not require the induction of an antigen-specific T cell response would be eliminated directly by the red pulp macrophages. In contrast, opportunistic infectious agents cleared by the red pulp macrophage do require a product T cell immune response for the eradication of the bacteria. It was therefore proposed that $\alpha_d$ expression on red pulp macrophages may serve to regulate macrophage/T cell interactions either by regulating the movement of macrophages from the red pulp into the marginal zones or by acting as an accessory molecule involved in macrophage/T cell interactions leading T cell activation.

To investigate the role of $\alpha_d$ during immune responses to infectious agents, $\alpha_d$ expression is evaluated in the spleen using a murine model of *Listeria monocytogens*. Expression of α$_d$ is examined on red pulp macrophages which have phagocytosed bacteria. Antibodies to α$_d$ are also tested in the model to determine the role played by α$_d$ in the induction of a protective T cell response to *L. monocytogenes*.

Numerous modifications and variations in the invention as set forth in the above illustrative examples are expected to occur to those skilled in the art. Consequently only such limitations as appear in the appended claims should be placed on the invention.

What is claimed is:

1. A method for identifying a modulator of binding between $\alpha_d$ and VCAM-1 comprising the steps of:
   a) contacting $\alpha_d$ and VCAM-1 in the presence and absence of a putative modulator compound;
   b) detecting binding between $\alpha_d$ and VCAM-1; and
   c) identifying a putative modulator compound in view of decreased or increased binding between $\alpha_d$ and VCAM-1 in the presence of the putative modulator as compared to binding in the absence of the putative modulator.

2. The method according to claim 1 which is carried out in a host cell containing a soluble $\alpha_d$ and a soluble VCAM-1 and wherein decreased or increased binding is quantitated through measurement of a binding-dependent phenotypic change in the host cell, said phenotypic change resulting from a change in expression or a reporter gene product.

3. A method for identifying a compound that modulates binding between $\alpha_d$ and VCAM-1 comprising the steps of:
   a) immobilizing $\alpha_d$ or a fragment thereof, or VCAM-1 or a fragment thereof, on a solid support;
   b) labelling the non-immobilized binding partner with a detectable agent;
   c) contacting said immobilized binding partner with said labelled binding partner in the presence and absence of a putative modulator compound capable of specifically reacting with $\alpha_d$ or VCAM-1;
   d) detecting binding between said immobilized binding partner and said labelled binding partner; and
   e) identifying modulating compounds as those compounds that affect binding between said immobilized binding partner and said labelled binding partner.

4. The method of claim 3 wherein $\alpha_d$ or VCAM-1 is immobilized on a solid support coated or impregnated with a fluorescent agent; said non-immobilized binding partner is labelled with a compound capable of exciting said fluorescent agent; and $\alpha_d$ interaction with the binding partner of $\alpha_d$ is detected by light emission from said fluorescent agent.

* * * * *

UNITED STATES PATENT AND TRADEMARK OFFICE
CERTIFICATE OF CORRECTION

PATENT NO. : 5,837,478
DATED : November 17, 1998
INVENTOR(S) : Gallatin et al.

It is certified that error appears in the above-identified patent and that said Letters Patent is hereby corrected as shown below:

Title page, Item [54] and Column 1, line 2,
-- αd -- should be added between "between" and "and"

Title page,
Item [56], References Cited, OTHER PUBLICATIONS,
"Danilenko, et al." reference, replace "(LeuCams)" with -- (LeuCAMS) --
"Metlay, et al." reference, replace "141:1753-1771 (1990)" with -- 171:1753-1771 (1990) --
"Moore et al." reference, replace "characteization" with -- characterization --
"Sanchez-Madrid, et al." reference, replace "distinct αa-subunits" with -- α-subunits --
"Tamura, et al." reference, replace "interin$α_6β_4$" with -- integrin$α_6β_4$ --
"Zhou, et al." reference, replace "Cd11b/Cd18" with -- CD116/CD18 --
"Rabb, et al.," reference, replace "patients [1.1]" with -- "patients [1.2] --
"Ward and Reynolds" reference, replace "Lymhoocytic" with -- Lymphocytic --

Column 1,
Line 1, -- αd -- need to be added after the word "between" and before the word "and" in the title
Line 6, "is not abandoned" should read -- now U.S. Patent No. 5,817,515 --

Column 2,
Line 44, replace "150kD and 90 kd" with -- 150kD and 90kD --

Column 5,
Line 1, replace "immobilizing $β_d$ or a" with -- immobilizing $α_d$ or a --

Column 6,
Line 12, replace "marker gene tinder" with -- marker gene under --
Line 64, replace "and the $_d$ fusion" with -- and the $α_d$ fusion --

Column 9,
Line 61, replace "Kapecchi, Science 244:1288-1292" with -- Capecchi: Science 244:1288-1292 --

Column 10,
Line 29, replace "$β_d$ mRNA" with -- $α_d$ mRNA --
Line 30, replace "$β_d$ gene" with -- $α_d$ gene --
Line 31, replace "express $β_d$ may have" with -- express $α_d$ may have --

UNITED STATES PATENT AND TRADEMARK OFFICE
CERTIFICATE OF CORRECTION

PATENT NO.    : 5,837,478
DATED         : November 17, 1998
INVENTOR(S)   : Gallatin et al.

It is certified that error appears in the above-identified patent and that said Letters Patent is hereby corrected as shown below:

Column 12,
Line 11, replace "unregulation" with -- upregulation --

Column 13,
Line 29, replace "grains" with -- grams --
Line 49, replace "α-mercaptoethanol" with -- β-mercaptoethanol --

Column 14,
Line 35, replace "λλZAP" with -- λZAP --

Column 15,
Line 9, replace "µCi λ $P^{32}$" with -- AµCi$\gamma^{32}$P --
Line 29, replace "canine $^{\alpha}{}_{TM1}$" with -- canine $\alpha_{TM1}$ --

Column 19,
Line 22, replace "the 1 (insertion) domain" with -- the I (insertion) domain --

Column 21,
Line 14, replace "10βg" with -- 10 µg --

Column 24,
Line 47, replace "human $\alpha_d$/CD18" with -- Human $\alpha_d$/CD18 --

Column 25,
Line 51, replace "reductase(DHFR)=Chinese" with -- reductase(DHFR)-Chinese --

Column 26,
Line 6, replace "Human $\alpha_d$ Binds" with -- Human $\alpha_d$ Binds --
Line 43, replace "ICAM-1IgG1" with -- ICAM-1/IgG1 --

Column 27,
Lines 3-4, replace "VCAM-1 IgG1" with -- VCAM-1/IgG1 --

Column 28,
Line 33, replace "CD11I" with -- CD11bI --
Line 51, replace "$\alpha_D$ Binding" with -- $\alpha_d$ Binding --

UNITED STATES PATENT AND TRADEMARK OFFICE
CERTIFICATE OF CORRECTION

PATENT NO.    : 5,837,478
DATED         : November 17, 1998
INVENTOR(S)   : Gallatin et al.

It is certified that error appears in the above-identified patent and that said Letters Patent is hereby corrected as shown below:

Column 29,
Line 30, replace "ICAM-1Ig" with -- ICAM-1/Ig --

Column 30,
Line 17, replace "E37A/1g" with -- E37A/Ig --

Column 31,
Line 36, replace "on the a chain construct" with -- on the α chain construct --
Line 36, delete the number "5" between "of" and "the"

Column 33,
Line 12, replace "(Phanmacia)" with -- (Pharmacia) --

Column 34,
Line 37, replace "two more tines" with -- two more times --

Column 36,
Line 37, replace "$\alpha_d$/CD18_JY cells" with -- $\alpha_d$/CD18-JY cells --

Column 37,
Line 48, replace "188G, 1881, 188J" with -- 188G, 188I, 188J --

Column 38,
Line 19, replace "anti-$a_d$" with -- anti-$\alpha_d$ --

Column 39,
Line 13, replace "αd binding" with -- $\alpha_d$ binding --

Column 40,
Line 27, replace "108 LFA-1" with -- $10^8$ LFA-1 --
Line 37, replace "anti-ad monoclonal with -- anti-$\alpha_d$ monoclonal --
Line 54, replace "anti-old antibody" with -- anti-$\alpha_d$ antibody --

Column 42,
Line 50, replace "120 ng/mil" with -- 120ng/ml --

UNITED STATES PATENT AND TRADEMARK OFFICE
CERTIFICATE OF CORRECTION

PATENT NO. : 5,837,478
DATED : November 17, 1998
INVENTOR(S) : Gallatin et al.

It is certified that error appears in the above-identified patent and that said Letters Patent is hereby corrected as shown below:

<u>Column 44,</u>
Line 3, replace "identical + $\alpha_d$" with -- identical to $\alpha_d$ --
Line 9, replace "well as ad)" with -- well as $\alpha_d$ --

<u>Column 45,</u>
Line 56, replace "10-8m" with -- $10^{-8}$ --
Line 65, replace "appropriate + $\alpha_d$" with -- appropriate to $\alpha_d$ --

<u>Column 46,</u>
Line 37, replace "upregulation of ad" with -- upregulation of $\alpha_d$ --
Line 46, replace "express $\alpha_d$d" with -- express $\alpha_d$. --

<u>Column 52,</u>
Line 15, replace "10mCi/ml $\lambda^{32}$ P-ATP" with -- 10mCi/ml$\gamma^{32}$P-ATP --
Line 37, replace "related + $\alpha_d$" with -- related to $\alpha_d$ --

<u>Column 53,</u>
Line 40, replace "βgIII" with -- βg/II --

<u>Column 56,</u>
Line 18, replace 5X108 splenocytes" with -- $5X10^8$ splenocytes --

<u>Column 57,</u>
Line 42, "1.15X108" with -- $1.15X10^8$ --
Line 48, replace "Free RPM1 over" with -- Free RPMI, over --
Line 54, replace "1.5X106" with -- $1.5X10^6$ --
Line 63, replace "5X105" with -- $5X10^5$ --

<u>Column 58,</u>
Line 3, replace "(RPM1, 2.0%" with -- RPMI 2.0% --
Line 16, replace "RPM1" with -- RPMI --
Line 27, replace "2.3X106" with -- $2.3X10^6$ --
Line 30, replace "2X106 rat $\alpha_d$S" with -- $2X10^6$ rat $\alpha_d$ --
Line 33, replace "5X106" with -- $5X10^6$ --
Line 43, replace "2X106 RAD" with -- $2X10^6$ RAD --

UNITED STATES PATENT AND TRADEMARK OFFICE
CERTIFICATE OF CORRECTION

PATENT NO. : 5,837,478
DATED : November 17, 1998
INVENTOR(S) : Gallatin et al.

It is certified that error appears in the above-identified patent and that said Letters Patent is hereby corrected as shown below:

Column 59,
Line 60, replace "a final washed" with -- a final wash --

Column 61,
Line 37, replace "1X106 cell/ml" with -- $1X10^6$ cell/ml --

Column 65,
Line 27, replace "1X106" cells/sample" with -- $1X10^6$ cells sample --

Column 66,
Line 23, replace "indicated t hat the" with -- indicated that the --
Line 65, replace "yak-i" with -- yak-1 --

Column 68,
Line 38, replace "Bluescript SK" with -- Bluescript SK- --

Column 70,
Line 43, replace "5X105 phage" with -- $5X10^5$ phage --

Column 71,
Line 45, replace "SDS at 65'C" with -- SDS at 65°C --

Column 72,
Line 18, replace "11.b-1/2 REV2 5' GTGGIJC" with -- 11.b-1/2REV25' GTGG ATC --

Signed and Sealed this

Twenty-second Day of April, 2003

JAMES E. ROGAN
*Director of the United States Patent and Trademark Office*